US011161886B2

(12) United States Patent
Hahn et al.

(10) Patent No.: US 11,161,886 B2
(45) Date of Patent: Nov. 2, 2021

(54) **BACTERIOCINS FOR CONTROL OF *SALMONELLA ENTERICA***

(71) Applicant: Nomad Bioscience GmbH, München (DE)

(72) Inventors: Simone Hahn, Merseburg (DE); Tobias Schneider, Halle (DE); Anett Stephan, Halle (DE); Steve Schulz, Halle (DE); Anatoli Giritch, Halle (DE); Yuri Gleba, Berlin (DE)

(73) Assignee: NOMAD BIOSCIENCE GMBH, Munich (DE)

( * ) Notice: Subject to any disclaimer, the term of this patent is extended or adjusted under 35 U.S.C. 154(b) by 0 days.

(21) Appl. No.: 16/577,484

(22) Filed: Sep. 20, 2019

(65) Prior Publication Data

US 2020/0010517 A1 Jan. 9, 2020

Related U.S. Application Data

(63) Continuation-in-part of application No. PCT/EP2018/055479, filed on Mar. 6, 2018.

(30) Foreign Application Priority Data

Mar. 24, 2017 (EP) .................................... 17162784

(51) Int. Cl.
*C07K 14/46* (2006.01)
*A23K 20/147* (2016.01)

(52) U.S. Cl.
CPC .......... *C07K 14/461* (2013.01); *A23K 20/147* (2016.05)

(58) Field of Classification Search
CPC ..... A23K 20/147; A61K 38/164; A61P 31/04; C07K 14/255; C07K 14/461; Y02A 50/481
See application file for complete search history.

(56) References Cited

U.S. PATENT DOCUMENTS 10,201,168 B2 2/2019 Giritch et al.
2015/0050253 A1* 2/2015 Gabant .................... C12N 1/16 424/93.21
2020/0263221 A1* 8/2020 Gabant ............. B01L 3/502738

FOREIGN PATENT DOCUMENTS

CA 2794603 * 4/2011 ............... C12N 9/52
WO WO2014009744 * 1/2014 ............ A61K 38/16

OTHER PUBLICATIONS

International Search Report and Written Opinion dated Jul. 31, 2018 from ISA/EP in Application No. PCT/EP2018/055479.
Database UniProt accession No. A0A1J4RAK5, Feb. 15, 2017 (Feb. 15, 2017).
S. Mills et al, "New Developments and Applications of Bacteriocins and Peptides in Foods," Annual Review of Food Science and Technology, vol. 2, No. 1, Apr. 10, 2011 (Apr. 10, 2011), p. 299-329.
Paul D. Cotter et al, "Bacteriocins—a viable alternative to antibiotics?", Nature Reviews. Microbiology,vol. 11, No. 2, Dec. 24, 2012 (Dec. 24, 2012), p. 95-105.
Yuri De Jesus Lopes et al, "Production of Bacteriocin EC2 and Its Interference in the Growth of *Salmonella typhi* in a Milk Matrix", Nitra Aug. 1, 2013 (Aug. 1, 2013), p. 26-29.
Chalón Miriam C et al, "Membrane-active bacteriocins to controlSalmonellain foods Are they the definite hurdle?", Food Research International,vol. 45, No. 2, 2012, p. 735-744.
Database UniProt accession No. A0A100QC05, Apr. 2016 (Apr. 13, 2016).
Database UniProt accession No. A0A098YNK1, Jan. 2015 (Jan. 7, 2015).
Database EMBL accession No. EM_STD:APW04102, Jan. 2017 (Jan. 19, 2017).
Database UniProt accession No. A0A1J4R8E3, Feb. 15, 2017 (Feb. 15, 2017).
S. Hahn-Löbmann, et al., "Colicins and Salmocins—New Classes of Plant-Made Non-antibiotic Food Antibacterials," Frontiers in Plant Science, vol. 10, Article 437, Apr. 9, 2019, pp. 1-16.
T. Schneider, et al., "Plant-made *Salmonella* bacteriocins salmocins for control of *Salmonella* pathovars," Scientific Reports, vol. 8, No. 4078, Mar. 6, 2018, pp. 1-10.
Database RefSeq [Online] Mar. 20, 2017 (Mar. 20, 2017), "colicin-10 [*Salmonella enterica*]", retrieved from EBI accession No. UNIPARC:UPI0009AA4FA3; Database accession No. WP079814137.

* cited by examiner

*Primary Examiner* — Marcela M Cordero Garcia
(74) *Attorney, Agent, or Firm* — David M. Saravitz; Williams Mullen

(57) ABSTRACT

The present invention relates to bacteriocins for control of *Salmonella enterica* (salmocins). The bacteriocins are derived from *Salmonella*. The salmocins can be expressed in plants and can be used in a method of preventing or reducing infection or contamination of an object with *Salmonella*.

20 Claims, 34 Drawing Sheets

Specification includes a Sequence Listing.

```
ScolE1a    KSKGKKIGNVDEALAAFE----KYKDVLDKKFSKADRDAIVNALKSFNYDDWAKHLDQFA    393
ScolE1b    QSKGKKISNVDEALAAFE----KYKDVLDKKFSKADRDAIVNALKSVDYADWAKHLDQFS    437
Spst       -----NFGDKHTTRREREAALVL-SDIVNNQYIYK-------------------------    296
ScolE3     ---DSQHGELEGYRASDGQHLGSFDPKTGKQLK---------GPDP------------K-    580
ScolE2     KLRDKEFKNFDDFRKKFWEE-VSKDPELSKQFIPGNKKRMSQGLAP------------RA    536
ScolE7     KLRDKEFRNFDDFRKKFWEE-VSKDPELSKQFIKGNRDRMQVGKAP------------KS    538
                :  : .             .   .::

ScolE1a    KY-LKITGHVSFGYDVVSDVLKASEIGDWKPLFITLEQKVLDTGMSYLVVLMFSLIAGTI    452
ScolE1b    RY-LKISGRVSTGYDIYSDIRKGMDTNDWRPLFLTLEKLAVDAGVGYIVALGFSVIASTA    496
Spst       ------------------------------------------------------------    296
ScolE3     --------------------------------------RNIKKYL---------------    587
ScolE2     RNKDIVGGRRSFELHHDKPISQDGGVYDMDNIRVTTPKLHIDIHRGK-------------    583
ScolE7     RKKDAAGKRTSFELHHDKPVSQDGGVYDMDNLRITTPKRHIDIHRGQ-------------    585

ScolE1a    LGIFGVAIITAILCSFVDKYILNALNDALGI    483
ScolE1b    LGIWGVAIITGVICSFVDKKDLEKLNEALGI    527
Spst       -------------------------------    296
ScolE3     -------------------------------    587
ScolE2     -------------------------------    583
ScolE7     -------------------------------    585
```

Fig. 20C a
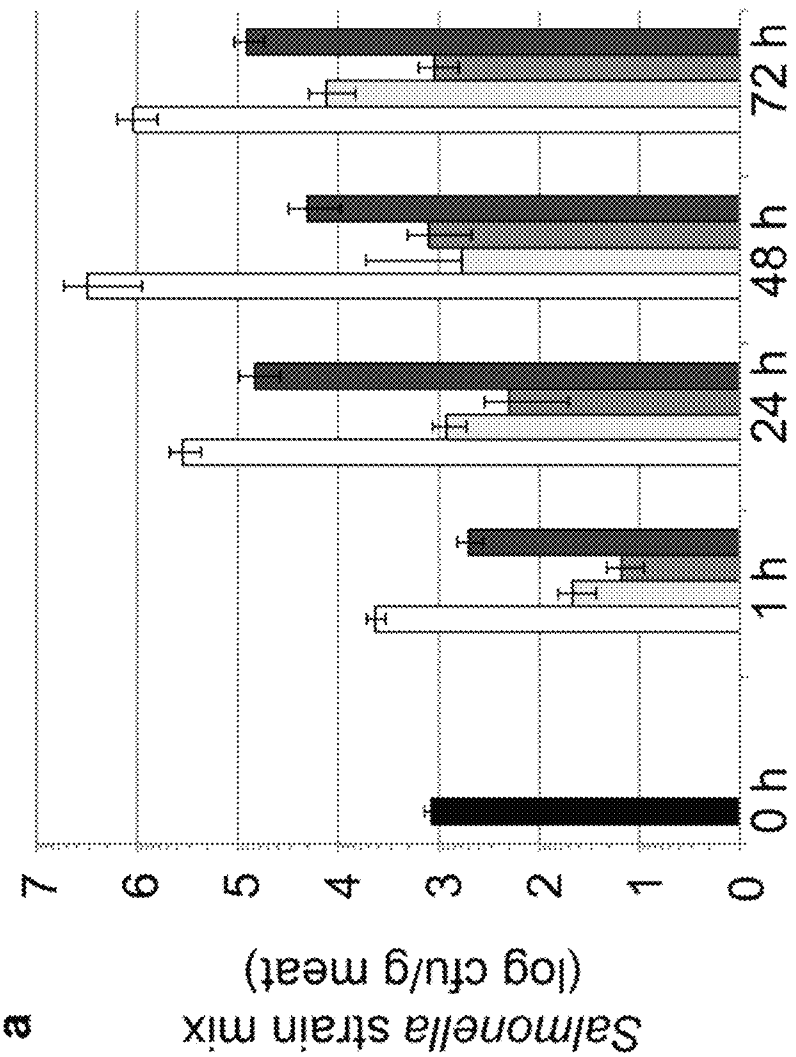
b
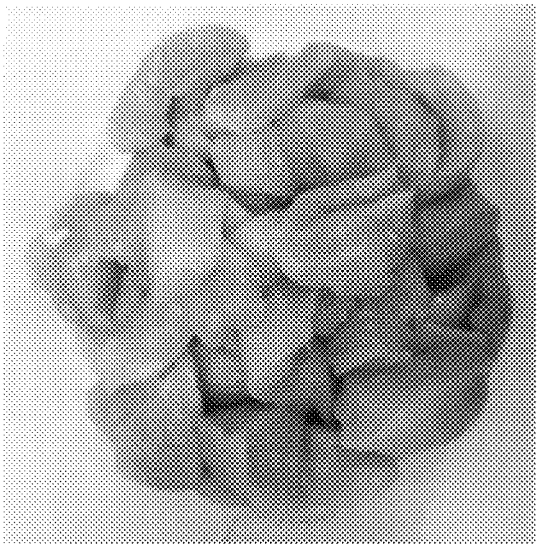
Fig. 25

```
ScolE1e  -MSGSIAYYEDGVPYSADGKVVIVITGKLPEGTGGSLTADLG---SAGVSESSAAIHATA  56
ScolE1a  MADNTIAYYEDGVPHSADGKVVIVIDGKNPVDTGAGGTGGGGGSKVGGTSESSAAIHATA  60
ScolE1c  MSDNTIAYYEDGVPYSADGKVLIIIDGKMPVDTG--GTGGGGGGKAGVTSESSAAIHATA  58
ScolE1d  MSDNTIAYYEDGVPYSADGKVLIIIDGKMPVDTG--GTGGGGGGKAGVTSESSAAIHATA  58
            ..:*********:******:*:* **:* .**   *.. *     . .***********

ScolE1e  KWSTAQLQKTKASQAVKVKEAAVAQAKAKEKRDALTQYLKDIVNQALSHNS-RPPAVTDL  115
ScolE1a  KWSTAQLKKTLAEKAAREREТAAAMAAAKAKRDALTQHLKDIVNDVLRHNASRTPSATDL  120
ScolE1c  KWSKAQLQKSLEEKAARERETAAAMAAAKAKRDALTQRLKDIVNDVLYHNAH-PPAVIDL  117
ScolE1d  KWSKAQLQKSLEEKAARERETAAAMAAAKAKRDALTQHLKDIVNDVLYHNAH-PPAVIDL  117
         ***.***:*:   *:*.: :*:*.* * ** *******:******:.* **:   *:. **

ScolE1e  AHANNMAMQAEAERLRLAKAEAKAREEAEAAEKAFQLAEQQRLASEREQAETERQLKLAE  175
ScolE1a  AHANNMAMQAEAQRLGRAKAEEKARKEAEAAELAFQEAERQREEAVRQLAETERQLKQAE  180
ScolE1c  AHANNMAMQAEAQRLGRAKAEEKARKEAEAAEKSLQEAERQCEEAARQRAEAERQLKQAE  177
ScolE1d  AHANNMAMQAEAQRLGRAKAEEKARKEAEAAEKSLQEAERQREEAARQRAEAERQLKQAE  177
         ************:**  **** ***:****** ::* **:*   : *: **:***** **

ScolE1e  AEEKRLAALSEEARAVEIAQKNLAATQSELTNMDGEIQNLNIRLNNNIHERDAETSSLSA  235
ScolE1a  -EEKRLAALSDEARAVENARKNLDTAKSELANVDSDIERQRSQLSSL-------------  226
ScolE1c  AEEKRLAALSEEARAVEIAQKNLAAAQSELSKMDGEIMSLNVRLSTSIHARDAEMNSLSG  237
ScolE1d  AEEKRLAALSEEARAVEIAQKNLAAAQSELSKMDGEIMSLNVRLSTSIHARDAEMNSLSG  237
          *********:****** *:*** :::***:::*.:*    . :*..

ScolE1e  KRNELFQVSEQYKEIDAQVKKLEPRANDPLQSRPFFAAMTRRANVYTVVQEKQGLVTASE  295
ScolE1a  ---------------DADVKKAEENLRLT---------MRIKGRIGRKMQAKSQAIVDDK  262
ScolE1c  KRNELAQASAKYKELDELVKKLEPRANDPLQNRPFFDAASRRARAGDTLAEKQKEVTASE  297
ScolE1d  KRNELAQASAKYKELDELVKKLEPRANDPLQNRPFFDAASRRARAGDTLAEKQKEVTASE  297
                        *  *** * . .                :..    :  *.  :. .:

ScolE1e  TRINQFNADISRLQEEIVKANEKRNMIITHIHEAESQLKIAKINLINSQIKDATDSVIGF  355
ScolE1a  KR--------IYSDAENVLNTMTVNPNLKAQQVTDAENELKVAIDNLNSSQMKNAVDATVSF  316
ScolE1c  TRINELNTEINQVQGAISQANNKRNLNVQQVTETENALKVAIDNLNSSQMKNAVDATVSF  357
ScolE1d  TRINELNTEINQVQGAISQANNKRNLNVQQVTETENALKVAIDNLNSSQMKNAVDATVSF  357
         .*          .  :  :    . :**:    :: ::*: **:*  ** .**:*:*.*:.:.*

ScolE1e  YQTLTEKYGQKYSLLAQELAEKSKGKKIGNVNEALAAFEKYQDVLNKKFSKADRDAIFNA  415
ScolE1a  YQTLTEKYGEKYSLIAQELAEKSKGKKIGNVDEALAAFEKYKDVLDKKFSKADRDAIVNA  376
ScolE1c  YQTLTEKYGEKYSLIAQELAEKSKGKKIGNVDEALAAFEKYKDVLDRKFSKADRDAIVNA  417
ScolE1d  YQTLTEKYGEKYSLIAQELAEKSKGKKIGNVDEALAAFEKYKDVLDRKFSKADRDAIVNA  417
         *********:****:****************:*********:***::**********.**

ScolE1e  LESVKYDDWAKHLDQFAKYLKITGRVSFGYDLVSDVLKVRDTGDWKPLFLTLEKKALDTG  475
ScolE1a  LKSFNYDDWAKHLDQFAKYLKITGHVSFGYDVVSDVLKASETGDWKPLFITLEQKVLDTG  436
ScolE1c  LKSFNYDDWAKHLDQFAKYLKITGHVSFGYDVVSDVLKARETGDWKPLFITLEQKALDTG  477
ScolE1d  LKSFNYDDWAKHLDQFAKYLKITGHVSFGYDVVSDVLKARETGDWKPLFITLEQKALDTG  477
         *:*.:*******************:******:******.  :********:***:*.****

ScolE1e  LSYLVVLMFSLIAGTTLGIWGVAIVTGILCSFIDKSMLNDLNEALGI  522
ScolE1a  MSYLVVLMFSLIAGTTLGIFGVAIITAILCSFVDKYILNALNDALGI  483
ScolE1c  MSYLVVLMFSLIAGTTLGIFGVAIITAILCSFVDKYILNALNDALGI  524
ScolE1d  MSYLVVLMFSLIAGTTLGIFGVAIITAILCSFVDKYILNALNDALGI  524
         :******************:****:*.*****:** :** **:****
```

Fig. 26

```
ColM      -METLTVHAPSPSTNLPSYGN-GAFSLSAPHVPGAGPLLVQVVYSFFQSPNMCLQALTQL 58
ScolMa    MTDTITVVAPVPPSGSALAGNYSASTMSAGNRISSGPTFLQFAYPYYQSPQLAVNCAKWI 60
            :*:** ** * :.     ** .* ::** :  .:** ::*..* ::***::.::. . :

ColM      EDYIKKHGASNPLTLQIISTNIGYFCNADRNLVLHPGISVYDAYHFAKPAPSQYDYRSMN 118
ScolMa    LDFVESHDMKNANNQKIFSENVGHFCFADKNLVNYPAMKVLDAFGG----DRKFIYSQDQ 116
           *:::.*. .*  . :*:* *:*:** **:*** :*.:.* **:        :: * . :

ColM      MKQMSGNVTTPIVALAHYLWGNGAERSVNIANIGLKISPMKINQIKDIIKSGVVGTFPVS 178
ScolMa    ISRLSGDVTTPITAWAHFLWGDGAARTVNLTDVGLRIQANQISPVMDLVKGGAVGTFPVN 176
          :.::**:*****.* **:***:** *:**:::::**:*.  :*. : *::*.*.******.

ColM      TKFTHATGDYNVITGAYLGNITLKTEGTLTISANGSWTYNGVVRSYDDKYDFNASTHRGI 238
ScolMa    AKFTRDTMLDGIIPASYLGNITLQTTGTLTINSLGAWSYDGVVKAYNDTYDANPSTHRGL 236
          :***: *   .:* .:*******:* *****.: *:*:*:***::*:*.** * *****:

ColM      IGESLTRLGAMFSGKEYQILLPGEIHIKESGKR 271
ScolMa    LGEYSTSVLGHFSGTPYEIQMPGMIPVKGNGMR 269
          :**  * : . ***. *:* :** * :* .* *
```

Fig. 27

SEQUENCE LISTING

```
<160> NUMBER OF SEQ ID NOS: 32

<210> SEQ ID NO 1
<211> LENGTH: 583
<212> TYPE: PRT
<213> ORGANISM: Salmonella enterica

<400> SEQUENCE: 1

Met Ser Gly Gly Asp Gly Ile Gly His Asn Ser Gly Ala His Ser Thr
1               5                   10                  15

Gly Gly Val Asn Gly Ser Ser Ser Gly Arg Gly Gly Ser Ser Ser Gly
            20                  25                  30

Gly Gly Asn Asn Pro Asn Ser Gly Pro Gly Trp Gly Thr Thr His Thr
        35                  40                  45

Pro Asp Gly His Asp Ile His Asn Tyr Asn Pro Gly Glu Phe Gly Gly
    50                  55                  60

Gly Gly His Lys Pro Gly Gly Asn Gly Gly Asn His Ser Gly Gly Thr
65                  70                  75                  80

Gly Asp Gly Gln Pro Pro Gly Ala Ala Met Ala Phe Gly Phe Pro Ala
                85                  90                  95

Leu Val Pro Ala Gly Ala Gly Gly Leu Ala Val Thr Val Ser Gly Asp
            100                 105                 110

Ala Leu Ala Ala Ala Ile Ala Asp Val Leu Ala Val Leu Lys Gly Pro
        115                 120                 125

Phe Lys Phe Gly Ala Trp Gly Ile Ala Leu Tyr Gly Ile Leu Pro Thr
    130                 135                 140

Glu Ile Ala Lys Asp Asp Pro Arg Met Met Ser Lys Ile Val Thr Ser
145                 150                 155                 160

Leu Pro Ala Asp Ala Val Thr Glu Ser Pro Val Ser Ser Leu Pro Leu
                165                 170                 175

Asp Gln Ala Thr Val Ser Val Thr Lys Arg Val Thr Asp Val Val Lys
            180                 185                 190

Asp Glu Arg Gln His Ile Ala Val Val Ala Gly Val Pro Ala Ser Ile
        195                 200                 205
```

-continued

```
Pro Val Val Asp Ala Lys Pro Thr Thr His Pro Gly Val Phe Ser Val
    210                 215                 220

Ser Val Pro Gly Leu Pro Asp Leu Gln Val Ser Thr Val Lys Asn Ala
225                 230                 235                 240

Pro Ala Met Thr Ala Leu Pro Arg Gly Val Thr Asp Glu Lys Asp Arg
                245                 250                 255

Thr Val His Pro Ala Gly Phe Thr Phe Gly Gly Ser Ser His Glu Ala
            260                 265                 270

Val Ile Arg Phe Pro Lys Glu Ser Gly Gln Ala Pro Val Tyr Val Ser
        275                 280                 285

Val Thr Asp Val Leu Thr Pro Glu Gln Val Lys Gln Arg Gln Asp Glu
    290                 295                 300

Glu Asn Arg Arg Gln Gln Glu Trp Asp Ala Thr His Pro Val Glu Val
305                 310                 315                 320

Ala Glu Arg Asn Tyr Arg Leu Ala Ser Asp Glu Leu Asn Arg Ala Asn
                325                 330                 335

Val Asp Val Ala Gly Lys Gln Glu Arg Gln Ile Gln Ala Ala Gln Ala
            340                 345                 350

Val Ala Ala Arg Lys Gly Glu Leu Asp Ala Ala Asn Lys Thr Phe Ala
        355                 360                 365

Asp Ala Lys Glu Glu Ile Lys Lys Phe Glu Arg Phe Ala His Asp Pro
    370                 375                 380

Met Ala Gly Gly His Arg Met Trp Gln Met Ala Gly Leu Lys Ala Gln
385                 390                 395                 400

Arg Ala Gln Asn Glu Val Asn Gln Lys Gln Ala Glu Phe Asn Ala Ala
                405                 410                 415

Glu Lys Glu Lys Ala Asp Ala Asp Ala Ala Leu Asn Val Ala Leu Glu
            420                 425                 430

Ser Arg Lys Gln Lys Glu Gln Lys Ala Lys Asp Ala Ser Asp Lys Leu
        435                 440                 445

Asp Lys Glu Asn Lys Arg Asn His Pro Gly Lys Ala Thr Gly Lys Gly
    450                 455                 460

Gln Pro Val Gly Asp Lys Trp Leu Glu Asp Ala Gly Lys Glu Ala Gly
465                 470                 475                 480

Ala Pro Val Pro Asp Arg Ile Ala Asp Lys Leu Arg Asp Lys Glu Phe
                485                 490                 495

Lys Asn Phe Asp Asp Phe Arg Lys Lys Phe Trp Glu Glu Val Ser Lys
            500                 505                 510

Asp Pro Glu Leu Ser Lys Gln Phe Ile Pro Gly Asn Lys Lys Arg Met
        515                 520                 525

Ser Gln Gly Leu Ala Pro Arg Ala Arg Asn Lys Asp Thr Val Gly Gly
    530                 535                 540

Arg Arg Ser Phe Glu Leu His His Asp Lys Pro Ile Ser Gln Asp Gly
545                 550                 555                 560

Gly Val Tyr Asp Met Asp Asn Ile Arg Val Thr Thr Pro Lys Leu His
                565                 570                 575

Ile Asp Ile His Arg Gly Lys
            580
```

<210> SEQ ID NO 2
<211> LENGTH: 587
<212> TYPE: PRT
<213> ORGANISM: Salmonella enterica

<400> SEQUENCE: 2

```
Met Ser Gly Gly Asp Gly Arg Gly His Asn Thr Gly Ala His Ser Thr
1               5                   10                  15

Ser Gly Asn Ile Asn Gly Gly Pro Thr Gly Leu Gly Val Ser Gly Gly
            20                  25                  30

Ala Ser Asp Gly Ser Gly Trp Ser Ser Glu Asn Asn Pro Trp Gly Gly
        35                  40                  45

Gly Ser Gly Ser Gly Ile His Trp Gly Gly Gly Ser Gly Arg Gly Asn
    50                  55                  60

Gly Gly Gly Asn Gly Asn Ser Gly Gly Gly Ser Gly Thr Gly Gly Asn
65                  70                  75                  80

Leu Ser Ala Val Ala Ala Pro Val Ala Phe Gly Phe Pro Ala Leu Ser
                85                  90                  95

Thr Pro Gly Ala Gly Gly Leu Ala Val Ser Ile Ser Ala Ser Glu Leu
            100                 105                 110

Ser Ala Ala Ile Ala Gly Ile Ile Ala Lys Leu Lys Lys Val Asn Leu
        115                 120                 125

Lys Phe Thr Pro Phe Gly Val Val Leu Ser Ser Leu Ile Pro Ser Glu
    130                 135                 140

Ile Ala Lys Asp Asp Pro Asn Met Met Ser Lys Ile Val Thr Ser Leu
145                 150                 155                 160

Pro Ala Asp Asp Ile Thr Glu Ser Pro Val Ser Ser Leu Pro Leu Asp
                165                 170                 175

Lys Ala Thr Val Asn Val Asn Val Arg Val Val Asp Asp Val Lys Asp
            180                 185                 190

Glu Arg Gln Asn Ile Ser Val Val Ser Gly Val Pro Met Ser Val Pro
        195                 200                 205

Val Val Asp Ala Lys Pro Thr Glu Arg Pro Gly Val Phe Thr Ala Ser
    210                 215                 220

Ile Pro Gly Ala Pro Val Leu Asn Ile Ser Val Asn Asn Ser Thr Pro
225                 230                 235                 240

Ala Val Gln Thr Leu Ser Pro Gly Val Thr Asn Asn Thr Asp Lys Asp
                245                 250                 255

Val Arg Pro Ala Gly Phe Thr Gln Gly Gly Asn Thr Arg Asp Ala Val
            260                 265                 270

Ile Arg Phe Pro Lys Asp Ser Gly His Asn Ala Val Tyr Val Ser Val
        275                 280                 285

Ser Asp Val Leu Ser Pro Asp Gln Val Lys Gln Arg Gln Asp Glu Glu
    290                 295                 300

Asn Arg Arg Gln Gln Glu Trp Asp Ala Thr His Pro Val Glu Val Ala
305                 310                 315                 320

Glu Arg Glu Tyr Glu Asn Ala Arg Ala Glu Leu Glu Ala Glu Asn Lys
                325                 330                 335

Asn Val His Ser Leu Gln Val Ala Leu Asp Gly Leu Lys Asn Thr Ala
            340                 345                 350

Glu Gly Leu Ala Leu Ser Asp Ala Gly Arg His Pro Leu Thr Ser Ser
        355                 360                 365

Glu Ser Arg Phe Val Ala Val Pro Gly Tyr Ser Gly Gly Gly Val His
    370                 375                 380

Phe Asp Ala Thr Ala Thr Val Asp Ser Arg Asp Arg Leu Asn Ser Leu
385                 390                 395                 400

Leu Ser Leu Gly Gly Ala Ala Tyr Val Asn Asn Val Leu Glu Leu Gly
                405                 410                 415
```

Glu Val Ser Ala Pro Thr Glu Asp Gly Leu Lys Val Gly Asn Ala Ile
420 425 430

Lys Asn Ala Met Ile Glu Val Tyr Asp Lys Leu Arg Gln Arg Leu Ile
435 440 445

Thr Arg Gln Asn Glu Ile Asn His Ala Gln Val Ser Leu Asn Thr Ala
450 455 460

Ile Glu Ser Arg Asn Lys Lys Glu Glu Lys Lys Arg Ser Ala Glu Asn
465 470 475 480

Lys Leu Asn Glu Glu Arg Asn Lys Pro Arg Lys Gly Thr Lys Asp Tyr
485 490 495

Gly His Asp Tyr His Pro Ala Pro Glu Thr Glu Glu Ile Lys Gly Leu
500 505 510

Gly Asp Ile Lys Lys Gly Ile Pro Lys Thr Pro Lys Gln Asn Gly Gly
515 520 525

Gly Lys Arg Lys Arg Trp Ile Gly Asp Lys Gly Arg Lys Ile Tyr Glu
530 535 540

Trp Asp Ser Gln His Gly Glu Leu Glu Gly Tyr Arg Ala Ser Asp Gly
545 550 555 560

Gln His Leu Gly Ser Phe Asp Pro Lys Thr Gly Lys Gln Leu Lys Gly
565 570 575

Pro Asp Pro Lys Arg Asn Ile Lys Lys Tyr Leu
580 585

<210> SEQ ID NO 3
<211> LENGTH: 585
<212> TYPE: PRT
<213> ORGANISM: Salmonella enterica

<400> SEQUENCE: 3

Met Ser Gly Gly Asp Gly Ile Gly His Asn Ser Gly Ala His Ser Thr
1 5 10 15

Gly Gly Val Asn Gly Ser Ser Ser Gly Ser Gly Gly Ser Ser Ser Gly
20 25 30

Ser Gly Asn Asn Pro Asn Ser Gly Pro Gly Trp Gly Thr Thr His Thr
35 40 45

Pro Asn Gly Asp Ile His Asn Tyr Asn Pro Gly Glu Phe Gly Gly Gly
50 55 60

Gly Asn Lys Pro Gly Gly His Gly Gly Asn Ser Gly Asn His Asp Gly
65 70 75 80

Ser Ser Gly Asn Gly Gln Pro Ser Ala Ala Pro Met Ala Phe Gly Phe
85 90 95

Pro Ala Leu Ala Pro Ala Gly Ala Gly Ser Leu Ala Val Thr Val Ser
100 105 110

Gly Glu Ala Leu Ser Ala Ala Ile Ala Asp Ile Phe Ala Ala Leu Lys
115 120 125

Gly Pro Phe Lys Phe Gly Ala Trp Gly Ile Ala Leu Tyr Gly Ile Met
130 135 140

Pro Thr Glu Ile Ala Lys Asp Asp Pro Asn Met Met Ser Lys Ile Met
145 150 155 160

Thr Ser Leu Pro Ala Asp Thr Val Thr Asp Thr Pro Val Ser Ser Leu
165 170 175

Pro Leu Asp Gln Ala Thr Val Ser Val Thr Lys Arg Val Ala Asp Val
180 185 190

Val Lys Asp Glu Arg Gln His Ile Ala Val Val Ala Gly Val Pro Met

-continued

```
        195                 200                 205

Ser Val Pro Val Val Asp Ala Lys Pro Thr Thr Arg Pro Gly Ile Phe
    210                 215                 220

Ser Ala Thr Val Pro Gly Leu Pro Ala Leu Glu Val Ser Thr Gly Lys
225                 230                 235                 240

Ser Ile Pro Ala Ser Thr Ala Leu Pro Arg Gly Ile Thr Glu Asp Lys
                245                 250                 255

Asp Arg Thr Glu His Pro Ala Gly Phe Thr Phe Gly Gly Ser Ser His
            260                 265                 270

Asp Ala Val Ile Arg Phe Pro Lys Glu Ser Gly Gln Ala Pro Val Tyr
        275                 280                 285

Val Ser Val Thr Asp Val Leu Thr Pro Glu Gln Val Lys Gln Arg Gln
    290                 295                 300

Asp Glu Glu Ser Arg Arg Gln Gln Glu Trp Asp Ala Thr His Pro Val
305                 310                 315                 320

Glu Val Ala Glu Arg Asn Tyr Arg Leu Ala Ser Asp Glu Leu Asn Arg
                325                 330                 335

Val Asn Ala Asp Val Ala Gly Lys Gln Glu Arg Gln Ala Gln Ala Gly
            340                 345                 350

Gln Ala Val Ala Ala Arg Lys Gly Glu Leu Asp Ala Ala Asn Lys Thr
        355                 360                 365

Phe Ala Asp Ala Lys Glu Glu Ile Lys Lys Phe Glu His Phe Ala Arg
    370                 375                 380

Asp Pro Met Ala Gly Gly His Arg Met Trp Gln Met Ala Gly Leu Lys
385                 390                 395                 400

Ala Gln Arg Ala Gln Asn Glu Val Asn Gln Lys Gln Ala Glu Phe Asp
                405                 410                 415

Ala Ala Glu Lys Glu Lys Ala Asp Ala Asp Ala Ala Leu Asn Ala Ala
            420                 425                 430

Leu Glu Ser Arg Lys Gln Lys Glu Gln Lys Ala Lys Asp Thr Lys Glu
        435                 440                 445

Arg Leu Asp Lys Glu Asn Lys Arg Asn Gln Pro Gly Lys Ala Thr Gly
    450                 455                 460

Lys Gly Gln Pro Val Ser Asp Lys Trp Leu Glu Asp Ala Gly Lys Glu
465                 470                 475                 480

Ser Gly Ser Pro Ile Pro Asp Ser Ile Ala Asp Lys Leu Arg Asp Lys
                485                 490                 495

Glu Phe Arg Asn Phe Asp Asp Phe Arg Lys Lys Phe Trp Glu Glu Val
            500                 505                 510

Ser Lys Asp Pro Glu Leu Ser Lys Gln Phe Ile Lys Gly Asn Arg Asp
        515                 520                 525

Arg Met Gln Val Gly Lys Ala Pro Lys Ser Arg Lys Lys Asp Ala Ala
    530                 535                 540

Gly Lys Arg Thr Ser Phe Glu Leu His His Asp Lys Pro Val Ser Gln
545                 550                 555                 560

Asp Gly Gly Val Tyr Asp Met Asp Asn Leu Arg Ile Thr Thr Pro Lys
                565                 570                 575

Arg His Ile Asp Ile His Arg Gly Gln
            580                 585
```

<210> SEQ ID NO 4
<211> LENGTH: 483
<212> TYPE: PRT
<213> ORGANISM: Salmonella enterica

<400> SEQUENCE: 4

Met Ala Asp Asn Thr Ile Ala Tyr Tyr Glu Asp Gly Val Pro His Ser
1               5                   10                  15

Ala Asp Gly Lys Val Val Ile Val Ile Asp Gly Lys Met Pro Val Asp
            20                  25                  30

Thr Gly Ala Gly Gly Thr Gly Gly Gly Gly Gly Gly Lys Val Gly Gly
        35                  40                  45

Thr Ser Glu Ser Ser Ala Ala Ile His Ala Thr Ala Lys Trp Ser Thr
    50                  55                  60

Ala Gln Leu Lys Lys Thr Leu Ala Glu Lys Ala Ala Arg Glu Arg Glu
65                  70                  75                  80

Thr Ala Ala Ala Met Ala Ala Ala Lys Ala Lys Arg Asp Ala Leu Thr
                85                  90                  95

Gln His Leu Lys Asp Ile Val Asn Asp Val Leu Arg His Asn Ala Ser
            100                 105                 110

Arg Thr Pro Ser Ala Thr Asp Leu Ala His Ala Asn Asn Met Ala Met
        115                 120                 125

Gln Ala Glu Ala Gln Arg Leu Gly Arg Ala Lys Ala Glu Glu Lys Ala
    130                 135                 140

Arg Lys Glu Ala Glu Ala Ala Glu Leu Ala Phe Gln Glu Ala Glu Arg
145                 150                 155                 160

Gln Arg Glu Glu Ala Val Arg Gln Leu Ala Glu Thr Glu Arg Gln Leu
                165                 170                 175

Lys Gln Ala Glu Glu Glu Lys Arg Leu Ala Ala Leu Ser Asp Glu Ala
            180                 185                 190

Arg Ala Val Glu Asn Ala Arg Lys Asn Leu Asp Thr Ala Lys Ser Glu
        195                 200                 205

Leu Ala Asn Val Asp Ser Asp Ile Glu Arg Gln Arg Ser Gln Leu Ser
    210                 215                 220

Ser Leu Asp Ala Asp Val Lys Lys Ala Glu Glu Asn Leu Arg Leu Thr
225                 230                 235                 240

Met Arg Ile Lys Gly Arg Ile Gly Arg Lys Met Gln Ala Lys Ser Gln
                245                 250                 255

Ala Ile Val Asp Asp Lys Lys Arg Ile Tyr Ser Asp Ala Glu Asn Val
            260                 265                 270

Leu Asn Thr Met Thr Val Asn Arg Asn Leu Lys Ala Gln Gln Val Thr
        275                 280                 285

Asp Ala Glu Asn Glu Leu Lys Val Ala Ile Asp Asn Leu Asn Ser Ser
    290                 295                 300

Gln Met Lys Asn Ala Val Asp Ala Thr Val Ser Phe Tyr Gln Thr Leu
305                 310                 315                 320

Thr Glu Lys Tyr Gly Glu Lys Tyr Ser Leu Ile Ala Gln Glu Leu Ala
                325                 330                 335

Glu Lys Ser Lys Gly Lys Lys Ile Gly Asn Val Asp Glu Ala Leu Ala
            340                 345                 350

Ala Phe Glu Lys Tyr Lys Asp Val Leu Asp Lys Lys Phe Ser Lys Ala
        355                 360                 365

Asp Arg Asp Ala Ile Val Asn Ala Leu Lys Ser Phe Asn Tyr Asp Asp
    370                 375                 380

Trp Ala Lys His Leu Asp Gln Phe Ala Lys Tyr Leu Lys Ile Thr Gly
385                 390                 395                 400

His Val Ser Phe Gly Tyr Asp Val Val Ser Asp Val Leu Lys Ala Ser 405 410 415

Glu Thr Gly Asp Trp Lys Pro Leu Phe Ile Thr Leu Glu Gln Lys Val
420 425 430

Leu Asp Thr Gly Met Ser Tyr Leu Val Val Leu Met Phe Ser Leu Ile
435 440 445

Ala Gly Thr Thr Leu Gly Ile Phe Gly Val Ala Ile Ile Thr Ala Ile
450 455 460

Leu Cys Ser Phe Val Asp Lys Tyr Ile Leu Asn Ala Leu Asn Asp Ala
465 470 475 480

Leu Gly Ile

<210> SEQ ID NO 5
<211> LENGTH: 527
<212> TYPE: PRT
<213> ORGANISM: Salmonella enterica

<400> SEQUENCE: 5

Met Ser Asp Asn Thr Ile Ala Tyr Tyr Glu Asp Gly Val Pro Tyr Ser
1 5 10 15

Ala Asp Gly Gln Val Val Ile Val Ile Asp Gly Lys Met Pro Val Asp
20 25 30

Thr Gly Ala Gly Gly Thr Gly Gly Gly Gly Gly Gly Lys Val Gly Gly
35 40 45

Thr Ser Glu Ser Ser Ala Ala Ile His Ala Thr Ala Lys Trp Ser Lys
50 55 60

Ala Gln Leu Gln Lys Ser Leu Glu Glu Lys Ala Ala Arg Glu Arg Glu
65 70 75 80

Thr Ala Ala Ala Met Ala Ala Ala Lys Ala Lys Arg Asp Ala Leu Thr
85 90 95

Gln His Leu Lys Asp Ile Val Asn Asp Val Leu Arg Tyr Asn Ala Ser
100 105 110

Arg Thr Pro Ser Ala Thr Asp Leu Ala His Ala Asn Asn Met Ala Met
115 120 125

Gln Ala Glu Ala Gln Arg Leu Gly Arg Ala Lys Ala Glu Glu Lys Ala
130 135 140

Arg Lys Glu Ala Glu Ala Ala Glu Lys Ser Leu Gln Glu Ala Glu Arg
145 150 155 160

Gln Arg Glu Glu Ala Ala Arg Gln Arg Ala Glu Ala Glu Arg Gln Leu
165 170 175

Lys Gln Ala Glu Ala Glu Glu Lys Arg Leu Ala Ala Leu Ser Glu Glu
180 185 190

Ala Arg Ala Val Glu Ile Thr Gln Lys Asn Leu Ala Ala Ala Gln Ser
195 200 205

Glu Leu Ser Lys Met Asp Gly Glu Ile Lys Ser Leu Asn Val Arg Leu
210 215 220

Ser Thr Ser Ile His Ala Arg Asp Ala Glu Met Asn Ser Leu Ser Gly
225 230 235 240

Lys Arg Asn Glu Leu Ala Gln Glu Ser Ala Lys Tyr Lys Glu Leu Asp
245 250 255

Glu Leu Val Lys Lys Leu Glu Pro Arg Ala Asn Asp Pro Leu Gln Asn
260 265 270

Arg Pro Phe Phe Asp Ala Thr Ser Arg Arg Ala Arg Ala Gly Asp Thr
275 280 285

Leu Ala Glu Lys Gln Lys Glu Val Thr Ala Ser Glu Thr Arg Ile Asn

```
    290                 295                 300

Glu Leu Asn Thr Glu Ile Asn Gln Val Arg Gly Ala Ile Ser Gln Ala
305                 310                 315                 320

Asn Asn Asn Arg Asn Leu Lys Val Gln Gln Val Thr Glu Thr Glu Asn
                325                 330                 335

Ala Leu Lys Val Ala Ile Asp Asn Leu Asn Ser Ser Gln Met Lys Asn
            340                 345                 350

Ala Val Asp Ala Thr Val Ser Phe Tyr Gln Thr Leu Thr Ala Lys Tyr
        355                 360                 365

Gly Glu Lys Tyr Ser Leu Ile Ala Gln Glu Leu Ala Glu Gln Ser Lys
    370                 375                 380

Gly Lys Lys Ile Ser Asn Val Asp Glu Ala Leu Ala Ala Phe Glu Lys
385                 390                 395                 400

Tyr Lys Asp Val Leu Asp Lys Lys Phe Ser Lys Ala Asp Arg Asp Ala
                405                 410                 415

Ile Val Asn Ala Leu Lys Ser Val Asp Tyr Ala Asp Trp Ala Lys His
            420                 425                 430

Leu Asp Gln Phe Ser Arg Tyr Leu Lys Ile Ser Gly Arg Val Ser Thr
        435                 440                 445

Gly Tyr Asp Ile Tyr Ser Asp Ile Arg Lys Gly Met Asp Thr Asn Asp
    450                 455                 460

Trp Arg Pro Leu Phe Leu Thr Leu Glu Lys Leu Ala Val Asp Ala Gly
465                 470                 475                 480

Val Gly Tyr Ile Val Ala Leu Gly Phe Ser Val Ile Ala Ser Thr Ala
                485                 490                 495

Leu Gly Ile Trp Gly Val Ala Ile Ile Thr Gly Val Ile Cys Ser Phe
            500                 505                 510

Val Asp Lys Lys Asp Leu Glu Lys Leu Asn Glu Ala Leu Gly Ile
        515                 520                 525


<210> SEQ ID NO 6
<211> LENGTH: 296
<212> TYPE: PRT
<213> ORGANISM: Salmonella enterica

<400> SEQUENCE: 6

Met Phe Ile Lys Ser Gly Gly Asn Leu Thr Ile Arg Thr Phe Gly Gly
1               5                   10                  15

Leu Gly Val Gly Gly Asp Phe Asp Ser Asp Thr Trp Arg Arg Arg Ser
            20                  25                  30

Thr Asp Ser Trp Val Pro Tyr Ser Glu Tyr Ile Ala Ile Glu Cys Ile
        35                  40                  45

Val Ala Pro Asn Gln Leu Tyr Gln Leu Leu Thr Asp Val Ala Gln Val
    50                  55                  60

Glu Thr Val Ala Ala Gln Leu Ala Gln Val Gly Tyr Gln Tyr Leu Gln
65                  70                  75                  80

Gly Arg Leu Arg Leu Val Arg Glu Asp Gly Ser Cys Thr Asp Phe Ser
                85                  90                  95

Gly Lys Ala Met Leu Asp Asn Leu Leu Asn Lys Ser Lys Asp Ile Leu
            100                 105                 110

Asp Leu Asp Phe Leu His Val Ser Glu Gly Tyr Arg Ser Glu Ala Tyr
        115                 120                 125

Trp Pro Gly Gln Ser Ser Gly Ile Thr Ile Gly Tyr Gly Val Asp Ile
    130                 135                 140
```

Gly His Gln Ser Glu Glu Gly Leu His Lys Trp Gly Val Pro Gln Ser
145 150 155 160

Ile Ile Asp Lys Ile Lys Asp Tyr Phe Gly Ile Thr Gly Glu Ala Ala
165 170 175

Asn Thr Leu Leu Lys Gly Leu Lys Asp Lys Thr Leu Gly Leu Ser Asp
180 185 190

Arg Glu Ile Lys Gln Phe Ser Asp Ile Val Lys Lys Gln Ala Thr Ala
195 200 205

Asp Ile Ile Asn Lys Tyr Asn Ala Ala Thr Lys Gly Ile Thr Phe Asp
210 215 220

Lys Ile Pro Tyr Asn Thr Arg Thr Ala Ile Ile Asp Leu Phe Tyr Gln
225 230 235 240

Tyr Ser Ala Pro Lys Gly Ala Pro Lys Ser Trp Gly Phe Ile Ile Asn
245 250 255

Asn Asp Trp Asn Gly Phe Tyr Asn Glu Leu Met Asn Phe Gly Asp Lys
260 265 270

His Thr Thr Arg Arg Glu Arg Glu Ala Ala Leu Val Leu Ser Asp Ile
275 280 285

Val Asn Asn Gln Tyr Ile Tyr Lys
290 295

<210> SEQ ID NO 7
<211> LENGTH: 100
<212> TYPE: PRT
<213> ORGANISM: Salmonella enterica

<400> SEQUENCE: 7

Met Glu Leu Lys Lys Ser Ile Ser Asp Tyr Thr Glu Ala Glu Phe Lys
1 5 10 15

Lys Ile Ile Glu Ala Ile Ile Asn Cys Glu Gly Asp Glu Lys Thr Gln
20 25 30

Asp Asp Asn Leu Glu Phe Phe Ile Arg Val Thr Glu Tyr Pro Ser Gly
35 40 45

Ser Asp Leu Ile Tyr Tyr Pro Glu Gly Asp Asn Asp Gly Ser Thr Glu
50 55 60

Ala Ile Ile Lys Glu Ile Lys Glu Trp Arg Ala Ala Asn Gly Lys Pro
65 70 75 80

Gly Phe Lys Gln Ala Asp Ser Ser Tyr Phe Val Ser Phe Asp Tyr Arg
85 90 95

Asp Gly Asp Trp
100

<210> SEQ ID NO 8
<211> LENGTH: 87
<212> TYPE: PRT
<213> ORGANISM: Salmonella enterica

<400> SEQUENCE: 8

Met Glu Leu Lys Asn Ser Ile Ser Asp Tyr Thr Glu Ala Glu Phe Ile
1 5 10 15

Glu Phe Met Lys Glu Ile Asp Lys Glu Asn Val Ala Glu Thr Asp Asp
20 25 30

Lys Leu Asp Leu Leu Leu Asn His Phe Glu Gln Val Thr Glu His Pro
35 40 45

Asp Gly Thr Asp Leu Ile Tyr Tyr Ala Ala Ser Asp Ala Glu Ser Thr
50 55 60

```
Pro Glu Ala Ile Thr Lys Lys Ile Lys Glu Trp Arg Ala Ala Asn Gly
65                  70                  75                  80

Lys Pro Gly Phe Lys Gln Gly
                85


<210> SEQ ID NO 9
<211> LENGTH: 499
<212> TYPE: PRT
<213> ORGANISM: Escherichia coli

<400> SEQUENCE: 9

Met Ala Lys Glu Leu Ser Val Tyr Gly Pro Thr Ala Gly Glu Ser Met
1               5                   10                  15

Gly Gly Thr Gly Ala Asn Leu Asn Gln Gln Gly Gly Asn Asn Asn Ser
            20                  25                  30

Asn Ser Gly Val His Trp Gly Gly Gly Ser Gly Ser Gly Asn Gly Gly
        35                  40                  45

Arg Glu His Gly Ser Gln Thr Gly Trp Gly Trp Ser Lys Thr Asn Asn
    50                  55                  60

Pro Asp Val Pro Pro Tyr Val Asp Asp Asn Gly Gln Val Arg Ile Thr
65                  70                  75                  80

Ile Thr Asn Gly Leu Val Lys Thr Pro Val Tyr Gly Val Pro Gly Ala
                85                  90                  95

Gly Gly Asn Ser Asp Val Gln Gly Gly Tyr Ile Pro Glu Asn Pro Asn
            100                 105                 110

Asp Glu Val Ala Arg Lys Trp Asp Lys Asn Asn Leu Pro Arg Glu Ile
        115                 120                 125

Asp Val Ser Ile Asp Gly Phe Lys Tyr Arg Val Thr Leu Asn Asp Asn
    130                 135                 140

Gly Arg Ala Ile Gly Ile Leu Arg Thr Gly Val Arg Pro Tyr Val Gly
145                 150                 155                 160

Ser Glu Lys Ala Lys Ala Gly Ile Met Glu Lys Ile Asn His Lys Thr
                165                 170                 175

Pro Glu Glu Ile Tyr Glu Ala Leu Gly Phe Asn Lys Asp Glu Ser Gln
            180                 185                 190

Arg Gln Glu Lys Ala Lys Gln Gln Ala Glu Asp Ala Trp Asp Arg Leu
        195                 200                 205

Pro Pro Asn Val Arg Lys Phe Asp Val Asp Val Glu Gln Phe His Tyr
    210                 215                 220

Leu Val Val Leu Asp Asp Tyr Gly Asn Val Leu Ser Val Thr Arg Thr
225                 230                 235                 240

Gly Val Arg Pro Tyr Val Gly Ser Glu Lys Ala Lys Ala Gly Ile Met
                245                 250                 255

Asp Lys Val Asp His Lys Thr Pro Glu Glu Ile Tyr Glu Ala Leu Gly
            260                 265                 270

Phe Asn Asn Glu Glu Pro Gln Arg Gln Asn Gln Ala Lys Lys Ala Ala
        275                 280                 285

Tyr Asp Val Phe Tyr Ser Phe Ser Met Asn Arg Asp Arg Ile Gln Ser
    290                 295                 300

Asp Val Leu Asn Lys Ala Ala Glu Val Ile Ser Asp Ile Gly Asn Lys
305                 310                 315                 320

Val Gly Asp Tyr Leu Gly Asp Ala Tyr Lys Ser Leu Ala Arg Glu Ile
                325                 330                 335

Ala Asp Asp Val Lys Asn Phe Gln Gly Lys Thr Ile Arg Ser Tyr Asp
            340                 345                 350
```

```
Asp Ala Met Ala Ser Leu Asn Lys Val Leu Ser Asn Pro Gly Phe Lys
        355                 360                 365

Phe Asn Arg Ala Asp Ser Asp Ala Leu Ala Asn Val Trp Arg Ser Ile
    370                 375                 380

Asp Ala Gln Asp Met Ala Asn Lys Leu Gly Asn Ile Ser Lys Ala Phe
385                 390                 395                 400

Lys Phe Ala Asp Val Val Met Lys Val Glu Lys Val Arg Glu Lys Ser
                405                 410                 415

Ile Glu Gly Tyr Glu Thr Gly Asn Trp Gly Pro Leu Met Leu Glu Val
            420                 425                 430

Glu Ser Trp Val Leu Ser Gly Ile Ala Ser Ala Val Ala Leu Gly Val
        435                 440                 445

Phe Ser Ala Thr Leu Gly Ala Tyr Ala Leu Ser Leu Gly Ala Pro Ala
    450                 455                 460

Ile Ala Val Gly Ile Val Gly Ile Leu Leu Ala Ala Val Val Gly Ala
465                 470                 475                 480

Leu Leu Asp Asp Lys Phe Ala Asp Ala Leu Asn Lys Glu Ile Ile Lys
                485                 490                 495

Pro Ala His


<210> SEQ ID NO 10
<211> LENGTH: 490
<212> TYPE: PRT
<213> ORGANISM: Escherichia coli

<400> SEQUENCE: 10

Met Asp Lys Val Thr Asp Asn Ser Pro Asp Val Glu Ser Thr Glu Ser
1               5                   10                  15

Thr Glu Gly Ser Phe Pro Thr Val Gly Val Asp Thr Gly Asp Thr Ile
            20                  25                  30

Thr Ala Thr Leu Ala Thr Gly Thr Glu Asn Val Gly Gly Gly Gly Gly
        35                  40                  45

Ala Phe Gly Gly Ala Ser Glu Ser Ser Ala Ala Ile His Ala Thr Ala
    50                  55                  60

Lys Trp Ser Thr Ala Gln Leu Lys Lys His Gln Ala Glu Gln Ala Ala
65                  70                  75                  80

Arg Ala Ala Ala Ala Glu Ala Ala Leu Ala Lys Ala Lys Ser Gln Arg
                85                  90                  95

Asp Ala Leu Thr Gln Arg Leu Lys Asp Ile Val Asn Asp Ala Leu Arg
            100                 105                 110

Ala Asn Ala Ala Arg Ser Pro Ser Val Thr Asp Leu Ala His Ala Asn
        115                 120                 125

Asn Met Ala Met Gln Ala Glu Ala Glu Arg Leu Arg Leu Ala Lys Ala
    130                 135                 140

Glu Gln Lys Ala Arg Glu Glu Ala Glu Ala Ala Glu Lys Ala Leu Arg
145                 150                 155                 160

Glu Ala Glu Arg Gln Arg Asp Glu Ile Ala Arg Gln Gln Ala Glu Thr
                165                 170                 175

Ala His Leu Leu Ala Met Ala Glu Ala Ala Glu Ala Glu Lys Asn Arg
            180                 185                 190

Gln Asp Ser Leu Asp Glu Glu His Arg Ala Val Glu Val Ala Glu Lys
        195                 200                 205

Lys Leu Ala Glu Ala Lys Ala Glu Leu Ala Lys Ala Glu Ser Asp Val
    210                 215                 220
```

Gln Ser Lys Gln Ala Ile Val Ser Arg Val Ala Gly Glu Leu Glu Asn
225 230 235 240

Ala Gln Lys Ser Val Asp Val Lys Val Thr Gly Phe Pro Gly Trp Arg
245 250 255

Asp Val Gln Lys Lys Leu Glu Arg Gln Leu Gln Asp Lys Lys Asn Glu
260 265 270

Tyr Ser Ser Val Thr Asn Ala Leu Asn Ser Ala Val Ser Ile Arg Asp
275 280 285

Ala Lys Lys Thr Asp Val Gln Asn Ala Glu Ile Lys Leu Lys Glu Ala
290 295 300

Lys Asp Ala Leu Glu Lys Ser Gln Val Lys Asp Ser Val Asp Thr Met
305 310 315 320

Val Gly Phe Tyr Gln Tyr Ile Thr Glu Gln Tyr Gly Glu Lys Tyr Ser
325 330 335

Arg Ile Ala Gln Asp Leu Ala Glu Lys Ala Lys Gly Ser Lys Phe Ser
340 345 350

Ser Val Asp Glu Ala Leu Ala Ala Phe Glu Lys Tyr Lys Asn Val Leu
355 360 365

Asp Lys Lys Ile Ser Lys Val Asp Arg Asp Ala Ile Phe Asn Ala Leu
370 375 380

Glu Ser Val Asn Tyr Asp Glu Leu Ser Lys Asn Leu Thr Lys Ile Ser
385 390 395 400

Lys Ser Leu Lys Ile Thr Ser Arg Val Ser Phe Leu Tyr Asp Val Gly
405 410 415

Ser Asp Phe Lys Asn Ala Ile Glu Thr Gly Asn Trp Arg Pro Leu Phe
420 425 430

Val Thr Leu Glu Lys Ser Ala Val Asp Val Gly Val Ala Lys Ile Val
435 440 445

Ala Leu Met Phe Ser Phe Ile Val Gly Val Pro Leu Gly Phe Trp Gly
450 455 460

Ile Ala Ile Val Thr Gly Ile Val Ser Ser Tyr Ile Gly Asp Asp Glu
465 470 475 480

Leu Asn Lys Leu Asn Glu Leu Leu Gly Ile
485 490

<210> SEQ ID NO 11
<211> LENGTH: 490
<212> TYPE: PRT
<213> ORGANISM: Escherichia coli

<400> SEQUENCE: 11

Met Asp Lys Val Thr Asp Asn Ser Pro Asp Val Glu Ser Thr Glu Ser
1 5 10 15

Thr Glu Gly Ser Phe Pro Thr Val Gly Val Asp Thr Gly Asp Thr Ile
20 25 30

Thr Ala Thr Leu Ala Thr Gly Thr Glu Asn Val Gly Gly Gly Gly Gly
35 40 45

Ala Phe Gly Gly Ala Ser Glu Ser Ser Ala Ala Ile His Ala Thr Ala
50 55 60

Lys Trp Ser Thr Ala Gln Leu Lys Lys His Gln Ala Glu Gln Ala Ala
65 70 75 80

Arg Ala Ala Ala Ala Glu Ala Ala Leu Ala Lys Ala Lys Ser Gln Arg
85 90 95

Asp Ala Leu Thr Gln Arg Leu Lys Asp Ile Val Asn Asp Ala Leu Arg

```
            100                 105                 110

Ala Asn Ala Ala Arg Ser Pro Ser Val Thr Asp Leu Ala His Ala Asn
        115                 120                 125

Asn Met Ala Met Gln Ala Glu Ala Glu Arg Leu Arg Leu Ala Lys Ala
    130                 135                 140

Glu Gln Lys Ala Arg Glu Glu Ala Glu Ala Ala Glu Lys Ala Leu Arg
145                 150                 155                 160

Glu Ala Glu Arg Gln Arg Asp Glu Ile Ala Arg Gln Gln Ala Glu Thr
                165                 170                 175

Ala His Leu Leu Ala Met Ala Glu Ala Ala Glu Ala Glu Lys Asn Arg
            180                 185                 190

Gln Asp Ser Leu Asp Glu Glu His Arg Ala Val Glu Val Ala Glu Lys
        195                 200                 205

Lys Leu Ala Glu Ala Lys Ala Glu Leu Ala Lys Ala Glu Ser Asp Val
    210                 215                 220

Gln Ser Lys Gln Ala Ile Val Ser Arg Val Ala Gly Glu Leu Glu Asn
225                 230                 235                 240

Ala Gln Lys Ser Val Asp Val Lys Val Thr Gly Phe Pro Gly Trp Arg
                245                 250                 255

Asp Val Gln Lys Lys Leu Glu Arg Gln Leu Gln Asp Lys Lys Asn Glu
            260                 265                 270

Tyr Ser Ser Val Thr Asn Ala Leu Asn Ser Ala Val Ser Ile Arg Asp
        275                 280                 285

Ala Lys Lys Thr Glu Val Gln Asn Ala Glu Ile Lys Leu Lys Glu Ala
    290                 295                 300

Lys Asp Ala Leu Glu Lys Ser Gln Val Lys Asp Ser Val Asp Thr Met
305                 310                 315                 320

Val Gly Phe Tyr Gln Tyr Ile Thr Glu Gln Tyr Gly Glu Lys Tyr Ser
                325                 330                 335

Arg Ile Ala Gln Asp Leu Ala Glu Lys Ala Lys Gly Ser Lys Phe Asn
            340                 345                 350

Ser Val Asp Glu Ala Leu Ala Ala Phe Glu Lys Tyr Lys Asn Val Leu
        355                 360                 365

Asp Lys Lys Phe Ser Lys Val Asp Arg Asp Asp Ile Phe Asn Ala Leu
    370                 375                 380

Glu Ser Ile Thr Tyr Asp Glu Trp Ala Lys His Leu Glu Lys Ile Ser
385                 390                 395                 400

Arg Ala Leu Lys Val Thr Gly Tyr Leu Ser Phe Gly Tyr Asp Val Trp
                405                 410                 415

Asp Gly Thr Leu Lys Gly Leu Lys Thr Gly Asp Trp Lys Pro Leu Phe
            420                 425                 430

Val Thr Leu Glu Lys Ser Ala Val Asp Phe Gly Val Ala Lys Ile Val
        435                 440                 445

Ala Leu Met Phe Ser Phe Ile Val Gly Ala Pro Leu Gly Phe Trp Gly
    450                 455                 460

Ile Ala Ile Ile Thr Gly Ile Val Ser Ser Tyr Ile Gly Asp Asp Glu
465                 470                 475                 480

Leu Asn Lys Leu Asn Glu Leu Leu Gly Ile
                485                 490
```

<210> SEQ ID NO 12
<211> LENGTH: 626
<212> TYPE: PRT
<213> ORGANISM: Escherichia coli -continued

<400> SEQUENCE: 12

Met Ser Asp Pro Val Arg Ile Thr Asn Pro Gly Ala Glu Ser Leu Gly
1 5 10 15

Tyr Asp Ser Asp Gly His Glu Ile Met Ala Val Asp Ile Tyr Val Asn
20 25 30

Pro Pro Arg Val Asp Val Phe His Gly Thr Pro Pro Ala Trp Ser Ser
35 40 45

Phe Gly Asn Lys Thr Ile Trp Gly Gly Asn Glu Trp Val Asp Asp Ser
50 55 60

Pro Thr Arg Ser Asp Ile Glu Lys Arg Asp Lys Glu Ile Thr Ala Tyr
65 70 75 80

Lys Asn Thr Leu Ser Ala Gln Gln Lys Glu Asn Glu Asn Lys Arg Thr
85 90 95

Glu Ala Gly Lys Arg Leu Ser Ala Ala Ile Ala Ala Arg Glu Lys Asp
100 105 110

Glu Asn Thr Leu Lys Thr Leu Arg Ala Gly Asn Ala Asp Ala Ala Asp
115 120 125

Ile Thr Arg Gln Glu Phe Arg Leu Leu Gln Ala Glu Leu Arg Glu Tyr
130 135 140

Gly Phe Arg Thr Glu Ile Ala Gly Tyr Asp Ala Leu Arg Leu His Thr
145 150 155 160

Glu Ser Arg Met Leu Phe Ala Asp Ala Asp Ser Leu Arg Ile Ser Pro
165 170 175

Arg Glu Ala Arg Ser Leu Ile Glu Gln Ala Glu Lys Arg Gln Lys Asp
180 185 190

Ala Gln Asn Ala Asp Lys Lys Ala Ala Asp Met Leu Ala Glu Tyr Glu
195 200 205

Arg Arg Lys Gly Ile Leu Asp Thr Arg Leu Ser Glu Leu Glu Lys Asn
210 215 220

Gly Gly Ala Ala Leu Ala Val Leu Asp Ala Gln Gln Ala Arg Leu Leu
225 230 235 240

Gly Gln Gln Thr Arg Asn Asp Arg Ala Ile Ser Glu Ala Arg Asn Lys
245 250 255

Leu Ser Ser Val Thr Glu Ser Leu Asn Thr Ala Arg Asn Ala Leu Thr
260 265 270

Arg Ala Glu Gln Gln Leu Thr Gln Gln Lys Asn Thr Pro Asp Gly Lys
275 280 285

Thr Ile Val Ser Pro Glu Lys Phe Pro Gly Arg Ser Ser Thr Asn His
290 295 300

Ser Ile Val Val Ser Gly Asp Pro Arg Phe Ala Gly Thr Ile Lys Ile
305 310 315 320

Thr Thr Ser Ala Val Ile Asp Asn Arg Ala Asn Leu Asn Tyr Leu Leu
325 330 335

Thr His Ser Gly Leu Asp Tyr Lys Arg Asn Ile Leu Asn Asp Arg Asn
340 345 350

Pro Val Val Thr Glu Asp Val Glu Gly Asp Lys Lys Ile Tyr Asn Ala
355 360 365

Glu Val Ala Glu Trp Asp Lys Leu Arg Gln Arg Leu Leu Asp Ala Arg
370 375 380

Asn Lys Ile Thr Ser Ala Glu Ser Ala Val Asn Ser Ala Arg Asn Asn
385 390 395 400

Leu Ser Ala Arg Thr Asn Glu Gln Lys His Ala Asn Asp Ala Leu Asn

```
                405                 410                 415

Ala Leu Leu Lys Glu Lys Glu Asn Ile Arg Asn Gln Leu Ala Gly Ile
            420                 425                 430

Asn Gln Lys Ile Ala Glu Glu Lys Arg Lys Gln Asp Glu Leu Lys Ala
        435                 440                 445

Thr Lys Asp Ala Ile Asn Phe Thr Thr Glu Phe Leu Lys Ser Val Ser
    450                 455                 460

Glu Lys Tyr Gly Ala Lys Ala Glu Gln Leu Ala Arg Glu Met Ala Gly
465                 470                 475                 480

Gln Ala Lys Gly Lys Lys Ile Arg Asn Val Glu Glu Ala Leu Lys Thr
                485                 490                 495

Tyr Glu Lys Tyr Arg Ala Asp Ile Asn Lys Lys Ile Asn Ala Lys Asp
            500                 505                 510

Arg Ala Ala Ile Ala Ala Ala Leu Glu Ser Val Lys Leu Ser Asp Ile
        515                 520                 525

Ser Ser Asn Leu Asn Arg Phe Ser Arg Gly Leu Gly Tyr Ala Gly Lys
    530                 535                 540

Phe Thr Ser Leu Ala Asp Trp Ile Thr Glu Phe Gly Lys Ala Val Arg
545                 550                 555                 560

Thr Glu Asn Trp Arg Pro Leu Phe Val Lys Thr Glu Thr Ile Ile Ala
                565                 570                 575

Gly Asn Ala Ala Thr Ala Leu Val Ala Leu Val Phe Ser Ile Leu Thr
            580                 585                 590

Gly Ser Ala Leu Gly Ile Ile Gly Tyr Gly Leu Leu Met Ala Val Thr
        595                 600                 605

Gly Ala Leu Ile Asp Glu Ser Leu Val Glu Lys Ala Asn Lys Phe Trp
    610                 615                 620

Gly Ile
625
```

<210> SEQ ID NO 13
<211> LENGTH: 626
<212> TYPE: PRT
<213> ORGANISM: Escherichia coli

<400> SEQUENCE: 13

```
Met Ser Asp Pro Val Arg Ile Thr Asn Pro Gly Ala Glu Ser Leu Gly
1               5                   10                  15

Tyr Asp Ser Asp Gly His Glu Ile Met Ala Val Asp Ile Tyr Val Asn
            20                  25                  30

Pro Pro Arg Val Asp Val Phe His Gly Thr Pro Pro Ala Trp Ser Ser
        35                  40                  45

Phe Gly Asn Lys Thr Ile Trp Gly Gly Asn Glu Trp Val Asp Asp Ser
    50                  55                  60

Pro Thr Arg Ser Asp Ile Glu Lys Arg Asp Lys Glu Ile Thr Ala Tyr
65                  70                  75                  80

Lys Asn Thr Leu Ser Ala Gln Gln Lys Glu Asn Glu Asn Lys Arg Thr
                85                  90                  95

Glu Ala Gly Lys Arg Leu Ser Ala Ala Ile Ala Ala Arg Glu Lys Asp
            100                 105                 110

Glu Asn Thr Leu Lys Thr Leu Arg Ala Gly Asn Ala Asp Ala Ala Asp
        115                 120                 125

Ile Thr Arg Gln Glu Phe Arg Leu Leu Gln Ala Glu Leu Arg Glu Tyr
    130                 135                 140
```

-continued

Gly Phe Arg Thr Glu Ile Ala Gly Tyr Asp Ala Leu Arg Leu His Thr
145 150 155 160

Glu Ser Arg Met Leu Phe Ala Asp Ala Asp Ser Leu Arg Ile Ser Pro
165 170 175

Arg Glu Ala Arg Ser Leu Ile Glu Gln Ala Glu Lys Arg Gln Lys Asp
180 185 190

Ala Gln Asn Ala Asp Lys Lys Ala Ala Asp Met Leu Ala Glu Tyr Glu
195 200 205

Arg Arg Lys Gly Ile Leu Asp Thr Arg Leu Ser Glu Leu Glu Lys Asn
210 215 220

Gly Gly Ala Ala Leu Ala Val Leu Asp Ala Gln Gln Ala Arg Leu Leu
225 230 235 240

Gly Gln Gln Thr Arg Asn Asp Arg Ala Ile Ser Glu Ala Arg Asn Lys
245 250 255

Leu Ser Ser Val Thr Glu Ser Leu Lys Thr Ala Arg Asn Ala Leu Thr
260 265 270

Arg Ala Glu Gln Gln Leu Thr Gln Gln Lys Asn Thr Pro Asp Gly Lys
275 280 285

Thr Ile Val Ser Pro Glu Lys Phe Pro Gly Arg Ser Ser Thr Asn His
290 295 300

Ser Ile Val Val Ser Gly Asp Pro Arg Phe Ala Gly Thr Ile Lys Ile
305 310 315 320

Thr Thr Ser Ala Val Ile Asp Asn Arg Ala Asn Leu Asn Tyr Leu Leu
325 330 335

Thr His Ser Gly Leu Asp Tyr Lys Arg Asn Ile Leu Asn Asp Arg Asn
340 345 350

Pro Val Val Thr Glu Asp Val Glu Gly Asp Lys Lys Ile Tyr Asn Ala
355 360 365

Glu Val Ala Glu Trp Asp Lys Leu Arg Gln Arg Leu Leu Asp Ala Arg
370 375 380

Asn Lys Ile Thr Ser Ala Glu Ser Ala Ile Asn Ser Ala Arg Asn Asn
385 390 395 400

Val Ser Ala Arg Thr Asn Glu Gln Lys His Ala Asn Asp Ala Leu Asn
405 410 415

Ala Leu Leu Lys Glu Lys Glu Asn Ile Arg Ser Gln Leu Ala Asp Ile
420 425 430

Asn Gln Lys Ile Ala Glu Glu Lys Arg Lys Arg Asp Glu Ile Asn Met
435 440 445

Val Lys Asp Ala Ile Lys Leu Thr Ser Asp Phe Tyr Arg Thr Ile Tyr
450 455 460

Asp Glu Phe Gly Lys Gln Ala Ser Glu Leu Ala Lys Glu Leu Ala Ser
465 470 475 480

Val Ser Gln Gly Lys Gln Ile Lys Ser Val Asp Asp Ala Leu Asn Ala
485 490 495

Phe Asp Lys Phe Arg Asn Asn Leu Asn Lys Lys Tyr Asn Ile Gln Asp
500 505 510

Arg Met Ala Ile Ser Lys Ala Leu Glu Ala Ile Asn Gln Val His Met
515 520 525

Ala Glu Asn Phe Lys Leu Phe Ser Lys Ala Phe Gly Phe Thr Gly Lys
530 535 540

Val Ile Glu Arg Tyr Asp Val Ala Val Glu Leu Gln Lys Ala Val Lys
545 550 555 560

Thr Asp Asn Trp Arg Pro Phe Phe Val Lys Leu Glu Ser Leu Ala Ala

```
                565                 570                 575

Gly Arg Ala Ala Ser Ala Val Thr Ala Trp Ala Phe Ser Val Met Leu
            580                 585                 590

Gly Thr Pro Val Gly Ile Leu Gly Phe Ala Ile Ile Met Ala Ala Val
        595                 600                 605

Ser Ala Leu Val Asn Asp Lys Phe Ile Glu Gln Val Asn Lys Leu Ile
    610                 615                 620

Gly Ile
625


<210> SEQ ID NO 14
<211> LENGTH: 271
<212> TYPE: PRT
<213> ORGANISM: Escherichia coli

<400> SEQUENCE: 14

Met Glu Thr Leu Thr Val His Ala Pro Ser Pro Ser Thr Asn Leu Pro
1               5                   10                  15

Ser Tyr Gly Asn Gly Ala Phe Ser Leu Ser Ala Pro His Val Pro Gly
            20                  25                  30

Ala Gly Pro Leu Leu Val Gln Val Val Tyr Ser Phe Phe Gln Ser Pro
        35                  40                  45

Asn Met Cys Leu Gln Ala Leu Thr Gln Leu Glu Asp Tyr Ile Lys Lys
    50                  55                  60

His Gly Ala Ser Asn Pro Leu Thr Leu Gln Ile Ile Ser Thr Asn Ile
65                  70                  75                  80

Gly Tyr Phe Cys Asn Ala Asp Arg Asn Leu Val Leu His Pro Gly Ile
                85                  90                  95

Ser Val Tyr Asp Ala Tyr His Phe Ala Lys Pro Ala Pro Ser Gln Tyr
            100                 105                 110

Asp Tyr Arg Ser Met Asn Met Lys Gln Met Ser Gly Asn Val Thr Thr
        115                 120                 125

Pro Ile Val Ala Leu Ala His Tyr Leu Trp Gly Asn Gly Ala Glu Arg
    130                 135                 140

Ser Val Asn Ile Ala Asn Ile Gly Leu Lys Ile Ser Pro Met Lys Ile
145                 150                 155                 160

Asn Gln Ile Lys Asp Ile Ile Lys Ser Gly Val Val Gly Thr Phe Pro
                165                 170                 175

Val Ser Thr Lys Phe Thr His Ala Thr Gly Asp Tyr Asn Val Ile Thr
            180                 185                 190

Gly Ala Tyr Leu Gly Asn Ile Thr Leu Lys Thr Glu Gly Thr Leu Thr
        195                 200                 205

Ile Ser Ala Asn Gly Ser Trp Thr Tyr Asn Gly Val Val Arg Ser Tyr
    210                 215                 220

Asp Asp Lys Tyr Asp Phe Asn Ala Ser Thr His Arg Gly Ile Ile Gly
225                 230                 235                 240

Glu Ser Leu Thr Arg Leu Gly Ala Met Phe Ser Gly Lys Glu Tyr Gln
                245                 250                 255

Ile Leu Leu Pro Gly Glu Ile His Ile Lys Glu Ser Gly Lys Arg
            260                 265                 270


<210> SEQ ID NO 15
<211> LENGTH: 1942
<212> TYPE: DNA
<213> ORGANISM: Artificial Sequence
<220> FEATURE:
```

<223> OTHER INFORMATION: codon-optimized sequence for expressing ScolE2

<400> SEQUENCE: 15

```
atgtctggtg gtgatggtat cggtcacaat agcggtgctc attctactgg tggtgtgaac     60
ggttcttcat ctggtagggg tggtagttct tcaggtggtg gtaacaaccc taactctggt    120
cctggttggg gtactactca tactcctgat ggtcacgata tccacaacta caaccctggt    180
gagtttggtg gtggtggaca taagcctggt ggaaacggtg gtaatcactc tggtggtact    240
ggtgatggac aacctcctgg tgctgctatg gcttttggtt tccctgctct tgttcctgct    300
ggtgctggtg gtcttgctgt tactgtttct ggtgatgctc tggctgctgc aattgctgat    360
gtgcttgctg ttctgaaggg acctttcaag tttggtgctt ggggtatcgc tctgtacggt    420
attcttccta ccgagatcgc taaggatgat ccaaggatga tgagcaagat cgtgacctct    480
ttgcctgctg atgctgtgac tgagtctcct gtgtcatctc tgcctcttga tcaggctact    540
gtgagcgtta ccaagagggt taccgatgtg gttaaggatg agaggcagca cattgctgtt    600
gttgctggtg tgcctgcttc tatccctgtt gttgatgcta agcctactac ccaccctggt    660
gtgttctctg tttctgttcc tggtctgcct gatctgcagg tttcaactgt gaagaacgct    720
cctgctatga ctgctttgcc taggggtgtt actgatgaga aggataggac tgttcaccct    780
gctggtttca ccttcggtgg ttcttctcat gaggctgtga tcaggttccc taaagagtct    840
ggtcaggctc ctgtttacgt gtcagtgacc gatgttctta cccctgagca ggttaagcag    900
agacaggatg aagagaatag aaggcagcaa gagtgggatg ctactcaccc tgttgaagtg    960
gctgagagga attacaggct ggcttctgat gagctgaaca gggctaatgt ggatgtggct   1020
ggtaagcaag agaggcagat tcaagctgct caagctgttg ctgctagaaa gggtgaactg   1080
gatgctgcta acaagacctt cgctgatgct aaagaagaga tcaagaagtt cgagaggttc   1140
gctcacgatc ctatggctgg tggacacaga atgtggcaaa tggctggtct taaggctcag   1200
agggctcaga atgaggttaa ccagaaacaa gctgagttca acgctgctga gaaagaaaag   1260
gctgatgcag atgctgctct gaacgtggca cttgagtcta ggaagcagaa agaacaaaag   1320
gcaaaggatg ctagcgataa gctggataag gaaaacaaga ggaaccaccc tggaaaggct   1380
actggtaagg gtcaacctgt tggtgataag tggcttgagg atgctggtaa agaagctgga   1440
gcacctgttc cagataggat cgctgataag ctgagagata aggaattcaa gaacttcgat   1500
gattttagga agaagttctg ggaagaggta aatttctagt ttttctcctt cattttcttg   1560
gttaggaccc ttttctcttt ttattttttt gagctttgat ctttctttaa actgatctat   1620
tttttaattg attggttatg gtgtaaatat tacatagctt taactgataa tctgattact   1680
ttatttcgtg tgtctatgat gatgatgata actgcaggtt agcaaggatc ctgagctgag   1740
caagcagttc atccctggta acaagaaaag gatgagccag ggtcttgctc ctagggctag   1800
aaacaaggat actgtgggtg gtagaagatc cttcgagctg catcacgata agccaatctc   1860
tcaggatggt ggtgtttacg atatggataa catcagggtg accaccccaa agctgcacat   1920
cgatattcat aggggaaagt aa                                            1942
```

<210> SEQ ID NO 16
<211> LENGTH: 1954
<212> TYPE: DNA
<213> ORGANISM: Artificial Sequence
<220> FEATURE:
<223> OTHER INFORMATION: codon-optimized coding sequence for expressing ScolE3

<400> SEQUENCE: 16

```
atgtctggtg gtgatggtag gggtcataat accggtgctc atagcaccag cggtaacatt     60
aacggtggtc ctactggtct tggtgtgtca ggtggtgctt ctgatggttc tggttggtcc    120
tctgagaaca atccttgggg tggtggtagc ggttctggta ttcactgggg aggtggaagt    180
ggtagaggta atggtggtgg aaacggtaac agtggtggtg gttctggaac tggtggtaac    240
ctttctgctg ttgctgctcc tgttgctttc ggtttccctg ctctttctac tcctggtgct    300
ggtggtttgg ctgtgtctat ttctgcttct gagctgagcg ctgctatcgc tggtattatc    360
gctaagctga agaaggtgaa cctgaagttc accccttcg gtgtggtgct gtcctctttg     420
attcctagcg agatcgctaa ggatgatcct aacatgatga gcaagatcgt gaccagcctg    480
cctgctgatg atattaccga gtctcctgtg tcctctctgc ctcttgataa ggctactgtg    540
aatgtgaacg tgagggtggt ggatgatgtg aaggatgaga ggcagaacat cagcgttgtg    600
tctggtgttc ctatgtctgt gcctgttgtg gatgctaagc ctactgaaag gcctggtgtg    660
ttcaccgctt ctattccagg tgctcctgtg ctgaacatct ccgtgaacaa ttctacccct    720
gctgtgcaga ctctttctcc tggtgtgact aacaacaccg ataaggatgt taggcctgct    780
ggtttcactc agggtggtaa taccagggat gctgtgatca ggttccctaa ggattctggt    840
cacaacgcag tgtacgtgtc cgtgtctgat gtgttgtctc cagatcaggt taagcagagg    900
caggatgaag agaatagaag gcagcaagag tgggatgcta ctcaccctgt tgaagttgct    960
gagagagagt acgagaacgc tagagctgaa cttgaggctg aaaacaagaa cgtgcacagc   1020
cttcaggtgg cacttgatgg tcttaagaat accgctgagg gtctggctct ttctgatgct   1080
ggtagacatc ctctgaccag cagcgagtct agatttgttg ctgtgcctgg ttactccggt   1140
ggtggtgttc attttgatgc taccgctacc gtggatagca gggataggct taactctctt   1200
ctgtctcttg gtggtgctgc ttacgtgaac aacgtgttgg agcttggtga ggtgtcagct   1260
cctactgagg atggtttgaa ggtgggaaac gctatcaaga acgctatgat cgaggtgtac   1320
gataagctga ggcagaggct tattaccagg cagaacgaga tcaaccacgc tcaggtgtca   1380
cttaacaccg ctatcgagtc taggaacaag aaagaggaaa agaagaggtc cgcagagaac   1440
aagctgaacg aagagagaaa caagcctaga aagggtacta aggattacgg acacgattac   1500
catcctgctc cagagactga agaaatcaag ggtctgggtg atatcaagaa gggtatccct   1560
aagaccccta agcagaacgg tggtggtaag agaaagagat ggatcggaga taagggtaga   1620
aagatctacg agtgggatag ccagcatggt gagcttgaag gtaaatttct agtttttctc   1680
cttcattttc ttggttagga cccttttctc tttttatttt tttgagcttt gatctttctt   1740
taaactgatc tattttttaa ttgattggtt atggtgtaaa tattacatag ctttaactga   1800
taatctgatt actttatttc gtgtgtctat gatgatgatg ataactgcag gttatagggc   1860
ttcagatggt cagcacctgg gaagctttga tcctaagact ggtaagcagc tgaagggtcc   1920
tgatccaaag aggaacatca agaagtacct ttaa                                1954
```

<210> SEQ ID NO 17
<211> LENGTH: 1948
<212> TYPE: DNA
<213> ORGANISM: Artificial Sequence
<220> FEATURE:
<223> OTHER INFORMATION: codon-optimized coding sequence for expressing ScolE7

<400> SEQUENCE: 17

```
atgtctggtg gtgatggtat cggtcacaat agcggtgctc attctactgg tggtgtgaac     60
ggttcctctt ctggttctgg tggaagctca tctggaagcg gtaacaaccc taattctggt    120
cctggttggg gtactactca taccccctaac ggtgatatcc acaactacaa ccctggtgag   180
tttggtggtg gtggaaacaa gcctggtgga catggtggta actctggtaa ccacgatggt    240
agctctggaa acggtcaacc ttctgctgct cctatggctt ttggtttccc tgctcttgct    300
cctgctggtg ctggttctct tgctgttact gtttctggtg aggctctgtc tgctgctatc    360
gctgatattt tcgctgctct gaagggacct ttcaagttcg gtgcttgggg tattgctctg    420
tacggtatta tgcctaccga gatcgctaag gatgatccta acatgatgag caagatcatg    480
accagcctgc ctgctgatac tgtgactgat actcctgtgt cctctctgcc tcttgatcag    540
gctactgtgt ctgtgactaa gagggttgca gatgtggtga aggatgagag gcagcatatt    600
gctgttgttg ctggtgtgcc tatgtctgtg cctgttgttg atgctaagcc taccactagg    660
cctggtatct tctctgctac tgttcctgga cttcctgctt tggaggtgtc aaccggtaag    720
tctattcctg cttctaccgc tctgcctagg ggtattactg aggataagga taggactgag    780
caccctgctg gtttcacttt cggtggttct tctcacgatg ctgtgatcag gttccctaaa    840
gagtctggtc aggctccagt ttacgtgtca gtgactgatg tgcttacccc tgagcaggtt    900
aagcagagac aggatgaaga gtctagaagg cagcaagagt gggatgctac tcatcctgtt    960
gaagtggctg agaggaacta caggcttgct tctgatgagc tgaacagggt gaacgctgat   1020
gtggctggta agcaagaaag acaagctcaa gctggacagg ctgttgctgc tagaaagggt   1080
gaacttgatg ctgctaacaa gaccttcgct gatgctaaag aagagatcaa gaagttcgag   1140
cacttcgcta gggatccaat ggctggtggt catagaatgt ggcagatggc tggtcttaag   1200
gctcagaggg ctcagaatga ggttaaccag aaacaagctg agttcgatgc tgcagagaaa   1260
gaaaaggctg atgctgatgc agctctgaac gctgctcttg aatctaggaa gcagaaagag   1320
cagaaggcta aggataccaa agagaggctg gataaggaaa acaagaggaa tcagcctggt   1380
aaggctaccg gtaagggtca gccagtttct gataagtggc ttgaggatgc tggtaaagag   1440
agcggttctc ctatccctga tagcattgct gataagctta gagataagga attcagaaac   1500
ttcgatgatt ttaggaagaa gttctgggag gaagttagca aggatcctga gctgagcaag   1560
cagttcatca agggtaacag agataggatg caggtaaatt tctagttttt ctccttcatt   1620
ttcttggtta ggaccctttt ctctttttat ttttttgagc tttgatcttt ctttaaactg   1680
atctattttt taattgattg gttatggtgt aaatattaca tagctttaac tgataatctg   1740
attactttat ttcgtgtgtc tatgatgatg atgataactg caggttggaa aggctcctaa   1800
gtccagaaag aaggatgctg ctggtaagag gacctctttc gagcttcatc acgataagcc   1860
tgtgagccag gatggtggtg tttacgatat ggataacctg aggatcacca cccctaagag   1920
gcacatcgat attcataggg gacagtaa                                      1948
```

```
<210> SEQ ID NO 18
<211> LENGTH: 1452
<212> TYPE: DNA
<213> ORGANISM: Artificial Sequence
<220> FEATURE:
<223> OTHER INFORMATION: codon-optimized coding sequence for expressing
      ScolE1a

<400> SEQUENCE: 18

atggctgata acaccattgc ttactacgag gatggtgtgc ctcacagcgc tgatggtaag     60
```

-continued

```
gtggtgattg tgatcgatgg taagatgcct gtggataccg gtgctggtgg tactggtggt    120

ggtggaggtg gtaaggttgg aggaacttct gaaagctctg ctgctattca cgctaccgct    180

aagtggtcta ccgctcagct taagaaaacc ctggctgaga aggctgctag agagagagaa    240

actgctgctg caatggctgc tgctaaggct aagagagatg ctcttaccca gcacctgaag    300

gatatcgtga acgatgtgct taggcacaac gcttctagga ccccttctgc tactgatctt    360

gctcacgcta acaacatggc tatgcaggct gaagctcaga gacttggtag agctaaggct    420

gaggaaaagg ctagaaaaga ggctgaggct gctgagcttg ctttccaaga agctgaaaga    480

cagagggaag aggctgttag acagcttgct gaaactgaga ggcagcttaa gcaagctgag    540

gaagagaaga ggcttgctgc tctttctgat gaggctaggg ctgttgagaa cgctaggaag    600

aatctggata ccgcaaagtc cgagctggct aatgtggatt ctgatatcga gaggcagagg    660

tcccagctgt catctcttga tgctgatgtg aagaaggctg aagagaacct gaggctgacc    720

atgaggatta agggtaggat cggtaggaag atgcaggcta agtcacaggc tatcgtggat    780

gataagaaaa ggatctactc cgatgctgag aacgtgctga ataccatgac cgtgaatagg    840

aacctgaagg ctcagcaggt taccgatgca gagaatgagc ttaaggtggc aatcgataac    900

ctgaacagca gccagatgaa gaacgctgtg gatgctaccg tgtctttcta ccagactctg    960

accgagaagt acggtgagaa gtacagcctt atcgctcaag agctggcaga gaagtccaag   1020

ggtaagaaaa tcggaaatgt ggatgaggct ctggctgcat tcgagaagta taaggatgtg   1080

ctggataaga agttcagcaa ggctgatagg gatgctattg tgaacgctct gaagtccttc   1140

aactacgatg attgggctaa gcacctggat cagttcgcta agtacctgaa gatcaccggt   1200

cacgtgagct tcggttacga tgttgtgtct gatgtgctga aggctagcga gactggtgat   1260

tggaagcctc tgttcattac ccttgagcag aaggtgttgg atactggtat gagctacctg   1320

gtggtgctga tgttctctct tattgctgga accaccctgg gaatcttcgg tgtggctatt   1380

attaccgcta tcctgtgcag cttcgtggat aagtacatcc tgaacgcact gaacgatgct   1440

ctgggaatct aa                                                       1452
```

<210> SEQ ID NO 19
<211> LENGTH: 1584
<212> TYPE: DNA
<213> ORGANISM: Artificial Sequence
<220> FEATURE:
<223> OTHER INFORMATION: codon-optimized coding sequence for expressing ScolE1b

<400> SEQUENCE: 19

```
atgagcgata acaccattgc ttactacgag gatggtgtgc cttacagcgc tgatggtcaa     60

gtggtgattg tgatcgatgg taagatgcct gtggataccg gtgctggtgg tactggtggt    120

ggtggaggtg gtaaggttgg aggaacttct gaaagctctg ctgctattca cgctaccgct    180

aagtggtcta aggctcagct tcagaagtcc ctggaagaga aggctgctag agagagagaa    240

actgctgctg caatggctgc tgctaaggct aagagagatg ctcttaccca gcacctgaag    300

gatatcgtga acgatgtgct gaggtacaac gcttctagga ctccttctgc taccgatctt    360

gctcacgcta acaacatggc tatgcaggct gaagctcaga gacttggtag agctaaggct    420

gaggaaaagg ctagaaaaga ggctgaggct gctgagaagt ctcttcaaga agctgagaga    480

cagagggaag aagctgctag gcaaagagct gaagcagaga ggcaacttaa gcaggcagag    540

gctgaagaga agaggttggc tgctctttct gaagaggcta gggcagttga gatcacccag    600
```

-continued

```
aagaatcttg ctgctgctca gagcgagctg tccaagatgg atggtgagat caagagcctt    660

aacgtgaggc tgtctacctc tatccatgct agggatgctg agatgaacag cctgtctggt    720

aagaggaacg agctggctca agagagcgct aagtacaaag aactggatga gctggtgaag    780

aagcttgagc ctagggctaa tgatcctctg cagaacaggc ctttcttcga tgctacatct    840

agaagggcaa gggctggtga tactttggct gagaagcaga aagaggtgac cgcttctgag    900

actaggatca acgagcttaa caccgagatc aaccaggtga ggggtgctat ttcacaggca    960

aacaacaata ggaacctgaa ggtgcagcag gttaccgaga ctgagaacgc tcttaaggtg   1020

gcaatcgata acctgaacag cagccagatg aagaacgctg tggatgctac cgtgtctttc   1080

taccagaccc tgactgctaa gtacggtgag aagtacagcc tgatcgctca agaacttgct   1140

gagcagtcca agggtaagaa aatcagcaat gtggatgagg ctctggctgc attcgagaag   1200

tataaggatg tgctggataa gaagttcagc aaggctgata gggatgcaat tgtgaacgct   1260

ctgaagtccg tggattacgc tgattgggct aagcacctgg atcagttcag cagatacctg   1320

aagatcagcg gtagggtgtc aaccggttac gatatctaca gcgatatcag aaagggtatg   1380

gataccaacg attggaggcc tctgttcctg acccttgaga agcttgctgt tgatgctggt   1440

gtgggttaca tcgtggctct tggtttctct gtgatcgctt ctaccgctct tggtatttgg   1500

ggtgtggcta ttatcaccgg tgtgatctgc agcttcgttg ataagaagga tttggagaag   1560

ctgaacgagg cactgggaat ctaa                                           1584
```

<210> SEQ ID NO 20
<211> LENGTH: 891
<212> TYPE: DNA
<213> ORGANISM: Artificial Sequence
<220> FEATURE:
<223> OTHER INFORMATION: codon-optimized coding sequence for expressing salmocin Spst

<400> SEQUENCE: 20

```
atgttcatca agagcggtgg taacctgacc atcaggactt ttggtggtct tggtgtgggt     60

ggtgatttcg atagcgatac ttggagaaga aggtccaccg attcttgggt gccatacagc    120

gagtacattg ctatcgagtg catcgtggct cctaaccagc tttaccagct tcttactgat    180

gtggctcagg tggaaactgt ggctgctcaa cttgctcagg ttggatacca gtatcttcag    240

ggtaggctta ggctggtgag agaggatggt tcttgcaccg atttcagcgg taaggctatg    300

ctggataacc tgctgaacaa gagcaaggat attctggatc tggatttcct gcacgtgagc    360

gagggttata ggtctgaagc ttattggcct ggtcagtcct ctggtatcac cattggttac    420

ggtgtggata tcggtcacca gtctgaagag ggacttcata agtggggtgt gcctcagagc    480

atcatcgata agatcaagga ttacttcggt attaccggtg aggctgctaa cacccttctt    540

aagggtctga aggataagac cctgggactg agcgatagag agatcaagca gttctccgat    600

atcgtgaaga agcaggctac cgctgatatc atcaacaagt acaacgctgc taccaagggt    660

atcacctttg ataagatccc ttacaacacc aggaccgcta tcatcgatct gttctaccag    720

tacagcgctc ctaagggtgc tcctaagtct tggggtttca ttatcaacaa cgattggaac    780

ggtttctaca acgagctgat gaacttcggt gataagcaca ccaccagaag agagagggaa    840

gctgctctgg ttctgtctga tattgtgaac aaccagtaca tctacaagta a             891
```

<210> SEQ ID NO 21
<211> LENGTH: 258
<212> TYPE: DNA

<213> ORGANISM: Artificial Sequence
<220> FEATURE:
<223> OTHER INFORMATION: codon-optimized coding sequence for expressing SImmE2

<400> SEQUENCE: 21
atggaactga agaagtccat cagcgattac accgaggctg agttcaagaa gatcatcgag 60
gctatcatca actgcgaggg tgatgagaaa acccaggatg ataaccttga gttcttcatc 120
agggtgaccg agtacccttc tggtagcgat cttatctact accctgaggg tgataacgat 180
ggtagcaccg aggcaattat caaagaaatc aaggaatgga gggctgctaa cggtaagcct 240
ggttttaagc aagcttaa 258

<210> SEQ ID NO 22
<211> LENGTH: 264
<212> TYPE: DNA
<213> ORGANISM: Artificial Sequence
<220> FEATURE:
<223> OTHER INFORMATION: codon-optimized coding sequence for expressing SImmE7

<400> SEQUENCE: 22
atggaactga agaacagcat cagcgattac accgaggctg agttcatcga gttcatgaaa 60
gaaatcgata aggaaaacgt ggcagagact gatgataagc tggatctgct gctgaaccac 120
ttcgagcagg ttacagaaca ccctgatgga accgatctga tctactacgc tgcttccgat 180
gctgagtcta cccctgaggc tatcaccaag aaaatcaaag aatggagggc tgctaacggt 240
aagcctggtt ttaagcaagg ttaa 264

<210> SEQ ID NO 23
<211> LENGTH: 15014
<212> TYPE: DNA
<213> ORGANISM: Artificial Sequence
<220> FEATURE:
<223> OTHER INFORMATION: nucleotide sequence of binary TMV-based vector used for salmocin ScolE1a expression

<400> SEQUENCE: 23
catggctgat aacaccattg cttactacga ggatggtgtg cctcacagcg ctgatggtaa 60
ggtggtgatt gtgatcgatg gtaagatgcc tgtggatacc ggtgctggtg gtactggtgg 120
tggtggaggt ggtaaggttg gaggaacttc tgaaagctct gctgctattc acgctaccgc 180
taagtggtct accgctcagc ttaagaaaac cctggctgag aaggctgcta gagagagaga 240
aactgctgct gcaatggctg ctgctaaggc taagagagat gctcttaccc agcacctgaa 300
ggatatcgtg aacgatgtgc ttaggcacaa cgcttctagg accccttctg ctactgatct 360
tgctcacgct aacaacatgg ctatgcaggc tgaagctcag agacttggta gagctaaggc 420
tgaggaaaag gctagaaaag aggctgaggc tgctgagctt gctttccaag aagctgaaag 480
acagagggaa gaggctgtta gacagcttgc tgaaactgag aggcagctta agcaagctga 540
ggaagagaag aggcttgctg ctctttctga tgaggctagg gctgttgaga acgctaggaa 600
gaatctggat accgcaaagt ccgagctggc taatgtggat tctgatatcg agaggcagag 660
gtcccagctg tcatctcttg atgctgatgt gaagaaggct gaagagaacc tgaggctgac 720
catgaggatt aagggtagga tcggtaggaa gatgcaggct aagtcacagg ctatcgtgga 780
tgataagaaa aggatctact ccgatgctga gaacgtgctg aataccatga ccgtgaatag 840
gaacctgaag gctcagcagg ttaccgatgc agagaatgag cttaaggtgg caatcgataa 900

```
cctgaacagc agccagatga agaacgctgt ggatgctacc gtgtctttct accagactct    960
gaccgagaag tacggtgaga agtacagcct tatcgctcaa gagctggcag agaagtccaa   1020
gggtaagaaa atcggaaatg tggatgaggc tctggctgca ttcgagaagt ataaggatgt   1080
gctggataag aagttcagca aggctgatag ggatgctatt gtgaacgctc tgaagtcctt   1140
caactacgat gattgggcta agcacctgga tcagttcgct aagtacctga agatcaccgg   1200
tcacgtgagc ttcggttacg atgttgtgtc tgatgtgctg aaggctagcg agactggtga   1260
ttggaagcct ctgttcatta cccttgagca gaaggtgttg gatactggta tgagctacct   1320
ggtggtgctg atgttctctc ttattgctgg aaccaccctg ggaatcttcg gtgtggctat   1380
tattaccgct atcctgtgca gcttcgtgga taagtacatc ctgaacgcac tgaacgatgc   1440
tctgggaatc taagcttact agagcgtggt gcgcacgata gcgcatagtg tttttctctc   1500
cacttgaatc gaagagatag acttacggtg taaatccgta ggggtggcgt aaaccaaatt   1560
acgcaatgtt ttgggttcca tttaaatcga aacccctat ttcctggatc acctgttaac    1620
gcacgtttga cgtgtattac agtgggaata agtaaaagtg agaggttcga atcctcccta   1680
accccgggta ggggcccagc ggccgctcta gctagagtca agcagatcgt tcaaacattt   1740
ggcaataaag tttcttaaga ttgaatcctg ttgccggtct tgcgatgatt atcatataat   1800
ttctgttgaa ttacgttaag catgtaataa ttaacatgta atgcatgacg ttatttatga   1860
gatgggtttt tatgattaga gtcccgcaat tatacattta atacgcgata gaaaacaaaa   1920
tatagcgcgc aaactaggat aaattatcgc gcgcggtgtc atctatgtta ctagatcgac   1980
ctgcatccac cccagtacat taaaaacgtc cgcaatgtgt tattaagttg tctaagcgtc   2040
aatttgttta caccacaata tatcctgcca ccagccagcc aacagctccc cgaccggcag   2100
ctcggcacaa aatcaccact cgatacaggc agcccatcag tcagatcagg atctcctttg   2160
cgacgctcac cgggctggtt gccctcgccg ctgggctggc ggccgtctat ggccctgcaa   2220
acgcgccaga aacgccgtcg aagccgtgtg cgagacaccg cggccgccgg cgttgtggat   2280
acctcgcgga aaacttggcc ctcactgaca gatgaggggc ggacgttgac acttgagggg   2340
ccgactcacc cggcgcggcg ttgacagatg aggggcaggc tcgatttcgg ccggcgacgt   2400
ggagctggcc agcctcgcaa atcggcgaaa acgcctgatt ttacgcgagt ttcccacaga   2460
tgatgtggac aagcctgggg ataagtgccc tgcggtattg acacttgagg ggcgcgacta   2520
ctgacagatg aggggcgcga tccttgacac ttgaggggca gagtgctgac agatgagggg   2580
cgcacctatt gacatttgag gggctgtcca caggcagaaa atccagcatt tgcaagggtt   2640
tccgcccgtt tttcggccac cgctaacctg tcttttaacc tgcttttaaa ccaatattta   2700
taaaccttgt ttttaaccag ggctgcgccc tgtgcgcgtg accgcgcacg ccgaaggggg   2760
gtgccccccc ttctcgaacc ctcccggccc gctaacgcgg gcctcccatc cccccagggg   2820
ctgcgcccct cggccgcgaa cggcctcacc ccaaaaatgg cagcgctggc caattcgtgc   2880
gcggaacccc tatttgttta tttttctaaa tacattcaaa tatgtatccg ctcatgagac   2940
aataaccctg ataaatgctt caataatatt gaaaaaggaa gagtatggct aaaatgagaa   3000
tatcaccgga attgaaaaaa ctgatcgaaa aataccgctg cgtaaaagat acggaaggaa   3060
tgtctcctgc taaggtatat aagctggtgg gagaaaatga aaacctatat ttaaaaatga   3120
cggacagccg gtataaaggg accacctatg atgtggaacg ggaaaaggac atgatgctat   3180
ggctggaagg aaagctgcct gttccaaagg tcctgcactt tgaacggcat gatggctgga   3240
gcaatctgct catgagtgag gccgatggcg tcctttgctc ggaagagtat gaagatgaac   3300
```

-continued aaagccctga aaagattatc gagctgtatg cggagtgcat caggctcttt cactccatcg 3360
acatatcgga ttgtccctat acgaatagct tagacagccg cttagccgaa ttggattact 3420
tactgaataa cgatctggcc gatgtggatt gcgaaaactg ggaagaagac actccattta 3480
aagatccgcg cgagctgtat gattttttaa agacggaaaa gcccgaagag gaacttgtct 3540
tttcccacgg cgacctggga gacagcaaca tctttgtgaa agatggcaaa gtaagtggct 3600
ttattgatct tgggagaagc ggcagggcgg acaagtggta tgacattgcc ttctgcgtcc 3660
ggtcgatcag ggaggatatc ggggaagaac agtatgtcga gctatttttt gacttactgg 3720
ggatcaagcc tgattgggag aaaataaaat attatatttt actggatgaa ttgttttagc 3780
tgtcagacca agtttactca tatatacttt agattgattt aaaacttcat ttttaattta 3840
aaaggatcta ggtgaagatc ctttttgata atctcatgac caaaatccct taacgtgagt 3900
tttcgttcca ctgagcgtca gaccccgtag aaaagatcaa aggatcttct tgagatcctt 3960
tttttctgcg cgtaatctgc tgcttgcaaa caaaaaaacc accgctacca gcggtggttt 4020
gtttgccgga tcaagagcta ccaactcttt ttccgaaggt aactggcttc agcagagcgc 4080
agataccaaa tactgtcctt ctagtgtagc cgtagttagg ccaccacttc aagaactctg 4140
tagcaccgcc tacatacctc gctctgctaa tcctgttacc agtggctgct gccagtggcg 4200
ataagtcgtg tcttaccggg ttggactcaa gacgatagtt accggataag gcgcagcggt 4260
cgggctgaac ggggggttcg tgcacacagc ccagcttgga gcgaacgacc tacaccgaac 4320
tgagatacct acagcgtgag ctatgagaaa gcgccacgct tcccgaaggg agaaaggcgg 4380
acaggtatcc ggtaagcggc agggtcggaa caggagagcg cacgagggag cttccagggg 4440
gaaacgcctg gtatctttat agtcctgtcg ggtttcgcca cctctgactt gagcgtcgat 4500
ttttgtgatg ctcgtcaggg gggcggagcc tatggaaaaa cgccagcaac gcggcctttt 4560
tacggttcct ggcagatcct agatgtggcg caacgatgcc ggcgacaagc aggagcgcac 4620
cgacttcttc cgcatcaagt gttttggctc tcaggccgag gcccacggca agtatttggg 4680
caaggggtcg ctggtattcg tgcagggcaa gattcggaat accaagtacg agaaggacgg 4740
ccagacggtc tacgggaccg acttcattgc cgataaggtg gattatctgg acaccaaggc 4800
accaggcggg tcaaatcagg aataagggca cattgccccg gcgtgagtcg gggcaatccc 4860
gcaaggaggg tgaatgaatc ggacgtttga ccggaaggca tacaggcaag aactgatcga 4920
cgcggggttt tccgccgagg atgccgaaac catcgcaagc cgcaccgtca tgcgtgcgcc 4980
ccgcgaaacc ttccagtccg tcggctcgat ggtccagcaa gctacggcca agatcgagcg 5040
cgacagcgtg caactggctc cccctgccct gcccgcgcca tcggccgccg tggagcgttc 5100
gcgtcgtctc gaacaggagg cggcaggttt ggcgaagtcg atgaccatcg acacgcgagg 5160
aactatgacg accaagaagc gaaaaaccgc cggcgaggac ctggcaaaac aggtcagcga 5220
ggccaagcag gccgcgttgc tgaaacacac gaagcagcag atcaaggaaa tgcagctttc 5280
cttgttcgat attgcgccgt ggccggacac gatgcgagcg atgccaaacg acacggcccg 5340
ctctgccctg ttcaccacgc gcaacaagaa aatcccgcgc gaggcgctgc aaaacaaggt 5400
cattttccac gtcaacaagg acgtgaagat cacctacacc ggcgtcgagc tgcgggccga 5460
cgatgacgaa ctggtgtggc agcaggtgtt ggagtacgcg aagcgcaccc ctatcggcga 5520
gccgatcacc ttcacgttct acgagctttg ccaggacctg ggctggtcga tcaatggccg 5580
gtattacacg aaggccgagg aatgcctgtc gcgcctacag gcgacggcga tgggcttcac 5640

-continued

```
gtccgaccgc gttgggcacc tggaatcggt gtcgctgctg caccgcttcc gcgtcctgga   5700
ccgtggcaag aaaacgtccc gttgccaggt cctgatcgac gaggaaatcg tcgtgctgtt   5760
tgctggcgac cactacacga aattcatatg ggagaagtac cgcaagctgt cgccgacggc   5820
ccgacggatg ttcgactatt tcagctcgca ccgggagccg tacccgctca agctggaaac   5880
cttccgcctc atgtgcggat cggattccac ccgcgtgaag aagtggcgcg agcaggtcgg   5940
cgaagcctgc gaagagttgc gaggcagcgg cctggtggaa cacgcctggg tcaatgatga   6000
cctggtgcat tgcaaacgct agggccttgt ggggtcagtt ccggctgggg gttcagcagc   6060
cagcgcctga tctggggaac cctgtggttg gcacatacaa atggacgaac ggataaacct   6120
tttcacgccc ttttaaatat ccgattattc taataaacgc tcttttctct taggtttacc   6180
cgccaatata tcctgtcaaa cactgatagt ttaaactgaa ggcgggaaac gacaatctga   6240
tctaagctag cttggaattg gtaccacgcg tttcgacaaa atttagaacg aacttaatta   6300
tgatctcaaa tacattgata catatctcat ctagatctag gttatcatta tgtaagaaag   6360
ttttgacgaa tatggcacga caaaatggct agactcgatg taattggtat ctcaactcaa   6420
cattatactt ataccaaaca ttagttagac aaaatttaaa caactatttt ttatgtatgc   6480
aagagtcagc atatgtataa ttgattcaga atcgttttga cgagttcgga tgtagtagta   6540
gccattattt aatgtacata ctaatcgtga atagtgaata tgatgaaaca ttgtatctta   6600
ttgtataaat atccataaac acatcatgaa agacactttc tttcacggtc tgaattaatt   6660
atgatacaat tctaatagaa aacgaattaa attacgttga attgtatgaa atctaattga   6720
acaagccaac cacgacgacg actaacgttg cctggattga ctcggtttaa gttaaccact   6780
aaaaaaacgg agctgtcatg taacacgcgg atcgagcagg tcacagtcat gaagccatca   6840
aagcaaaaga actaatccaa gggctgagat gattaattag tttaaaaatt agttaacacg   6900
agggaaaagg ctgtctgaca gccaggtcac gttatcttta cctgtggtcg aaatgattcg   6960
tgtctgtcga ttttaattat tttttgaaa ggccgaaaat aaagttgtaa gagataaacc   7020
cgcctatata aattcatata ttttcctctc cgctttgaag ttttagtttt attgcaacaa   7080
caacaacaaa ttacaataac aacaaacaaa atacaaacaa caacaacatg gcacaatttc   7140
aacaaacaat tgacatgcaa actctccaag ccgctgcggg acgcaacagc ttggtgaatg   7200
atttggcatc tcgtcgcgtt tacgataatg cagtcgagga gctgaatgct cgttccagac   7260
gtcccaaggt aataggaact ttctggatct actttatttg ctggatctcg atcttgtttt   7320
ctcaatttcc ttgagatctg gaattcgttt aatttggatc tgtgaacctc cactaaatct   7380
tttggtttta ctagaatcga tctaagttga ccgatcagtt agctcgatta tagctaccag   7440
aatttggctt gaccttgatg gagagatcca tgttcatgtt acctgggaaa tgatttgtat   7500
atgtgaattg aaatctgaac tgttgaagtt agattgaatc tgaacactgt caatgttaga   7560
ttgaatctga acactgttta aggttagatg aagtttgtgt atagattctt cgaaacttta   7620
ggatttgtag tgtcgtacgt tgaacagaaa gctatttctg attcaatcag ggtttatttg   7680
actgtattga actctttttg tgtgtttgca ggtccacttc tccaaggcag tgtctacgga   7740
acagaccctg attgcaacaa acgcatatcc ggagttcgag atttccttta ctcatacgca   7800
atccgctgtg cactccttgg ccggaggcct tcggtcactt gagttggagt atctcatgat   7860
gcaagttccg ttcggttctc tgacgtacga catcggcggt aacttttccg cgcacctttt   7920
caaagggcgc gattacgttc actgctgcat gcctaatctg gatgtacgtg acattgctcg   7980
ccatgaagga cacaaggaag ctatttacag ttatgtgaat cgtttgaaaa ggcagcagcg   8040
```

-continued

```
tcctgtgcct gaataccaga gggcagcttt caacaactac gctgagaacc cgcacttcgt   8100
ccattgcgac aaacctttcc aacagtgtga attgacgaca gcgtatggca ctgacaccta   8160
cgctgtagct ctccatagca tttatgatat ccctgttgag gagttcggtt ctgcgctact   8220
caggaagaat gtgaaaactt gtttcgcggc ctttcatttc catgagaata tgcttctaga   8280
ttgtgataca gtcacactcg atgagattgg agctacgttc cagaaatcag gtaacattcc   8340
ttagttacct ttcttttctt tttccatcat aagtttatag attgtacatg ctttgagatt   8400
tttctttgca aacaatctca ggtgataacc tgagcttctt cttccataat gagagcactc   8460
tcaattacac ccacagcttc agcaacatca tcaagtacgt gtgcaagacg ttcttccctg   8520
ctagtcaacg cttcgtgtac cacaaggagt tcctggtcac tagagtcaac acttggtact   8580
gcaagttcac gagagtggat acgttcactc tgttccgtgg tgtgtaccac aacaatgtgg   8640
attgcgaaga gttttacaag gctatggacg atgcgtggca ctacaaaaag acgttagcaa   8700
tgcttaatgc cgagaggacc atcttcaagg ataacgctgc gttaaacttc tggttcccga   8760
aggtgctctt gaaattggaa gtcttctttt gttgtctaaa cctatcaatt tctttgcgga   8820
aatttatttg aagctgtaga gttaaaattg agtcttttaa acttttgtag gtgagagaca   8880
tggttatcgt ccctctcttt gacgcttcta tcacaactgg taggatgtct aggagagagg   8940
ttatggtgaa caaggacttc gtctacacgg tcctaaatca catcaagacc tatcaagcta   9000
aggcactgac gtacgcaaac gtgctgagct tcgtggagtc tattaggtct agagtgataa   9060
ttaacggtgt cactgccagg taagttgtta cttatgattg ttttcctctc tgctacatgt   9120
attttgttgt tcatttctgt aagatataag aattgagttt tcctctgatg atattattag   9180
gtctgaatgg gacacagaca aggcaattct aggtccatta gcaatgacat tcttcctgat   9240
cacgaagctg ggtcatgtgc aagatgaaat aatcctgaaa aagttccaga agttcgacag   9300
aaccaccaat gagctgattt ggacaagtct ctgcgatgcc ctgatggggg ttattccctc   9360
ggtcaaggag acgcttgtgc gcggtggttt tgtgaaagta gcagaacaag ccttagagat   9420
caaggttagt atcatatgaa gaaataccta gtttcagttg atgaatgcta ttttctgacc   9480
tcagttgttc tcttttgaga attatttctt ttctaatttg cctgattttt ctattaattc   9540
attaggttcc cgagctatac tgtaccttcg ccgaccgatt ggtactacag tacaagaagg   9600
cggaggagtt ccaatcgtgt gatctttcca aacctctaga agagtcagag aagtactaca   9660
acgcattatc cgagctatca gtgcttgaga atctcgactc ttttgactta gaggcgttta   9720
agactttatg tcagcagaag aatgtggacc cggatatggc agcaaaggta aatcctggtc   9780
cacactttta cgataaaaac acaagatttt aaactatgaa ctgatcaata atcattccta   9840
aaagaccaca cttttgtttt gtttctaaag taatttttac tgttataaca ggtggtcgta   9900
gcaatcatga agtcagaatt gacgttgcct ttcaagaaac ctacagaaga ggaaatctcg   9960
gagtcgctaa aaccaggaga ggggtcgtgt gcagagcata aggaagtgtt gagcttacaa  10020
aatgatgctc cgttcccgtg tgtgaaaaat ctagttgaag gttccgtgcc ggcgtatgga  10080
atgtgtccta agggtggtgg tttcgacaaa ttggatgtgg acattgctga tttccatctc  10140
aagagtgtag atgcagttaa aaagggaact atgatgtctg cggtgtacac agggtctatc  10200
aaagttcaac aaatgaagaa ctacatagat tacttaagtg cgtcgctggc agctacagtc  10260
tcaaacctct gcaaggtaag aggtcaaaag gtttccgcaa tgatccctct ttttttgttt  10320
ctctagtttc aagaatttgg gtatatgact aacttctgag tgttccttga tgcatatttg  10380
```

-continued

```
tgatgagaca aatgtttgtt ctatgtttta ggtgcttaga gatgttcacg gcgttgaccc  10440
agagtcacag gagaaatctg gagtgtggga tgttaggaga ggacgttggt tacttaaacc  10500
taatgcgaaa agtcacgcgt ggggtgtggc agaagacgcc aaccacaagt tggttattgt  10560
gttactcaac tgggatgacg gaaagccggt ttgtgatgag acatggttca gggtggcggt  10620
gtcaagcgat tccttgatat attcggatat gggaaaactt aagacgctca cgtcttgcag  10680
tccaaatggt gagccaccgg agcctaacgc caaagtaatt ttggtcgatg gtgttcccgg  10740
ttgtggaaaa acgaaggaga ttatcgaaaa ggtaagttct gcatttggtt atgctccttg  10800
cattttaggt gttcgtcgct cttccatttc catgaatagc taagattttt tttctctgca  10860
ttcattcttc ttgcctcagt tctaactgtt tgtggtattt ttgttttaat tattgctaca  10920
ggtaaacttc tctgaagact tgattttagt ccctgggaag gaagcttcta agatgatcat  10980
ccggagggcc aaccaagctg gtgtgataag agcggataag gacaatgtta gaacggtgga  11040
ttccttcttg atgcatcctt ctagaagggt gtttaagagg ttgtttatcg atgaaggact  11100
aatgctgcat acaggttgtg taaatttcct actgctgcta tctcaatgtg acgtcgcata  11160
tgtgtatggg gacacaaagc aaattccgtt catttgcaga gtcgcgaact ttccgtatcc  11220
agcgcatttt gcaaaactcg tcgctgatga gaaggaagtc agaagagtta cgctcaggta  11280
aagcaactgt gttttaatca atttcttgtc aggatatatg gattataact taatttttga  11340
gaaatctgta gtatttggcg tgaaatgagt ttgctttttg gtttctcccg tgttataggt  11400
gcccggctga tgttacgtat ttccttaaca agaagtatga cggggcggtg atgtgtacca  11460
gcgcggtaga gagatccgtg aaggcagaag tggtgagagg aaagggtgca ttgaacccaa  11520
taaccttacc gttggagggt aaaattttga ccttcacaca agctgacaag ttcgagttac  11580
tggagaaggg ttacaaggta aagtttccaa ctttccttta ccatatcaaa ctaaagttcg  11640
aaacttttta tttgatcaac ttcaaggcca cccgatcttt ctattcctga ttaatttgtg  11700
atgaatccat attgactttt gatggttacg caggatgtga acactgtgca cgaggtgcaa  11760
ggggagacgt acgagaagac tgctattgtg cgcttgacat caactccgtt agagatcata  11820
tcgagtgcgt cacctcatgt tttggtggcg ctgacaagac acacaacgtg ttgtaaatat  11880
tacaccgttg tgttggaccc gatggtgaat gtgatttcag aaatggagaa gttgtccaat  11940
ttccttcttg acatgtatag agttgaagca ggtctgtctt tcctatttca tatgtttaat  12000
cctaggaatt tgatcaattg attgtatgta tgtcgatccc aagactttct tgttcactta  12060
tatcttaact ctctctttgc tgtttcttgc aggtgtccaa tagcaattac aaatcgatgc  12120
agtattcagg ggacagaact tgtttgttca gacgcccaag tcaggagatt ggcgagatat  12180
gcaattttac tatgacgctc ttcttcccgg aaacagtact attctcaatg aatttgatgc  12240
tgttacgatg aatttgaggg atatttcctt aaacgtcaaa gattgcagaa tcgacttctc  12300
caaatccgtg caacttccta aagaacaacc tattttcctc aagcctaaaa taagaactgc  12360
ggcagaaatg ccgagaactg caggtaaaat attggatgcc agacgatatt ctttcttttg  12420
atttgtaact ttttcctgtc aaggtcgata aattttattt tttttggtaa aaggtcgata  12480
attttttttt ggagccatta tgtaattttc ctaattaact gaaccaaaat tatacaaacc  12540
aggtttgctg gaaaatttgg ttgcaatgat caaaagaaac atgaatgcgc cggatttgac  12600
agggacaatt gacattgagg atactgcatc tctggtggtt gaaaagtttt gggattcgta  12660
tgttgacaag gaatttagtg gaacgaacga aatgaccatg acaagggaga gcttctccag  12720
gtaaggactt ctcatgaata ttagtggcag attagtgttg ttaaagtctt tggttagata  12780
```

-continued atcgatgcct cctaattgtc catgttttac tggttttcta caattaaagg tggctttcga 12840
aacaagagtc atctacagtt ggtcagttag cggactttaa ctttgtggat ttgccggcag 12900
tagatgagta caagcatatg atcaagagtc aaccaaagca aaagttagac ttgagtattc 12960
aagacgaata tcctgcattg cagacgatag tctaccattc gaaaaagatc aatgcgattt 13020
tcggtccaat gttttcagaa cttacgagga tgttactcga aaggattgac tcttcgaagt 13080
ttctgttcta caccagaaag acacctgcac aaatagagga cttcttttct gacctagact 13140
caacccaggc gatggaaatt ctggaactcg acatttcgaa gtacgataag tcacaaaacg 13200
agttccattg tgctgtagag tacaagatct gggaaaagtt aggaattgat gagtggctag 13260
ctgaggtctg gaaacaaggt gagttcctaa gttccatttt tttgtaatcc ttcaatgtta 13320
ttttaacttt tcagatcaac atcaaaatta ggttcaattt tcatcaacca aataatattt 13380
ttcatgtata tataggtcac agaaaaacga ccttgaaaga ttatacggcc ggaatcaaaa 13440
catgtctttg gtatcaaagg aaaagtggtg atgtgacaac ctttattggt aataccatca 13500
tcattgccgc atgtttgagc tcaatgatcc ccatggacaa agtgataaag gcagcttttt 13560
gtggagacga tagcctgatt tacattccta aaggtttaga cttgcctgat attcaggcgg 13620
gcgcgaacct catgtggaac ttcgaggcca aactcttcag gaagaagtat ggttacttct 13680
gtggtcgtta tgttattcac catgatagag gagccattgt gtattacgat ccgcttaaac 13740
taatatctaa gttaggttgt aaacatatta gagatgttgt tcacttagaa gagttacgcg 13800
agtctttgtg tgatgtagct agtaacttaa ataattgtgc gtatttttca cagttagatg 13860
aggccgttgc cgaggttcat aagaccgcgg taggcggttc gtttgctttt tgtagtataa 13920
ttaagtattt gtcagataag agattgttta gagatttgtt ctttgtttga taatgtcgat 13980
agtctcgtac gaacctaagg tgagtgattt cctcaatctt tcgaagaagg aagagatctt 14040
gccgaaggct ctaacgaggt taaaaaccgt gtctattagt actaaagata ttatatctgt 14100
caaggagtcg gagactttgt gtgatataga tttgttaatc aatgtgccat tagataagta 14160
tagatatgtg ggtatcctag gagccgtttt taccggagag tggctagtgc cagacttcgt 14220
taaaggtgga gtgacgataa gtgtgataga taagcgtctg gtgaactcaa aggagtgcgt 14280
gattggtacg tacagagccg cagccaagag taagaggttc cagttcaaat tggttccaaa 14340
ttactttgtg tccaccgtgg acgcaaagag gaagccgtgg caggtaagga tttttatgat 14400
atagtatgct tatgtatttt gtactgaaag catatcctgc ttcattggga tattactgaa 14460
agcatttaac tacatgtaaa ctcacttgat gatcaataaa cttgattttg caggttcatg 14520
ttcgtataca agacttgaag attgaggcgg gttggcagcc gttagctctg gaagtagttt 14580
cagttgctat ggtcaccaat aacgttgtca tgaagggttt gagggaaaag gtcgtcgcaa 14640
taaatgatcc ggacgtcgaa ggtttcgaag gtaagccatc ttcctgctta tttttataat 14700
gaacatagaa ataggaagtt gtgcagagaa actaattaac ctgactcaaa atctaccctc 14760
ataattgttg tttgatattg gtcttgtatt ttgcaggtgt ggttgacgaa ttcgtcgatt 14820
cggttgcagc atttaaagcg gttgacaact ttaaaagaag gaaaaagaag gttgaagaaa 14880
agggtgtagt aagtaagtat aagtacagac cggagaagta cgccggtcct gattcgttta 14940
atttgaaaga agaaaacgtc ttacaacatt acaaacccga atcagtacca gtatttcgat 15000
aagaaacaag aaac 15014

<210> SEQ ID NO 24

<211> LENGTH: 11586
<212> TYPE: DNA
<213> ORGANISM: Artificial Sequence
<220> FEATURE:
<223> OTHER INFORMATION: nucleotide sequence of binary PVX-based vector used for salmocin ImmScolE2 expression

<400> SEQUENCE: 24
gatcggtcgt atcactggaa caacaaccgc tgaggctgtt gtcactctac caccaccata 60
actacgtcta cataaccgac gcctacccca gtttcatagt attttctggt ttgattgtat 120
gaataatata aataaaaaaa aaaaaaaaaa aaaaaaacta gtgagctctt ctgtcagcgg 180
gcccactgca tccaccccag tacattaaaa acgtccgcaa tgtgttatta agttgtctaa 240
gcgtcaattt gtttacacca caatatatcc tgccaccagc cagccaacag ctccccgacc 300
ggcagctcgg cacaaaatca ccactcgata caggcagccc atcagtcaga tcaggatctc 360
ctttgcgacg ctcaccgggc tggttgccct cgccgctggg ctggcggccg tctatggccc 420
tgcaaacgcg ccagaaacgc cgtcgaagcc gtgtgcgaga caccgcggcc gccggcgttg 480
tggatacctc gcggaaaact tggccctcac tgacagatga ggggcggacg ttgacacttg 540
aggggccgac tcacccggcg cggcgttgac agatgagggg caggctcgat ttcggccggc 600
gacgtggagc tggccagcct cgcaaatcgg cgaaaacgcc tgattttacg cgagtttccc 660
acagatgatg tggacaagcc tggggataag tgccctgcgg tattgacact tgaggggcgc 720
gactactgac agatgagggg cgcgatcctt gacacttgag ggcagagtg ctgacagatg 780 aggggcgcac ctattgacat ttgaggggct gtccacaggc agaaaatcca gcatttgcaa 840
gggtttccgc ccgtttttcg gccaccgcta acctgtcttt taacctgctt ttaaaccaat 900
atttataaac cttgttttta accagggctg cgccctgtgc gcgtgaccgc gcacgccgaa 960
ggggggtgcc cccccttctc gaaccctccc ggcccgctaa cgcgggcctc ccatcccccc 1020
aggggctgcg cccctcggcc gcgaacggcc tcaccccaaa aatggcagcg ctggccaatt 1080
cgtgcgcgga acccctattt gtttattttt ctaaatacat tcaaatatgt atccgctcat 1140
gagacaataa ccctgataaa tgcttcaata atattgaaaa aggaagagta tggctaaaat 1200
gagaatatca ccggaattga aaaaactgat cgaaaaatac cgctgcgtaa aagatacgga 1260
aggaatgtct cctgctaagg tatataagct ggtgggagaa aatgaaaacc tatatttaaa 1320
aatgacggac agccggtata aagggaccac ctatgatgtg gaacgggaaa aggacatgat 1380
gctatggctg gaaggaaagc tgcctgttcc aaaggtcctg cactttgaac ggcatgatgg 1440
ctggagcaat ctgctcatga gtgaggccga tggcgtcctt tgctcggaag agtatgaaga 1500
tgaacaaagc cctgaaaaga ttatcgagct gtatgcggag tgcatcaggc tctttcactc 1560
catcgacata tcggattgtc cctatacgaa tagcttagac agccgcttag ccgaattgga 1620
ttacttactg aataacgatc tggccgatgt ggattgcgaa aactgggaag aagacactcc 1680
atttaaagat ccgcgcgagc tgtatgattt tttaaagacg gaaaagcccg aagaggaact 1740
tgtcttttcc cacggcgacc tgggagacag caacatcttt gtgaaagatg gcaaagtaag 1800
tggctttatt gatcttggga gaagcggcag ggcggacaag tggtatgaca ttgccttctg 1860
cgtccggtcg atcagggagg atatcgggga agaacagtat gtcgagctat tttttgactt 1920
actggggatc aagcctgatt gggagaaaat aaaatattat attttactgg atgaattgtt 1980
ttagctgtca gaccaagttt actcatatat actttagatt gatttaaaac ttcattttta 2040
atttaaaagg atctaggtga agatcctttt tgataatctc atgaccaaaa tcccttaacg 2100

-continued

```
tgagttttcg ttccactgag cgtcagaccc cgtagaaaag atcaaaggat cttcttgaga   2160
tcctttttt ctgcgcgtaa tctgctgctt gcaaacaaaa aaaccaccgc taccagcggt   2220
ggtttgtttg ccggatcaag agctaccaac tctttttccg aaggtaactg gcttcagcag   2280
agcgcagata ccaaatactg tccttctagt gtagccgtag ttaggccacc acttcaagaa   2340
ctctgtagca ccgcctacat acctcgctct gctaatcctg ttaccagtgg ctgctgccag   2400
tggcgataag tcgtgtctta ccgggttgga ctcaagacga tagttaccgg ataaggcgca   2460
gcggtcgggc tgaacggggg gttcgtgcac acagcccagc ttggagcgaa cgacctacac   2520
cgaactgaga tacctacagc gtgagctatg agaaagcgcc acgcttcccg aagggagaaa   2580
ggcggacagg tatccggtaa gcggcagggt cggaacagga gagcgcacga gggagcttcc   2640
agggggaaac gcctggtatc tttatagtcc tgtcgggttt cgccacctct gacttgagcg   2700
tcgatttttg tgatgctcgt caggggggcg gagcctatgg aaaaacgcca gcaacgcggc   2760
ctttttacgg ttcctggcag atcctagatg tggcgcaacg atgccggcga caagcaggag   2820
cgcaccgact tcttccgcat caagtgtttt ggctctcagg ccgaggccca cggcaagtat   2880
ttgggcaagg ggtcgctggt attcgtgcag ggcaagattc ggaataccaa gtacgagaag   2940
gacggccaga cggtctacgg gaccgacttc attgccgata aggtggatta tctggacacc   3000
aaggcaccag gcgggtcaaa tcaggaataa gggcacattg ccccggcgtg agtcggggca   3060
atcccgcaag gagggtgaat gaatcggacg tttgaccgga aggcatacag gcaagaactg   3120
atcgacgcgg ggttttccgc cgaggatgcc gaaaccatcg caagccgcac cgtcatgcgt   3180
gcgccccgcg aaaccttcca gtccgtcggc tcgatggtcc agcaagctac ggccaagatc   3240
gagcgcgaca gcgtgcaact ggctccccct gccctgcccg cgccatcggc cgccgtggag   3300
cgttcgcgtc gtctcgaaca ggaggcggca ggtttggcga agtcgatgac catcgacacg   3360
cgaggaacta tgacgaccaa gaagcgaaaa accgccggcg aggacctggc aaaacaggtc   3420
agcgaggcca agcaggccgc gttgctgaaa cacacgaagc agcagatcaa ggaaatgcag   3480
ctttccttgt tcgatattgc gccgtggccg gacacgatgc gagcgatgcc aaacgacacg   3540
gcccgctctg ccctgttcac cacgcgcaac aagaaaatcc cgcgcgaggc gctgcaaaac   3600
aaggtcattt tccacgtcaa caaggacgtg aagatcacct acaccggcgt cgagctgcgg   3660
gccgacgatg acgaactggt gtggcagcag gtgttggagt acgcgaagcg cacccctatc   3720
ggcgagccga tcaccttcac gttctacgag ctttgccagg acctgggctg gtcgatcaat   3780
ggccggtatt acacgaaggc cgaggaatgc ctgtcgcgcc tacaggcgac ggcgatgggc   3840
ttcacgtccg accgcgttgg gcacctggaa tcggtgtcgc tgctgcaccg cttccgcgtc   3900
ctggaccgtg gcaagaaaac gtcccgttgc caggtcctga tcgacgagga aatcgtcgtg   3960
ctgtttgctg gcgaccacta cacgaaattc atatgggaga agtaccgcaa gctgtcgccg   4020
acggcccgac ggatgttcga ctatttcagc tcgcaccggg agccgtaccc gctcaagctg   4080
gaaaccttcc gcctcatgtg cggatcggat tccacccgcg tgaagaagtg gcgcgagcag   4140
gtcggcgaag cctgcgaaga gttgcgaggc agcggcctgg tggaacacgc ctgggtcaat   4200
gatgacctgg tgcattgcaa acgctagggc cttgtggggt cagttccggc tgggggttca   4260
gcagccagcg cctgatctgg ggaaccctgt ggttggcaca tacaaatgga cgaacggata   4320
aaccttttca cgccctttta aatatccgat tattctaata aacgctcttt tctcttaggt   4380
ttacccgcca atatatcctg tcaaacactg atagtttaaa ctgaaggcgg gaaacgacaa   4440
tctgatctaa gctaggcatg cctgcaggtc aacatggtgg agcacgacac gcttgtctac   4500
```

tccaaaaata tcaaagatac agtctcagaa gaccaaaggg caattgagac ttttcaacaa 4560
agggtaatat ccggaaacct cctcggattc cattgcccag ctatctgtca ctttattgtg 4620
aagatagtgg aaaaggaagg tggctcctac aaatgccatc attgcgataa aggaaaggcc 4680
atcgttgaag atgcctctgc cgacagtggt cccaaagatg gacccccacc cacgaggagc 4740
atcgtggaaa aagaagacgt tccaaccacg tcttcaaagc aagtggattg atgtgatatc 4800
tccactgacg taagggatga cgcacaatcc cactatcctt cgcaagaccc ttcctctata 4860
taaggaagtt catttcattt ggagaggaga aaactaaacc atacaccacc aacacaacca 4920
aacccaccac gcccaattgt tacacacccg cttgaaaaag aaagtttaac aaatggccaa 4980
ggtgcgcgag gtttaccaat cttttacaga ctccaccaca aaaactctca tccaagatga 5040
ggcttataga aacattcgcc ccatcatgga aaaacacaaa ctagctaacc cttacgctca 5100
aacggttgaa gcggctaatg atctagaggg gttcggcata gccaccaatc cctatagcat 5160
tgaattgcat acacatgcag ccgctaagac catagagaat aaacttctag aggtgcttgg 5220
ttccatccta ccacaagaac ctgttacatt tatgtttctt aaacccagaa agctaaacta 5280
catgagaaga aacccgcgga tcaaggacat tttccaaaat gttgccattg aaccaagaga 5340
cgtagccagg taccccaagg aaacaataat tgacaaactc acagagatca caacggaaac 5400
agcatacatt agtgacactc tgcacttctt ggatccgagc tacatagtgg agacattcca 5460
aaactgccca aaattgcaaa cattgtatgc gaccttagtt ctccccgttg aggcagcctt 5520
taaaatggaa agcactcacc cgaacatata cagcctcaaa tacttcggag atggtttcca 5580
gtatatacca ggcaaccatg gtggcggggc ataccatcat gaattcgctc atctacaatg 5640
gctcaaagtg ggaaagatca agtggaggga ccccaaggat agctttctcg gacatctcaa 5700
ttacacgact gagcaggttg agatgcacac agtgacagta cagttgcagg aatcgttcgc 5760
ggcaaaccac ttgtactgca tcaggagagg agacttgctc acaccggagg tgcgcacttt 5820
cggccaacct gacaggtacg tgattccacc acagatcttc ctcccaaaag ttcacaactg 5880
caagaagccg attctcaaga aactatgat gcagctcttc ttgtatgtta ggacagtcaa 5940
ggtcgcaaaa aattgtgaca tttttgccaa agtcagacaa ttaattaaat catctgactt 6000
ggacaaatac tctgctgtgg aactggttta cttagtaagc tacatggagt tccttgccga 6060
tttacaagct accacctgct tctcagacac actttctggt ggcttgctaa caaagaccct 6120
tgcaccggtg agggcttgga tacaagagaa aaagatgcag ctgtttggtc ttgaggacta 6180
cgcgaagtta gtcaaagcag ttgatttcca cccggtggat ttttctttca aagtggaaac 6240
ttgggacttc agattccacc ccttgcaagc gtggaaagcc ttccgaccaa gggaagtgtc 6300
ggatgtagag gaaatggaaa gtttgttctc agatggggac ctgcttgatt gcttcacaag 6360
aatgccagct tatgcggtaa acgcagagga agatttagct gcaatcagga aaacgcccga 6420
gatggatgtc ggtcaagaag ttaaagagcc tgcaggagac agaaatcaat actcaaaccc 6480
tgcagaaact ttcctcaaca agctccacag gaaacacagt agggaggtga aacaccaggc 6540
cgcaaagaaa gctaaacgcc tagctgaaat ccaggagtca atgagagctg aaggtgatgc 6600
cgaaccaaat gaaataagcg ggacgatggg ggcaataccc agcaacgccg aacttcctgg 6660
cacgaatgat gccagacaag aactcacact cccaaccact aaacctgtcc ctgcaaggtg 6720
ggaagatgct tcattcacag attctagtgt ggaagaggag caggttaaac tccttggaaa 6780
agaaaccgtt gaaacagcga cgcaacaagt catcgaagga cttccttgga aacactggat 6840

-continued

```
tcctcaatta aatgctgttg gattcaaggc gctggaaatt cagagggata ggagtggaac   6900
aatgatcatg cccatcacag aaatggtgtc cgggctggaa aaagaggact tccctgaagg   6960
aactccaaaa gagttggcac gagaattgtt cgctatgaac agaagccctg ccaccatccc   7020
tttggacctg cttagagcca gagactacgg cagtgatgta aagaacaaga gaattggtgc   7080
catcacaaag acacaggcaa cgagttgggg cgaatacttg acaggaaaga tagaaagctt   7140
aactgagagg aaagttgcga cttgtgtcat tcatggagct ggaggttctg gaaaaagtca   7200
tgccatccag aaggcattga gagaaattgg caagggctcg gacatcactg tagtcctgcc   7260
gaccaatgaa ctgcggctag attggagtaa gaaagtgcct aacactgagc cctatatgtt   7320
caagacctct gaaaaggcgt taattggggg aacaggcagc atagtcatct ttgacgatta   7380
ctcaaaactt cctcccggtt acatagaagc cttagtctgt ttctactcta aaatcaagct   7440
aatcattcta acaggagata gcagacaaag cgtctaccat gaaactgctg aggacgcctc   7500
catcaggcat ttgggaccag caacagagta cttctcaaaa tactgccgat actatctcaa   7560
tgccacacac cgcaacaaga aagatcttgc gaacatgctt ggtgtctaca gtgagagaac   7620
gggagtcacc gaaatcagca tgagcgccga gttcttagaa ggaatcccaa ctttggtacc   7680
ctcggatgag aagagaaagc tgtacatggg caccgggagg aatgacacgt tcacatacgc   7740
tggatgccag gggctaacta agccgaaggt acaaatagtg ttggaccaca acacccaagt   7800
gtgtagcgcg aatgtgatgt acacggcact ttctagagcc accgatagga ttcacttcgt   7860
gaacacaagt gcaaattcct ctgccttctg ggaaaagttg gacagcaccc cttacctcaa   7920
gactttccta tcagtggtga gagaacaagc actcagggag tacgagccgg cagaggcaga   7980
gccaattcaa gagcctgagc cccagacaca catgtgtgtc gagaatgagg agtccgtgct   8040
agaagagtac aaagaggaac tcttggaaaa gtttgacaga gagatccact ctgaatccca   8100
tggtcattca aactgtgtcc aaactgaaga cacaaccatt cagttgtttt cgcatcaaca   8160
agcaaaagat gagactctcc tctgggcgac tatagatgcg cggctcaaga ccagcaatca   8220
agaaacaaac ttccgagaat tcctgagcaa gaaggacatt ggggacgttc tgtttttaaa   8280
ctaccaaaaa gctatgggtt tacccaaaga gcgtattcct tttcccaag aggtctggga    8340
agcttgtgcc cacgaagtac aaagcaagta cctcagcaag tcaaagtgca acttgatcaa   8400
tgggactgtg agacagagcc cagacttcga tgaaaataag attatggtat tcctcaagtc   8460
gcagtgggtc acaaaggtgg aaaaactagg tctacccaag attaagccag gtcaaaccat   8520
agcagccttt taccagcaga ctgtgatgct tttggaact atggctaggt acatgcgatg    8580
gttcagacag gctttccagc caaaagaagt cttcataaac tgtgagacga cgccagatga   8640
catgtctgca tgggccttga acaactggaa tttcagcaga cctagcttgg ctaatgacta   8700
cacagctttc gaccagtctc aggatggagc catgttgcaa tttgaggtgc tcaaagccaa   8760
acaccactgc ataccagagg aaatcattca ggcatacata gatattaaga ctaatgcaca   8820
gattttccta ggcacgttat caattatgcg cctgactggt gaaggtccca cttttgatgc   8880
aaacactgag tgcaacatag cttacaccca tacaaagttt gacatcccag ccggaactgc   8940
tcaagtttat gcaggagacg actccgcact ggactgtgtt ccagaagtga agcatagttt   9000
ccacaggctt gaggacaaat tactcctaaa gtcaaagcct gtaatcacgc agcaaaagaa   9060
gggcagttgg cctgagtttt gtggttggct gatcacacca aaaggggtga tgaaagaccc   9120
aattaagctc catgttagct taaaattggc tgaagctaag ggtgaactca agaaatgtca   9180
agattcctat gaaattgatc tgagttatgc ctatgaccac aaggactctc tgcatgactt   9240
```

```
gttcgatgag aaacagtgtc aggcacacac actcacttgc agaacactaa tcaagtcagg   9300
gagaggcact gtctcacttt cccgcctcag aaactttctt taaccgttaa gttaccttag   9360
agatttgaat aagatgtcag caccagctag tacaacacag cccatagggt caactacctc   9420
aactaccaca aaaactgcag gcgcaactcc tgccacagct tcaggcctgt tcactatccc   9480
ggatggggat ttctttagta cagcccgtgc catagtagcc agcaatgctg tcgcaacaaa   9540
tgaggacctc agcaagattg aggctatttg gaaggacatg aaggtgccca cagacactat   9600
ggcacaggct gcttgggact tagtcagaca ctgtgctgat gtaggatcat ccgctcaaac   9660
agaaatgata gatacaggtc cctattccaa cggcatcagc agagctagac tggcagcagc   9720
aattaaagag gtgtgcacac ttaggcaatt ttgcatgaag tatgccccag tggtatggaa   9780
ctggatgtta actaacaaca gtccacctgc taactggcaa gcacaaggtt tcaagcctga   9840
gcacaaattc gctgcattcg acttcttcaa tggagtcacc aacccagctg ccatcatgcc   9900
caaagagggg ctcatccggc caccgtctga agctgaaatg aatgctgccc aaactgctgc   9960
ctttgtgaag attacaaagg ccagggcaca atccaacgac tttgccagcc tagatgcagc  10020
tgtcactcga ggaaggatca ccggaacgac cacagcagag gcagtcgtta ctctgcctcc  10080
tccataacag aaactttctt taaccgttaa gttaccttag agatttgaat aagatggata  10140
ttctcatcag tagtttgaaa agtttaggtt attctaggac ttccaaatct ttagattcag  10200
gacctttggt agtacatgca gtagccggag ccggtaagtc cacagcccta aggaagttga  10260
tcctcagaca cccaacattc accgtgcata cactcggtgt ccctgacaag gtgagtatca  10320
gaactagagg catacagaag ccaggaccta ttcctgaggg caacttcgca atcctcgatg  10380
agtatacttt ggacaacacc acaaggaact cataccaggc actttttgct gacccttatc  10440
aggcaccgga gtttagccta gagccccact tctacttgga aacatcattt cgagttccga  10500
ggaaagtggc agatttgata gctggctgtg gcttcgattt cgagacgaac tcaccggaag  10560
aagggcactt agagatcact ggcatattca aagggcccct actcggaaag gtgatagcca  10620
ttgatgagga gtctgagaca acactgtcca ggcatggtgt tgagtttgtt aagccctgcc  10680
aagtgacggg acttgagttc aaagtagtca ctattgtgtc tgccgcacca atagaggaaa  10740
ttggccagtc cacagctttc tacaacgcta tcaccaggtc aaagggattg acatatgtcc  10800
gcgcagggcc ataggctgac cgctccggtc aattctgaaa aagtgtacat agtattaggt  10860
ctatcatttg ctttagtttc aattaccttt ctgctttcta gaaatagctt accccacgtc  10920
ggtgacaaca ttcacagctt gccacacgga ggagcttaca gagacggcac caaagcaatc  10980
ttgtacaact ccccaaatct agggtcacga gtgagtctac acaacggaaa gaacgcagca  11040
tttgctgccg ttttgctact gactttgctg atctatggaa gtaaatacat atctcaacgc  11100
aatcatactt gtgcttgtgg taacaatcat agcagtcatt agcacttcct tagtgaggac  11160
tgaaccttgt gtcatcaaga ttactgggga atcaatcaca gtgttggctt gcaaactaga  11220
tgcagaaacc ataagggcca ttgccgatct caagccactc tccgttgaac ggttaagttt  11280
ccattgatac tcgaaagagg tcagcaccag ctagcaacaa acaagaacat ggaactgaag  11340
aagtccatca gcgattacac cgaggctgag ttcaagaaga tcatcgaggc tatcatcaac  11400
tgcgagggtg atgagaaaac ccaggatgat aaccttgagt tcttcatcag ggtgaccgag  11460
taccettctg gtagcgatct tatctactac cctgagggtg ataacgatgg tagcaccgag  11520
gcaattatca aagaaatcaa ggaatggagg gctgctaacg gtaagcctgg ttttaagcaa  11580
```

-continued gcttaa 11586

<210> SEQ ID NO 25
<211> LENGTH: 524
<212> TYPE: PRT
<213> ORGANISM: Salmonella enterica

<400> SEQUENCE: 25

```
Met Ser Asp Asn Thr Ile Ala Tyr Tyr Glu Asp Gly Val Pro Tyr Ser
1               5                   10                  15

Ala Asp Gly Lys Val Leu Ile Ile Ile Asp Gly Lys Met Pro Val Asp
            20                  25                  30

Thr Gly Gly Thr Gly Gly Gly Gly Gly Gly Lys Ala Gly Val Thr Ser
        35                  40                  45

Glu Ser Ser Ala Ala Ile His Ala Thr Ala Lys Trp Ser Lys Ala Gln
    50                  55                  60

Leu Gln Lys Ser Leu Glu Glu Lys Ala Ala Arg Glu Arg Glu Thr Ala
65                  70                  75                  80

Ala Ala Met Ala Ala Ala Lys Ala Lys Arg Asp Ala Leu Thr Gln His
                85                  90                  95

Leu Lys Asp Ile Val Asn Asp Val Leu Tyr His Asn Ala His Pro Pro
            100                 105                 110

Ala Val Ile Asp Leu Ala His Ala Asn Asn Met Ala Met Gln Ala Glu
        115                 120                 125

Ala Gln Arg Leu Gly Arg Ala Lys Ala Glu Glu Lys Ala Arg Lys Glu
    130                 135                 140

Ala Glu Ala Ala Glu Lys Ser Leu Gln Glu Ala Glu Arg Gln Cys Glu
145                 150                 155                 160

Glu Ala Ala Arg Gln Arg Ala Glu Ala Glu Arg Gln Leu Lys Gln Ala
                165                 170                 175

Glu Ala Glu Glu Lys Arg Leu Ala Ala Leu Ser Glu Glu Ala Arg Ala
            180                 185                 190

Val Glu Ile Ala Gln Lys Asn Leu Ala Ala Ala Gln Ser Glu Leu Ser
        195                 200                 205

Lys Met Asp Gly Glu Ile Met Ser Leu Asn Val Arg Leu Ser Thr Ser
    210                 215                 220

Ile His Ala Arg Asp Ala Glu Met Asn Ser Leu Ser Gly Lys Arg Asn
225                 230                 235                 240

Glu Leu Ala Gln Ala Ser Ala Lys Tyr Lys Glu Leu Asp Glu Leu Val
                245                 250                 255

Lys Lys Leu Glu Pro Arg Ala Asn Asp Pro Leu Gln Asn Arg Pro Phe
            260                 265                 270

Phe Asp Ala Ala Ser Arg Arg Ala Arg Ala Gly Asp Thr Leu Ala Glu
        275                 280                 285

Lys Gln Lys Glu Val Thr Ala Ser Glu Thr Arg Ile Asn Glu Leu Asn
    290                 295                 300

Thr Glu Ile Asn Gln Val Gln Gly Ala Ile Ser Gln Ala Asn Asn Asn
305                 310                 315                 320

Arg Asn Leu Asn Val Gln Gln Val Thr Glu Thr Glu Asn Ala Leu Lys
                325                 330                 335

Val Ala Ile Asp Asn Leu Asn Ser Ser Gln Met Lys Asn Ala Val Asp
            340                 345                 350

Ala Thr Val Ser Phe Tyr Gln Thr Leu Thr Glu Lys Tyr Gly Glu Lys
        355                 360                 365
```

```
Tyr Ser Leu Ile Ala Gln Glu Leu Ala Glu Lys Ser Lys Gly Lys Lys
    370                 375                 380

Ile Gly Asn Val Asp Glu Ala Leu Ala Ala Phe Glu Lys Tyr Lys Asp
385                 390                 395                 400

Val Leu Asp Arg Lys Phe Ser Lys Ala Asp Arg Asp Ala Ile Val Asn
                405                 410                 415

Ala Leu Lys Ser Phe Asn Tyr Asp Asp Trp Ala Lys His Leu Asp Gln
            420                 425                 430

Phe Ala Lys Tyr Leu Lys Ile Thr Gly His Val Ser Phe Gly Tyr Asp
        435                 440                 445

Val Val Ser Asp Val Leu Lys Ala Arg Glu Thr Gly Asp Trp Lys Pro
    450                 455                 460

Leu Phe Ile Thr Leu Glu Gln Lys Ala Leu Asp Thr Gly Met Ser Tyr
465                 470                 475                 480

Leu Val Val Leu Met Phe Ser Leu Ile Ala Gly Thr Thr Leu Gly Ile
                485                 490                 495

Phe Gly Val Ala Ile Ile Thr Ala Ile Leu Cys Ser Phe Val Asp Lys
            500                 505                 510

Tyr Ile Leu Asn Ala Leu Asn Asp Ala Leu Gly Ile
        515                 520


<210> SEQ ID NO 26
<211> LENGTH: 524
<212> TYPE: PRT
<213> ORGANISM: Salmonella enterica

<400> SEQUENCE: 26

Met Ser Asp Asn Thr Ile Ala Tyr Tyr Glu Asp Gly Val Pro Tyr Ser
1               5                   10                  15

Ala Asp Gly Lys Val Leu Ile Ile Ile Asp Gly Lys Met Pro Val Asp
            20                  25                  30

Thr Gly Gly Thr Gly Gly Gly Gly Gly Gly Lys Ala Gly Val Thr Ser
        35                  40                  45

Glu Ser Ser Ala Ala Ile His Ala Thr Ala Lys Trp Ser Lys Ala Gln
    50                  55                  60

Leu Gln Lys Ser Leu Glu Glu Lys Ala Ala Arg Glu Arg Glu Thr Ala
65                  70                  75                  80

Ala Ala Met Ala Ala Ala Lys Ala Lys Arg Asp Ala Leu Thr Gln His
                85                  90                  95

Leu Lys Asp Ile Val Asn Asp Val Leu Tyr His Asn Ala His Pro Pro
            100                 105                 110

Ala Val Ile Asp Leu Ala His Ala Asn Asn Met Ala Met Gln Ala Glu
        115                 120                 125

Ala Gln Arg Leu Gly Arg Ala Lys Ala Glu Glu Lys Ala Arg Lys Glu
    130                 135                 140

Ala Glu Ala Ala Glu Lys Ser Leu Gln Glu Ala Glu Arg Gln Arg Glu
145                 150                 155                 160

Glu Ala Ala Arg Gln Arg Ala Glu Ala Glu Arg Gln Leu Lys Gln Ala
                165                 170                 175

Glu Ala Glu Glu Lys Arg Leu Ala Ala Leu Ser Glu Glu Ala Arg Ala
            180                 185                 190

Val Glu Ile Ala Gln Lys Asn Leu Ala Ala Ala Gln Ser Glu Leu Ser
        195                 200                 205

Lys Met Asp Gly Glu Ile Met Ser Leu Asn Val Arg Leu Ser Thr Ser
    210                 215                 220
```

Ile His Ala Arg Asp Ala Glu Met Asn Ser Leu Ser Gly Lys Arg Asn
225 230 235 240

Glu Leu Ala Gln Ala Ser Ala Lys Tyr Lys Glu Leu Asp Glu Leu Val
245 250 255

Lys Lys Leu Glu Pro Arg Ala Asn Asp Pro Leu Gln Asn Arg Pro Phe
260 265 270

Phe Asp Ala Ala Ser Arg Arg Ala Arg Ala Gly Asp Thr Leu Ala Glu
275 280 285

Lys Gln Lys Glu Val Thr Ala Ser Glu Thr Arg Ile Asn Glu Leu Asn
290 295 300

Thr Glu Ile Asn Gln Val Gln Gly Ala Ile Ser Gln Ala Asn Asn Asn
305 310 315 320

Arg Asn Leu Asn Val Gln Gln Val Thr Glu Thr Glu Asn Ala Leu Lys
325 330 335

Val Ala Ile Asp Asn Leu Asn Ser Ser Gln Met Lys Asn Ala Val Asp
340 345 350

Ala Thr Val Ser Phe Tyr Gln Thr Leu Thr Glu Lys Tyr Gly Glu Lys
355 360 365

Tyr Ser Leu Ile Ala Gln Glu Leu Ala Glu Lys Ser Lys Gly Lys Lys
370 375 380

Ile Gly Asn Val Asp Glu Ala Leu Ala Ala Phe Glu Lys Tyr Lys Asp
385 390 395 400

Val Leu Asp Arg Lys Phe Ser Lys Ala Asp Arg Asp Ala Ile Val Asn
405 410 415

Ala Leu Lys Ser Phe Asn Tyr Asp Asp Trp Ala Lys His Leu Asp Gln
420 425 430

Phe Ala Lys Tyr Leu Lys Ile Thr Gly His Val Ser Phe Gly Tyr Asp
435 440 445

Val Val Ser Asp Val Leu Lys Ala Arg Glu Thr Gly Asp Trp Lys Pro
450 455 460

Leu Phe Ile Thr Leu Glu Gln Lys Ala Leu Asp Thr Gly Met Ser Tyr
465 470 475 480

Leu Val Val Leu Met Phe Ser Leu Ile Ala Gly Thr Thr Leu Gly Ile
485 490 495

Phe Gly Val Ala Ile Ile Thr Ala Ile Leu Cys Ser Phe Val Asp Lys
500 505 510

Tyr Ile Leu Asn Ala Leu Asn Asp Ala Leu Gly Ile
515 520

<210> SEQ ID NO 27
<211> LENGTH: 522
<212> TYPE: PRT
<213> ORGANISM: Salmonella enterica

<400> SEQUENCE: 27

Met Ser Gly Ser Ile Ala Tyr Tyr Glu Asp Gly Val Pro Tyr Ser Ala
1 5 10 15

Asp Gly Lys Val Val Ile Val Ile Thr Gly Lys Leu Pro Glu Gly Thr
20 25 30

Gly Gly Ser Leu Thr Ala Asp Leu Gly Ser Ala Gly Val Ser Glu Ser
35 40 45

Ser Ala Ala Ile His Ala Thr Ala Lys Trp Ser Thr Ala Gln Leu Gln
50 55 60

Lys Thr Lys Ala Glu Gln Ala Val Lys Val Lys Glu Ala Ala Val Ala

-continued 65 70 75 80

Gln Ala Lys Ala Lys Glu Lys Arg Asp Ala Leu Thr Gln Tyr Leu Lys
85 90 95

Asp Ile Val Asn Gln Ala Leu Ser His Asn Ser Arg Pro Pro Ala Val
100 105 110

Thr Asp Leu Ala His Ala Asn Asn Met Ala Met Gln Ala Glu Ala Glu
115 120 125

Arg Leu Arg Leu Ala Lys Ala Glu Ala Lys Ala Arg Glu Glu Ala Glu
130 135 140

Ala Ala Glu Lys Ala Phe Gln Leu Ala Glu Gln Gln Arg Leu Ala Ser
145 150 155 160

Glu Arg Glu Gln Ala Glu Thr Glu Arg Gln Leu Lys Leu Ala Glu Ala
165 170 175

Glu Glu Lys Arg Leu Ala Ala Leu Ser Glu Glu Ala Arg Ala Val Glu
180 185 190

Ile Ala Gln Lys Asn Leu Ala Ala Thr Gln Ser Glu Leu Thr Asn Met
195 200 205

Asp Gly Glu Ile Gln Asn Leu Asn Ile Arg Leu Asn Asn Asn Ile His
210 215 220

Glu Arg Asp Ala Glu Thr Ser Ser Leu Ser Ala Arg Arg Asn Glu Leu
225 230 235 240

Phe Gln Val Ser Glu Gln Tyr Lys Glu Ile Asp Ala Gln Val Lys Lys
245 250 255

Leu Glu Pro Arg Ala Asn Asp Pro Leu Gln Ser Arg Pro Phe Phe Ala
260 265 270

Ala Met Thr Arg Arg Ala Asn Val Tyr Thr Val Val Gln Glu Lys Gln
275 280 285

Gly Leu Val Thr Ala Ser Glu Thr Arg Ile Asn Gln Phe Asn Ala Asp
290 295 300

Ile Ser Arg Leu Gln Glu Glu Ile Val Lys Ala Asn Glu Lys Arg Asn
305 310 315 320

Met Ile Ile Thr His Ile His Glu Ala Glu Glu Gln Leu Lys Ile Ala
325 330 335

Lys Ile Asn Leu Ile Asn Ser Gln Ile Lys Asp Ala Thr Asp Ser Val
340 345 350

Ile Gly Phe Tyr Gln Thr Leu Thr Glu Lys Tyr Gly Gln Lys Tyr Ser
355 360 365

Leu Leu Ala Gln Glu Leu Ala Glu Lys Ser Lys Gly Lys Lys Ile Gly
370 375 380

Asn Val Asn Glu Ala Leu Ala Ala Phe Glu Lys Tyr Gln Asp Val Leu
385 390 395 400

Asn Lys Lys Phe Ser Lys Ala Asp Arg Asp Ala Ile Phe Asn Ala Leu
405 410 415

Glu Ser Val Lys Tyr Asp Asp Trp Ala Lys His Leu Asp Gln Phe Ala
420 425 430

Lys Tyr Leu Lys Ile Thr Gly Arg Val Ser Phe Gly Tyr Asp Leu Val
435 440 445

Ser Asp Val Leu Lys Val Arg Asp Thr Gly Asp Trp Lys Pro Leu Phe
450 455 460

Leu Thr Leu Glu Lys Lys Ala Leu Asp Thr Gly Leu Ser Tyr Leu Val
465 470 475 480

Val Leu Met Phe Ser Leu Ile Ala Gly Thr Thr Leu Gly Ile Trp Gly
485 490 495

```
Val Ala Ile Val Thr Gly Ile Leu Cys Ser Phe Ile Asp Lys Ser Met
            500                 505                 510

Leu Asn Asp Leu Asn Glu Ala Leu Gly Ile
        515                 520


<210> SEQ ID NO 28
<211> LENGTH: 269
<212> TYPE: PRT
<213> ORGANISM: Salmonella enterica

<400> SEQUENCE: 28

Met Thr Asp Thr Ile Thr Val Val Ala Pro Val Pro Pro Ser Gly Ser
1               5                   10                  15

Ala Leu Ala Gly Asn Tyr Ser Ala Ser Thr Met Ser Ala Gly Asn Arg
            20                  25                  30

Ile Ser Ser Gly Pro Thr Phe Leu Gln Phe Ala Tyr Pro Tyr Tyr Gln
        35                  40                  45

Ser Pro Gln Leu Ala Val Asn Cys Ala Lys Trp Ile Leu Asp Phe Val
    50                  55                  60

Glu Ser His Asp Met Lys Asn Ala Asn Asn Gln Lys Ile Phe Ser Glu
65                  70                  75                  80

Asn Val Gly His Phe Cys Phe Ala Asp Lys Asn Leu Val Asn Tyr Pro
                85                  90                  95

Ala Met Lys Val Leu Asp Ala Phe Gly Gly Asp Arg Lys Phe Ile Tyr
            100                 105                 110

Ser Gln Asp Gln Ile Ser Arg Leu Ser Gly Asp Val Thr Thr Pro Ile
        115                 120                 125

Thr Ala Trp Ala His Phe Leu Trp Gly Asp Gly Ala Ala Arg Thr Val
    130                 135                 140

Asn Leu Thr Asp Val Gly Leu Arg Ile Gln Ala Asn Gln Ile Ser Pro
145                 150                 155                 160

Val Met Asp Leu Val Lys Gly Gly Ala Val Gly Thr Phe Pro Val Asn
                165                 170                 175

Ala Lys Phe Thr Arg Asp Thr Met Leu Asp Gly Ile Ile Pro Ala Ser
            180                 185                 190

Tyr Leu Gly Asn Ile Thr Leu Gln Thr Thr Gly Thr Leu Thr Ile Asn
        195                 200                 205

Ser Leu Gly Ala Trp Ser Tyr Asp Gly Val Val Lys Ala Tyr Asn Asp
    210                 215                 220

Thr Tyr Asp Ala Asn Pro Ser Thr His Arg Gly Leu Leu Gly Glu Tyr
225                 230                 235                 240

Ser Thr Ser Val Leu Gly His Phe Ser Gly Thr Pro Tyr Glu Ile Gln
                245                 250                 255

Met Pro Gly Met Ile Pro Val Lys Gly Asn Gly Met Arg
            260                 265


<210> SEQ ID NO 29
<211> LENGTH: 1575
<212> TYPE: DNA
<213> ORGANISM: Artificial Sequence
<220> FEATURE:
<223> OTHER INFORMATION: Nucleotide sequence used for salmocin ScolE1c
      expression

<400> SEQUENCE: 29

atgagcgaca acaccattgc ctactacgag gatggtgtgc cttacagcgc tgatggtaag      60
```

-continued

```
gtgctgatca tcatcgatgg caagatgcct gttgataccg gtggtactgg tggtggtggc    120

ggtggtaagg ctggtgttac ttctgaatct agcgctgcta ttcacgctac cgccaagtgg    180

tctaaggctc agcttcagaa gtctctggaa gagaaggctg ctagagagag ggaaactgct    240

gctgctatgg ctgctgcaaa ggctaagaga gatgctctta cccagcacct gaaggacatc    300

gtgaacgatg tgctttacca taacgctcac cctccagctg tgattgatct tgctcacgct    360

aacaacatgg ctatgcaggc tgaagctcag aggcttggta gagctaaggc tgaggaaaag    420

gctcgtaaag aagctgaggc tgctgagaag tcacttcaag aggctgaaag acagtgcgag    480

gaagctgcta gacaaagagc tgaagcagag aggcaactta agcaggctga ggcagaagag    540

aagaggcttg ctgctctttc tgaagaggct agggctgttg agatcgctca gaagaatctt    600

gctgctgcac agagcgagct gtccaagatg gatggtgaga tcatgtctct gaacgtgcgg    660

ctgtctactt ctatccatgc tagggatgcc gagatgaaca gcctttctgg taagaggaat    720

gagctggctc aggctagcgc caagtacaaa gaacttgatg agctggtgaa gaagctcgag    780

cctagggcta atgatccact tcagaacagg ccattcttcg acgctgctag tagaagggct    840

agagctggcg atactcttgc cgagaagcag aaagaggtta ccgcttctga gactcggatc    900

aacgagctta acaccgagat taaccaggtg cagggtgcta tctcacaggc caacaacaat    960

aggaacctca acgtgcagca ggtcaccgag actgagaacg ctcttaaggt ggcaatcgac   1020

aacctgaaca gcagccagat gaagaacgct gtggatgcta ccgtgagctt ctaccagact   1080

ttgaccgaga agtacgggga gaagtacagc cttattgctc aagagctggc cgagaagtcc   1140

aagggtaaga aaattggtaa cgtggacgag gctctcgctg ccttcgaaaa gtacaaggat   1200

gtgctggacc ggaagttcag caaggctgat agggatgcta ttgtgaacgc cctgaagtcc   1260

ttcaactacg acgattgggc taagcacctg gaccagttcg ctaagtacct taagatcacc   1320

ggccacgtgt ccttcggtta cgatgttgtt tctgacgtgc tgaaggctcg tgagactggt   1380

gattggaagc ctctgttcat taccctcgag cagaaggctt tggataccgg catgtcttac   1440

cttgtggtgc tgatgttctc tctgatcgct ggtactaccc ttggcatttt cggtgtggct   1500

atcatcaccg ctatcctgtg ctcattcgtg gacaagtaca tcctgaacgc tctgaacgat   1560

gctctgggaa tctaa                                                    1575
```

```
<210> SEQ ID NO 30
<211> LENGTH: 1575
<212> TYPE: DNA
<213> ORGANISM: Artificial Sequence
<220> FEATURE:
<223> OTHER INFORMATION: Nucleotide sequence used for salmocin ScolE1d
      expression

<400> SEQUENCE: 30

atgagcgaca acaccattgc ctactacgag gatggtgtgc cttacagcgc tgatggtaag     60

gtgctgatca tcatcgatgg caagatgcct gttgataccg gtggtactgg tggtggtggc    120

ggtggtaagg ctggtgttac ttctgaatct agcgctgcta ttcacgctac cgccaagtgg    180

tctaaggctc agcttcagaa gtctctggaa gagaaggctg ctagagagag ggaaactgct    240

gctgctatgg ctgctgcaaa ggctaagaga gatgctctta cccagcacct gaaggacatc    300

gtgaacgatg tgctttacca taacgctcac cctccagctg tgattgatct tgctcacgct    360

aacaacatgg ctatgcaggc tgaagctcag aggcttggta gagctaaggc tgaggaaaag    420

gctcgtaaag aagctgaggc tgctgagaag tcacttcaag aggctgaaag gcagagagag    480
```

-continued

```
gaagctgcaa gacaaagagc agaggctgag agacaactta agcaggctga ggcagaagag    540

aagaggcttg ctgctctttc tgaagaggct agggctgttg agatcgctca gaagaatctt    600

gctgctgcac agagcgagct gtccaagatg gatggtgaga tcatgtctct gaacgtgcgg    660

ctgtctactt ctatccatgc tagggatgcc gagatgaaca gcctttctgg taagaggaat    720

gagctggctc aggctagcgc caagtacaaa gaacttgatg agctggtgaa gaagctcgag    780

cctagggcta atgatccact tcagaacagg ccattcttcg acgctgctag tagaagggct    840

agagctggcg atactcttgc cgagaagcag aaagaggtta ccgcttctga gactcggatc    900

aacgagctta acaccgagat taaccaggtg cagggtgcta tctcacaggc caacaacaat    960

aggaacctca acgtgcagca ggtcaccgag actgagaacg ctcttaaggt ggcaatcgac   1020

aacctgaaca gcagccagat gaagaacgct gtggatgcta ccgtgagctt ctaccagact   1080

ttgaccgaga agtacgggga gaagtacagc cttattgctc aagagctggc cgagaagtcc   1140

aagggtaaga aaattggtaa cgtggacgag gctctcgctg ccttcgaaaa gtacaaggat   1200

gtgctggacc ggaagttcag caaggctgat agggatgcta ttgtgaacgc cctgaagtcc   1260

ttcaactacg acgattgggc taagcacctg gaccagttcg ctaagtacct taagatcacc   1320

ggccacgtgt ccttcggtta cgatgttgtt tctgacgtgc tgaaggctcg tgagactggt   1380

gattggaagc ctctgttcat taccctcgag cagaaggctt tggataccgg catgtcttac   1440

cttgtggtgc tgatgttctc tctgatcgct ggtactaccc ttggcatttt cggtgtggct   1500

atcatcaccg ctatcctgtg ctcattcgtg gacaagtaca tcctgaacgc tctgaacgat   1560

gctctgggaa tctaa                                                    1575
```

<210> SEQ ID NO 31
<211> LENGTH: 1569
<212> TYPE: DNA
<213> ORGANISM: Artificial Sequence
<220> FEATURE:
<223> OTHER INFORMATION: Nucleotide sequence used for salmocin ScolE1e expression

<400> SEQUENCE: 31

```
atgagcggct ctatcgctta ctacgaggat ggtgttcctt acagcgctga tggtaaggtg     60

gtgatcgtga ttaccggcaa gcttcctgaa ggtactggtg gttctcttac cgctgatctt    120

ggatctgctg gtgtgtctga aagctctgct gctattcatg ctaccgccaa gtggtctact    180

gctcagcttc aaaagactaa ggctgagcag gccgtgaagg tgaaagaagc tgctgttgct    240

caggccaagg ccaaagaaaa gagggatgct cttacccagt acctgaagga tatcgtgaac    300

caggctctga gccataactc tagacctcca gctgtgactg atctggctca cgctaacaat    360

atggctatgc aggctgaggc tgagaggctt agacttgcta aagctgaggc taaggctcgt    420

gaagaagctg aagctgcaga gaaggctttt cagcttgctg aacagcagag gcttgcttct    480

gaaagagaac aggctgagac agagcggcag cttaagttgg ctgaagcaga ggaaaagagg    540

ctggctgctc tttctgaaga ggctagggct gttgagatcg ctcagaagaa tcttgctgct    600

acccagtctg agctgaccaa catggatggt gagatccaga acctgaacat ccggctgaac    660

aacaacatcc atgagaggga cgctgagaca agctctctgt ctgctagacg gaacgagctt    720

ttccaggtta gcgagcagta caaagagatc gacgcccagg ttaagaagct tgagcctagg    780

gctaatgacc ctcttcagtc taggcctttc ttcgctgcta tgaccagacg ggctaatgtg    840

tacactgtgg tgcaagagaa gcagggtctt gtgactgctt ctgagactcg gatcaaccag    900
```

-continued ttcaacgctg acatctctag gctgcaagaa gagatcgtca aggccaacga gaagcggaac 960
atgatcatta cccacatcca cgaggctgag gaacagctga agatcgctaa gatcaacctg 1020
atcaactccc agatcaagga cgctaccgat agcgtgatcg gtttctacca gactctgacc 1080
gagaagtacg gccagaagta ctctttgctt gctcaagagc tggccgagaa gtccaagggt 1140
aagaaaatcg gtaacgtgaa cgaggccctt gctgcctttg agaagtacca ggatgtgctg 1200
aacaagaagt tctccaaggc tgacagggac gctatcttca acgctcttga gtccgtgaag 1260
tacgacgatt gggctaagca ccttgaccag ttcgccaagt accttaagat caccggtagg 1320
gtgagcttcg gttacgatct tgtgtccgat gtcctcaagg tgagagatac tggtgattgg 1380
aagccgctgt tcttgaccct tgagaagaag gctcttgata ccggcctgtc ttaccttgtg 1440
gtgctgatgt tctctcttat cgccggtact acccttggca tttggggtgt tgctattgtg 1500
accggtatcc tgtgctcctt catcgacaag agcatgctga acgacctcaa cgaggctctt 1560
ggtatctaa 1569

<210> SEQ ID NO 32
<211> LENGTH: 810
<212> TYPE: DNA
<213> ORGANISM: Artificial Sequence
<220> FEATURE:
<223> OTHER INFORMATION: Nucleotide sequence used for salmocin ScolMa expression

<400> SEQUENCE: 32
atgaccgaca ctattactgt ggttgctcct gtgcctcctt ctggttctgc tcttgctggt 60
aactacagcg cctctactat gtctgctggc aacaggattt ctagcggtcc tacctttctg 120
cagttcgctt acccttacta ccagtctcct cagcttgctg tgaattgcgc taagtggatc 180
ctggacttcg ttgagagcca cgacatgaag aacgccaaca accagaaaat cttcagcgag 240
aacgtgggcc acttctgctt cgctgataag aaccttgtga actacccggc catgaaggtg 300
ttggatgctt ttggtggtga ccggaagttc atctacagcc aggatcagat ctctcggctg 360
tctggtgatg tgactactcc tattactgct tgggctcact tcctgtgggg tgatggtgct 420
gctaggactg tgaatcttac cgatgttggt ctgcggatcc aggccaatca gatttctcct 480
gtgatggacc tggtgaaagg tggtgctgtt ggtactttcc ctgtgaacgc taagttcacc 540
agggatacca tgctggacgg tatcatccct gctagctacc ttggtaacat tacccttcag 600
accaccggca ccttgaccat caattctctt ggtgcttgga gctacgatgg cgtggtgaag 660
gcttacaacg atacctacga tgctaacccg tctactcaca ggggtttgct tggtgagtac 720
agcacttctg tgctcggtca tttctctgga accccttacg agattcagat gcctggtatg 780
atcccggtga aaggcaatgg tatgaggtaa 810

BACTERIOCINS FOR CONTROL OF *SALMONELLA ENTERICA*

CROSS-REFERENCE TO RELATED APPLICATIONS

This application is a continuation-in-part of International Application PCT/EP2018/055479, filed Mar. 6, 2018, which designates the U.S. and was published by the International Bureau in English on Sep. 27, 2018, and which claims the benefit of European Patent Application No. 17 162 784.7, filed Mar. 24, 2017; both of which are hereby incorporated herein in their entirety by reference.

REFERENCE TO A SEQUENCE LISTING SUBMITTED AS A TEXT FILE

The official copy of the sequence listing is submitted electronically via EFS-Web as an ASCII formatted sequence listing with a file named 070313-0030SEQLST.TXT, created on Sep. 20, 2019 and having a size of 125 kilobytes, and is filed concurrently with the specification. The sequence listing contained in this ASCII formatted document is part of the specification and is herein incorporated by reference in its entirety.

FIELD OF THE INVENTION

The present invention provides proteins capable of exerting a cytotoxic effect on *Salmonella*, referred to as salmocins. The invention also provides compositions, including pharmaceutical compositions, comprising one or more of said proteins. Also provided is a method of preventing or reducing infection or contamination of an object with *Salmonella*, a method of treating infection with *Salmonella* of a subject or patient in need thereof, and a process of producing a composition comprising the protein.

BACKGROUND OF THE INVENTION

*Salmonella* is a rod-shaped Gram-positive bacterium of Enterobacteriaceae family. *Salmonella enterica* is the type species and is further divided into six subspecies with *S. enterica* ssp. *enterica* as subspecies that includes over 2500 serovars. *Salmonella* infections are common and can result in protean clinical manifestations, ranging from an asymptomatic state to very severe diseases. *Salmonella enterica* causes an estimated 1 million illnesses in the United States each year, resulting in an estimated 19,000 hospitalizations and 380 deaths. Over the last 5 years, 46 *Salmonella* outbreaks have been recorded in USA, most of the food poisonings being due to contaminated poultry or vegetables, but also red meats and fish (CDC website).

Prevention *Salmonella* infections or reducing contamination of food with *Salmonella* requires control measures at all stages of the food chain, from agricultural production on the farm to processing, manufacturing and preparation of foods in both commercial establishments and household kitchens. Good hygienic practices reduce contamination of food with *Salmonella*, but do not guarantee the absence of *Salmonella* from products. Preventive measures for *Salmonella* in the home are similar to those used against other foodborne bacteria. Basic food hygiene practices, such as "cook thoroughly", are recommended as a preventive measure against salmonellosis, cf. WHO at www.who.int/mediacentre/factsheets/fs139/en/.

Antimicrobial therapy may be used to treat humans or animals suffering from *Salmonella* infections. However, antimicrobial resistance is a global public health concern and *Salmonella* is one of the microorganisms in which some resistant serotypes have emerged, affecting the food chain.

Most of the above mentioned methods of preventing or treating *Salmonella* infections or reducing contamination with *Salmonella* are methods that are essentially independent from a particular pathogenic bacterium or from a particular serotype of *Salmonella*. This has the advantage that little prior knowledge of the specific *Salmonella* strain or *Salmonella enterica* serotype in question is necessary before counter-measures are taken. However, the above mentioned methods of preventing *Salmonella* infection or reducing contamination with *Salmonella* such as heating are not always applicable or change the treated good or food in undesirable ways. Other methods may have turned out non-effective with a particular patient. There is therefore a need for further methods of preventing or treating *Salmonella* infections or contamination, or methods for reducing or preventing contamination of objects with *Salmonella*, notably with *Salmonella enterica* ssp. *enterica*.

It is an object of the invention to provide methods for preventing or treating *Salmonella* infections such as food-borne *Salmonella* infections. It is another object to provide methods for preventing or reducing contamination of objects, notably food, with *Salmonella*. It is a further object to provide methods for preventing or treating *Salmonella* infections and/or methods for reducing contamination of objects with *Salmonella*, that are effective against a wide range of *Salmonella* serogroups. Further, compounds, agents and compositions for such methods are desired.

SUMMARY OF THE INVENTION

Accordingly, the invention provides:

(1) A protein, preferably capable of exerting a cytotoxic effect on *Salmonella*, said protein comprising at least any one of the following amino acid sequence segments (a-i) to (a-x) or derivatives thereof as defined in (b-i) to (b-x), (c-i) to (c-x) or (d-i) to (d-x):

- (a-i) the segment from amino acid residue 316 to 449 of ScolE2 (SEQ ID NO: 1),
- (a-ii) the segment from amino acid residue 315 to 483 of ScolE3 (SEQ ID NO: 2),
- (a-iii) the segment from amino acid residue 318 to 451 of ScolE7 (SEQ ID NO: 3),
- (a-iv) the segment from amino acid residue 174 to 297 of ScolE1a (SEQ ID NO: 4),
- (a-v) the segment from amino acid residue 198 to 322 of ScolE1b (SEQ ID NO: 5),
- (a-vi) a segment comprising at least 200 contiguous amino acid residues of Spst of SEQ ID NO: 6,
- (a-vii) the segment from amino acid residue 195 to 319 of ScolE1c (SEQ ID NO: 25),
- (a-viii) the segment from amino acid residue 195 to 319 of ScolE1d (SEQ ID NO: 26),
- (a-ix) the segment from amino acid residue 193 to 317 of ScolE1e (SEQ ID NO: 27), or
- (a-x) the segment from amino acid residue 38 to 138 of ScolMa (SEQ ID NO: 28); or
- (b-i) a segment having at least 75% sequence identity to the segment from amino acid residue 316 to 449 of ScolE2 (SEQ ID NO: 1),
- (b-ii) a segment having at least 70% sequence identity to the segment from amino acid residue 315 to 483 of ScolE3 (SEQ ID NO: 2), (b-iii) a segment having at least 77% sequence identity to the segment from amino acid residue 318 to 451 of ScolE7 (SEQ ID NO: 3),
(b-iv) a segment having at least 70% sequence identity to the segment from amino acid residue 174 to 297 of ScolE1a (SEQ ID NO: 4),
(b-v) a segment having at least 70% sequence identity to the segment from amino acid residue 198 to 322 of ScolE1b (SEQ ID NO: 5),
(b-vi) a segment having at least 70% sequence identity to a segment comprising at least 200 contiguous amino acid residues of Spst of SEQ ID NO: 6,
(b-vii) a segment having at least 70% sequence identity to the segment from amino acid residue 195 to 319 of ScolE1c (SEQ ID NO: 25),
(b-viii) a segment having at least 70% sequence identity to the segment from amino acid residue 195 to 319 of ScolE1d (SEQ ID NO: 26),
(b-ix) a segment having at least 70% sequence identity to the segment from amino acid residue 193 to 317 of ScolE1e (SEQ ID NO: 27), or
(b-x) a segment having at least 70% sequence identity to the segment from amino acid residue 38 to 138 of ScolMa (SEQ ID NO: 28);

or (c-i) a segment having at least 85% sequence similarity to the segment from amino acid residue 316 to 449 of ScolE2 (SEQ ID NO: 1),
(c-ii) a segment having at least 80% sequence similarity to the segment from amino acid residue 315 to 483 of ScolE3 (SEQ ID NO: 2),
(c-iii) a segment having at least 85% sequence similarity to the segment from amino acid residue 318 to 451 of ScolE7 (SEQ ID NO: 3),
(c-iv) a segment having at least 80% sequence similarity to the segment from amino acid residue 174 to 297 of ScolE1a (SEQ ID NO: 4),
(c-v) a segment having at least 80% sequence similarity to the segment from amino acid residue 198 to 322 of ScolE1b (SEQ ID NO: 5),
(c-vi) a segment having at least 80% sequence similarity to a segment comprising at least 200 contiguous amino acid residues of Spst of SEQ ID NO: 6,
(c-vii) a segment having at least 80% sequence similarity to the segment from amino acid residue 195 to 319 of ScolE1c (SEQ ID NO: 25),
(c-viii) a segment having at least 80% sequence similarity to the segment from amino acid residue 195 to 319 of ScolE1d (SEQ ID NO: 26),
(c-ix) a segment having at least 80% sequence similarity to the segment from amino acid residue 193 to 317 of ScolE1e (SEQ ID NO: 27), or
(c-x) a segment having at least 80% sequence similarity to the segment from amino acid residue 38 to 138 of ScolMa (SEQ ID NO: 28);

or (d-i) a segment having from 1 to 25 amino acid substitutions, additions, insertions or deletions to the segment from amino acid residue 316 to 449 of ScolE2 (SEQ ID NO: 1),
(d-ii) a segment having from 1 to 40 amino acid substitutions, additions, insertions or deletions to the segment from amino acid residue 315 to 483 of ScolE3 (SEQ ID NO: 2),
(d-iii) a segment having from 1 to 30 amino acid substitutions, additions, insertions or deletions to the segment from amino acid residue 318 to 451 of ScolE7 (SEQ ID NO: 3),
(d-iv) a segment having from 1 to 40 amino acid substitutions, additions, insertions or deletions to the segment from amino acid residue 174 to 297 of ScolE1a (SEQ ID NO: 4),
(d-v) a segment having from 1 to 40 amino acid substitutions, additions, insertions or deletions to the segment from amino acid residue 198 to 322 of ScolE1b (SEQ ID NO: 5),
(d-vi) a segment having from 1 to 40 amino acid substitutions, additions, insertions or deletions to a segment comprising at least 200 contiguous amino acid residues of Spst of SEQ ID NO: 6,
(d-vii) a segment having from 1 to 40 amino acid substitutions, additions, insertions or deletions to the segment from amino acid residue 195 to 319 of ScolE1c (SEQ ID NO: 25),
(d-viii) a segment having from 1 to 40 amino acid substitutions, additions, insertions or deletions to the segment from amino acid residue 195 to 319 of ScolE1d (SEQ ID NO: 26),
(d-ix) a segment having from 1 to 40 amino acid substitutions, additions, insertions or deletions to the segment from amino acid residue 193 to 317 of ScolE1e (SEQ ID NO: 27), or
(d-x) a segment having from 1 to 30 amino acid substitutions, additions, insertions or deletions to the segment from amino acid residue 38 to 138 of ScolMa (SEQ ID NO: 28).

(2) The protein according to (1), comprising a cytotoxic or catalytic domain having any one or more of the following activities: a membrane pore-forming activity, DNase activity, RNase activity, or a cell wall degrading activity such as muramidase activity.

(3) The protein according to (1) or (2), comprising a cytotoxic or catalytic domain comprising or consisting of any one of the following amino acid sequence segments (a-i)' to (a-x)', or derivatives thereof or amino acid sequence segments as defined in any one of (b-i)' to (b-x)', (c-i)' to (c-x)' or (d-i)' to (d-x)':

(a-i)' the segment from amino acid residue 453 to 582 of ScolE2 (SEQ ID NO: 1),
(a-ii)' the segment from amino acid residue 501 to 584 of ScolE3 (SEQ ID NO: 2),
(a-iii)' the segment from amino acid residue 455 to 584 of ScolE7 (SEQ ID NO: 3),
(a-iv)' the segment from amino acid residue 306 to 478 of ScolE1a (SEQ ID NO: 4),
(a-v)' the segment from amino acid residue 350 to 522 of ScolE1b (SEQ ID NO: 5),
(a-vi)' the segment from amino acid residue 112 to 288 of Spst (SEQ ID NO: 6),
(a-vii)' the segment from amino acid residue 347 to 519 of ScolE1c (SEQ ID NO: 25),
(a-viii)' the segment from amino acid residue 347 to 519 of ScolE1d (SEQ ID NO: 26),
(a-ix)' the segment from amino acid residue 345 to 517 of ScolE1e (SEQ ID NO: 27), or
(a-x)' the segment from amino acid residue 139 to 269 of ScolMa (SEQ ID NO: 28);

or (b-i)' a segment having at least 70% sequence identity to the segment from amino acid residue 453 to 582 of ScolE2 (SEQ ID NO: 1), (b-ii)' a segment having at least 70% sequence identity to the segment from amino acid residue 501 to 584 of ScolE3 (SEQ ID NO: 2), (b-iii)' a segment having at least 70% sequence identity to the segment from amino acid residue 455 to 584 of ScolE7 (SEQ ID NO: 3), (b-iv)' a segment having at least 70% sequence identity to the segment from amino acid residue 306 to 478 of ScolE1a (SEQ ID NO: 4), (b-v)' a segment having at least 70% sequence identity to the segment from amino acid residue 350 to 522 of ScolE1b (SEQ ID NO: 5), (b-vi)' a segment having at least 70% sequence identity to the segment from amino acid residue 112 to 288 of Spst (SEQ ID NO: 6), (b-vii)' a segment having at least 70% sequence identity to the segment from amino acid residue 347 to 519 ScolE1c (SEQ ID NO: 25), (b-viii)' a segment having at least 70% sequence identity to the segment from amino acid residue 347 to 519 ScolE1d (SEQ ID NO: 26), (b-ix)' a segment having at least 70% sequence identity to the segment from amino acid residue 345 to 517 ScolE1e (SEQ ID NO: 27), or (b-x)' a segment having at least 70% sequence identity to the segment from amino acid residue 139 to 269 ScolMa (SEQ ID NO: 28);

or (c-i)' a segment having at least 80% sequence similarity to the segment from amino acid residue 453 to 582 of ScolE2 (SEQ ID NO: 1), (c-ii)' a segment having at least 80% sequence similarity to the segment from amino acid residue 501 to 584 of ScolE3 (SEQ ID NO: 2), (c-iii)' a segment having at least 80% sequence similarity to the segment from amino acid residue 455 to 584 of ScolE7 (SEQ ID NO: 3), (c-iv)' a segment having at least 80% sequence similarity to the segment from amino acid residue 306 to 478 of ScolE1a (SEQ ID NO: 4), (c-v)' a segment having at least 80% sequence similarity to the segment from amino acid residue 350 to 522 of ScolE1b (SEQ ID NO: 5), (c-vi)' a segment having at least 80% sequence similarity to the segment from amino acid residue 112 to 288 of Spst (SEQ ID NO: 6), (c-vii)' a segment having at least 80% sequence similarity to the segment from amino acid residue 347 to 519 ScolE1c (SEQ ID NO: 25), (c-viii)' a segment having at least 80% sequence similarity to the segment from amino acid residue 347 to 519 ScolE1d (SEQ ID NO: 26), (c-ix)' a segment having at least 80% sequence similarity to the segment from amino acid residue 345 to 517 ScolE1e (SEQ ID NO: 27), or (c-x)' a segment having at least 80% sequence similarity to the segment from amino acid residue 139 to 269 ScolMa (SEQ ID NO: 28);

or (d-i)' a segment having from 1 to 20 amino acid substitutions, additions, insertions or deletions to the segment from amino acid residue 453 to 582 of ScolE2 (SEQ ID NO: 1), (d-ii)' a segment having from 1 to 20 amino acid substitutions, additions, insertions or deletions to the segment from amino acid residue 501 to 584 of ScolE3 (SEQ ID NO: 2), (d-iii)' a segment having from 1 to 20 amino acid substitutions, additions, insertions or deletions to the segment from amino acid residue 455 to 584 of ScolE7 (SEQ ID NO: 3), (d-iv)' a segment having from 1 to 20 amino acid substitutions, additions, insertions or deletions to the segment from amino acid residue 306 to 478 of ScolE1a (SEQ ID NO: 4), (d-v)' a segment having from 1 to 20 amino acid substitutions, additions, insertions or deletions to the segment from amino acid residue 350 to 522 of ScolE1b (SEQ ID NO: 5), (d-vi)' a segment having from 1 to 20 amino acid substitutions, additions, insertions or deletions to the segment from amino acid residue 112 to 288 of Spst (SEQ ID NO: 6), (d-vii)' a segment having from 1 to 40 amino acid substitutions, additions, insertions or deletions to the segment from amino acid residue 347 to 519 ScolE1c (SEQ ID NO: 25), (d-viii)' a segment having from 1 to 40 amino acid substitutions, additions, insertions or deletions to the segment from amino acid residue 347 to 519 ScolE1d (SEQ ID NO: 26), (d-ix)' a segment having from 1 to 40 amino acid substitutions, additions, insertions or deletions to the segment from amino acid residue 345 to 517 ScolE1e (SEQ ID NO: 27), or (d-x)' a segment having from 1 to 30 amino acid substitutions, additions, insertions or deletions to the segment from amino acid residue 139 to 269 ScolMa (SEQ ID NO: 28).

(4) The protein according to any one of (1), (2) or (3), comprising a translocation domain comprising (or consisting of) any one of the following amino acid sequence segments (a-i)" to (a-v)" and (a-vii)" to (a-x)", or derivatives thereof (or amino acid sequence segments) as defined in any one of (b-i)" to (b-v)" and (b-vii)" to (b-x)", (c-i)" to (c-v)" and (c-vii)" to (c-x)", or (d-i)" to (d-v)" and (d-vii)" to (d-x)":

(a-i)" the segment from amino acid residue 43 to 313 of ScolE2 (SEQ ID NO: 1), (a-ii)" the segment from amino acid residue 35 to 315 of ScolE3 (SEQ ID NO: 2), (a-iii)" the segment from amino acid residue 43 to 316 of ScolE7 (SEQ ID NO: 3), (a-iv)" the segment from amino acid residue 1 to 170 of ScolE1a (SEQ ID NO: 4), (a-v)" the segment from amino acid residue 1 to 195 of ScolE1b (SEQ ID NO: 5), (a-vii)" the segment from amino acid residue 6 to 194 of ScolE1c (SEQ ID NO: 25), (a-viii)" the segment from amino acid residue 6 to 194 of ScolE1d (SEQ ID NO: 26), (a-ix)" the segment from amino acid residue 5 to 192 of ScolE1e (SEQ ID NO: 27), or (a-x)" the segment from amino acid residue 1 to 37 of ScolMa (SEQ ID NO: 28);

or (b-i)" a segment having at least 75%, preferably at least 80%, more preferably at least 85%, more preferably at least 90% and most preferably at least 95% sequence identity to the segment from amino acid residue 43 to 313 of ScolE2 (SEQ ID NO: 1), (b-ii)" a segment having at least 75%, preferably at least 80%, more preferably at least 85%, more preferably at least 90% and most preferably at least 95% sequence identity to the segment from amino acid residue 35 to 315 of ScolE3 (SEQ ID NO: 2), (b-iii)" a segment having at least 80%, preferably at least 85%, more preferably at least 90% and most preferably at least 95% sequence identity to the segment from amino acid residue 43 to 316 of ScolE7 (SEQ ID NO: 3), (b-iv)" a segment having at least 70%, preferably at least 80%, more preferably at least 85%, more preferably at least 90% and most preferably at least 95% sequence identity to the segment from amino acid residue 1 to 170 of ScolE1a (SEQ ID NO: 4), (b-v)" a segment having at least 70%, preferably at least 80%, more preferably at least 85%, more preferably at least 90% and most preferably at least 95% sequence identity to the segment from amino acid residue 1 to 195 of ScolE1b (SEQ ID NO: 5), (b-vii)" a segment having at least 70%, preferably at least 80%, more preferably at least 85%, more preferably at least 90% and most preferably at least 95% sequence identity to the segment from amino acid residue 6 to 194 of ScolE1c (SEQ ID NO: 25), (b-viii)" a segment having at least 70%, preferably at least 80%, more preferably at least 85%, more preferably at least 90% and most preferably at least 95% sequence identity to the segment from amino acid residue 6 to 194 of ScolE1d (SEQ ID NO: 26), (b-ix)" a segment having at least 70%, preferably at least 80%, more preferably at least 85%, more preferably at least 90% and most preferably at least 95% sequence identity to the segment from amino acid residue 5 to 192 of ScolE1e (SEQ ID NO: 27), or (b-x)" a segment having at least 70%, preferably at least 80%, more preferably at least 85%, more preferably at least 90% and most preferably at least 95% sequence identity to the segment from amino acid residue 1 to 37 of ScolMa (SEQ ID NO: 28);

or (c-i)" a segment having at least 85%, preferably at least 90% and more preferably at least 95% sequence similarity to the segment from amino acid residue 43 to 313 of ScolE2 (SEQ ID NO: 1), (c-ii)" a segment having at least 85%, preferably at least 90% and more preferably at least 95% sequence similarity to the segment from amino acid residue 35 to 315 of ScolE3 (SEQ ID NO: 2), (c-iii)" a segment having at least 90%, preferably at least 95% sequence similarity to the segment from amino acid residue 43 to 316 of ScolE7 (SEQ ID NO: 3), (c-iv)" a segment having at least 80%, preferably at least 90, more preferably at least 95% sequence similarity to the segment from amino acid residue 1 to 170 of ScolE1a (SEQ ID NO: 4), (c-v)" a segment having at least 80%, preferably at least 90%, more preferably at least 95% sequence similarity to the segment from amino acid residue 1 to 195 of ScolE1b (SEQ ID NO: 5), (c-vii)" a segment having at least 80%, preferably at least 90%, more preferably at least 95% sequence similarity to the segment from amino acid residue 6 to 194 of ScolE1c (SEQ ID NO: 25), (c-viii)" a segment having at least 80%, preferably at least 90%, more preferably at least 95% sequence similarity to the segment from amino acid residue 6 to 194 of ScolE1d (SEQ ID NO: 26), (c-ix)" a segment having at least 80%, preferably at least 90%, more preferably at least 95% sequence similarity to the segment from amino acid residue 5 to 192 of ScolE1e (SEQ ID NO: 27), or (c-x)" a segment having at least 80%, preferably at least 90%, more preferably at least 95% sequence similarity to the segment from amino acid residue 1 to 37 of ScolMa (SEQ ID NO: 28);

or (d-i)" a segment having from 1 to 50, preferably from 1 to 40, more preferably from 1 to 30, even more preferably from 1 to 20 and most preferably from 1 to 10 amino acid substitutions, additions, insertions or deletions to the segment from amino acid residue 43 to 313 of ScolE2 (SEQ ID NO: 1), (d-ii)" a segment having from 1 to 50, preferably from 1 to 40, more preferably from 1 to 30, even more preferably from 1 to 20 and most preferably from 1 to 10 amino acid substitutions, additions, insertions or deletions to the segment from amino acid residue 35 to 315 of ScolE3 (SEQ ID NO: 2), (d-iii)" a segment having from 1 to 30, preferably from 1 to 20 and most preferably from 1 to 10 amino acid substitutions, additions, insertions or deletions to the segment from amino acid residue 43 to 316 of ScolE7 (SEQ ID NO: 3), (d-iv)" a segment having from 1 to 40, preferably from 1 to 30, more preferably from 1 to 20, and most preferably from 1 to 10 amino acid substitutions, additions, insertions or deletions to the segment from amino acid residue 1 to 170 of ScolE1a (SEQ ID NO: 4), (d-v)" a segment having from 1 to 40, preferably from 1 to 30, more preferably from 1 to 20, and most preferably from 1 to 10 amino acid substitutions, additions, insertions or deletions to the segment from amino acid residue 1 to 195 of ScolE1b (SEQ ID NO: 5), (d-vii)" a segment having from 1 to 40, preferably from 1 to 30, more preferably from 1 to 20, and most preferably from 1 to 10 amino acid substitutions, additions, insertions or deletions to the segment from amino acid residue 6 to 194 of ScolE1c (SEQ ID NO: 25), (d-viii)" a segment having from 1 to 40, preferably from 1 to 30, more preferably from 1 to 20, and most preferably from 1 to 10 amino acid substitutions, additions, insertions or deletions to the segment from amino acid residue 6 to 194 of ScolE1d (SEQ ID NO: 26), (d-ix)" a segment having from 1 to 40, preferably from 1 to 30, more preferably from 1 to 20, and most preferably from 1 to 10 amino acid substitutions, additions, insertions or deletions to the segment from amino acid residue 5 to 192 of ScolE1e (SEQ ID NO: 27), or (d-x)" a segment having from 1 to 7, preferably from 1 to 5, more preferably from 1 to 3, and most preferably from 1 to 3 amino acid substitutions, additions, insertions or deletions to the segment from amino acid residue 1 to 37 of ScolMa (SEQ ID NO: 28).

(5) The protein according to any one of (1) to (4), for use in a method of treating infection or contamination with *Salmonella* such as *Salmonella enterica*, preferably *Salmonella enterica* ssp. *enterica*.

(6) The protein according to any one of (1) to (5), wherein the toxicity of a protein of claim 1, notably of classes (b) to (d) of claim 1, against *Salmonella enterica* is such that it and the protein of SEQ ID NO: 1 produce spots free of viable bacteria of *Salmonella enterica* ssp. *enterica* serovar Newport strain ATCC® 6962™* of the same diameter 12 hours after spotting 5 microliters of a solution of said protein of classes (b) to (d) and the protein of SEQ ID NO: 1 onto a softagar overlay plate seeded with 0.14 mL bacterial solution of 1×107 cfu/mL per cm2 of the sensitive *Salmonella enterica* strain and subsequent incubation of the agar plate at 37° C., wherein the concentration of the protein of classes (b) to (d) is at most 5 times that of the comparative solution of the protein of SEQ ID NO: 1.

(7) A composition comprising one or more proteins as defined in any one of (1) to (6).

(8) The composition according to (7), wherein said one or more proteins is or comprises ScolE1a, ScolE1b, ScolE1c, ScolE1d, ScolE1e, or ScolMa or a derivative of ScolE1a, ScolE1b, ScolE1c, ScolE1d, ScolE1e, or ScolMa.

(9) The composition according to (7) or (8), comprising two or more proteins selected from at least two different classes (i) to (x) as defined in claim 1.

(10) The composition according to (9), comprising at least a protein of a sub-class (i) (of any of classes (a) to (d)) and a protein of a sub-class (v) (of any of classes (a) to (d)).

(11) The composition according to any one of (7) to (10) for use in a method of treating infection with *Salmonella*; preferably *Salmonella enterica*, more preferably *Salmonella enterica* ssp. *enterica.*

(12) The composition according to any one of (7) to (11), wherein said composition is a plant material or extract thereof, wherein the plant material is a material from a plant having expressed said protein, preferably an edible plant having expressed said protein.

(13) The composition according to (12), wherein said plant material is material from a plant selected from the group consisting of spinach, chard, beetroot, carrot, sugar beet, leafy beet, amaranth, *Nicotiana*, and/or said plant material is one or more leaves, roots, tubers, or seeds, or a crushed, milled or comminuted product of said leaves, roots, tubers, or seeds.

(14) The composition according to any one of (7) to (13), wherein said composition is an aqueous solution containing said protein.

(15) The composition according to (14), wherein the concentration of said protein, or if the compositions contains two or more different proteins, said proteins, in said aqueous solution is from 0.0001 to 1 mg/ml, preferably from 0.001 to 0.1 mg/ml, more preferably from 0.005 to 0.05 mg/ml; or from 0.1 to 15 mg/kg food, preferably from 0.5 to 10 mg/kg, more preferably from 0.1 to 5 mg/kg food.

(16) The composition according to any one of (7) to (15), comprising ScolE1a and/or a derivative thereof or ScolE1a or a derivative thereof; or comprising a protein according to item (A-iv), (B-iv), (C-iv), (D-iv) or (E-iv), and/or a protein according to item (A-v), (B-v), (C-v), (D-v) or (E-v) defined below; or comprising a protein according to item (A-iv), (B-iv), (D-iv) or (E-iv), and/or a protein according to item (A-v), (B-v), (D-v) or (E-v) defined below; or comprising a protein according to item (A-iv), (B-iv), (D-iv) or (E-iv), and a protein according to item (A-v), (B-v), (D-v) or (E-v) defined below; wherein preferred embodiments defined herein may be combined with the embodiments defined in this item (16).

(17) A method of preventing or reducing infection or contamination of an object with *Salmonella*, comprising contacting said object with a protein as defined in any one of (1) to (6) or a composition as defined in any one of (7) to (16).

(18) The method according to (17), wherein said object is sprayed with said aqueous solution or is immersed into said aqueous solution.

(19) The method according to (17) to (18), wherein said object is immersed for at least 10 seconds, preferably for at least 1 minute, preferably for at least 5 minutes into an aqueous solution of said protein.

(20) The method according to any one of (17) to (19), wherein said object is food or animal feed.

(21) The method according to (20), wherein said food is whole animal carcass, meat, eggs, raw fruit or vegetable, preferably said food is meet, raw fruit or vegetable, more preferably said food is meat.

(22) A method of treating infection with *Salmonella* of a subject in need thereof, comprising administering to said subject a protein as defined in any one of (1) to (6) or a composition as defined in any one of (7) to (16).

(23) The method according to any one of (17) to (22), wherein said *Salmonella* is *Salmonella enterica*, preferably *Salmonella enterica* ssp. *enterica.*

(24) A process of producing a composition comprising a protein as defined in any one of (1) to (6), said process comprising the following steps:

(i) expressing said protein in a plant, preferably an edible plant or *Nicotiana,*

(ii) harvesting plant material containing expressed protein from said plant, (iii) extracting said protein from said plant material using an aqueous buffer to obtain a composition containing said protein, (iv) optionally removing undesired contaminants from said composition.

(25) The protein according to (1), wherein said protein is that of item (a-iv), (b-iv), (c-iv), or (d-iv), each optionally in combination with item (3), or (A-iv), (B-iv), (C-iv), (D-iv) or (E-iv);

or wherein said protein is that of item (a-v), (b-v), (c-v), or (d-v), each optionally in combination with item (3), or (A-v), (B-v), (C-v), (D-v) or (E-v);

or wherein said protein is that of item (a-vii), (b-vii), (c-vii), or (d-vii), each optionally in combination with item (3), or (A-vii), (B-vii), (C-vii), (D-vii) or (E-vii);

or wherein said protein is that of item (a-viii), (b-viii), (c-viii), or (d-viii), each optionally in combination with item (3), or (A-viii), (B-viii), (C-viii), (D-viii) or (E-viii);

or wherein said protein is that of item (a-x), (b-x), (c-x), or (d-x), each optionally in combination with item (3), or (A-x), (B-x), (C-x), (D-x) or (E-x).

*Salmonella* bacteriocins, herein together with derivatives thereof referred to as "salmocins", are natural non-antibiotic antimicrobial proteins produced by certain *Salmonella* strains that kill or inhibit the growth of other *Salmonella* strains. Unlike relatively well studied *Escherichia coli* protein analogues termed colicins, salmocins have been given little attention. There is a number of *Salmonella* sequences with similarity to colicin sequences in the publicly available genome databases, most of them showing high identity to colicins M, la, lb, 5 and 10. The inventors have identified salmocins similar to but different from colicins that can be used to prevent or reduce infection or contamination with *Salmonella*, notably with *Salmonella enterica* ssp. *enterica.*

The inventors have found that all salmocins tested can be expressed efficiently in plants. Expression processes as those used in this study have already been brought to the level of GMP compliance, and are currently being used in different clinical trials as manufacturing processes. Most salmocins are expressed at high yields (up to 1.7 g active protein per kilogram of fresh green biomass), meaning low commercially viable manufacturing costs. Production can be made using, inter alia, tobacco and edible plants such as leaf beets or spinach. Among different salmocins, salmocins E1a (ScolE1a) and E1b (ScolE1b) or their derivatives are preferred, since they were found to possess the broadest antimicrobial activity against major pathogenic *Salmonella* strains. Each of these two salmocins shows also a very high activity against all 36 major pathogenic strains tested. Treatments with low amounts of colicins (e.g. less than 10 mg colicin per kg of treated food product) reduce the bacterial load of different pathogenic strains by 3 to >6 logs in the assay employed. In spike experiments using poultry meats spiked with two to four pathogen serovars, colicins (colicins M, la and 5) efficiently reduced the titer of pathogenic bacteria. Therefore, it is expected that salmocins possessing higher antimicrobial activity towards *S. enterica* ssp. *enterica* serovars mentioned above than the colicins mentioned will reduce the titer of a *Salmonella* contamination on poultry even more effectively.

The experimental data of the present invention demonstrate that the non-antibiotic antibacterial salmocins can be expressed at very high levels in plants such as *Nicotiana benthamiana*, a standard manufacturing host for multiple biopharmaceuticals currently undergoing clinical trials, and the plant-expressed proteins are apparently fully active. The expression levels in most cases reach 37% of total soluble protein or 1.74 g/kg of fresh leaf biomass without process optimization, meaning that salmocins are not toxic to plants and that optimized industrial procedures of transfection or induction in transgenic hosts could be developed that are inexpensive. In contrast, attempts to express bacteriocin proteins in bacterial hosts at a high level were usually met with general toxicity of this bacteriocin class even in species other than homologous bacterial species (e.g. Medina et al., PLoS One, 2011; 6(8):e23055; Diaz et al., 1994). Thus, plants are excellent hosts for manufacturing salmocins.

The data of this invention demonstrate that salmocins can efficiently control most or all major pathogenic serotypes of *Salmonella enterica* ssp. *enterica* under actual exposure modelling. There is a limited variety among salmocins produced by *Salmonella*. Studied salmocins have quite diverse structure within the general three-domain (translocation, receptor and cytotoxic domains) architecture, similar to more studied *E. coli* colicins. Surprisingly, practically all tested salmocins and colicins, alone or together with antitoxin (immunity protein), are expressed very well in plants. This may be explained by a low toxicity of salmocins and colicins to plant cells and by the fact that these bacteriocin proteins, being classical representatives of 'inherently disordered proteins' (a feature essential for ability to unfold/refold during the bacterial cell wall and membrane translocation), probably do not impose unusual requirements on translation and post-translational machinery of the plant cell.

To the best of our knowledge, this invention includes the first study on the inhibition efficacy of salmocins on major enteropathogenic strains of *Salmonella*. Unlike the list of major *E. coli* strains defined by FDA based on a historical analysis of food poisoning due to *E. coli*, a list of major foodborne *Salmonella* strains has not been defined by regulatory agencies, primarily due to higher diversity of the pathovars responsible for the outbreaks. Being confronted with this lack of guidance in the prior art, the inventors decided to pool three existing major studies that ranked the pathovars based on their prevalence and poisoning severity.

In our study, 36 serovars have been selected to be analyzed, 29 of them caused at least 100 incidences reported to Centers for Disease Control in 2003-2012 (National Enteric Disease Surveillance: *Salmonella* Annual Report, 2013 (CDC, June 2016): laboratory-confirmed human *Salmonella* infections (US) reported to CDC 2003-2012) with 17 most notorious pathovars on CDCs top 20 list; the number being five times higher than the number of *E. coli* pathovars defined by the FDA (seven).

The data presented in this patent application show that, based on their ability to control major pathogenic *Salmonella* strains, five different *Salmonella* salmocins can be divided into three groups. *Salmonella* salmocins E1a and E1b turned out to be universally active, each being able to kill all tested pathovars and showing the highest average activity. Average activity of the two salmocins on all tested strains was over $10^7$ AU/μg. For example, the individual activity of salmocin E1a was: >$10^3$ AU/μg for 35 out of 36 strains, >$10^4$ AU/μg for 24 out of 36 strains and >$10^6$ AU/μg for 13 out of 36 strains. The remaining salmocins fell into two groups with Salmocins E2 and E7 being inhibitory to over 80% of strains but having a 100-fold lower average activity (less than $10^5$ AU/μg), whereas salmocin E3 inhibited approx. 60% of strains at lower average activity (about $10^2$ AU/μg). Also the salmocins ScolE1c, ScolE1d, ScolE1e, and ScolMa demonstrated significant antimicrobial activities.

These results are unexpected, because colicins (salmocin analogues produced by *E. coli* cells) exhibit a much narrower spectrum of antimicrobial activity against seven *E. coli* pathovars, and mixtures of two to five colicins had to be preferably used to efficiently inhibit all seven STEC serotypes defined by FDA. Colicins also demonstrated much lower average activity against 'Big Seven' STEC strains (average <$10^3$ AU/μg), although much higher activity has been observed on strain H104:H4 (>$10^5$ AU/μg) that caused a major outbreak in 2011 in Europe, and a common laboratory strain.

The inventors' analysis of cross specific activity of salmocins and colicins on *E. coli* and *Salmonella*, respectively, demonstrates low activity against bacteria of different genus/species. In particular, activity of salmocins against 'Big Seven' STEC strains was low (less than $10^2$ AU/μg) although some salmocins (such as E2, E7 and E1b, but surprisingly not E1a) were fairly active against H104:H4 ($10^3$ AU/μg) and laboratory strain DH10B ($10^5$ AU/μg). Similarly, activity of colicins on *Salmonella* pathovars was found to be low, with colicins la and lb being active on over 80% of strains, but with average activity of only colicin la being higher than $3\times10^3$ AU/μg (or three to four orders of magnitude less than salmocin E1a/b). The inventors conclude from these studies that, to combat both pathogenic species, one has to use mixtures of colicins and salmocins. These results are also in seeming partial disagreement with the recent studies of ecological efficacy of colicin-like proteins in competitions between bacteria of different genera (Nedialkova et al., PLoS Pathog. 2014 January; 10(1): e1003844).

The invention provides new agents and compositions for controlling *Salmonella*. The salmocins of the invention have the advantage that marketing authorization can be obtained in an uncomplicated manner. For example, the FDA recently granted plant-produced colicins GRAS (Generally Regarded As Safe) status (GRN573, FDA website). Because of the unmet need for natural non-antibiotic antibacterials for

*Salmonella* control, the inventors conceived exploring *Salmonella* bacteriocins ("salmocins"). Thereby, the present invention was accomplished.

Figure 1A:
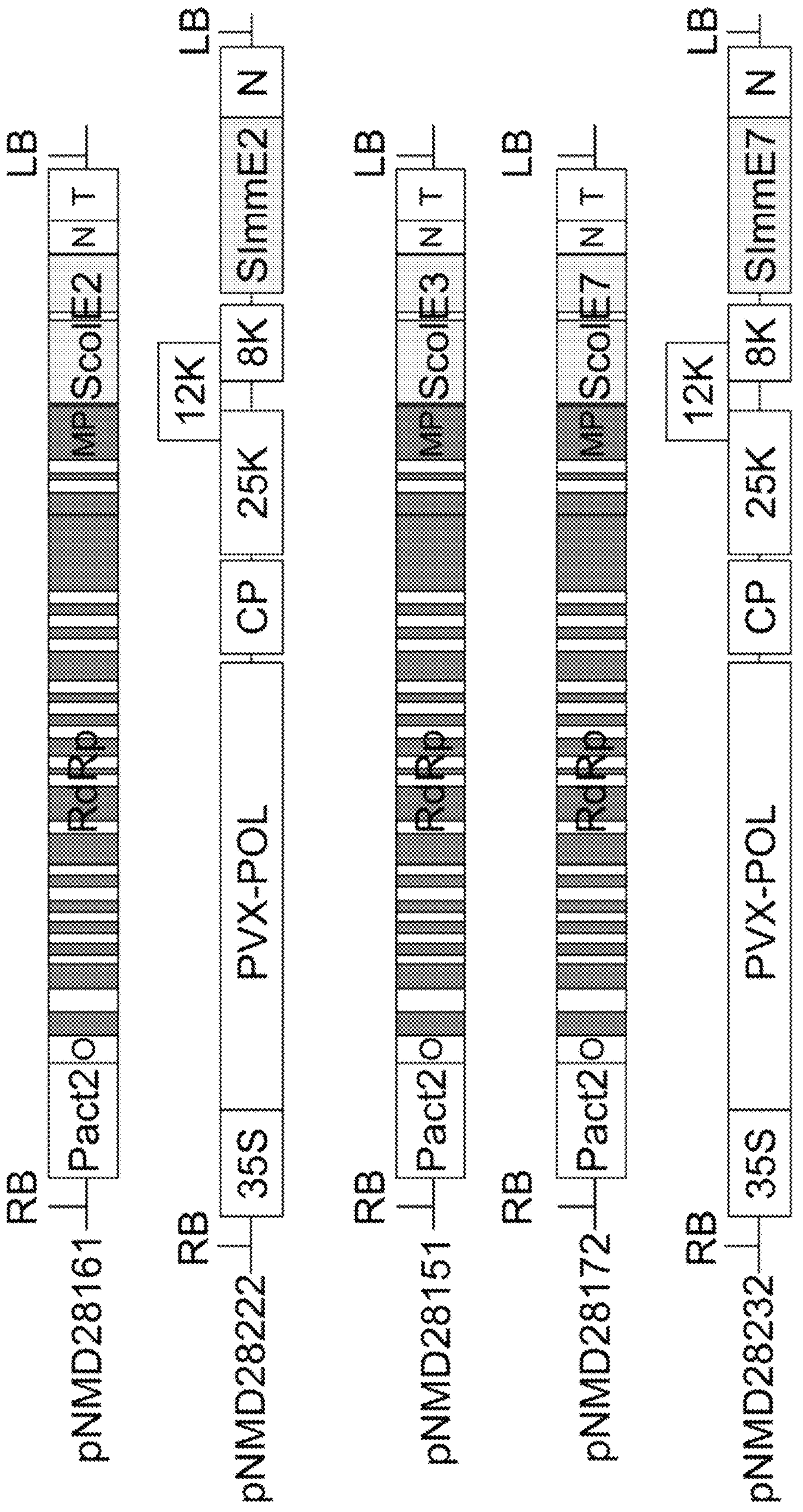
FIG. 1 shows schematically viral vectors for the expression of salmocins and corresponding immunity proteins used in the Examples. Constructs for the expression of salmocins are based on Tobacco mosaic virus (TMV), whereas constructs for the expression of immunity proteins are based on Potato Virus X (PVX).
Figure 1B:
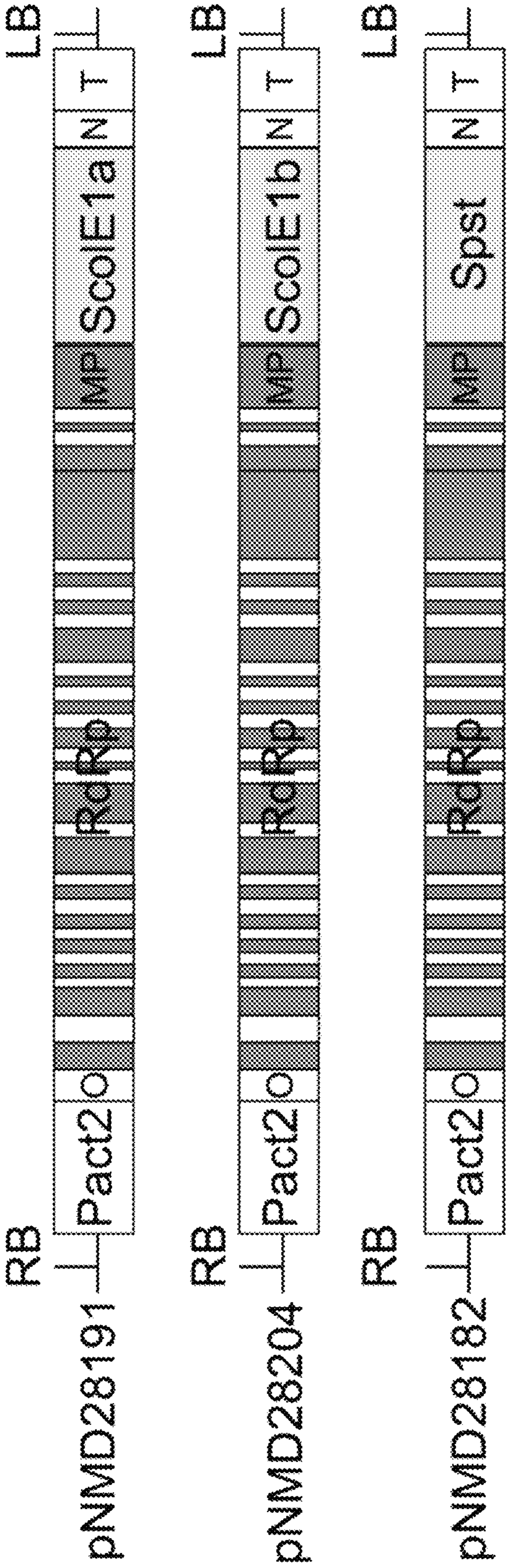

Salmocin expression vectors include pNMD28161, pNMD28151 and pNMD28172 for the expression of salmocins ScolE2, ScolE3 and ScolE7, respectively (FIG. 1A), pNMD28191, pNMD28204, and pNMD28182 for the expression of salmocins ScolE1a, ScolE1b and Spst, respectively (FIG. 1B).

RB and LB indicate the right and left borders of T-DNA of binary vectors. Pact2: promoter of *Arabidopsis* actin2 gene; o: 5' end from TVCV (turnip vein clearing virus); RdRp: RNA-dependent RNA polymerase open reading frame (ORF) from cr-TMV (crucifer-infecting tobamovirus); MP: movement protein ORF from cr-TMV; ScolE2: salmocin ScolE2 coding sequence; ScolE3: salmocin ScolE3 coding sequence; ScolE7: salmocin ScolE7 coding sequence; ScolE1a: salmocin ScolE1a coding sequence; ScolE1b: salmocin ScolE1b coding sequence; Spst: salmocin Spst coding sequence; N: 3'-non-translated region from cr-TMV; T: *Agrobacterium* nopaline synthase terminator; white segments interrupting grey segments in the RdRp and MP ORFs indicate introns inserted into these ORFs for increasing the likelihood of RNA replicon formation in the cytoplasm of plant cells, which is described in detail in WO2005049839. An intron was also inserted into ScolE2, ScolE3 and ScolE7 ORFs for preventing the cytotoxic effect of these proteins on *E. coli* cells used for plasmid cloning.

PVX-based vectors for the expression of immunity proteins include pNMD28222 and pNMD28232 for the expression of salmocin ScolE2 and ScolE7 immunity proteins, respectively (FIG. 1A). P35S: cauliflower mosaic virus 35S promoter; PVX-pol: RNA-dependent RNA polymerase from PVX; CP: coat protein ORF; 25K, 12K and 8K together indicate the 25 kDa, 12 kDa and 8 kDa triple gene block modules from PVX; N: 3'-untranslated region from PVX. SlmmE2 and SlmmE7 stand for coding sequences of salmocin ScolE2 and ScolE7 immunity proteins, respectively.

Figure 2:
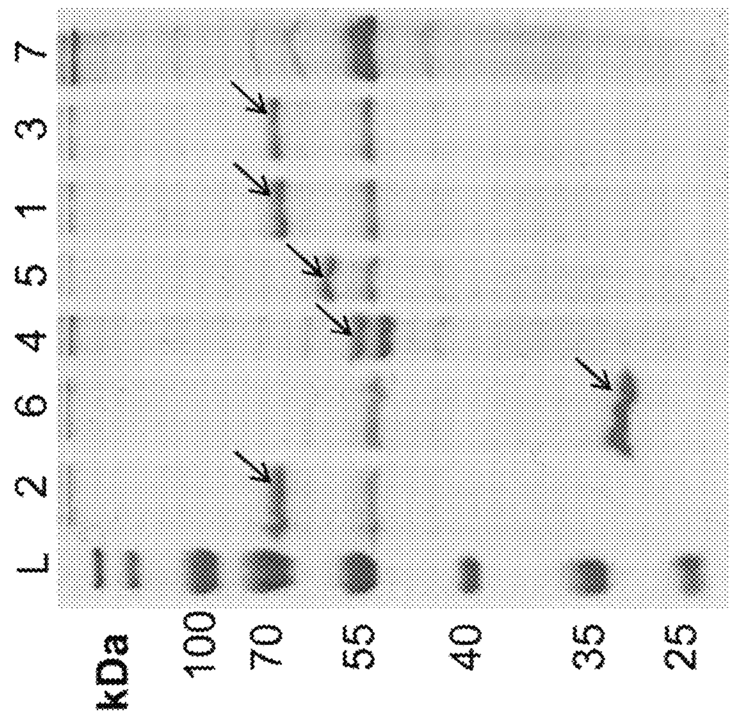

FIG. 2 shows comparative SDS-PAGE analysis of expression for salmocins after the infiltration of *Nicotiana benthamiana* plants with agrobacteria carrying viral vectors. Plant leaf material was extracted with 5 volumes of buffer containing 50 mM HEPES (pH 7.0), 10 mM potassium acetate, 5 mM magnesium acetate, 10% (v/v) glycerol, 0.05% (v/v) Tween-20 and 300 mM NaCl. Protein extracts were resolved in 12% polyacrylamide gels. For gel loading, aliquots containing the extract volumes corresponding to 0.4 mg fresh weight of plant tissue were used. Before loading on the gel, aliquots of protein extracts were mixed with 2×Laemmli buffer in the proportion 1:1 and incubated at 95° C. for 10 min. Numerals above gel lanes stand for protein extracts from plant tissues expressing the following recombinant proteins: 1—salmocin ScolE2; 2—salmocin ScolE3; 3—salmocin ScolE7; 4—salmocin ScolE1a; 5—salmocin ScolE1b; 6—salmocin Spst. Numeral 7 corresponds to the extract from uninfected leaf tissue used as a negative control. L—PageRuler™ Prestainded Protein Ladder (Thermo Fisher Scientific Inc. (Waltham, USA), #SM0671). Arrows indicate specific protein bands corresponding to expressed recombinant colicins.

Figure 3:
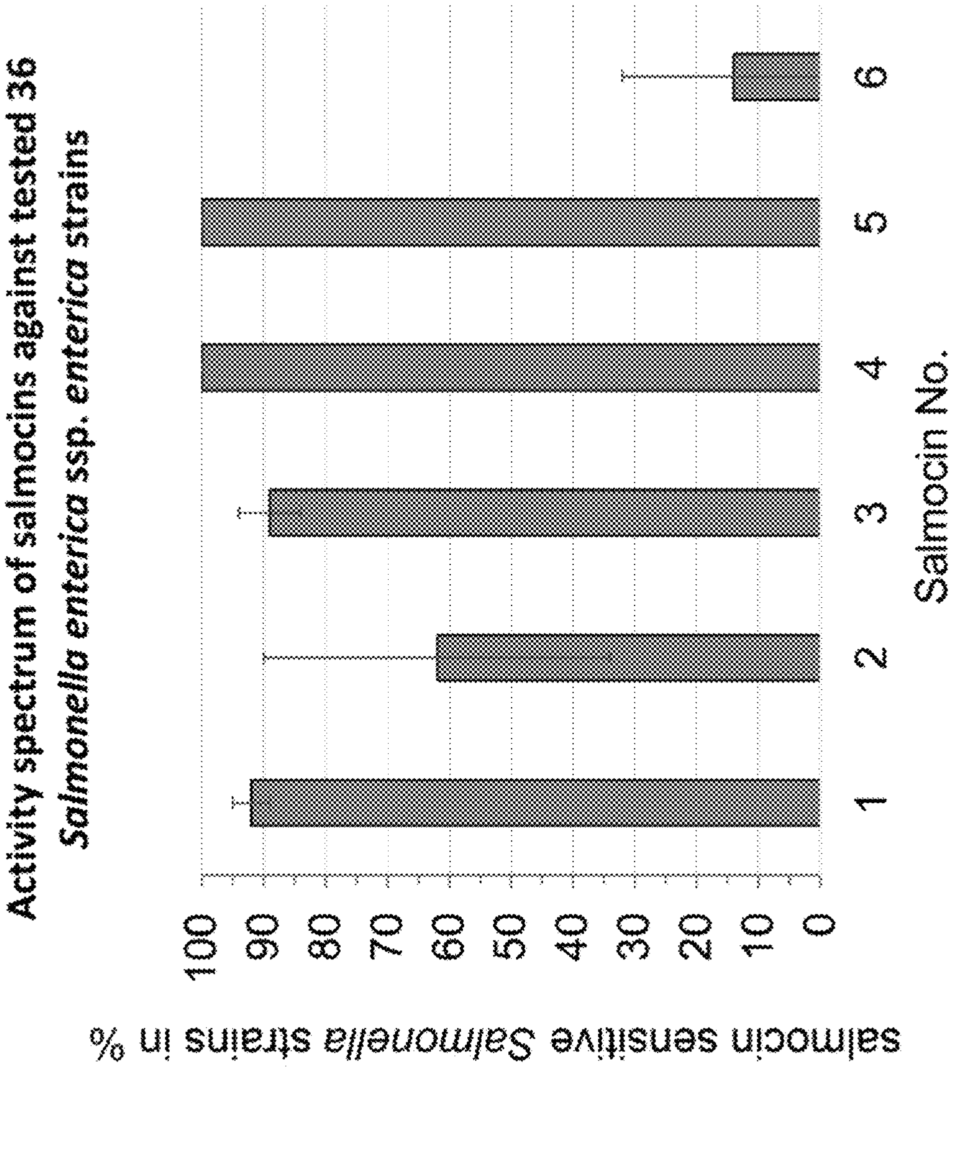

FIG. 3 shows the semi-quantitative evaluation of specific antimicrobial activity of salmocin-containing plant extracts against 36 *S. enterica* ssp. *enterica* strains listed in Tables 5A and 5B. The antimicrobial activity was tested using a radial diffusion assay via spot-on-lawn-method. The percentage of salmocin-sensitive *Salmonella* strains (average of 3 independent experiments) is given for salmocins: 1—salmocin ScolE2; 2—salmocin ScolE3; 3—salmocin ScolE7; 4—salmocin ScolE1a; 5—salmocin ScolE1b; 6—salmocin Spst.

Figure 4:
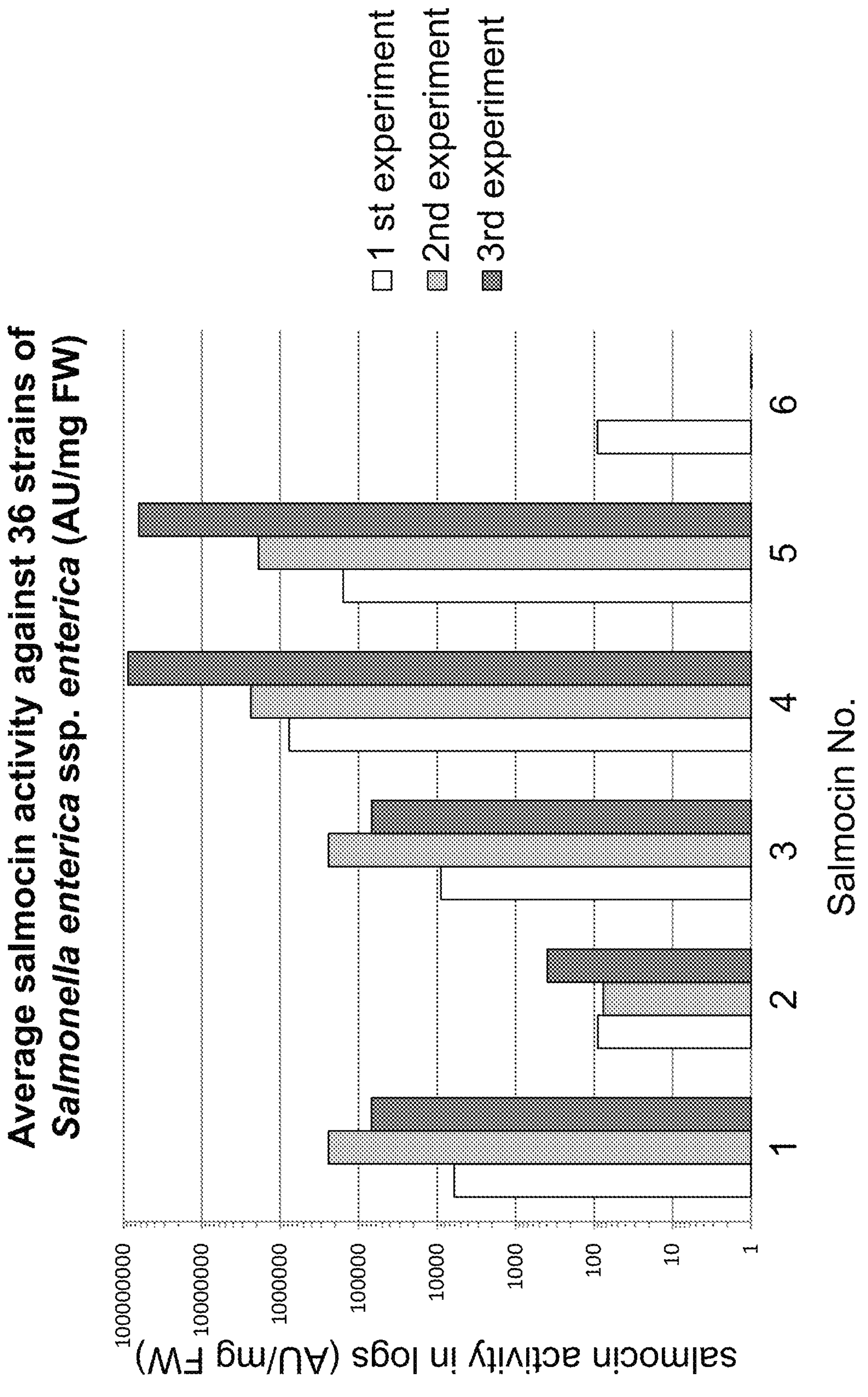

FIG. 4 shows the semi-quantitative evaluation of the average antimicrobial activity of salmocin-containing plant extracts against 36 *S. enterica* ssp. *enterica* strains listed in Tables 5A and 5B. The antimicrobial activity was tested using radial diffusion assay via spot-on-lawn-method and calculated in arbitrary units (AU) per mg fresh weight (FW) of plant biomass expressing recombinant salmocins (average of 3 independent experiments). Thereby it reflects the yield of specific active agent per unit of biomass; i. e. the specific production capacity of the host. Arbitrary units are calculated as a dilution factor for the highest dilution of protein extract causing a detectable clearing effect in the radial diffusion assay. Tested recombinant salmocins are given as: 1—salmocin ScolE2; 2—salmocin ScolE3; 3—salmocin ScolE7; 4—salmocin ScolE1a; 5—salmocin ScolE1b; 6—salmocin Spst.

Figure 5:
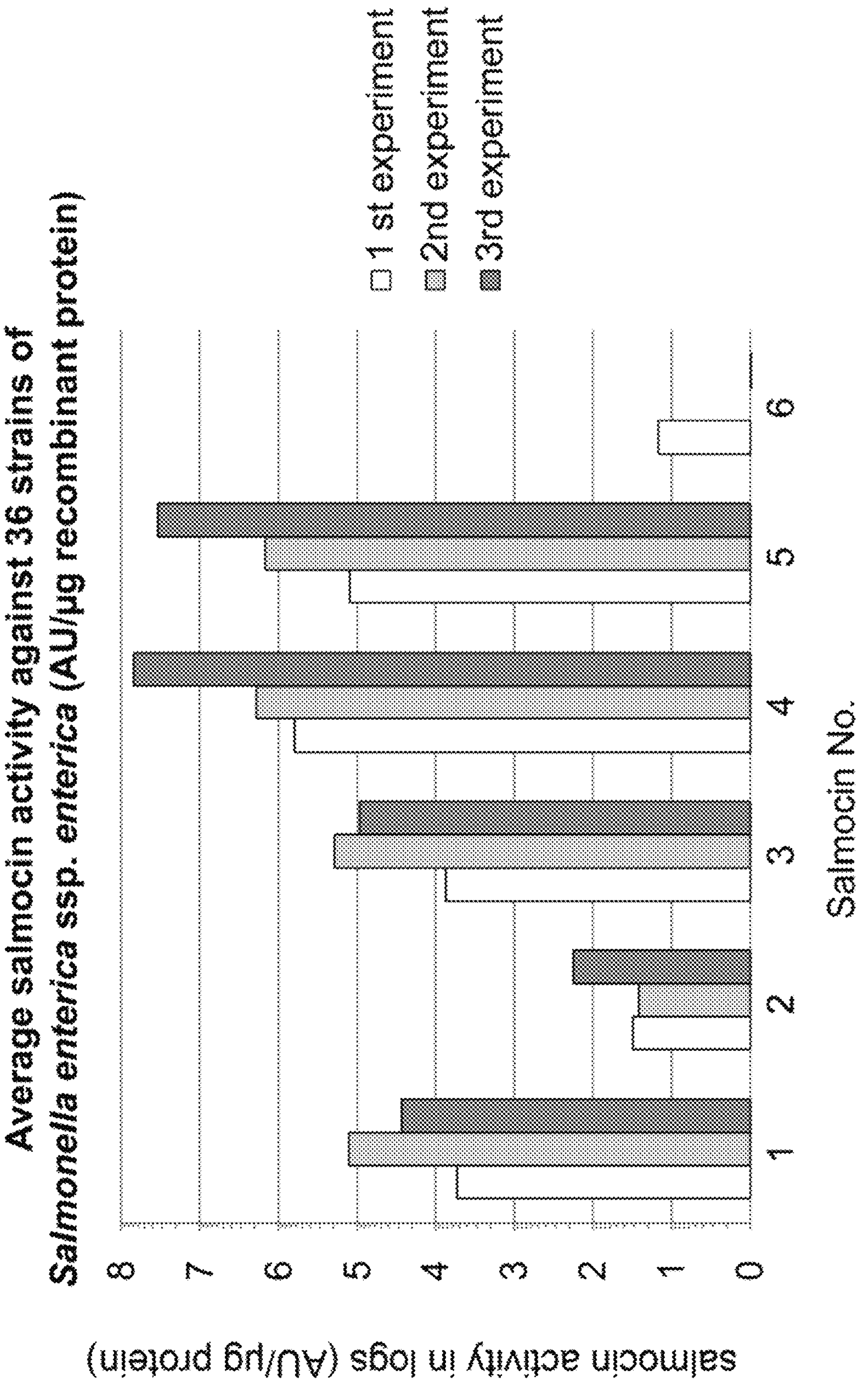

FIG. 5 shows the semi-quantitative evaluation of the average specific antimicrobial activity of salmocin-containing plant extracts against 36 *S. enterica* ssp. *enterica* strains listed in Tables 5A and 5B. The antimicrobial activity was tested using radial diffusion assay via spot-on-lawn-method and calculated in arbitrary units (AU) per µg of recombinant salmocin (average of 3 independent experiments) which reflects the specific activity of salmocins against particular strains; i. e. the specific antimicrobial potency of salmocins is being evaluated. Tested recombinant salmocins are given as: 1—salmocin ScolE2; 2—salmocin ScolE3; 3—salmocin ScolE7; 4—salmocin ScolE1a; 5—salmocin ScolE1b; 6—salmocin Spst.

Figure 6:
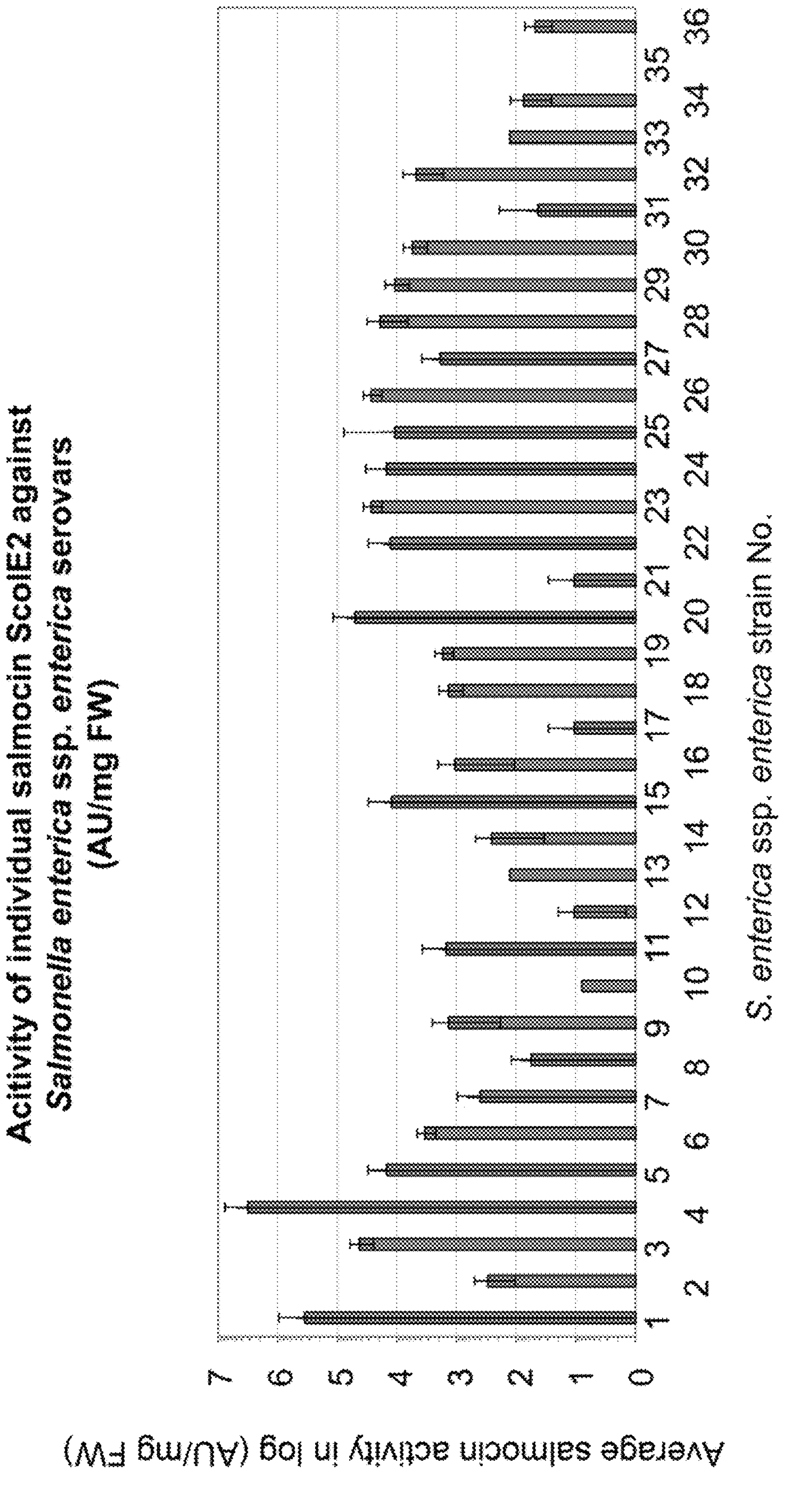

FIG. 6 shows the semi-quantitative evaluation of the average specific antimicrobial activity of salmocin ScolE2-containing plant extracts against 36 *S. enterica* ssp. *enterica* strains listed in Tables 5A and 5B. The antimicrobial activity was tested using radial diffusion assay via spot-on-lawn-method and calculated in arbitrary units (AU) per mg FW plant biomass (average of 3 independent experiments).

Figure 7:
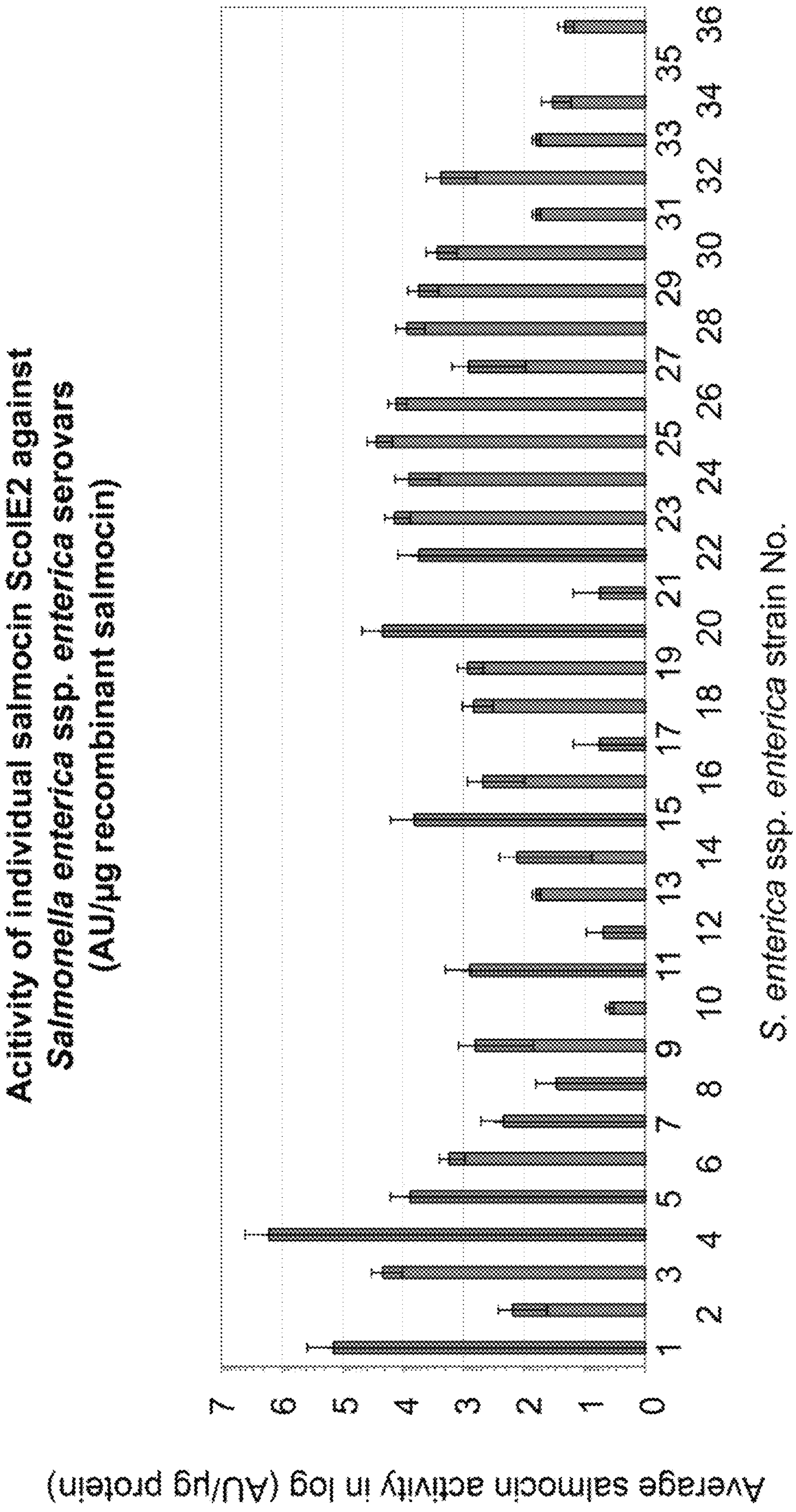

FIG. 7 shows the semi-quantitative evaluation of the average specific antimicrobial activity of salmocin ScolE2-containing plant extracts against 36 *S. enterica* ssp. *enterica* strains listed in tables 5A and 5B. The antimicrobial activity was tested using radial diffusion assay via spot-on-lawn-method and calculated in arbitrary units (AU) per µg of recombinant salmocin (average of 3 independent experiments).

Figure 8:
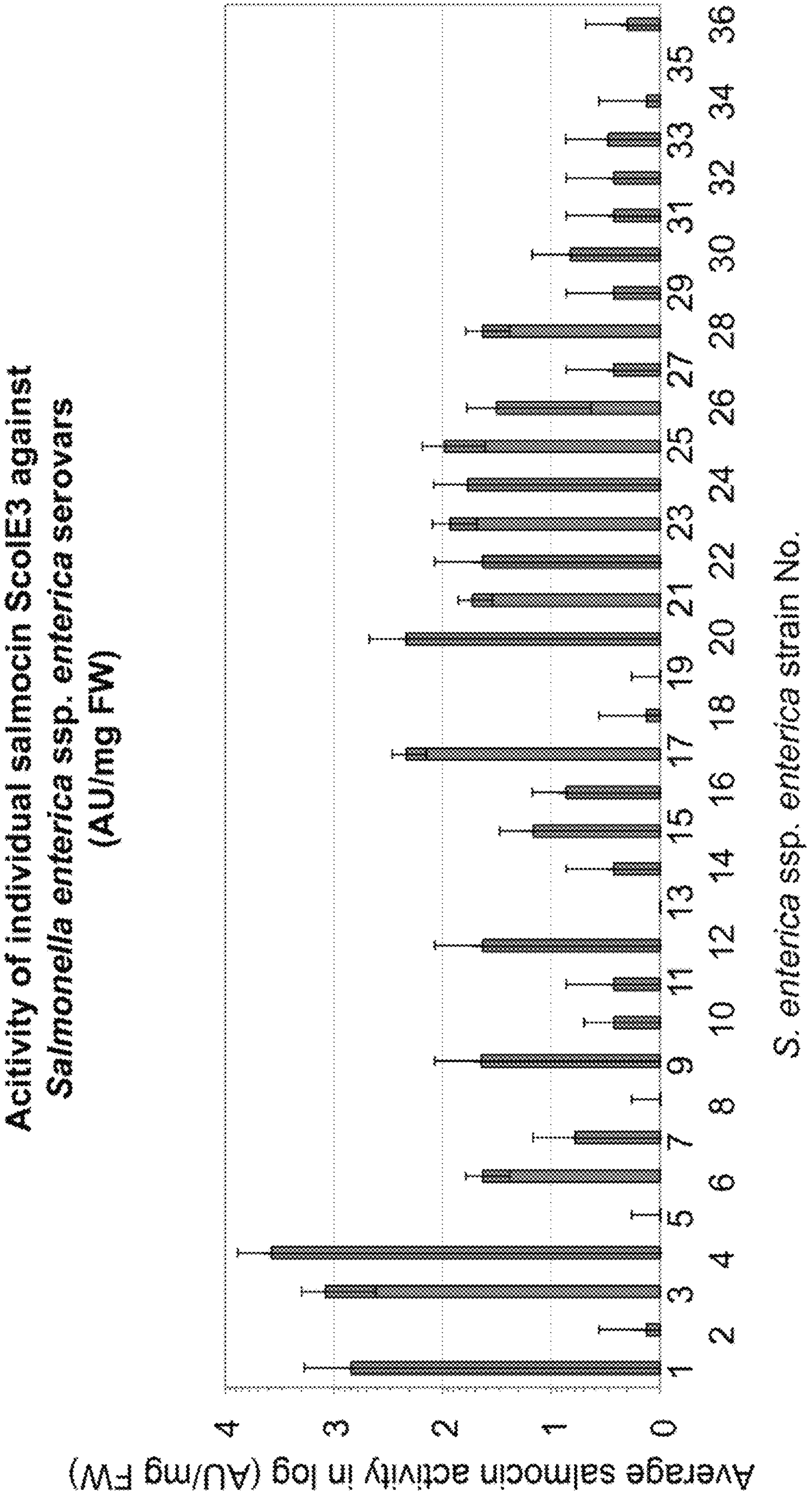

FIG. 8 shows the semi-quantitative evaluation of the average specific antimicrobial activity of salmocin ScolE3-containing plant extracts against 36 *S. enterica* ssp. *enterica* strains listed in tables 5A and 5B. The antimicrobial activity was tested using radial diffusion assay via spot-on-lawn-method and calculated in arbitrary units (AU) per mg FW plant biomass (average of 3 independent experiments).

Figure 9:
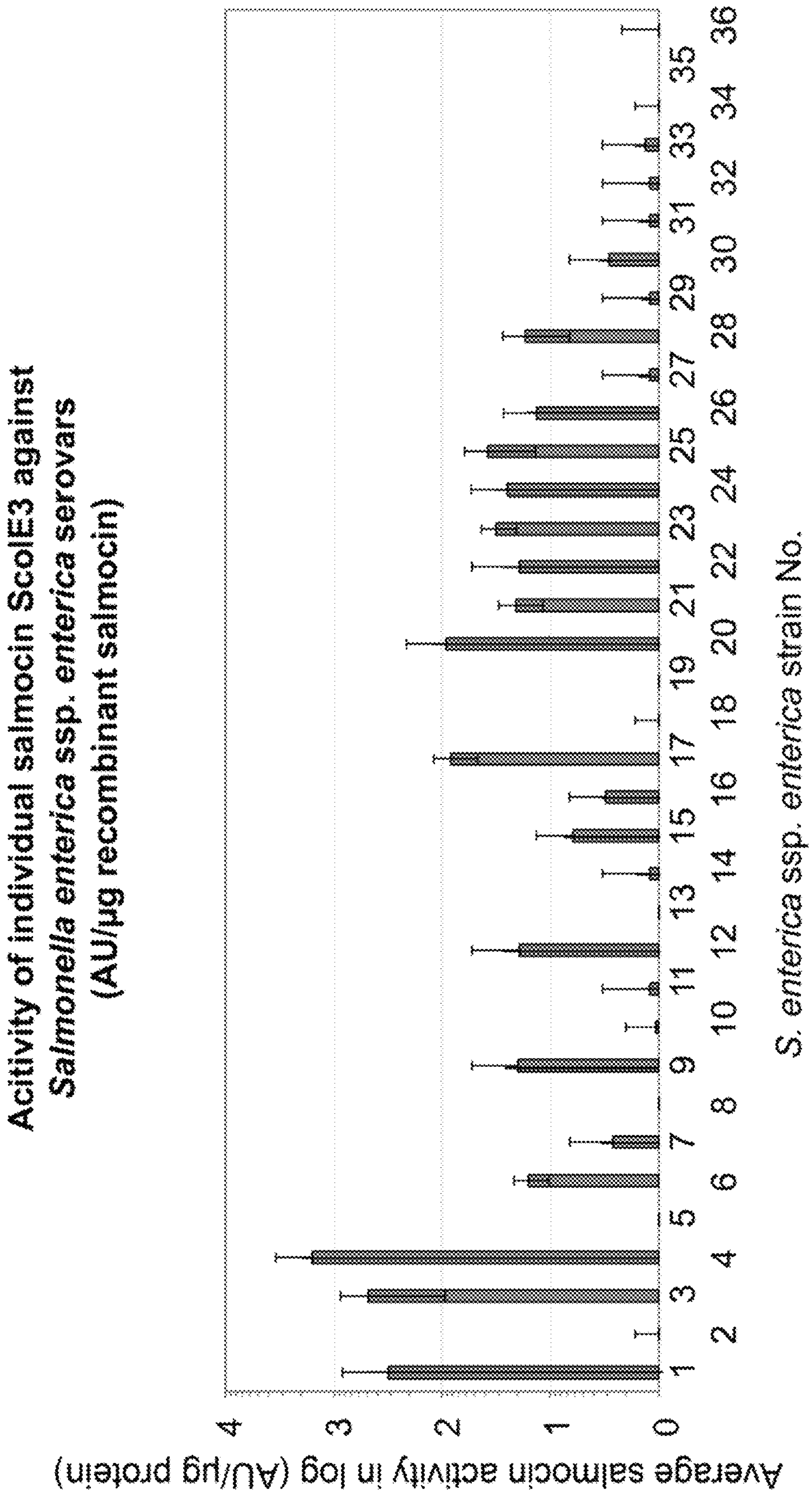

FIG. 9 shows the semi-quantitative evaluation of the average specific antimicrobial activity of salmocin ScolE3-containing plant extracts against 36 *S. enterica* ssp. *enterica* strains listed in tables 5A and 5B. The antimicrobial activity was tested using radial diffusion assay via spot-on-lawn-method and calculated in arbitrary units (AU) per μg of recombinant salmocin (average of 3 independent experiments).

Figure 10:
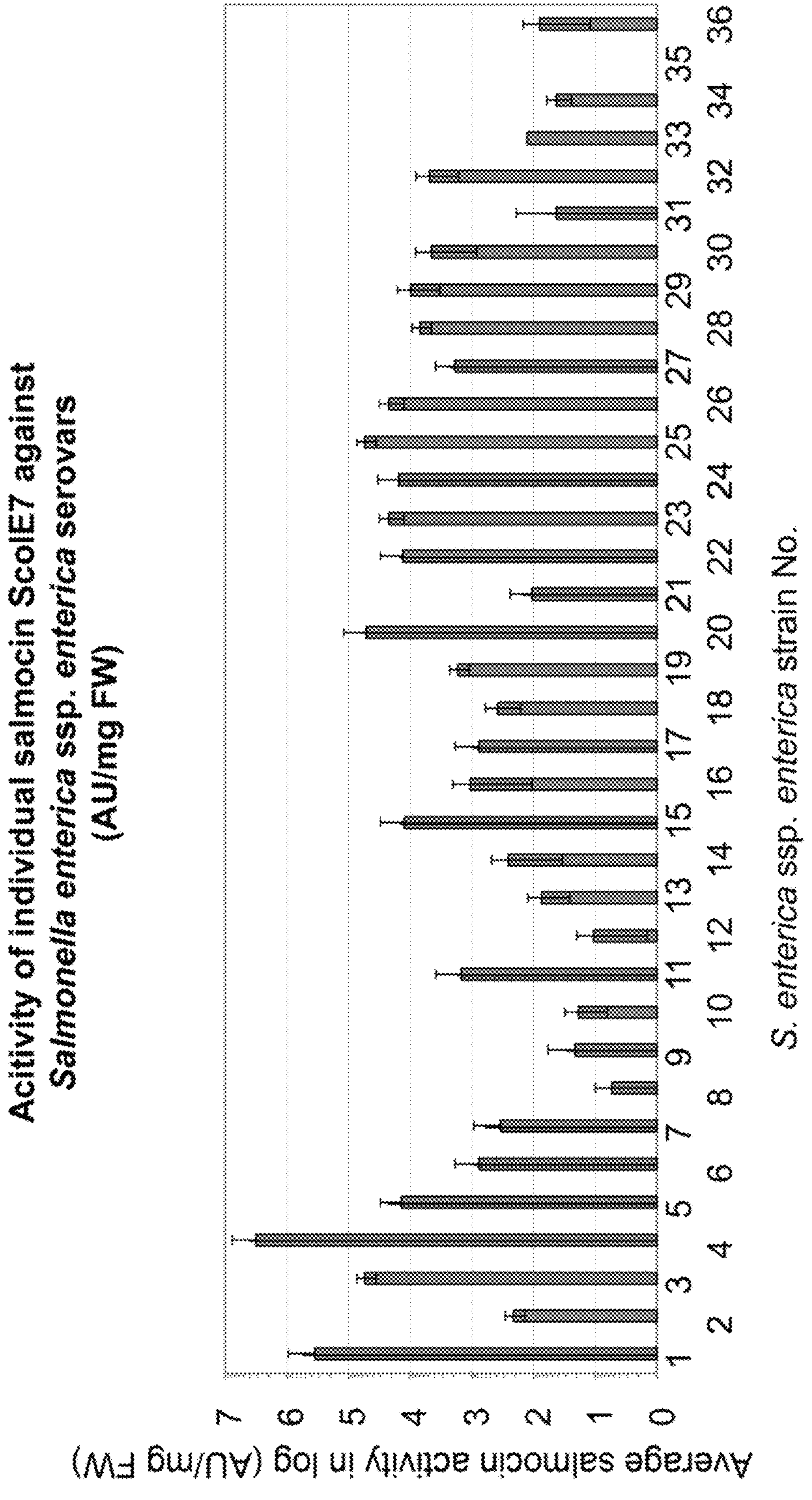

FIG. 10 shows the semi-quantitative evaluation of the average specific antimicrobial activity of salmocin ScolE7-containing plant extracts against 36 *S. enterica* ssp. *enterica* strains listed in tables 5A and 5B. The antimicrobial activity was tested using radial diffusion assay via spot-on-lawn-method and calculated in arbitrary units (AU) per mg FW plant biomass (average of 3 independent experiments).

Figure 11:
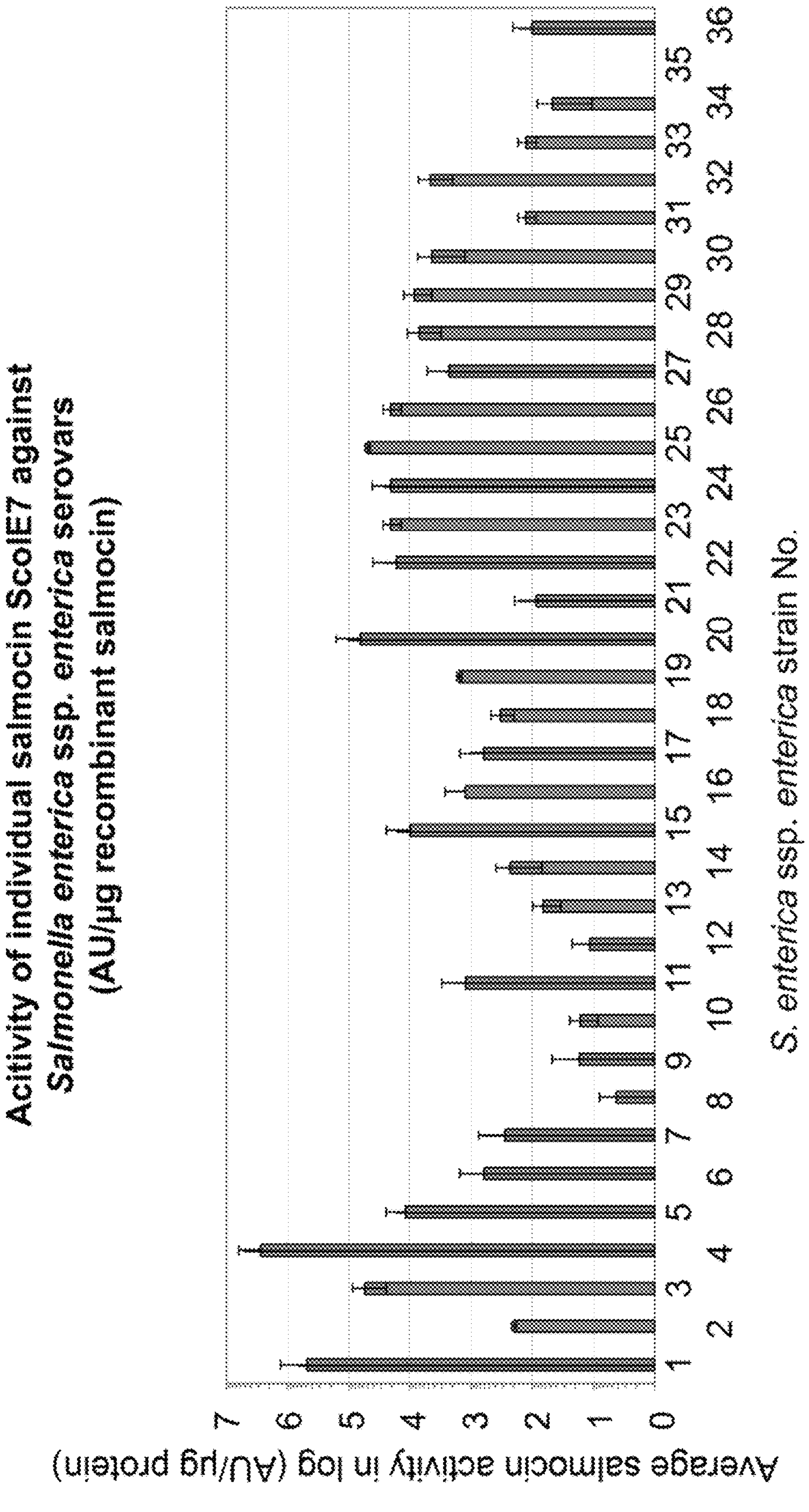

FIG. 11 shows the semi-quantitative evaluation of the average specific antimicrobial activity of salmocin ScolE7-containing plant extracts against 36 *S. enterica* ssp. *enterica* strains listed in tables 5A and 5B. The antimicrobial activity was tested using radial diffusion assay via spot-on-lawn-method and calculated in arbitrary units (AU) per μg of recombinant salmocin (average of 3 independent experiments).

Figure 12:
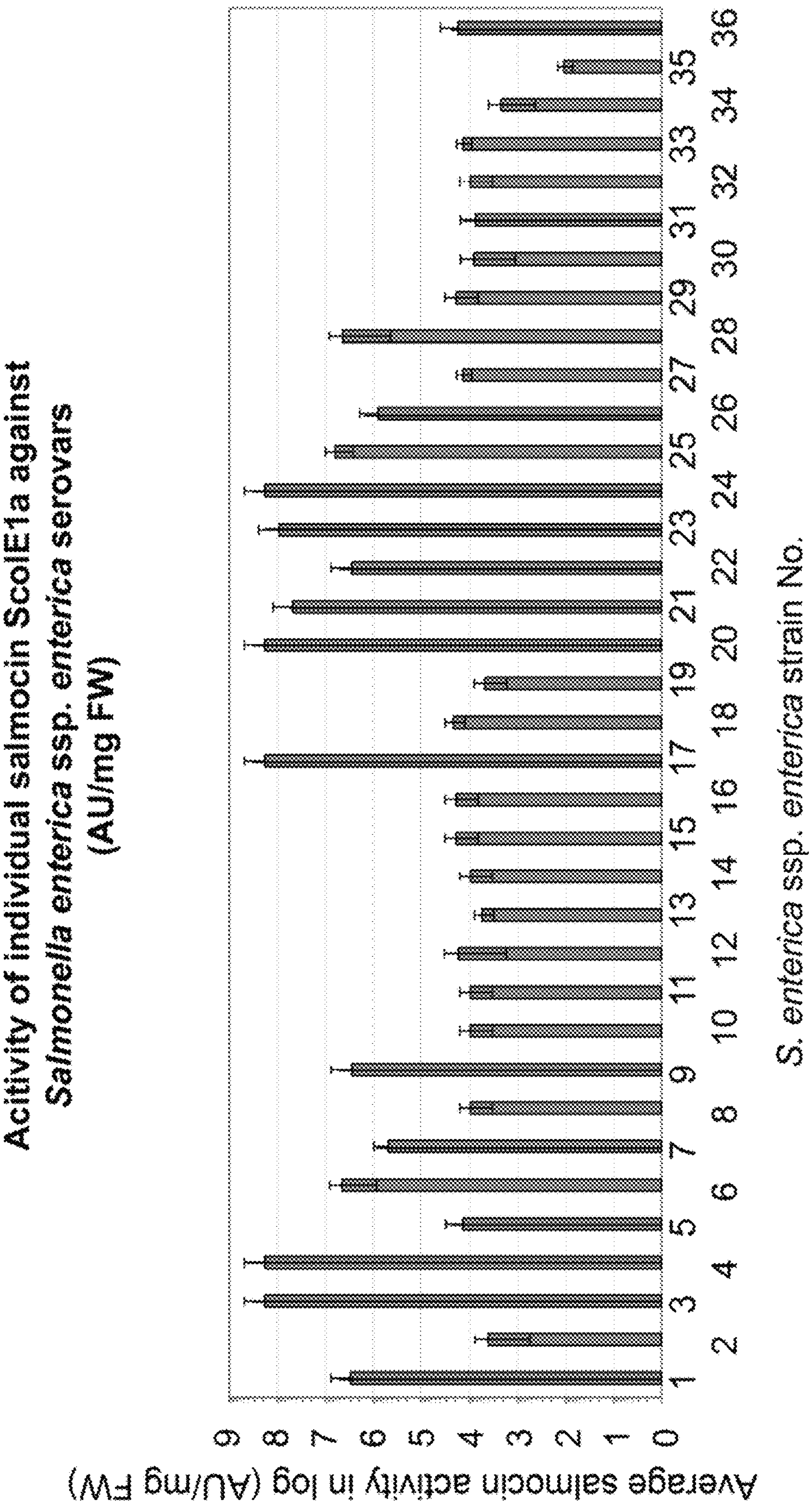

FIG. 12 shows the semi-quantitative evaluation of the average specific antimicrobial activity of salmocin ScolE1a-containing plant extracts against 36 *S. enterica* ssp. *enterica* strains listed in tables 5A and 5B. The antimicrobial activity was tested using radial diffusion assay via spot-on-lawn-method and calculated in arbitrary units (AU) per mg FW plant biomass (average of 3 independent experiments).

Figure 13:
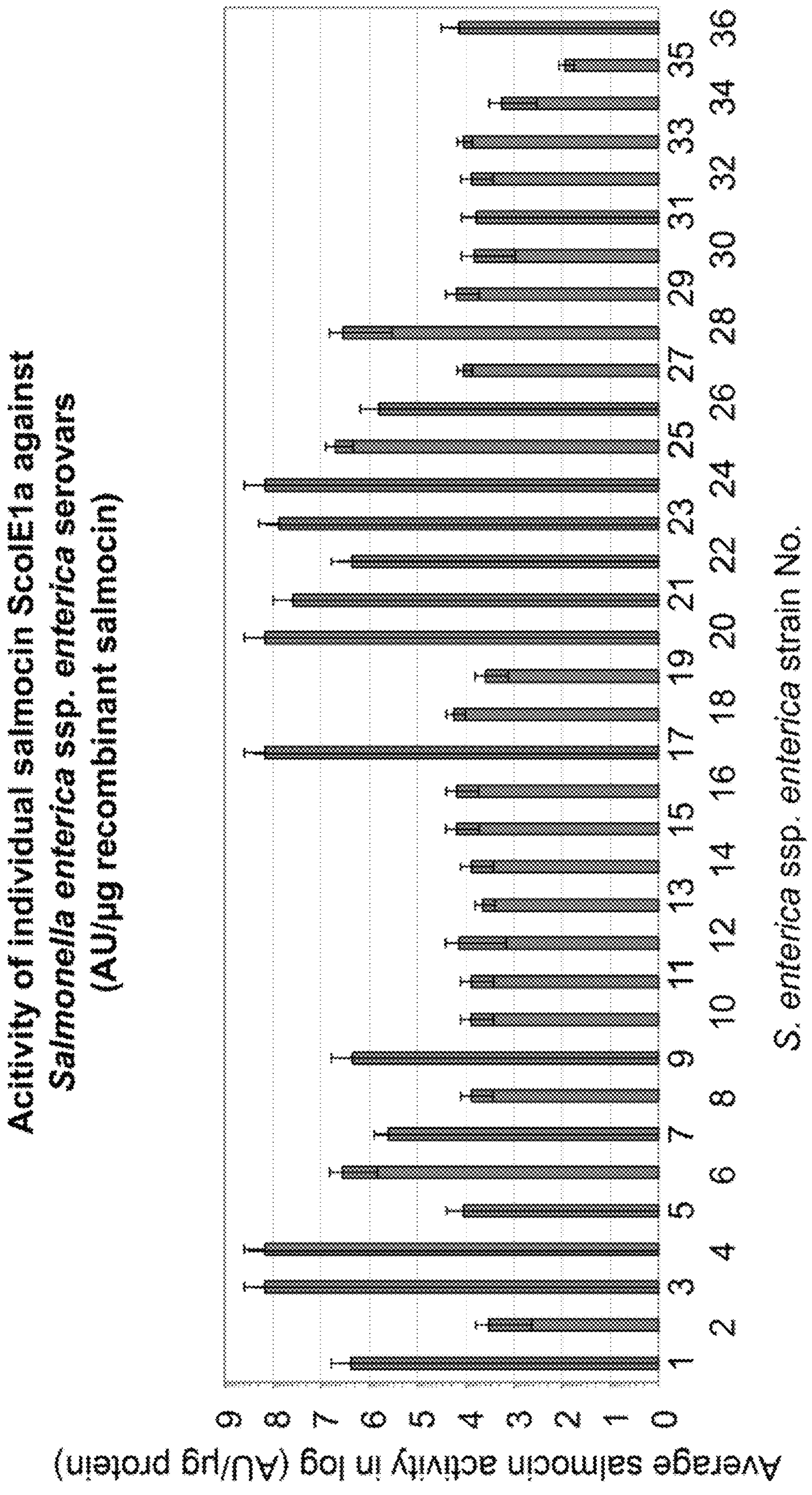

FIG. 13 shows the semi-quantitative evaluation of the average specific antimicrobial activity of salmocin ScolE1a-containing plant extracts against 36 *S. enterica* ssp. *enterica* strains listed in tables 5A and 5B. The antimicrobial activity was tested using radial diffusion assay via spot-on-lawn-method and calculated in arbitrary units (AU) per μg of recombinant salmocin (average of 3 independent experiments).

Figure 14:
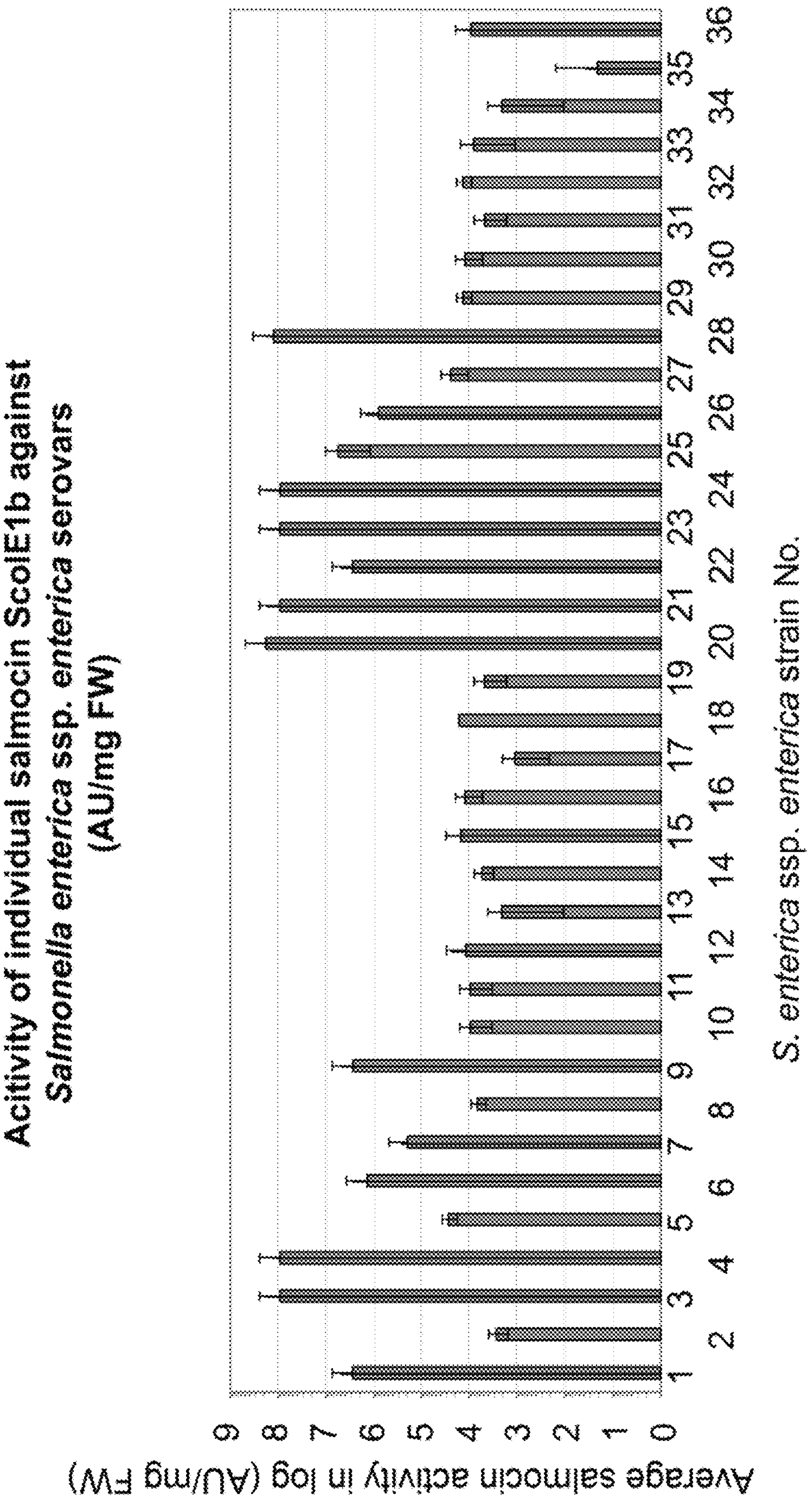

FIG. 14 shows the semi-quantitative evaluation of the average specific antimicrobial activity of salmocin ScolE1b-containing plant extracts against 36 *S. enterica* ssp. *enterica* strains listed in tables 5A and 5B. The antimicrobial activity was tested using radial diffusion assay via spot-on-lawn-method and calculated in arbitrary units (AU) per mg FW plant biomass (average of 3 independent experiments).

Figure 15:
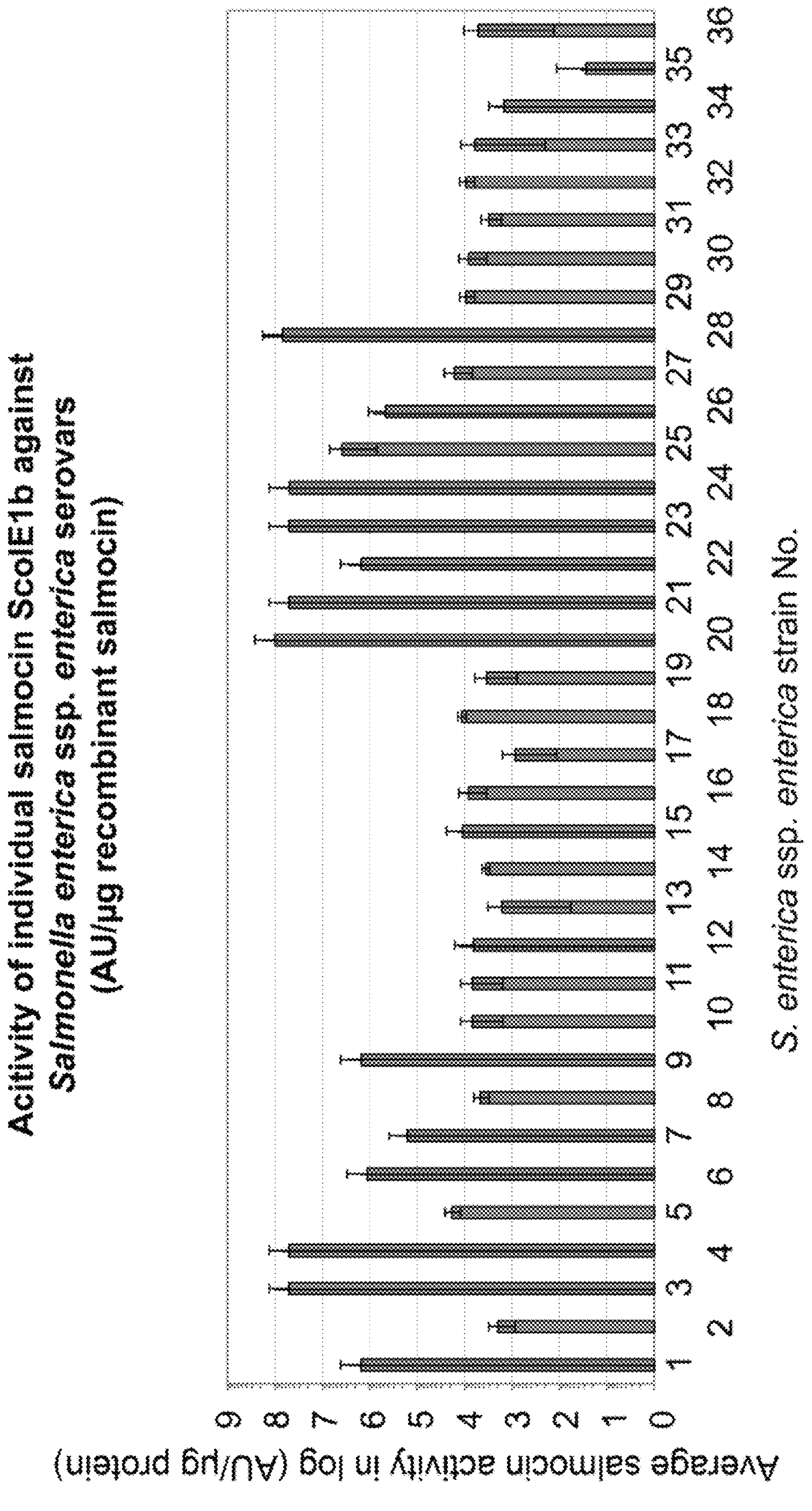

FIG. 15 shows the semi-quantitative evaluation of the average specific antimicrobial activity of salmocin ScolE1b-containing plant extracts against 36 *S. enterica* ssp. *enterica* strains listed in tables 5A and 5B. The antimicrobial activity was tested using radial diffusion assay via spot-on-lawn-method and calculated in arbitrary units (AU) per μg of recombinant salmocin (average of 3 independent experiments).

Figure 16:
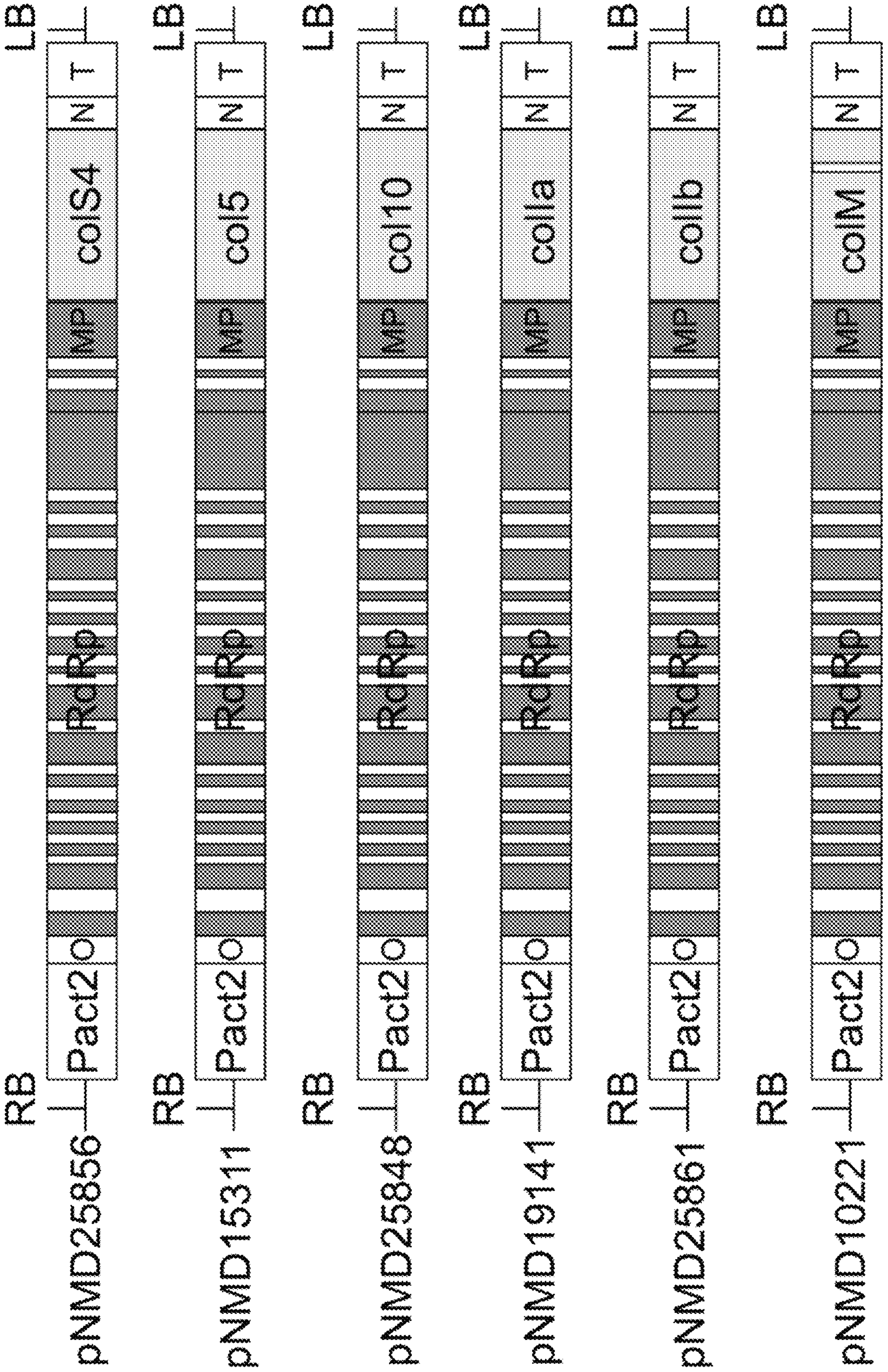

FIG. 16 shows schematically viral vectors based on Tobacco mosaic virus (TMV) for the expression of colicins used in the Examples. Colicin expression vectors include pNMD25856, pNMD15311, pNMD25848, pNMD19141, pNMD25861 and pNMD10221 for the expression of colicins colS4, col5, col10, colla, collb and colM, respectively.

RB and LB indicate the right and left borders of T-DNA of binary vectors. Pact2: promoter of *Arabidopsis* actin2 gene; o: 5' end from TVCV (turnip vein clearing virus); RdRp: RNA-dependent RNA polymerase open reading frame (ORF) from cr-TMV (crucifer-infecting tobamovirus); MP: movement protein ORF from cr-TMV; colS4: colicin S4 coding sequence; col5: colicin 5 coding sequence; col10: colicin 10 coding sequence; colla: colicin la coding sequence; collb: colicin lb coding sequence; colM: colicin M coding sequence; N: 3'-non-translated region from cr-TMV; T: *Agrobacterium* nopaline synthase terminator; white segments interrupting grey segments in the RdRp and MP ORFs indicate introns inserted into these ORFs for increasing the likelihood of RNA replicon formation in the cytoplasm of plant cells, which is described in detail in WO2005049839.

Figure 17:
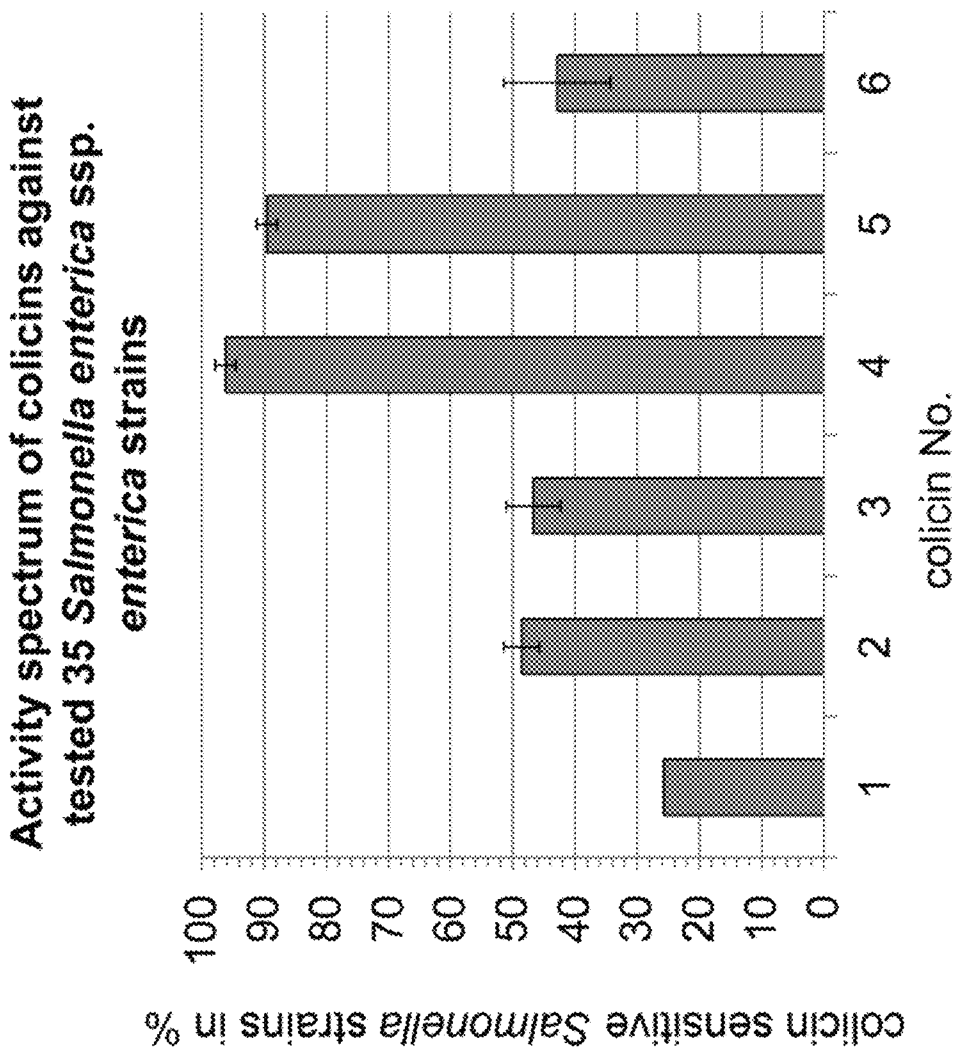

FIG. 17 shows the semi-quantitative evaluation of specific antimicrobial activity of colicin-containing plant extracts against 35 *S. enterica* ssp. *enterica* strains (No. 1-35) listed in tables 5A and 5B. The antimicrobial activity was tested using radial diffusion assay via spot-on-lawn-method. The percentage of colicin-sensitive *Salmonella* strains (average of 3 independent experiments) is given for colicins: 1—colicin S4; 2—colicin 5; 3—colicin 10; 4—colicin la; 5—colicin lb; 6—colicin M.

Figure 18:
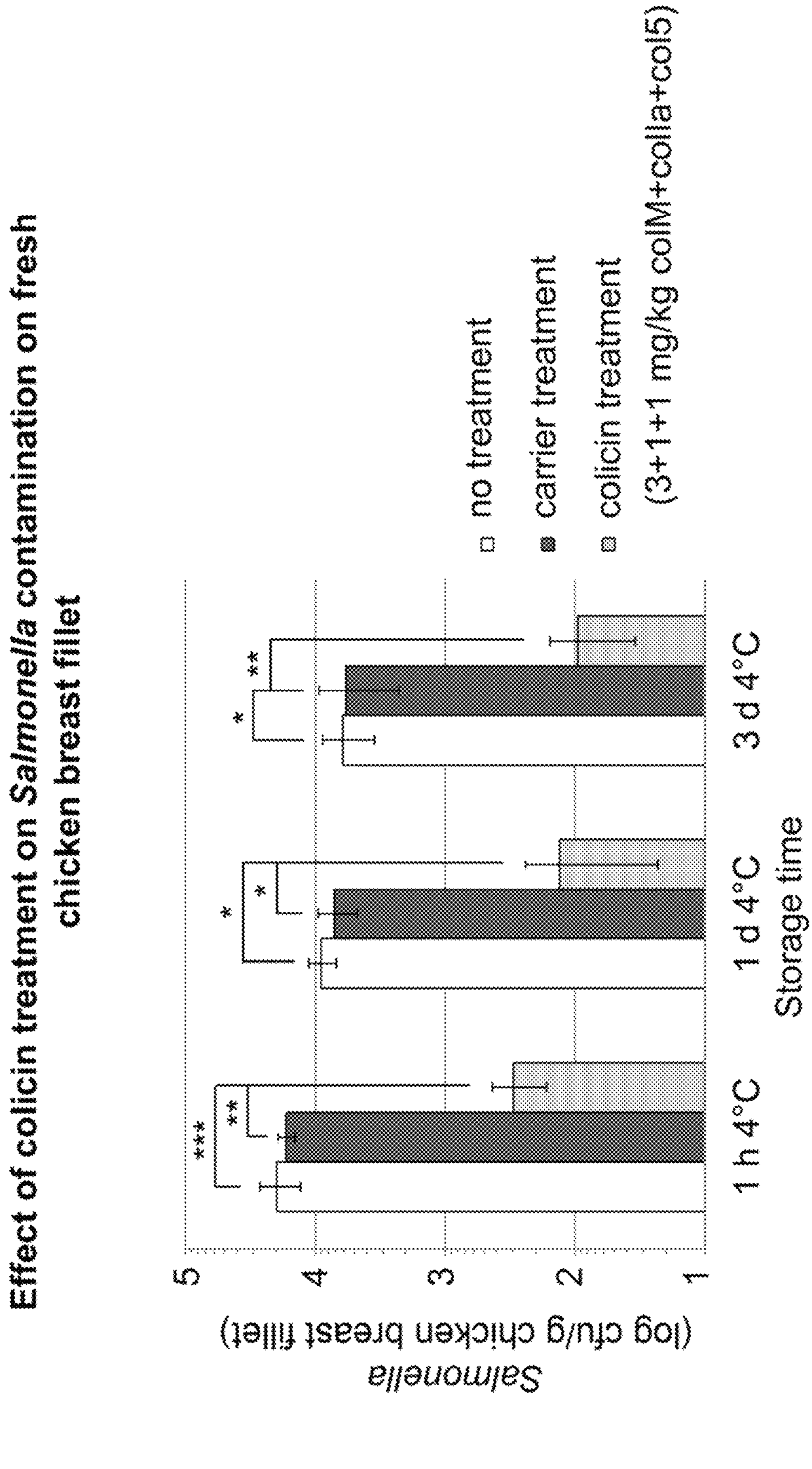

FIG. 18 shows the reduction of *S. enterica* ssp. *enterica* cell population in contaminated chicken breast meat pieces by treatment with a three-component colicin blend comprising colicin M, colicin la and colicin 5. Meat was contaminated with a two-strain mixture of *S. enterica* ssp. *enterica* strains ATCC®14028™* and ATCC®13076™* of serotypes *Typhimurium* and *Enteritidis*, respectively. Asteriks indicate statistically significant differences in bacterial numbers.

Figure 19:
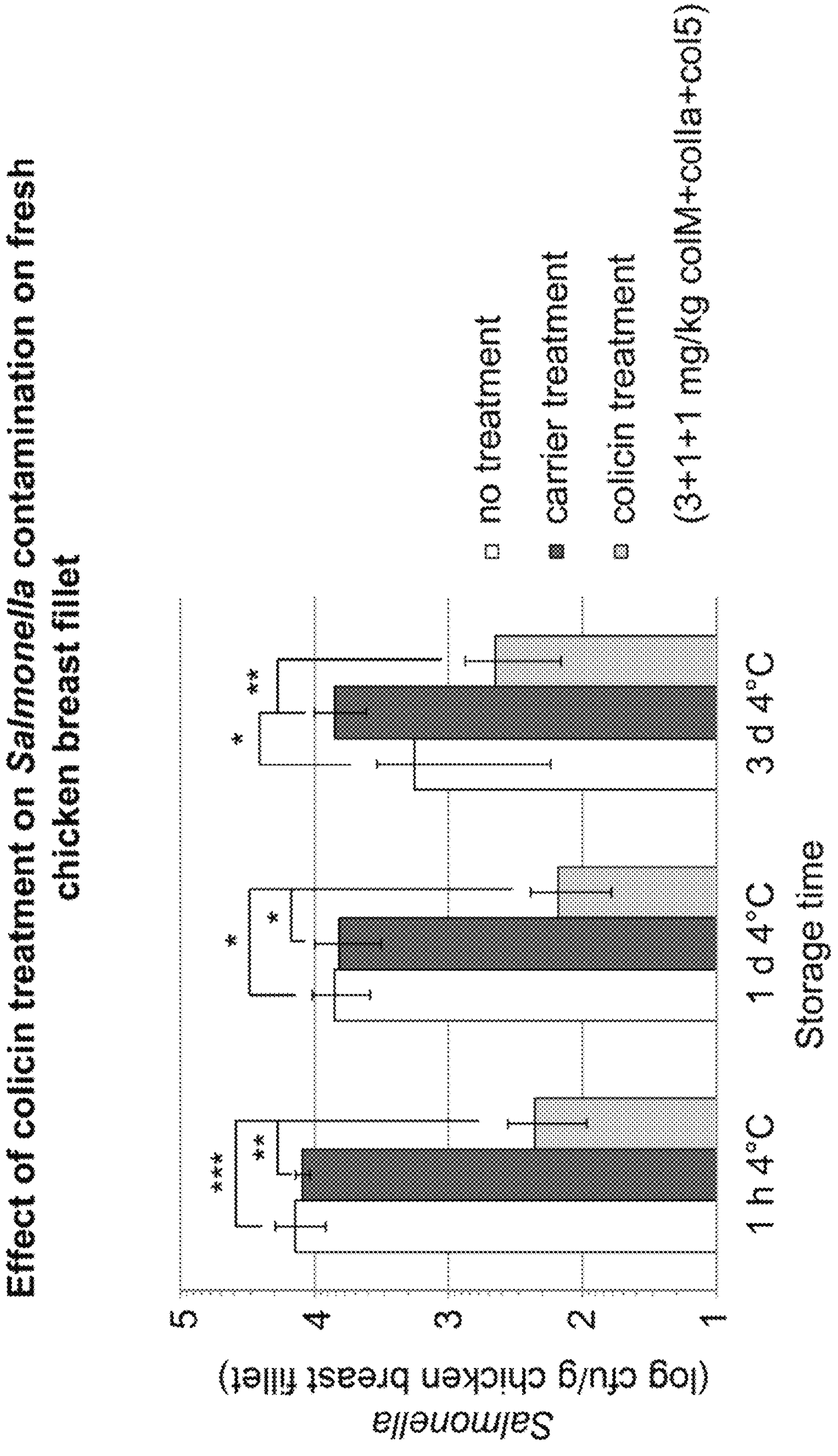

FIG. 19 shows the reduction of *S. enterica* ssp. *enterica* cell population in contaminated chicken breast meat pieces by treatment with a three-component colicin blend comprising colicin M, colicin la and colicin 5. Meat was contaminated with a four-strain mixture of *S. enterica* ssp. *enterica* strains ATCC®14028™*, ATCC®13076™*, ATCC®9270™* and ATCC®6962™* of serotypes *Typhimurium, Enteritidis*, Anatum and Newport, respectively. Asteriks indicate statistically significant differences in bacterial numbers.

Figure 20A:
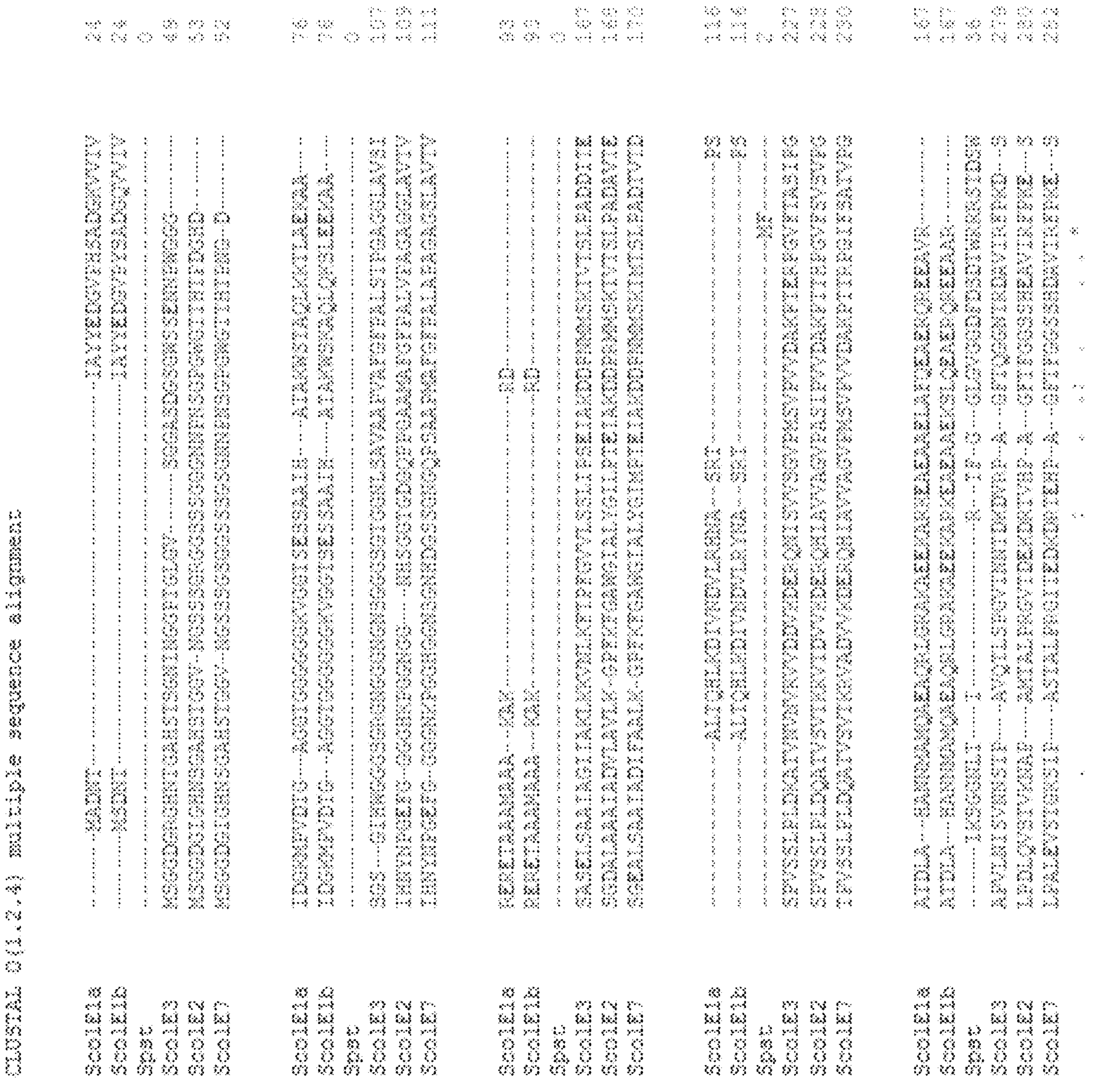
Figure 20B:
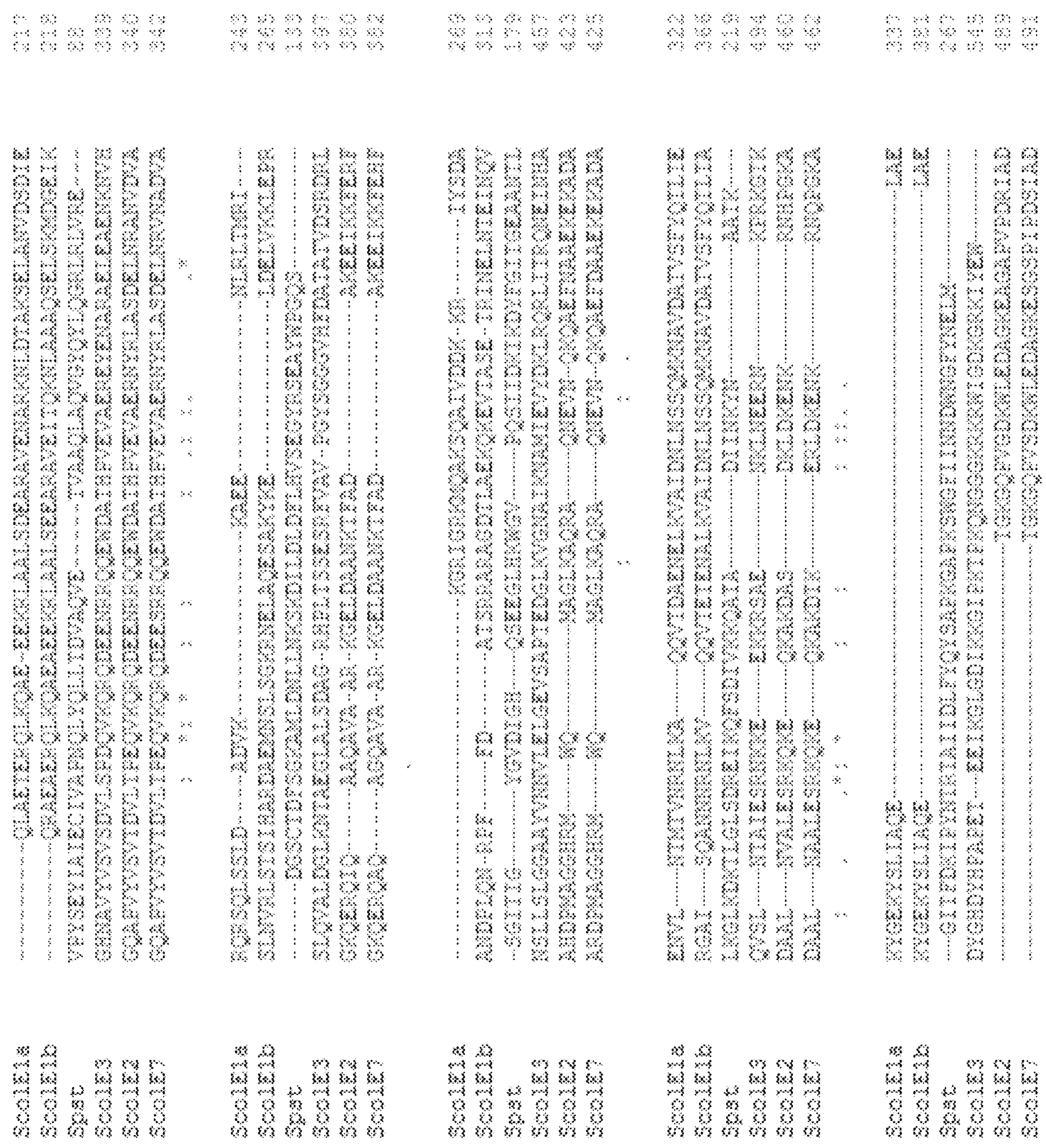

FIG. 20 A-C shows a multiple sequence alignment of salmocin amino acid sequences generated using Clustal Omega tool (Fast, scalable generation of high-quality protein multiple sequence alignments using Clustal Omega. (2011 Oct. 11) Molecular systems biology 7:539). ScolE2, ScolE3, ScolE7, ScolE1a, ScolE1b and Spst refer to SEQ ID NOs: 1-6, respectively. Colour labels indicate properties of amino acid residues (red residues as AVFPMILW (small, hydrophobic and aromatic-Y); blue residues as DE (acidic); magenta residues as RK (basic) and green residues as STYHCNGQ (hydroxyl sulfhydryl amine and G)). Consensus symbol * (asterisk) indicates positions in alignment which have a single, fully conserved residue, a: (colon) indicates conservation between groups of strongly similar properties and a. (period) indicates conservation between groups of weakly similar properties.

Figure 21:
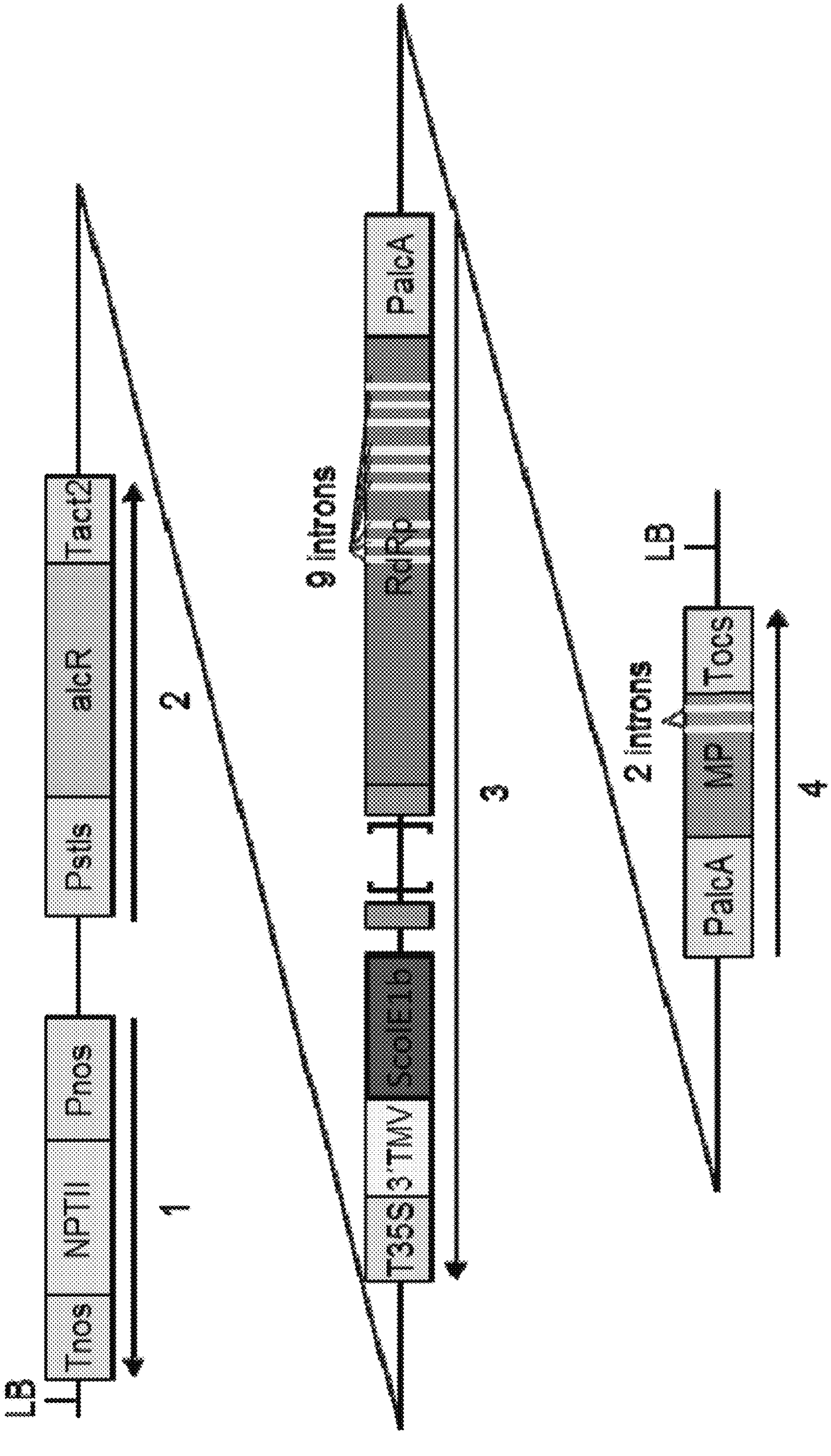

FIG. 21 is a schematic representation of T-DNA regions of ScolE1b-encoding plasmid construct (pNMD35541) used for stable plant transformation. The T-DNA region is composed of 4 expression cassettes for: 1) constitutive expression of kanamycine resistance transgenic plant selection marker, 2) constitutive expression of alcR transcriptional activator, 3) ethanol-inducible expression of salmocin ScolE1b and 4) ethanol-inducible expression of TMV MP. Arrows indicate orientation of expression cassettes. For tight control of viral replicon activation in non-induced state, the viral vector is deconstructed in the 2 components, replicon and MP (expression cassettes 3 and 4) (Werner et al. Proc. Natl. Acad. Sci. USA 108, 14061-14066 (2011). LB and RB, binary left and right borders, respectively; Tnos and Pnos, terminator and promoter of the *Agrobacterium* nopaline synthase gene; NPTII, neomycin phosphotransferase II; Pstls, promoter of potato ST-LS1 gene; alcR, *Aspergillus nidulans* alcR ORF; Tact2, *Arabidopsis thaliana* actin 2 terminator; T35S, CaMV 35S terminator; 3"TMV, 3" untranslated region of TMV; RdRp, RNA-dependent RNA polymerase; pAlcA, ScolE1b, coding sequence of salmocin E1b (ScolE1b); *Aspergillus nidulans* alcohol dehydrogenase (alcA) promoter; MP, movement protein; Tocs terminator of *Agrobacterium* octopine synthase gene; [ ] deletion of MP in expression cassette 3.

Figure 22:
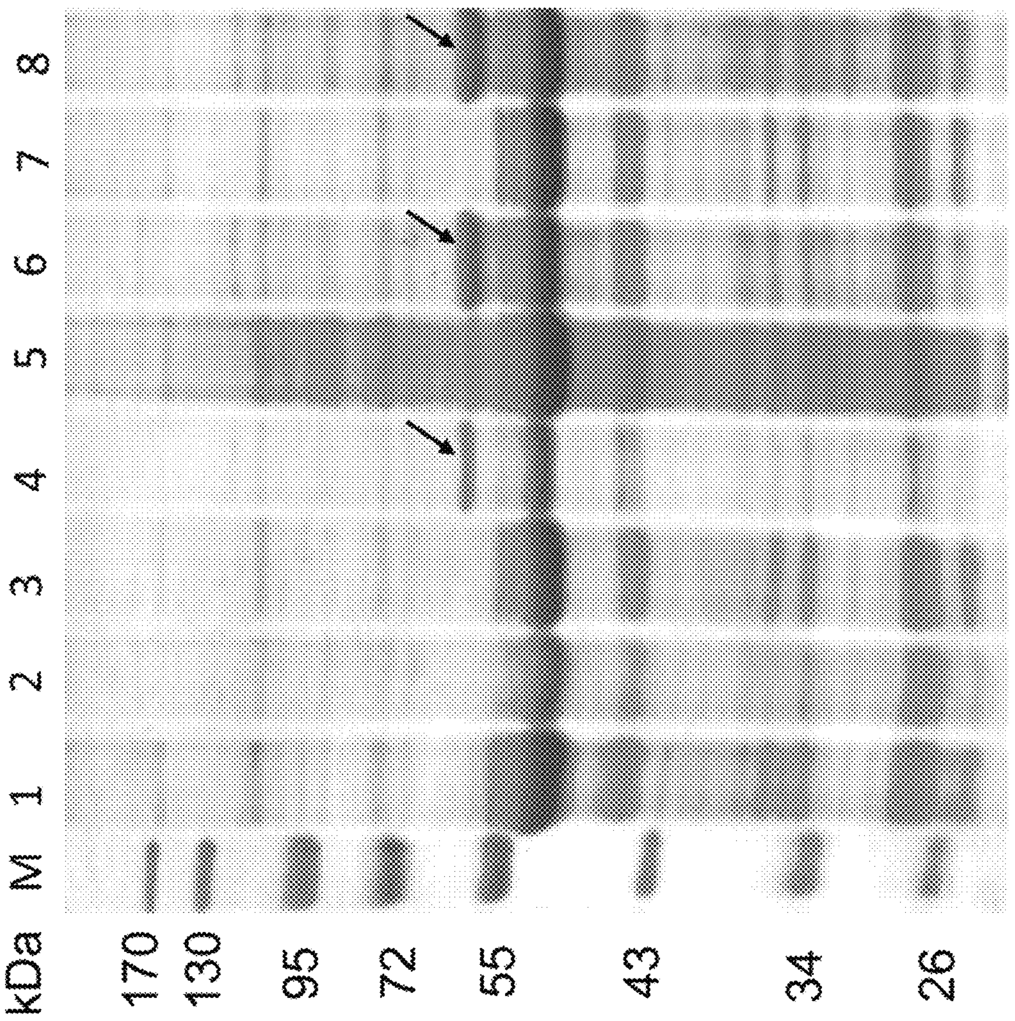

FIG. 22 shows the results of inducible expression of salmocin ScolE1b in stable transgenic *Nicotiana benthamiana* plants. Loading with crude extracts corresponds to 3 mg FW extracted with 2×Laemmli buffer from (lanes 1, 3, 5, 7) non-induced plant material or (lanes 2, 4, 6, 8) plant material 4 dp induction with ethanol. (lanes 1, 2) *N. benthamiana* WT plant, (lanes 3, 4), (lanes 5, 6), (lanes 7, 8) different transgenic plant candidates for single copy T-DNA insertion of TO generation (#4, 12, 37 for ScolE1b). Arrows mark recombinant proteins.

Figure 23:
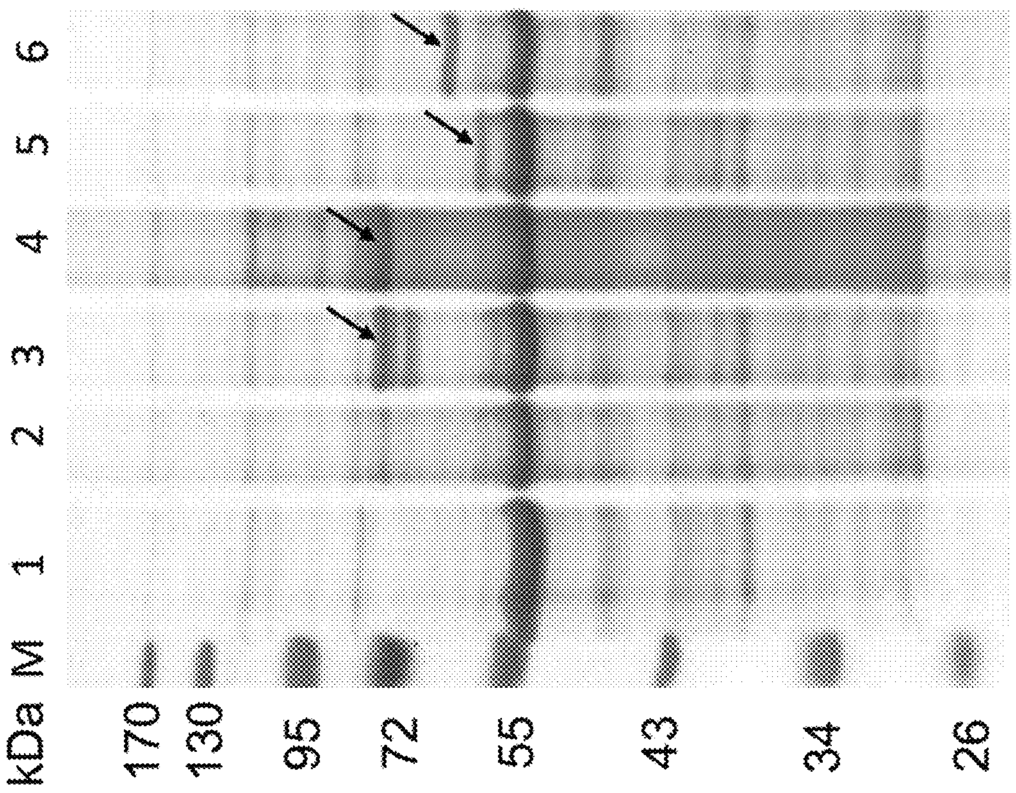

FIG. 23 shows the results of transient expression of salmocins in *Spinacia oleracea* cv. Frühes Riesenblatt upon syringe infiltration with agrobacteria carrying TMV or TMV and PVX vectors. Loading of TSP extracts corresponds to 3 mg FW plant material extracted with 5 vol. 150 mM NaCl. Plant material was harvested (a) 5 dpi (days post infiltration) for 6 dpi for ScolE3, ScolE7 and ScolE1a or 7 dpi for ScolE2 or (b) 4 dpi for ScolE1b, 5 dpi for ScolE3, ScolE7 and ScolE1a and 6 dpi for ScolE2 or (c) 8 dpi for ScolE2, ScolE3, ScolE7, ScolE1a and ScolE1b. (a, b, c) Analyzed extracts were prepared from plant material expressing ScolE2 (lane 1), ScolE3 (lane 2), ScolE7 (lane 3), ScolE1a (lane 4) and ScolE1b (lane 5) or from (WT) non-transfected leaf tissue. ScolE2 and ScolE7 were co-expressed with their respective immunity proteins. Arrows mark recombinant proteins.

Figure 24:
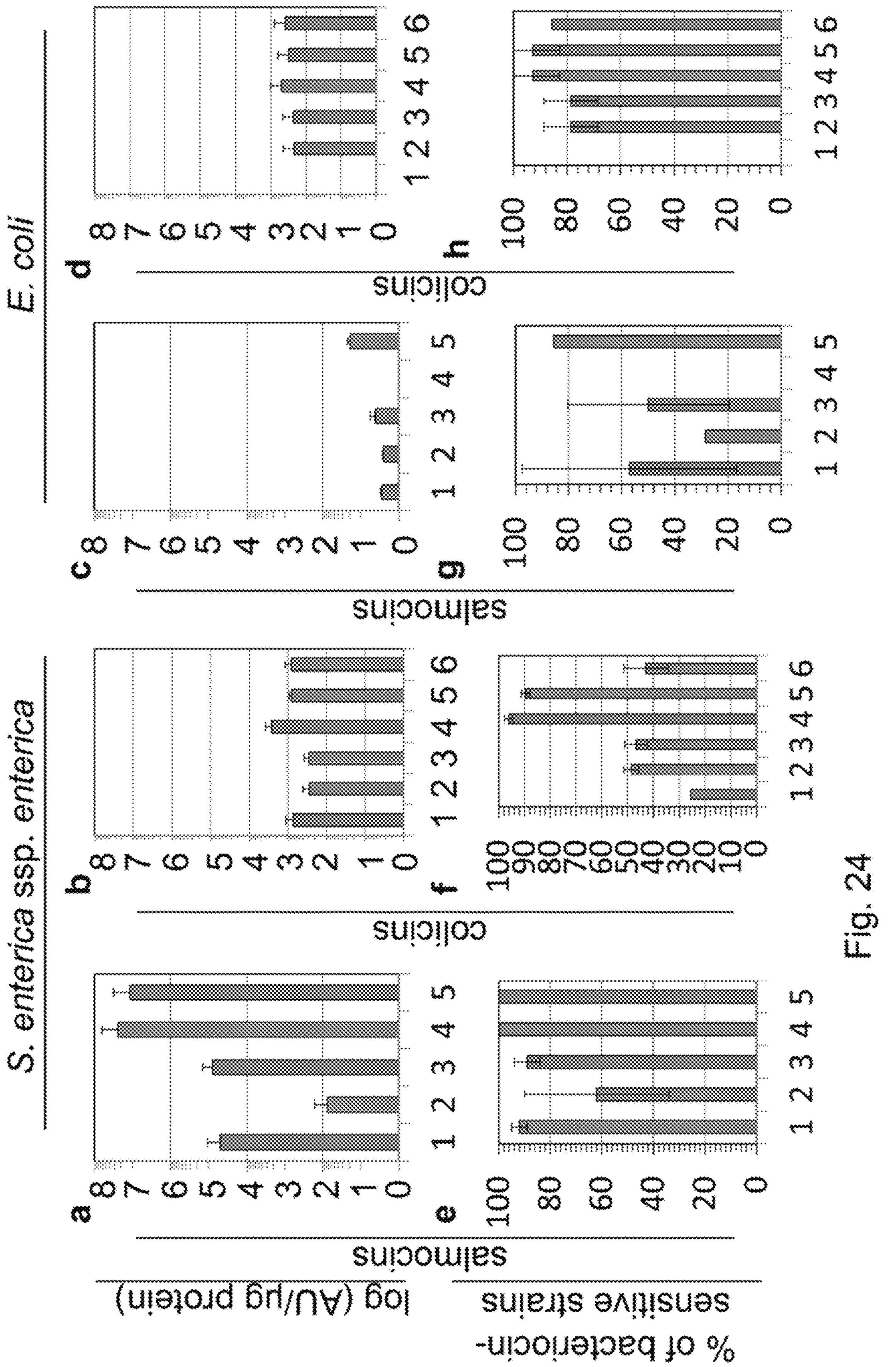

FIG. 24 shows activity spectrum of bacteriocins from *Salmonella* and *E. coli* against *Salmonella enterica* ssp. *enterica* and *E. coli* Big 7 STEC serotypes. Semi-quantitative evaluation of the specific antimicrobial activity by radial diffusion assay via spot-on-lawn-method of (a, c, e, g) salmocin- and (b, d, f, h) colicin-containing plant extracts against 36 (a, e) or 35 (b, f) *S. enterica* ssp. *enterica* strains listed in Table 9 or 7 *E. coli* Big 7 STEC strains (c, d, g, h) listed in Table 10. Average and STDV of N=3 and N=2 independent experiments is given in (a, b, e, f) and (c, d, g, h), respectively, for the percentage of bacteriocin-sensitive strains (e, f, g, h) and for the specific bacteriocin activity calculated in arbitrary units (AU) per µg of recombinant protein (a, b, c, d) on all tested strains. 1—ScolE2 (a, c, e, g) or colS4 (b, d, f, h); 2—ScolE3 (a, c, e, g) or col5 (b, d, f, h); 3—ScolE7 (a, c, e, g) or col10 (b, d, f, h); 4—ScolE1a (a, c, e, g) or colla (b, d, f, h); 5—ScolE1b (a, c, e, g) or collb (b, d, f, h); 6—colM (b, d, f, h).

FIG. 25 shows the reduction of a *S. enterica* ssp. *enterica* contamination on fresh chicken breast fillet by salmocins. (a) Bacterial populations recovered from meat upon storage for various periods of time at 10° C. upon salmocin treatment (black bar at 0 h, initial contamination level; white bars, carrier treatment; at 1 h, 24 h, 48 h and 72 h: light grey bars, bacteriocin treatment ScolE1a in concentration of 3 mg/kg meat; grey bars, bacteriocin treatment ScolE1a+ScolE1b+ScolE2+ScolE7 in concentration of 3+1+1+1 mg/kg meat; dark grey bars, bacteriocin treatment ScolE1a+ScolE1b+ScolE2+ScolE7 in concentration of 0.3+0.1+0.1+0.1 mg/kg meat) of contaminated meat by spray-application. Error bars indicate standard deviation of biological replicates, N=4. (b) Chicken breast trims used in (a).

FIG. 26 shows a multiple sequence alignment of salmocin amino acid sequences generated using Clustal Omega tool. ScolE1a, ScolE1c, ScolE1d, ScolE1e refer to SEQ ID NOs: 4, 25, 26 and 27, respectively. Consensus symbol * (asterisk) indicates positions in alignment which have a single, fully conserved residue, a: (colon) indicates conservation between groups of strongly similar properties and a. (period) indicates conservation between groups of weakly similar properties.

FIG. 27 shows a multiple sequence alignment of salmocin ScolMa and colicin ColM amino acid sequences generated using Clustal Omega tool. ScolMa and ColM refer to SEQ ID NOs: 28 and 14, respectively.

Figure 28:
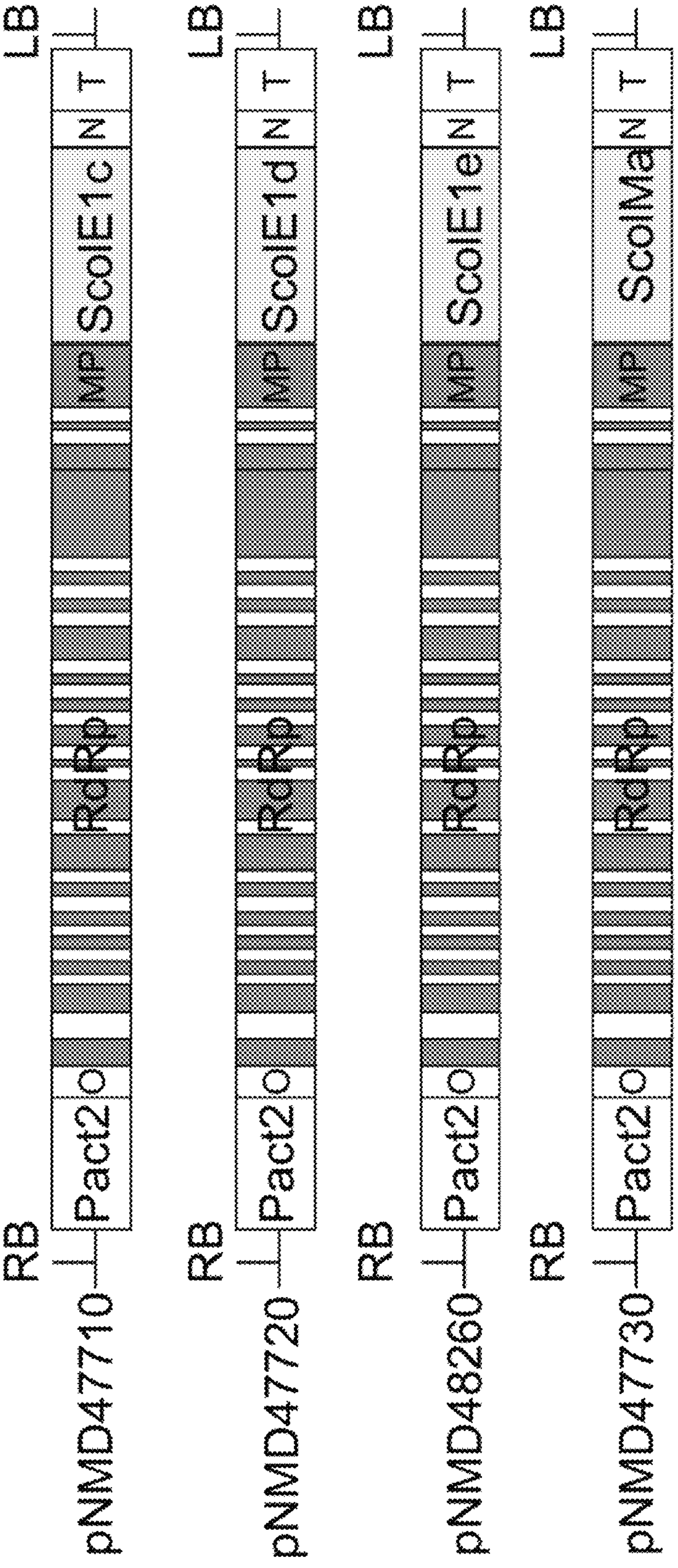

FIG. 28 shows schematically viral vectors pNMD47710, pNMD47720, pNMD48260 and pNMD47730 for the expression of salmocins ScolE1c, ScolE1d, ScolE1e and ScolEMa, respectively. These constructs are based on Tobacco mosaic virus (TMV).

ScolE1c: salmocin ScolE1c coding sequence; ScolE1d: salmocin ScolE1d coding sequence; ScolE1e: salmocin ScolE1e coding sequence; ScolMa: salmocin ScolMa coding sequence.

Figure 29:
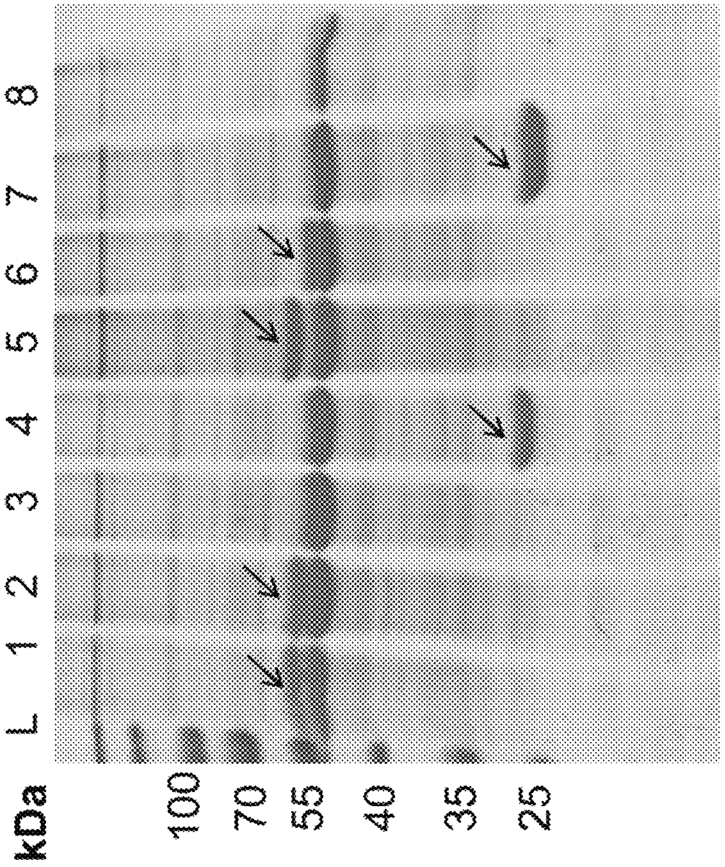

FIG. 29 shows comparative SDS-PAGE analysis of expression for salmocins after the infiltration of *Nicotiana benthamiana* plants with agrobacteria carrying viral vectors. Plant leaf material was extracted with 5 volumes of buffer containing 50 mM HEPES (pH 7.0), 10 mM potassium acetate, 5 mM magnesium acetate, 10% (v/v) glycerol, 0.05% (v/v) Tween-20 and 300 mM NaCl. Protein extracts were resolved in 12% polyacrylamide gels. For gel loading, aliquots containing the extract volumes corresponding to 0.4 mg fresh weight of plant tissue were used. Before loading on the gel, aliquots of protein extracts were mixed with 2×Laemmli buffer in the proportion 1:1 and incubated at 95° C. for 10 min. Numerals above gel lanes stand for protein extracts from plant tissues expressing the following recombinant proteins: 1—salmocin ScolE1c; 2—salmocin ScolE1d; 3—salmocin ScolE1e; 4—salmocin ScolMa; 5—salmocin ScolE1b; 6—salmocin ScolE1a, 7—colicin M. Numeral 8 corresponds to the extract from uninfected leaf tissue used as a negative control. L—PageRuler™ Prestainded Protein Ladder (Thermo Fisher Scientific Inc. (Waltham, USA), #SM0671). Arrows indicate specific protein bands corresponding to expressed recombinant colicins.

Figure 30:
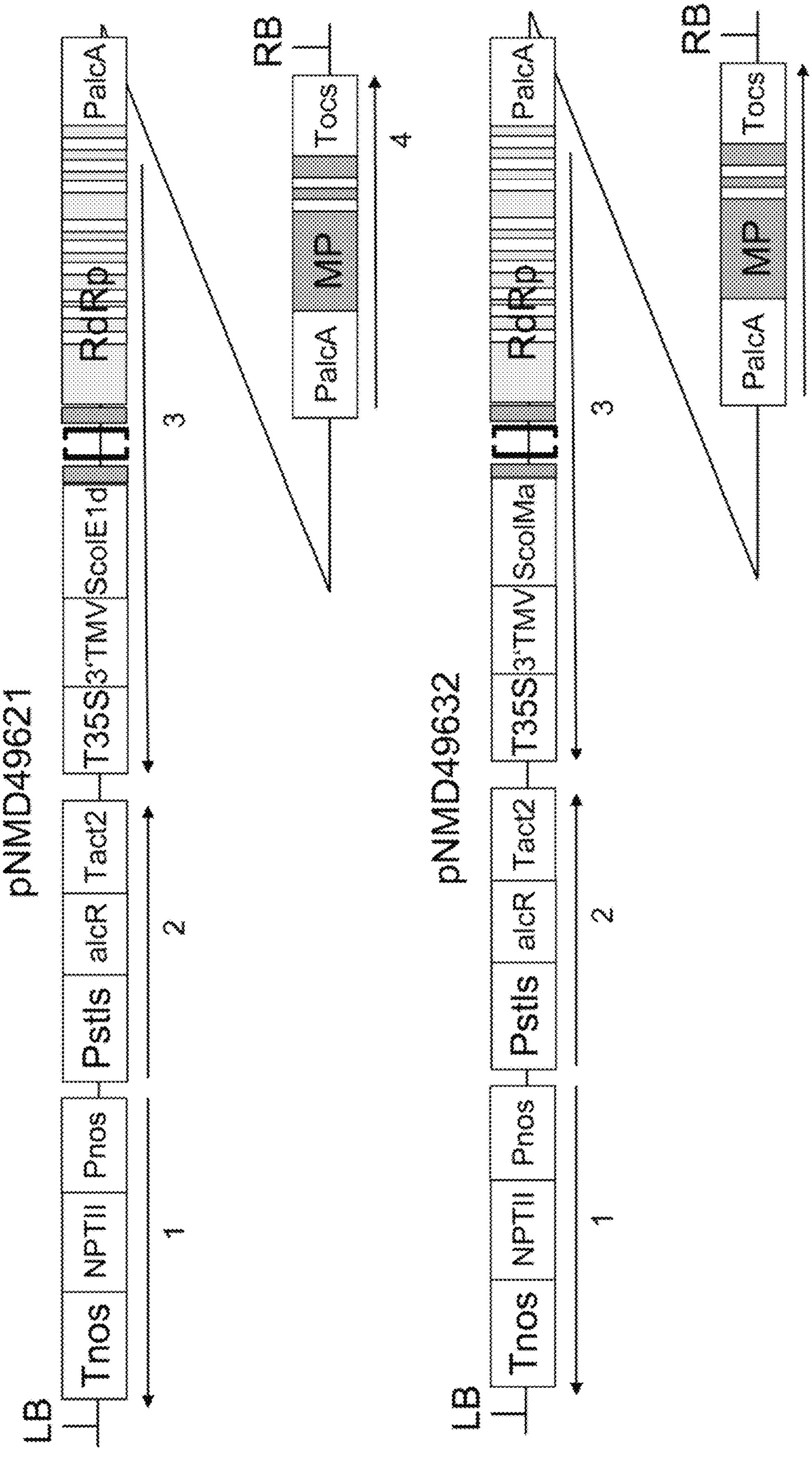

FIG. 30 shows a schematic representation of T-DNA regions of ScolE1d- and ScolMa-encoding plasmid constructs (pNMD49621 and pNMD49632, respectively) used for stable plant transformation. The T-DNA region is composed of 4 expression cassettes for: 1) constitutive expression of kanamycine resistance transgenic plant selection marker, 2) constitutive expression of alcR transcriptional activator, 3) ethanol-inducible expression of salmocin ScolE1b and 4) ethanol-inducible expression of TMV MP. Arrows indicate orientation of expression cassettes. ScolE1d stands for coding sequence of salmocin E1d (ScolE1d); ScolMa stands for coding sequence of salmocin Ma (ScolMa). For details, see the description to FIG. 21.

Figure 31:
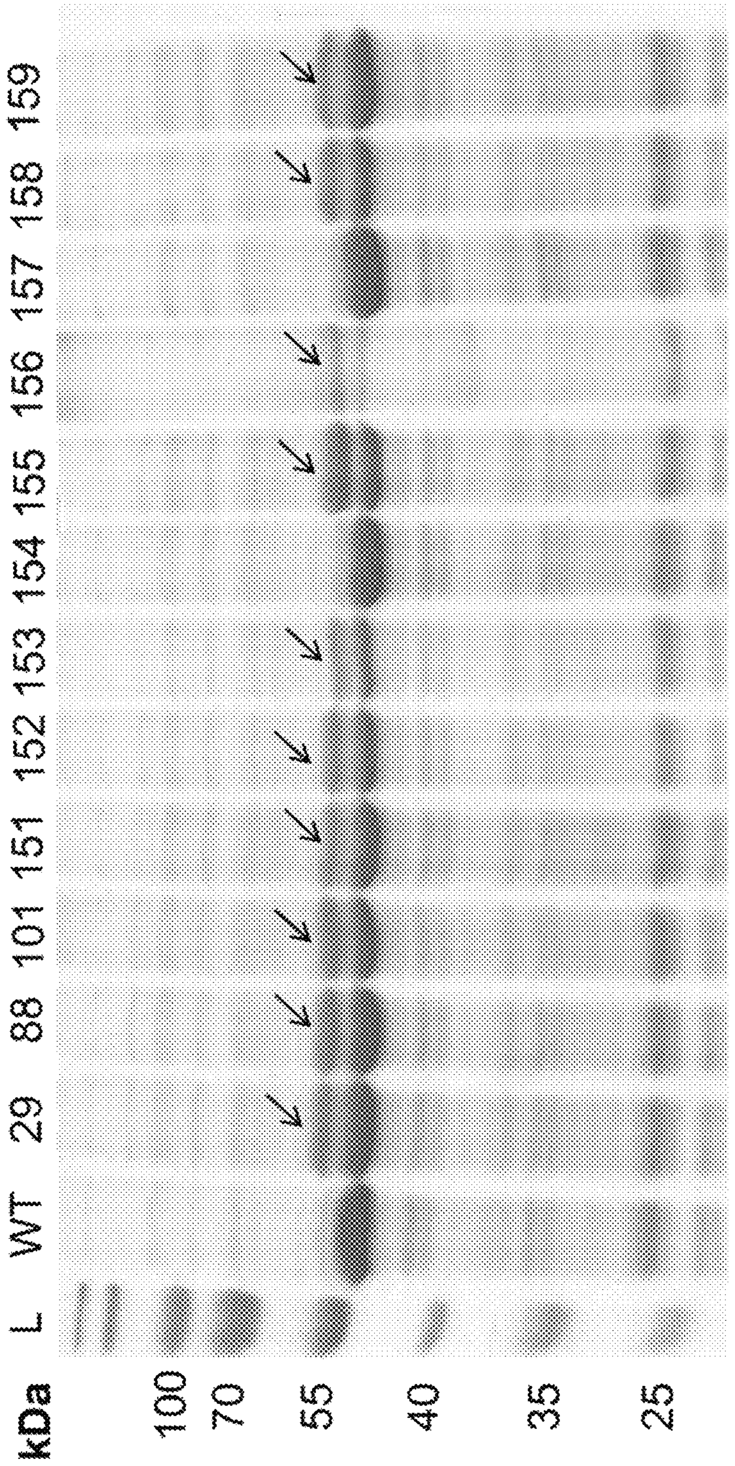

FIG. 31 shows the results of inducible expression of salmocin ScolE1d in stable transgenic *Nicotiana benthamiana* plants of TO generation. Loading with crude extracts corresponds to 3 mg FW extracted with 2×Laemmli buffer from *N. benthamiana* wild type plants (WT) and individual plant TO plants transformed with pNMD49621 construct (lines 29, 88, 101, 151, 152, 153, 154, 155, 156, 157, 158, and 159) 4 days post induction with ethanol. Arrows mark recombinant proteins.

DETAILED DESCRIPTION OF THE INVENTION

The proteins of the invention are proteins that have a cytotoxic effect on *Salmonella* and are referred to herein as "salmocins". The salmocins generally have at least a binding domain (also referred to as "receptor binding domain") that allows binding of the salmocin to a surface receptor structure of cells of the target *Salmonella*. Salmocins further have a cytotoxic domain that may be a catalytic or a pore-forming domain. The catalytic domain may have an RNase or DNase catalytic activity, an inhibitory activity against cell wall peptidoglycan (murein) biosynthesis, or may degrade cell wall structures of *Salmonella*. Further, the salmocins may have a translocation domain that may interact with membrane proteins of cells of the target *Salmonella* so that the salmocin is translocated to a compartment where the salmocin exerts its cytotoxic function.

For the specificity to *Salmonella*, the binding domain is of importance and (inter alia) distinguishes the salmocins from otherwise similar colicins. Thus, the protein of the invention may be defined by having at least a binding domain that comprises or consists of or is contained in any one of the amino acid sequence segments as defined in item (1) above or in claim 1. Items (a-i) to (a-v) of item (1) or claim 1 define binding domains of the salmocins ScolE2, ScolE3, ScolE7, ScolE1a, and ScolE1b, respectively. Items (a-vii) to (a-x) of item (1) or claim 1 define binding domains of the salmocins ScolE1c, ScolE1d, ScolE1e, and ScolMa, respectively. The binding domain of Spst is contained in the amino acid sequence segment defined in item (a-vi) of item (1) or claim 1. The amino acid sequences of salmocins ScolE2, ScolE3, ScolE7, ScolE1a, ScolE1b, and Spst are given as SEQ ID NO: 1 to 6, respectively. The amino acid sequence of the salmocins ScolE1c, ScolE1d, ScolE1e, and ScolMa are given as SEQ ID NO: 25 to 28, respectively. Items (b) to (d) of item (1) above define derivatives of ScolE2, ScolE3, ScolE7, ScolE1a, ScolE1b, Spst, ScolE1c, ScolE1d, ScolE1e, and ScolMa having or containing derivative binding domains (or amino acid sequence segments). Analogously, items (B) to (E) and items (a) to (8) (defined below) define derivatives of ScolE2, ScolE3, ScolE7, ScolE1a, ScolE1b, Spst, ScolE1c, ScolE1d, ScolE1e and ScolMa. Derivatives of ScolE2, ScolE3, ScolE7, ScolE1a, ScolE1b, Spst, ScolE1c, ScolE1d, ScolE1e, and ScolMa are preferably capable of exerting a cytotoxic effect on *Salmonella*. In the present invention, salmocins ScolE1a and ScolE1b and derivatives thereof as defined herein are preferred.

Herein, an amino acid sequence segment (or, briefly, segment) refers to a plurality of contiguous amino acid residues of a protein or polypeptide having a larger number of amino acid residues than the segment. Domains are also referred to herein as "amino acid sequence segments" or briefly "segments".

The protein of the invention comprises at least a binding domain. The following items (i) to (v) and (vii) to (x) of each of items (b) to (d) define preferred binding domains. Most preferred binding domains are those of items (a-i) to (a-v) and (a-vii) to (a-x). Items (vi) of each of the following items (b) to (d), i.e. sub-items (b-vi), (c-vi) and (d-vi), define preferred amino acid sequence segments that contain a binding domain and are derivatives of salmocin Spst. The protein of the invention preferably comprises any one of the following amino acid sequence segments:

(b-i) a segment having at least 80%, preferably at least 85%, more preferably at least 90% and most preferably at least 95% sequence identity to the segment from amino acid residue 316 to 449 of ScolE2 (SEQ ID NO: 1), (b-ii) a segment having at least 75%, preferably 80%, more preferably at least 85%, more preferably at least 90% and most preferably at least 95% sequence identity to the segment from amino acid residue 315 to 483 of ScolE3 (SEQ ID NO: 2), (b-iii) a segment having at least 80%, preferably at least 85%, more preferably at least 90% and most preferably at least 95% sequence identity to the segment from amino acid residue 318 to 451 of ScolE7 (SEQ ID NO: 3), (b-iv) a segment having at least 80%, preferably at least 85%, more preferably at least 90% and most preferably at least 95% sequence identity to the segment from amino acid residue 174 to 297 of ScolE1a (SEQ ID NO: 4), (b-v) a segment having at least 80%, preferably at least 85%, more preferably at least 90% and most preferably at least 95% sequence identity to the segment from amino acid residue 198 to 322 of ScolE1b (SEQ ID NO: 5), (b-vi) a segment having at least 80%, preferably at least 85%, more preferably at least 90% and most preferably at least 95% sequence identity to a segment comprising at least 200 contiguous amino acid residues of Spst of SEQ ID NO: 6; in one embodiment, a segment having at least 80%, preferably at least 85%, more preferably at least 90% and most preferably at least 95% sequence identity to a segment comprising at least 250 contiguous amino acid residues of Spst of SEQ ID NO: 6; in a further embodiment; in a further embodiment, the protein comprises or consists of an amino acid sequence having at least 80%, preferably at least 85%, more preferably at least 90% and most preferably at least 95% sequence identity to the (entire) amino acid sequence of SEQ ID NO: 6, (b-vii) a segment having at least 80%, preferably at least 85%, more preferably at least 90% and most preferably at least 95% sequence identity to the segment from amino acid residue 195 to 319 of ScolE1c (SEQ ID NO: 25), (b-viii) a segment having at least 80%, preferably at least 85%, more preferably at least 90% and most preferably at least 95% sequence identity to the segment from amino acid residue 195 to 319 of ScolE1d (SEQ ID NO: 26), (b-ix) a segment having at least 80%, preferably at least 85%, more preferably at least 90% and most preferably at least 95% sequence identity to the segment from amino acid residue 193 to 317 of ScolE1e (SEQ ID NO: 27), or (b-x) a segment having at least 80%, preferably at least 85%, more preferably at least 90% and most preferably at least 95% sequence identity to the segment from amino acid residue 38 to 138 of ScolMa (SEQ ID NO: 28);

or (c-i) a segment having at least 90%, preferably at least 95% sequence similarity to the segment from amino acid residue 316 to 449 of ScolE2 (SEQ ID NO: 1), (c-ii) a segment having at least 85%, preferably at least 90%, more preferably at least 95% sequence similarity to the segment from amino acid residue 315 to 483 of ScolE3 (SEQ ID NO: 2), (c-iii) a segment having at least 90%, preferably at least 95% sequence similarity to the segment from amino acid residue 318 to 451 of ScolE7 (SEQ ID NO: 3), (c-iv) a segment having at least 90%, preferably at least 95% sequence similarity to the segment from amino acid residue 174 to 297 of ScolE1a (SEQ ID NO: 4), (c-v) a segment having at least 90%, preferably at least 95% sequence similarity to the segment from amino acid residue 198 to 322 of ScolE1b (SEQ ID NO: 5), (c-vi) a segment having at least 90%, preferably at least 95% sequence similarity to a segment comprising at least 200 contiguous amino acid residues of Spst of SEQ ID NO: 6; in one embodiment, a segment having at least 90%, preferably at least 95% sequence similarity to a segment comprising at least 250 contiguous amino acid residues of Spst of SEQ ID NO: 6; in a further embodiment, the protein comprises or consists of an amino acid sequence having at least 80%, preferably at least 90% and most preferably at least 95% sequence similarity to the (entire) amino acid sequence of SEQ ID NO: 6;

(c-vii) a segment having at least 90%, preferably at least 95% sequence similarity to the segment from amino acid residue 195 to 319 of ScolE1c (SEQ ID NO: 25), (c-viii) a segment having at least 90%, preferably at least 95% sequence similarity to the segment from amino acid residue 195 to 319 of ScolE1d (SEQ ID NO: 26), (c-ix) a segment having at least 90%, preferably at least 95% sequence similarity to the segment from amino acid residue 193 to 317 of ScolE1e (SEQ ID NO: 27), or (c-x) a segment having at least 90%, preferably at least 95% sequence similarity to the segment from amino acid residue 38 to 138 of ScolMa (SEQ ID NO: 28);

or (d-i) a segment having from 1 to 20, preferably from 1 to 15, more preferably from 1 to 10 amino acid substitutions, additions, insertions or deletions to the segment from amino acid residue 316 to 449 of ScolE2 (SEQ ID NO: 1), (d-ii) a segment having from 1 to 30, preferably from 1 to 29, more preferably from 1 to 10 amino acid substitutions, additions, insertions or deletions to the segment from amino acid residue 315 to 483 of ScolE3 (SEQ ID NO: 2), (d-iii) a segment having from 1 to 20, preferably from 1 to 15, more preferably from 1 to 10 amino acid substitutions, additions, insertions or deletions to the segment from amino acid residue 318 to 451 of ScolE7 (SEQ ID NO: 3), (d-iv) a segment having from 1 to 30, preferably from 1 to 20, more preferably from 1 to 15, even more preferably from 1 to 10 amino acid substitutions, additions, insertions or deletions to the segment from amino acid residue 174 to 297 of ScolE1a (SEQ ID NO: 4), (d-v) a segment having from 1 to 30, preferably from 1 to 20, more preferably from 1 to 15, and even more preferably from 1 to 10 amino acid substitutions, additions, insertions or deletions to the segment from amino acid residue 198 to 322 of ScolE1b (SEQ ID NO: 5), (d-vi) a segment having from 1 to 30, preferably from 1 to 20, more preferably from 1 to 15, and even more preferably from 1 to 10 amino acid substitutions, additions, insertions or deletions to a segment comprising at least 200 contiguous amino acid residues of Spst of SEQ ID NO: 6; in one embodiment, a segment having from 1 to 30, preferably from 1 to 20, more preferably from 1 to 15, and even more preferably from 1 to 10 amino acid substitutions, additions, insertions or deletions to a segment comprising at least 250 contiguous amino acid residues of Spst of SEQ ID NO: 6; in a further embodiment, the protein comprises or consists of an amino acid sequence having from 1 to 30, preferably from 1 to 20, more preferably from 1 to 15, and even more preferably from 1 to 10 amino acid substitutions, additions, insertions or deletions to the (entire) amino acid sequence of SEQ ID NO: 6.

(d-vii) a segment having from 1 to 30, preferably from 1 to 20, more preferably from 1 to 15, and even more preferably from 1 to 10 amino acid substitutions, additions, insertions or deletions to the segment from amino acid residue 195 to 319 of ScolE1c (SEQ ID NO: 25), (d-viii) a segment having from 1 to 30, preferably from 1 to 20, more preferably from 1 to 15, and even more preferably from 1 to 10 amino acid substitutions, additions, insertions or deletions to the segment from amino acid residue 195 to 319 of ScolE1d (SEQ ID NO: 26), (d-ix) a segment having from 1 to 30, preferably from 1 to 20, more preferably from 1 to 15, and even more preferably from 1 to 10 amino acid substitutions, additions, insertions or deletions to the segment from amino acid residue 193 to 317 of ScolE1e (SEQ ID NO: 27), or (d-x) a segment having from 1 to 30, preferably from 1 to 20, more preferably from 1 to 15, even more preferably from 1 to 10, and most preferably from 1 to 5 amino acid substitutions, additions, insertions or deletions to the segment from amino acid residue 38 to 138 of ScolMa (SEQ ID NO: 28).

In another embodiment, the invention provides a protein that is preferably capable of exerting a cytotoxic effect on *Salmonella*, wherein the amino acid sequence of said protein is defined by, or by comprising the segments of, any one of items (a-i) to (a-vi), (a-vii) to (a-x), (b-i) to (b-vi), (b-vii) to (b-x), (c-i) to (c-vi), (c-vii) to (c-x), (d-i) to (d-vi), or (d-vii) to (d-x) above.

Where a protein is defined herein by a number or number range of amino acid substitutions, additions, insertions or deletions, amino acid substitutions, additions, insertions or deletions may be combined, but the given number or number range refers to the sum of all amino acid substitutions, additions, insertions and deletions. Among amino acid substitutions, additions, insertions and deletions, amino acid substitutions, additions, and deletions are preferred. The term "insertion" relates to insertions within the amino acid sequence of a reference sequence, i.e. excluding additions at the C- or N-terminal end. The term additions means additions at the C- or N-terminal end of the amino acid sequence of a reference sequence. A deletion may be a deletion of a terminal or an internal amino acid residue of a reference sequence. Herein, where the protein or any domain thereof is defined by a number or number range of amino acid substitutions, additions, insertions or deletions relative to an indicated amino acid sequence of segment, in a further embodiment, the protein or domain may have from 1 to several amino acid substitutions, additions, insertions or deletions relative to the indicated amino acid sequence of segment.

The cytotoxic or catalytic domain of the protein of the invention may be as defined in item (3) above. In preferred embodiments, the protein of the invention comprises a cytotoxic or catalytic domain that comprises or consists of any one of the following amino acid sequence segments:

(b-i)' a segment having at least 80%, preferably at least 85%, more preferably at least 90% and most preferably at least 95% sequence identity to the segment from amino acid residue 453 to 582 of ScolE2 (SEQ ID NO: 1), (b-ii)' a segment having at least 80%, preferably at least 85%, more preferably at least 90% and most preferably at least 95% sequence identity to the segment from amino acid residue 501 to 584 of ScolE3 (SEQ ID NO: 2), (b-iii)' a segment having at least 80%, preferably at least 85%, more preferably at least 90% and most preferably at least 95% sequence identity to the segment from amino acid residue 455 to 584 of ScolE7 (SEQ ID NO: 3), (b-iv)' a segment having at least 80%, preferably at least 85%, more preferably at least 90% and most preferably at least 95% sequence identity to the segment from amino acid residue 306 to 478 of ScolE1a (SEQ ID NO: 4), (b-v)' a segment having at least 80%, preferably at least 85%, more preferably at least 90% and most preferably at least 95% sequence identity to the segment from amino acid residue 350 to 522 of ScolE1b (SEQ ID NO: 5), (b-vi)' a segment having at least 80%, preferably at least 85%, more preferably at least 90% and most preferably at least 95% sequence identity to the segment from amino acid residue 112 to 288 of Spst (SEQ ID NO: 6), (b-vii)' a segment having at least 80%, preferably at least 85%, more preferably at least 90% and most preferably at least 95% sequence identity to the segment from amino acid residue 347 to 519 ScolE1c (SEQ ID NO: 25), (b-viii)' a segment having at least 80%, preferably at least 85%, more preferably at least 90% and most preferably at least 95% sequence identity to the segment from amino acid residue 347 to 519 ScolE1d (SEQ ID NO: 26), (b-ix)' a segment having at least 80%, preferably at least 85%, more preferably at least 90% and most preferably at least 95% sequence identity to the segment from amino acid residue 345 to 517 ScolE1e (SEQ ID NO: 27), or (b-x)' a segment having at least 80%, preferably at least 85%, more preferably at least 90% and most preferably at least 95% sequence identity to the segment from amino acid residue 139 to 269 ScolMa (SEQ ID NO: 28);

or (c-i)' a segment having at least 90%, preferably at least 95% sequence similarity to the segment from amino acid residue 453 to 582 of ScolE2 (SEQ ID NO: 1), (c-ii)' a segment having at least 90%, preferably at least 95% sequence similarity to the segment from amino acid residue 501 to 584 of ScolE3 (SEQ ID NO: 2), (c-iii)' a segment having at least 90%, preferably at least 95% sequence similarity to the segment from amino acid residue 455 to 584 of ScolE7 (SEQ ID NO: 3), (c-iv)' a segment having at least 90%, preferably at least 95% sequence similarity to the segment from amino acid residue 306 to 478 of ScolE1a (SEQ ID NO: 4), (c-v)' a segment having at least 90%, preferably at least 95% sequence similarity to the segment from amino acid residue 350 to 522 of ScolE1b (SEQ ID NO: 5), (c-vi)' a segment having at least 90%, preferably at least 95% sequence similarity to the segment from amino acid residue 112 to 288 of Spst (SEQ ID NO: 6), (c-vii)' a segment having at least 90%, preferably at least 95% sequence similarity to the segment from amino acid residue 347 to 519 ScolE1c (SEQ ID NO: 25), (c-viii)' a segment having at least 90%, preferably at least 95% sequence similarity to the segment from amino acid residue 347 to 519 ScolE1d (SEQ ID NO: 26), (c-ix)' a segment having at least 90%, preferably at least 95% sequence similarity to the segment from amino acid residue 345 to 517 ScolE1e (SEQ ID NO: 27), or (c-x)' a segment having at least 90%, preferably at least 95% sequence similarity to the segment from amino acid residue 139 to 269 ScolMa (SEQ ID NO: 28);

or (d-i)' a segment having from 1 to 20, preferably from 1 to 15, more preferably from 1 to 10 amino acid substitutions, additions, insertions or deletions to the segment from amino acid residue 453 to 582 of ScolE2 (SEQ ID NO: 1), (d-ii)' a segment having from 1 to 20, preferably from 1 to 15, preferably from 1 to 10 amino acid substitutions, additions, insertions or deletions to the segment from amino acid residue 501 to 584 of ScolE3 (SEQ ID NO: 2), (d-iii)' a segment having from 1 to 20, preferably from 1 to 15, preferably from 1 to 10 amino acid substitutions, additions, insertions or deletions to the segment from amino acid residue 455 to 584 of ScolE7 (SEQ ID NO: 3), (d-iv)' a segment having from 1 to 30, preferably from 1 to 20, more preferably from 1 to 15, preferably from 1 to 10 amino acid substitutions, additions, insertions or deletions to the segment from amino acid residue 306 to 478 of ScolE1a (SEQ ID NO: 4), (d-v)' a segment having from 1 to 30, preferably from 1 to 20, more preferably from 1 to 15, preferably from 1 to 10 amino acid substitutions, additions, insertions or deletions to the segment from amino acid residue 350 to 522 of ScolE1b (SEQ ID NO: 5), (d-vi)' a segment having from 1 to 20, preferably from 1 to 15, more preferably from 1 to 10 amino acid substitutions, additions, insertions or deletions to the segment from amino acid residue 112 to 288 of Spst (SEQ ID NO: 6), (d-vii)' a segment having from 1 to 30, preferably from 1 to 20, more preferably from 1 to 15, preferably from 1 to 10 amino acid substitutions, additions, insertions or deletions to the segment from amino acid residue 347 to 519 ScolE1c (SEQ ID NO: 25), (d-viii)' a segment having from 1 to 30, preferably from 1 to 20, more preferably from 1 to 15, preferably from 1 to 10 amino acid substitutions, additions, insertions or deletions to the segment from amino acid residue 347 to 519 ScolE1d (SEQ ID NO: 26), (d-ix)' a segment having from 1 to 30, preferably from 1 to 20, more preferably from 1 to 15, preferably from 1 to 10 amino acid substitutions, additions, insertions or deletions to the segment from amino acid residue 345 to 517 ScolE1e (SEQ ID NO: 27), or (d-x)' a segment having from 1 to 30, preferably from 1 to 20, more preferably from 1 to 15, preferably from 1 to 10 amino acid substitutions, additions, insertions or deletions to the segment from amino acid residue 139 to 269 ScolMa (SEQ ID NO: 28).

In more preferred embodiments, the protein of the invention comprises a cytotoxic or catalytic domain that comprises, or consists of, any one of the sequence segments (a-i)' to (a-v)' or (a-vii)' to (a-x)'.

Herein, in any item (x-y)' (wherein x stands for any one of a, b, c, or d, and y stands for any roman numeral i to x), the prime ' indicates catalytic domains or segments. Items (x-y) lacking the prime indicates binding domains or segments. Items (x-y)" carrying the double prime" indicates translocation domains or segments. Among items (a) to (d), those of items (a), (b) and (d) are preferred and items (a) and (d) are more preferred. Similarly, among items (a)' to (d)', those of items (a)', (b)' and (d)' are preferred and items (a)' and (d)' are more preferred. Similarly, among items (a)" to (d)", those of items (a)", (b)" and (d)" are preferred and items (a)" and (d)" are more preferred:

Where the protein of the invention comprises a binding domain as defined herein and a catalytic domain as defined herein, any binding domain (or segment) as defined above may be combined with any catalytic domain (or segment). In a preferred embodiment, a binding domain of any sub-item from (i) to (x) is combined, in a protein of the invention, with a catalytic domain of sub-item (i)' to (x)', respectively (e.g. a binding domain of item (iii) is combined with a catalytic domain of item (iii)'), whereby the catalytic domain may be on the C-terminal side of the protein. In one embodiment, a binding domain of any item (a) to (d) is combined with a catalytic domain of item (a)' to (d)', respectively, whereby the catalytic domain may be on the C-terminal side of the protein.

In certain embodiments, the protein of the invention may be capable of exerting a cytotoxic effect on *Salmonella*, and the protein comprises at least any one of the following combinations of amino acid sequence segments, preferably in the given order from N-terminus to the C-terminus of the protein:

(α-i) the segment from amino acid residue 316 to 449 SEQ ID NO: 1 and the segment from amino acid residue 453 to 582 of SEQ ID NO: 1, (α-ii) the segment from amino acid residue 315 to 483 of ScolE3 of SEQ ID NO: 2 and the segment from amino acid residue 501 to 584 of SEQ ID NO: 2, (α-iii) the segment from amino acid residue 318 to 451 of SEQ ID NO: 3 and the segment from amino acid residue 455 to 584 of SEQ ID NO: 3, (α-iv) the segment from amino acid residue 174 to 297 of SEQ ID NO: 4 and the segment from amino acid residue 306 to 478 of SEQ ID NO: 4, (α-v) the segment from amino acid residue 198 to 322 of SEQ ID NO: 5 and the segment from amino acid residue 350 to 522 of SEQ ID NO: 5, (α-vi) a segment comprising at least 200 contiguous amino acid residues of SEQ ID NO: 6 including the segment from amino acid residue 112 to 288 of SEQ ID NO: 6, (α-vii) the segment from amino acid residue 195 to 319 of SEQ ID NO: 25 and the segment from amino acid residue 347 to 519 of SEQ ID NO: 25, (α-viii) the segment from amino acid residue 195 to 319 of SEQ ID NO: 26 and the segment from amino acid residue 347 to 519 of SEQ ID NO: 26, (α-ix) the segment from amino acid residue 193 to 317 of SEQ ID NO: 27 and the segment from amino acid residue 345 to 517 of SEQ ID NO: 27, or (α-x) the segment from amino acid residue 38 to 138 of SEQ ID NO: 28 and the segment from amino acid residue 139 to 269 of SEQ ID NO: 28;

or (β-i) a segment having at least 75% sequence identity to the segment from amino acid residue 316 to 449 of SEQ ID NO: 1 and a segment having at least 70% sequence identity to the segment from amino acid residue 453 to 582 of SEQ ID NO: 1, (β-ii) a segment having at least 70% sequence identity to the segment from amino acid residue 315 to 483 of SEQ ID NO: 2 and a segment having at least 70% sequence identity to the segment from amino acid residue 501 to 584 of SEQ ID NO: 2, (β-iii) a segment having at least 77% sequence identity to the segment from amino acid residue 318 to 451 of SEQ ID NO: 3 and a segment having at least 70% sequence identity to the segment from amino acid residue 455 to 584 of SEQ ID NO: 3, (β-iv) a segment having at least 70% sequence identity to the segment from amino acid residue 174 to 297 of SEQ ID NO: 4 and a segment having at least 70% sequence identity to the segment from amino acid residue 306 to 478 of SEQ ID NO: 4, (β-v) a segment having at least 70% sequence identity to the segment from amino acid residue 198 to 322 of SEQ ID NO: 5 and a segment having at least 70% sequence identity to the segment from amino acid residue 350 to 522 of SEQ ID NO: 5, (β-vi) a segment having at least 70% sequence identity to a segment comprising at least 200 contiguous amino acid residues of SEQ ID NO: 6 including a segment having at least 70% sequence identity to the segment from amino acid residue 112 to 288 of SEQ ID NO: 6, (β-vii) a segment having at least 70% sequence identity to the segment from amino acid residue 195 to 319 of SEQ ID NO: 25 and a segment having at least 70% sequence identity to the segment from amino acid residue 347 to 519 of SEQ ID NO: 25, (β-viii) a segment having at least 70% sequence identity to the segment from amino acid residue 195 to 319 of SEQ ID NO: 26 and a segment having at least 70% sequence identity to the segment from amino acid residue 347 to 519 of SEQ ID NO: 26, (β-ix) a segment having at least 70% sequence identity to the segment from amino acid residue 193 to 317 of SEQ ID NO: 27 and a segment having at least 70% sequence identity to the segment from amino acid residue 345 to 517 of SEQ ID NO: 27, (β-x) a segment having at least 70% sequence identity to the segment from amino acid residue 38 to 138 of SEQ ID NO: 28 and a segment having at least 70% sequence identity to the segment from amino acid residue 139 to 269 of SEQ ID NO: 28; or (χ-i) a segment having at least 85% sequence similarity to the segment from amino acid residue 316 to 449 of SEQ ID NO: 1 and a segment having at least 80% sequence similarity to the segment from amino acid residue 453 to 582 of SEQ ID NO: 1, (χ-ii) a segment having at least 80% sequence similarity to the segment from amino acid residue 315 to 483 of SEQ ID NO: 2 and a segment having at least 80% sequence similarity to the segment from amino acid residue 501 to 584 of SEQ ID NO: 2, (χ-iii) a segment having at least 85% sequence similarity to the segment from amino acid residue 318 to 451 of SEQ ID NO: 3 and a segment having at least 80% sequence similarity to the segment from amino acid residue 455 to 584 of SEQ ID NO: 3, (χ-iv) a segment having at least 80% sequence similarity to the segment from amino acid residue 174 to 297 of SEQ ID NO: 4 and a segment having at least 80% sequence similarity to the segment from amino acid residue 306 to 478 of SEQ ID NO: 4, (χ-v) a segment having at least 80% sequence similarity to the segment from amino acid residue 198 to 322 of SEQ ID NO: 5 and a segment having at least 80% sequence similarity to the segment from amino acid residue 350 to 522 of SEQ ID NO: 5, (χ-vi) a segment having at least 80% sequence similarity to a segment comprising at least 200 contiguous amino acid residues of SEQ ID NO: 6 including a segment having at least 80% sequence similarity to the segment from amino acid residue 112 to 288 of SEQ ID NO: 6, (χ-vii) a segment having at least 80% sequence similarity to the segment from amino acid residue 195 to 319 of SEQ ID NO: 25 and a segment having at least 80% sequence similarity to the segment from amino acid residue 347 to 519 of SEQ ID NO: 25, (χ-viii) a segment having at least 80% sequence similarity to the segment from amino acid residue 195 to 319 of SEQ ID NO: 26 and a segment having at least 80% sequence similarity to the segment from amino acid residue 347 to 519 of SEQ ID NO: 26, (χ-ix) a segment having at least 80% sequence similarity to the segment from amino acid residue 193 to 317 of SEQ ID NO: 27 and a segment having at least 80% sequence similarity to the segment from amino acid residue 345 to 517 of SEQ ID NO: 27, or (χ-x) a segment having at least 80% sequence similarity to the segment from amino acid residue 38 to 138 of SEQ ID NO: 28 and a segment having at least 80% sequence similarity to the segment from amino acid residue 139 to 269 of SEQ ID NO: 28; or (δ-i) a segment having from 1 to 25 amino acid substitutions, additions, insertions or deletions to the segment from amino acid residue 316 to 449 of SEQ ID NO: 1 and a segment having from 1 to 30 amino acid substitutions, additions, insertions or deletions to the segment from amino acid residue 453 to 582 of SEQ ID NO: 1, (δ-ii) a segment having from 1 to 40 amino acid substitutions, additions, insertions or deletions to the segment from amino acid residue 315 to 483 of SEQ ID NO: 2 and a segment having from 1 to 30 amino acid substitutions, additions, insertions or deletions to the segment from amino acid residue 501 to 584 of SEQ ID NO: 2, (δ-iii) a segment having from 1 to 30 amino acid substitutions, additions, insertions or deletions to the segment from amino acid residue 318 to 451 of SEQ ID NO: 3 and a segment having from 1 to 30 amino acid substitutions, additions, insertions or deletions to the segment from amino acid residue 455 to 584 of SEQ ID NO: 3, (δ-iv) a segment having from 1 to 40 amino acid substitutions, additions, insertions or deletions to the segment from amino acid residue 174 to 297 of SEQ ID NO: 4 and a segment having from 1 to 40 amino acid substitutions, additions, insertions or deletions to the segment from amino acid residue 306 to 478 of SEQ ID NO: 4, (δ-v) a segment having from 1 to 40 amino acid substitutions, additions, insertions or deletions to the segment from amino acid residue 198 to 322 of SEQ ID NO: 5 and a segment having from 1 to 40 amino acid substitutions, additions, insertions or deletions to the segment from amino acid residue 350 to 522 of SEQ ID NO: 5, (δ-vi) a segment having from 1 to 40 amino acid substitutions, additions, insertions or deletions to a segment comprising at least 200 contiguous amino acid residues of SEQ ID NO: 6 including a segment having from 1 to 30 amino acid substitutions, additions, insertions or deletions to the segment from amino acid residue 112 to 288 of SEQ ID NO: 6, (δ-vii) a segment having from 1 to 40 amino acid substitutions, additions, insertions or deletions to the segment from amino acid residue 195 to 319 of SEQ ID NO: 25 and a segment having from 1 to 40 amino acid substitutions, additions, insertions or deletions to the segment from amino acid residue 347 to 519 of SEQ ID NO: 25, (δ-viii) a segment having from 1 to 40 amino acid substitutions, additions, insertions or deletions to the segment from amino acid residue 195 to 319 of SEQ ID NO: 26 and a segment having from 1 to 40 amino acid substitutions, additions, insertions or deletions to the segment from amino acid residue 347 to 519 of SEQ ID NO: 26, (δ-ix) a segment having from 1 to 40 amino acid substitutions, additions, insertions or deletions to the segment from amino acid residue 193 to 317 of SEQ ID NO: 27 and a segment having from 1 to 40 amino acid substitutions, additions, insertions or deletions to the segment from amino acid residue 345 to 517 of SEQ ID NO: 27, or (δ-x) a segment having from 1 to 30 amino acid substitutions, additions, insertions or deletions to the segment from amino acid residue 38 to 138 of SEQ ID NO: 28 and a segment having from 1 to 40 amino acid substitutions, additions, insertions or deletions to the segment from amino acid residue 139 to 269 of SEQ ID NO: 28.

All these embodiments may be combined with the preferred values for minimum sequence identities or similarities or preferred numbers of amino acid substitutions, additions, insertions or deletions of the respective segments defined herein.

Item (4) above defines translocation domains and derivatives thereof of ScolE2, ScolE3 ScolE7, ScolE1a, ScolE1b, ScolE1c, ScolE1d, ScolE1e and ScolMa. The definitions of the translocation domains and derivatives thereof may be combined with the definitions of the cytotoxic and binding domains or derivatives thereof. The definitions of the translocation domains and derivatives thereof may be combined with the definitions of the protein as inter alia defined below.

A protein of the invention may have a binding domain (or binding segment) according to any one of items (a-i) to (a-x) or according to any of the derivatives of items (b-i) to (b-x), (c-i) to (c-x) or (d-i) to (d-x). Any such binding domain may be combined with a catalytic/cytotoxic domain according to any one items (a-i)' to (a-x)', (b-i)' to (b-x)', (c-i)' to (c-x)' or (d-i)' to (d-x)'. The domain structure of the salmocins allows establishing artificial salmocins wherein domains from different salmocins of the invention, or derivatives thereof as defined herein, are combined to form novel salmocins (chimeric salmocins). In such chimeric salmocins, the domain sequence of natural salmocins, from the N-terminus to the C-terminus, of a translocation domain (if present), a binding domain, and a catalytic or activity domain may or may not be maintained; preferably, it is maintained. Thus, the protein of the invention may comprise, from the N-terminus to the C-terminus, a binding domain of any one of items (a-i) to (a-x), or according to any of the derivatives of items (b-i) to (b-x), (c-i) to (c-x) or (d-i) to (d-x), and a catalytic domain (segment) of any one of items (a-i)' to (a-x)', (b-i)' to (b-x)', (c-i)' to (c-x)' or (d-i)' to (d-x)'. In a preferred embodiment, the protein of the invention may comprise, from the N-terminus to the C-terminus, a translocation domain of any one of items (a-i)" to (a-ix)", (b-i)" to (b-ix)", (c-i)" to (c-ix)" or (d-i)" to (d-ix)", a binding domain of any one of items (a-i) to (a-x), or according to any of the derivatives of items (b-i) to (b-x), (c-i) to (c-x) or (d-i) to (d-x), and a catalytic domain (segment) of any one of items (a-i)' to (a-x)', (b-i)' to (b-x)', (c-i)' to (c-x)' or (d-i)' to (d-x)'.

Within the three cytotoxic activities of the salmocins nuclease, pore-forming and muramidase (Table 1), domains may be exchanged between salmocins of the same type of cytotoxic activity. For example, a new salmocin with RNase-type cytotoxicity may be formed from the translocation and binding domains of ScolE2 or ScolE7 (or derivatives of these domains) and the cytotoxic domain of ScolE3. Preferably, however, a binding domain of any one of sub-items (i) to (x) is combined with a catalytic domain of any one of sub-items (i)' to (x)', respectively, for increased similarity to natural salmocins, preferably each of any of items (a) to (d). More preferably, however, a binding domain of any one of sub-items (i) to (v) or (vii) to (x) may be combined with a catalytic domain of any one of sub-items (i)' to (v)' or (vii)' to (x)', respectively, and a translocation domain of any one of sub-items (i)" to (v)" or (vii)" to (x)", respectively, preferably of any of items (a) to (d), for increased similarity to natural salmocins.

In another embodiment, a binding domain of sub-items (i) to (v) is combined with a catalytic domain of sub-items (i)' to (vi)' (preferably (i)' to (v)'), respectively, for increased similarity to natural salmocins, preferably each of any of items (a) to (d). In a further embodiment, a binding domain of any one of sub-items (i) to (v) is combined with a catalytic domain of any one of sub-items (i)' to (v)', respectively, and a translocation domain of any one of sub-items (i)" to (v)", respectively, preferably of any of items (a) to (d), for increased similarity to natural salmocins.

The invention also provides a protein that is preferably capable of exerting a cytotoxic effect on *Salmonella*, said protein comprising or consisting of the following amino acid sequences:

(A-i) SEQ ID NO: 1, (A-ii) SEQ ID NO: 2, (A-iii) SEQ ID NO: 3, (A-iv) SEQ ID NO: 4, (A-v) SEQ ID NO: 5, (A-vi) SEQ ID NO: 6, (A-vii) SEQ ID NO: 25, (A-viii) SEQ ID NO: 26, (A-ix) SEQ ID NO: 27, or (A-x) SEQ ID NO: 28;

or (B-i) an amino acid sequence having at least 75%, preferably at least 80%, more preferably at least 85%, even more preferably at least 90%, and even more preferably at least 95% sequence identity to the amino acid sequence of SEQ ID NO: 1, (B-ii) an amino acid sequence having at least 80%, preferably at least 85%, more preferably at least 93%, and even more preferably at least 96% sequence identity to the amino acid sequence of SEQ ID NO: 2, (B-iii) an amino acid sequence having at least 80%, preferably at least 85%, more preferably at least 90%, and even more preferably at least 95% sequence identity to the amino acid sequence of SEQ ID NO: 3, (B-iv) an amino acid sequence having at least 70%, preferably at least 80%, more preferably at least 85%, even more preferably at least 90%, and even more preferably at least 95% sequence identity to the amino acid sequence of SEQ ID NO: 4, (B-v) an amino acid sequence having at least 70%, preferably at least 80%, more preferably at least 85%, even more preferably at least 90%, and even more preferably at least 95% sequence identity to the amino acid sequence of SEQ ID NO: 5, (B-vi) an amino acid sequence having at least 70%, preferably at least 80%, more preferably at least 85%, even more preferably at least 90%, and even more preferably at least 95% sequence identity to the amino acid sequence of SEQ ID NO: 6, (B-vii) an amino acid sequence having at least 70%, preferably at least 80%, more preferably at least 85%, even more preferably at least 90%, and even more preferably at least 95% sequence identity to the amino acid sequence of SEQ ID NO: 25, (B-viii) an amino acid sequence having at least 70%, preferably at least 80%, more preferably at least 85%, even more preferably at least 90%, and even more preferably at least 95% sequence identity to the amino acid sequence of SEQ ID NO: 26, (B-ix) an amino acid sequence having at least 70%, preferably at least 80%, more preferably at least 85%, even more preferably at least 90%, and even more preferably at least 95% sequence identity to the amino acid sequence of SEQ ID NO: 27, or (B-x) an amino acid sequence having at least 70%, preferably at least 80%, more preferably at least 85%, even more preferably at least 90%, and even more preferably at least 95% sequence identity to the amino acid sequence of SEQ ID NO: 28;

or (C-i) an amino acid sequence having at least 85%, preferably at least 90%, and more preferably at least 95% sequence similarity to the amino acid sequence of SEQ ID NO: 1, (C-ii) an amino acid sequence having at least 85%, preferably at least 90%, and more preferably at least 95% sequence similarity to the amino acid sequence of SEQ ID NO: 2, (C-iii) an amino acid sequence having at least 85%, preferably at least 90%, and more preferably at least 95% sequence similarity to the amino acid sequence of SEQ ID NO: 3, (C-iv) an amino acid sequence having at least 80%, preferably at least 85%, more preferably at least 90%, and even more preferably at least 95% sequence similarity to the amino acid sequence of SEQ ID NO: 4, (C-v) an amino acid sequence having at least 80%, preferably at least 85%, more preferably at least 90%, and even more preferably at least 95% sequence similarity to the amino acid sequence of SEQ ID NO: 5, (C-vi) an amino acid sequence having at least 80%, preferably at least 85%, more preferably at least 90%, and even more preferably at least 95% sequence similarity to the amino acid sequence of SEQ ID NO: 6, (C-vii) an amino acid sequence having at least 80%, preferably at least 85%, more preferably at least 90%, and even more preferably at least 95% sequence similarity to the amino acid sequence of SEQ ID NO: 25, (C-viii) an amino acid sequence having at least 80%, preferably at least 85%, more preferably at least 90%, and even more preferably at least 95% sequence similarity to the amino acid sequence of SEQ ID NO: 26, (C-ix) an amino acid sequence having at least 80%, preferably at least 85%, more preferably at least 90%, and even more preferably at least 95% sequence similarity to the amino acid sequence of SEQ ID NO: 27, or (C-x) an amino acid sequence having at least 80%, preferably at least 85%, more preferably at least 90%, and even more preferably at least 95% sequence similarity to the amino acid sequence of SEQ ID NO: 28;

or (D-i) an amino acid sequence having from 1 to 40, preferably from 1 to 30, more preferably from 1 to 20, and most preferably from 1 to 10 amino acid substitutions, additions, insertions or deletions to the amino acid sequence of SEQ ID NO: 1, (D-ii) an amino acid sequence having from 1 to 40, preferably from 1 to 30, more preferably from 1 to 20, and most preferably from 1 to 10 amino acid substitutions, additions, insertions or deletions to the amino acid sequence of SEQ ID NO: 2, (D-iii) an amino acid sequence having from 1 to 40, preferably from 1 to 30, more preferably from 1 to 20, and most preferably from 1 to 10 amino acid substitutions, additions, insertions or deletions to the amino acid sequence of SEQ ID NO: 3, (D-iv) an amino acid sequence having from 1 to 40, preferably from 1 to 30, more preferably from 1 to 20, and most preferably from 1 to 10 amino acid substitutions, additions, insertions or deletions to the amino acid sequence of SEQ ID NO: 4, (D-v) an amino acid sequence having from 1 to 40, preferably from 1 to 30, more preferably from 1 to 20, and most preferably from 1 to 10 amino acid substitutions, additions, insertions or deletions to the amino acid sequence of SEQ ID NO: 5, (D-vi) an amino acid sequence having from 1 to 40, preferably from 1 to 30, more preferably from 1 to 20, and most preferably from 1 to 10 amino acid substitutions, additions, insertions or deletions to the amino acid sequence of SEQ ID NO: 6, (D-vii) an amino acid sequence having from 1 to 40, preferably from 1 to 30, more preferably from 1 to 20, and most preferably from 1 to 10 amino acid substitutions, additions, insertions or deletions to the amino acid sequence of SEQ ID NO: 25, (D-viii) an amino acid sequence having from 1 to 40, preferably from 1 to 30, more preferably from 1 to 20, and most preferably from 1 to 10 amino acid substitutions, additions, insertions or deletions to the amino acid sequence of SEQ ID NO: 26, (D-ix) an amino acid sequence having from 1 to 40, preferably from 1 to 30, more preferably from 1 to 20, and most preferably from 1 to 10 amino acid substitutions, additions, insertions or deletions to the amino acid sequence of SEQ ID NO: 27, or (D-x) an amino acid sequence having from 1 to 40, preferably from 1 to 30, more preferably from 1 to 20, and most preferably from 1 to 10 amino acid substitutions, additions, insertions or deletions to the amino acid sequence of SEQ ID NO: 28;

or (E-i) an amino acid sequence comprising or consisting of at least 470, preferably at least 525, more preferably at least 555, contiguous amino acid residues of SEQ ID NO: 1, (E-ii) an amino acid sequence comprising or consisting of at least 470, preferably at least 525, more preferably at least 555, contiguous amino acid residues of SEQ ID NO: 2, (E-iii) an amino acid sequence comprising or consisting of at least 470, preferably at least 525, more preferably at least 555, contiguous amino acid residues of SEQ ID NO: 3, (E-iv) an amino acid sequence comprising or consisting of at least 390, preferably at least 435, more preferably at least 460, contiguous amino acid residues of SEQ ID NO: 4, (E-v) an amino acid sequence comprising or consisting of at least 425, preferably at least 475, more preferably at least 500, contiguous amino acid residues of SEQ ID NO: 5, (E-vi) an amino acid sequence comprising or consisting of at least 250, preferably at least 270, more preferably at least 282, contiguous amino acid residues of SEQ ID NO: 6, (E-vii) an amino acid sequence comprising or consisting of at least 425, preferably at least 475, more preferably at least 500, contiguous amino acid residues of SEQ ID NO: 25, (E-viii) an amino acid sequence comprising or consisting of at least 425, preferably at least 475, more preferably at least 500, contiguous amino acid residues of SEQ ID NO: 26, (E-ix) an amino acid sequence comprising or consisting of at least 425, preferably at least 475, more preferably at least 500, contiguous amino acid residues of SEQ ID NO: 27, or (E-x) an amino acid sequence comprising or consisting of at least 215, preferably at least 240, more preferably at least 260, contiguous amino acid residues of SEQ ID NO: 28.

In another embodiment, the invention provides a protein that is preferably capable of exerting a cytotoxic effect on *Salmonella*, wherein the amino acid sequence of said protein is as defined any one of items (A-i) to (A-x), (B-i) to (B-x), (C-i) to (C-x), (D-i) to (D-x) or (E-i) to (E-x).

The above definitions of the proteins with respect to the entire sequence of SEQ ID NOs 1 to 6 or 25 to 28 may be combined with the above definitions of the protein based on one or more particular domains such as a binding and/or catalytic or cytotoxic domains and/or translocation domain where available.

Herein, the determination of sequence identities and similarities is done using Align Sequences Protein BLAST (BLASTP 2.6.1+) (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.).

The derivatives of domains and/or protein of the invention as defined above in items (b) to (d), (b)' to (d)', (b)" to (d)", or items (B) to (D) or (E) may, notwithstanding the sequence varieties allowed by the embodiments defined above, preserve amino acid residues as defined in the following. In preferred embodiments, the amino acid residue(s) corresponding to residue 125 of SEQ ID NO: 4 is Asn or Ser;
residue 145 of SEQ ID NO: 4 is Lys or Arg;
residue 151 of SEQ ID NO: 4 is Ala or Gly;
residue 154 of SEQ ID NO: 4 is Ala, Ser or Gly;
residue 155 of SEQ ID NO: 4 is Phe, Leu or Ile;
residue 158 of SEQ ID NO: 4 is Ala or Gly;
residue 163 of SEQ ID NO: 4 is Glu, Asp, Ser, Leu or Ile, preferably Glu, Asp, or Ser;
residue 165 of SEQ ID NO: 4 is Ala, Thr, Val or Ser, preferably Ala, Thr, or Val;
residue 167 of SEQ ID NO: 4 is Arg;
residue 172 of SEQ ID NO: 4 is Thr, Ala, or Ser;
residue 175 of SEQ ID NO: 4 is Gln;
residue 176 of SEQ ID NO: 4 is Val or Leu;
residue 178 of SEQ ID NO: 4 is Gln or Leu, preferably Gln;
residue 181 of SEQ ID NO: 4 is Glu or Asp, preferably Glu;
residue 184 of SEQ ID NO: 4 is Arg or Gln, preferably Arg;
residue 192 of SEQ ID NO: 4 is Ala or Thr;
residue 195 of SEQ ID NO: 4 is Ala or Val;
residue 196 of SEQ ID NO: 4 is Glu or Gln, preferably Glu;
residue 198 of SEQ ID NO: 4 is Ala or Thr;
residue 209 of SEQ ID NO: 4 is Leu or Ile, preferably Leu;
residue 273 of SEQ ID NO: 4 is Leu or Ile;
residue 280 of SEQ ID NO: 4 Arg;
residue 283 of SEQ ID NO: 4 Lys;
residue 286 of SEQ ID NO: 4 Gln or Lys;
residue 290 of SEQ ID NO: 4 Ala, or Thr;
residue 299 of SEQ ID NO: 4 Asp, Asn or Glu;
residue 301 of SEQ ID NO: 4 Leu;
residue 302 of SEQ ID NO: 4 Asn or Asp;
residue 346 of SEQ ID NO: 4 Asn, Asp, or Glu;
residue 363 of SEQ ID NO: 4 Lys, Asn or Arg;
residue 364 of SEQ ID NO: 4 Lys or Gln.

The wording "amino acid residue(s) corresponding to the amino acid residue . . . " refers to the alignments shown in FIGS. 20A-C and FIG. 26 and means amino acid residues in SEQ ID NO: 4 (ScolE1a) or amino acid residues in SEQ ID NO: 1 to 3, 5, 6, 25, 26 or 27 having the same position (i.e. written on top of each other) in said alignment as the indicated amino acid residues in SEQ ID NO: 4 (ScolE1a).

In derivatives of ScolE1a and ScolE1b, and/or in derivative domains of ScolE1a and ScolE1b, corresponding amino acid residues that are the same in the alignment of ScolE1a and ScolE1b of FIG. 20 may be the same amino acid residue as in ScolE1a and ScolE1b; and/or corresponding to amino acid residues that differ among ScolE1a and ScolE1b, some or all such differing amino acid residues may be an amino acid residue as in ScolE1a or in ScolE1b (but not another amino acid residue).

In derivatives of ScolE2 and ScolE7, and/or in derivative domains of ScolE2 and ScolE7, corresponding amino acid residues that are the same in the alignment of ScolE2 and ScolE7 of FIG. 20 may be the same amino acid residue as in ScolE2 or ScolE7; and/or corresponding to amino acid residues that differ among ScolE2 and ScolE7, some or all such differing amino acid residues may be an amino acid residue as in ScolE2 or ScolE7 (but not another amino acid residue).

A salmocin according to the invention may comprise an additional N- or C-terminal amino acid sequence stretch such as purification tags, e.g. as a His-tag of 6 or more contiguous histidine residues; the derivative has, preferably, no N-terminal amino acid residue addition.

The protein (salmocin) of the invention is preferably capable of exerting a cytotoxic effect on *Salmonella*, notably of *Salmonella enterica* and more preferably *Salmonella enterica* ssp. *enterica*. Whether this condition is fulfilled can be tested experimentally using a radial diffusion assays via spot-on-lawn-method. The cytotoxicity of a protein to be tested against *Salmonella enterica* is such that it and the protein of SEQ ID NO: 1 produce spots free of viable bacteria of *Salmonella enterica* ssp. *enterica* serovar Newport strain ATCC® 6962™* of the same diameter 12 hours after spotting 5 microliters of a solution of said protein to be tested and the protein of SEQ ID NO: 1 onto a softagar overlay plate seeded with 0.14 mL bacterial solution of $1\times10^7$ cfu/mL per $cm^2$ of the sensitive *Salmonella enterica* strain and subsequent incubation of the agar plate at 37° C., wherein the concentration of the protein to be tested is at most 5 times that of the comparative solution of the protein SEQ ID NO: 1. In a preferred embodiment, the point of reference is not the protein of SEQ ID NO: 1, but the protein of SEQ ID NO: 4 or 5 under otherwise identical conditions.

The composition of the invention comprises a protein (salmocin) as described above and optionally further components as the case requires such as a carrier. The composition preferably comprises ScolE1a and/or ScolE1b or a derivative thereof as described above and optionally further components as the case requires such as a carrier. The composition may comprise one or more different proteins (salmocins) as defined herein, such as two, three or four different proteins (salmocins) as defined herein. "Different" means that the proteins differ in at least one amino acid residue. The composition may comprise two, three or more salmocins from the same class represented by any one of items (i) to (x) above or, preferably, from different classes represented by any one of items (i) to (x) above. The composition may comprise at least a protein of class (i) and a protein of class (iv) or (v). The composition may further comprise one or more *E. coli* colicin or a derivative thereof e.g. as described in EP 3 097 783 A1, e.g. for concomitantly controlling pathogenic *E. coli* such as EHEC.

As the protein of the invention is preferably produced by expression in plants or cells thereof, the composition may be a plant material or extract thereof, wherein the plant material is a material from a plant having expressed the protein, preferably *Nicotiana* or an edible plant having expressed said protein. An extract of plant material is an aqueous solution containing water-soluble proteins including a salmocin of the invention that is present or expressed in said plant material, or a dried product of such aqueous solution. The extract preferably has water-insoluble components of the plant material removed e.g. by filtration or centrifugation. The plant material may be a material from a plant selected from the group consisting of spinach, chard, beetroot, carrot, sugar beet, leafy beet, amaranth, *Nicotiana*, and/or said plant material is one or more leaves, roots, tubers, or seeds, or a crushed, milled or comminuted product of said leaves, roots, tubers, or seeds.

The composition or said extract from a plant material may be a solid or liquid composition, such as a solution or a dispersion, containing said salmocin(s). The liquid composition may be aqueous, such as an aqueous solution. The concentration of said protein in said aqueous dispersion or solution may be from 0.0001 to 1 mg/ml, preferably from 0.001 to 0.1 mg/ml, more preferably from 0.005 to 0.05 mg/ml. If more than one salmocin capable of exerting a cytotoxic effect on *Salmonella* is employed, these concentrations relate to the total concentration of all such salmocins.

The aqueous solution may, apart from the one or more salmocin, contain a buffer. The buffer may be an inorganic or organic acid or salts thereof. An example of an inorganic acid is phosphoric acid or salts thereof. Examples of the organic acid are HEPES, acetic acid, succinic acid, tartaric acid, malic acid, benzoic acid, cinnamic acid, glycolic acid, lactic acid, citric acid, and ascorbic acid. Preferred organic acids are malic acid, lactic acid, citric acid, and ascorbic acid. The pH of the solution may generally be from 4 to 8, preferably from 5 to 8, more preferably from 6.0 to 7.5. If the object to which the composition is applied is meat, the pH of the solution may generally be from 4 to 8, preferably from 4.5 to 7, more preferably from 5.0 to 6.5, and even more preferably from 5.0 to 6.0. Further, the solution may contain isotonic agents such as glycerol or a salt. A preferred salt to be used is sodium chloride. The aqueous solution containing the one or more salmocin may be a buffered aqueous solution that may contain further solutes e.g. salts such as from 50 to 400 mM NaCl, preferably from 100 to 200 mM NaCl. The aqueous solution may further contain a sulfhydryl compound such as dithiothreitol (DTT), dithioerythritol, thioethanol or glutathione, preferably DTT. The concentration of the total of sulfhydryl compounds in the aqueous solution may be from 1 to 50 mM, preferably from 2 to 20 mM and more preferably from 4 to 10 mM.

If the composition of the invention is a solid composition, it may be a powder such as a lyophilized solid composition obtained by lyophilization of the extract or solution mentioned above. The powder may contain additional solid components such as those mentioned above for the aqueous solution. Before use, it may be reconstituted with a suitable liquid, such as water or buffer. The solid composition may contain buffer, salts or other components as mentioned above, such that the concentrations given above may be achieved upon reconstitution or dissolution of the solid composition.

Examples of carriers of the composition are solvents such as water or an aqueous buffer (as described above), salts, sugars such as monosaccharides and disaccharides, sugar alcohols, and other carriers such as those known from pharmaceutical compositions. Examples of the latter are starch, cellulose and other proteins such as albumin. Examples of sugars are glucose, fructose, lactose, sucrose, and maltose.

The composition of the invention may contain at least 10, preferably at least 20, more preferably at least 30, even more preferably at least 50, even more preferably at least 75% by weight of one or more salmocins of the invention based on the total weight of protein in the composition. The content of salmocin(s) in the composition may be determined by subjecting the composition to SDS-PAGE and analyzing the obtained gel, after staining, by determining the intensity of bands on the gel. Thereby, intensity of bands due to salmocins can be determined in relation to the sum of intensities of bands due to all proteins in the composition. The total protein content in the composition may be determined using the well-known Bradford protein assay.

In one embodiment, the composition of the invention is a pharmaceutical composition. The pharmaceutical composition may, apart from one or more salmocin(s) of the invention, optionally contain an *E. coli* colicin, and/or one or more suitable pharmaceutically acceptable excipients.

The invention provides a method of preventing or reducing infection or contamination of an object with *Salmonella*, comprising contacting said object with one or more proteins (salmocins) as described above or a composition as described above. The object may be a surface of any non-organic object or an organic object such as food. Contamination of an object with *Salmonella* means adhesion of viable *Salmonella* cells to the object. Reducing contamination with *Salmonella* means reducing the number of viable *Salmonella* cells adhering to the object. Determining contamination of objects with *Salmonella* is part of the general knowledge. For example, dilution plating of solutions or dispersions of homogenized food as done in the Examples or dilution plating of a rinsing solution of other objects may be used, followed by counting bacterial colonies. Preferably, the object is food or animal feed. The food may be meat such as whole poultry carcasses, raw meat, cooked meat, and minced meat, eggs such raw eggs, whole eggs, peeled cooked eggs, scrambled eggs, fried eggs, raw fruit, or raw or cooked vegetable.

For treating or contacting the object with the protein or composition, a solution of the protein or a liquid composition as described above is generally contacted with the object. For example, said object is sprayed with an aqueous solution or is immersed into the aqueous solution as a composition of the invention. The object may be immersed for at least 10 seconds, preferably for at least 1 minute, preferably for at least 5 minutes into the aqueous solution. Contacting the object with a liquid composition helps to distribute the composition over the surface of the object. Where sufficiently even distribution can be achieved, it is possible to contact the object with a solid composition according to the invention, e.g. upon mincing meat.

The invention also provides a method of treating infection with *Salmonella* of a subject in need thereof, comprising administering to said subject one or more proteins (salmocins) as described above or a composition as described above. The subject may be a human being or a mammal such as a farm animal. Examples of farm animals are poultry and cattle. Generally, a liquid or solid pharmaceutical composition containing the salmocin(s) and optionally further components as described above is prepared for administration to the animal or human. Liquid compositions may be aqueous solutions as described above. Solid compositions may be powder containing the at least one salmocin(s) e.g. in freeze-dried form, or tablets obtained from such powder or capsules filled with such powder. Administration may be oral. In this case, the pharmaceutical preparation is one that allows passage through the stomach without being attacked by the acid medium in the stomach. The salmocin(s) should then be released from the pharmaceutical preparation in the intestine. Such pharmaceutical preparations are known in the art. Examples are tablets and capsules resistant to the acid medium in the stomach. It is further possible to administer orally a biological material such as *E. coli* or plant material containing expressed salmocin(s) to a patient. The salmocin(s) may be administered to a human adult in amounts of 1 mg to 1000 mg per day, preferably of from 10 mg to 250 mg per day to a human patient. Such amounts may also be administered to an animal. In a probiotic approach, a patient may be treated by administering to the patient a genetically-modified microorganism expressing the at least one salmocin(s). The genetically-modified microorganism may be a genetically-modified non-pathogenic *E. coli* or a lactic acid-producing microorganism as commonly employed in fermentation of milk products. Examples of lactic acid-producing microorganism are bacteria from the genera *Lactobacillus* such as *Lactobacillus lactis* and *Bifidobacterium* such as *Bifidobacterium bifidum* or *Bifidobacterium breve*. Another route of administration is by injection into the blood stream of a patient for preventing infection with *Salmonella*. For this purpose, the salmocin(s) may be dissolved in a physiological saline and the solution be sterilized.

In the methods described above, the *Salmonella* is *Salmonella enterica*, preferably *Salmonella enterica* ssp. *enterica*.

Salmocins ScolE1a and ScolE1b have a particularly wide activity against many different serovars of *Salmonella*, notably of *Salmonella enterica*, preferably of *Salmonella enterica* ssp. *enterica*, as demonstrated in the Examples below. Therefore, ScolE1a and ScolE1b, or derivatives thereof, are preferably used for treating infection or for preventing or reducing contamination with any *Salmonella enterica*, preferably any *Salmonella enterica* ssp. *enterica*. Salmocins E2, E3, E7 and Spst also have a wide activity against target *Salmonella*. However, ScolE2 and derivatives thereof may be preferably used against strains 1, 3, 4, 15, 20, 22 to 30 as defined in Tables 5A and 5B. ScolE3 and derivatives thereof may be preferably used against strains 1, 3, 4, 17, and 20 to 25 as defined in Tables 5A and 5B. ScolE7 and derivatives thereof may be preferably used against strains 1, 3, 4, 5, 15, 20, 22 to 30 and 32 as defined in Tables 5A and 5B.

A salmocin according to the invention may be produced by known methods of protein expression in a standard expression system. For producing the salmocin, a nucleotide sequence encoding it may be expressed in a suitable host organism. Methods usable for producing and purifying a protein of interest have been described in the prior art and any such methods may be used. An *E. coli* expression system as generally known in the art may, for example, be used. If a eukaryotic expression system is used, one or more introns may be inserted in the coding sequence of the salmocin to prevent toxicity on the bacterial organism used for cloning.

Particularly efficient expression methods are plant expression systems that are also known in the prior art. Plant expression systems usable for expressing a salmocin according to the invention are described in the Examples. A possible way of achieving expression of a nucleotide sequence of interest in plants is the use of self-replicating (viral) replicons containing the nucleotide sequence encoding the salmocin. The coding sequence of the salmocin may be codon optimized for expression in plants or in the particular plant used as expression host. Plant viral expression systems have been described in many publications, such as in WO2012019660, WO2008028661, WO2006003018, WO2005071090, WO2005049839, WO2006012906, WO02101006, WO2007137788 or WO02068664 and many more publications are cited in these documents. Various methods for introducing a nucleic acid molecule, such as a DNA molecule, into a plant or plant part for transient expression are known. Agrobacteria may be used for transfecting plants with the nucleic acid molecule (vector) or nucleic acid construct e.g. by agroinfiltration or spraying with agrobacterial suspensions. For references, see WO 2012019660, WO 2014187571, or WO 2013149726.

In embodiments wherein strong expression of a salmocin as a protein of interest is desired, a nucleic acid construct containing a nucleotide sequence encoding the salmocin may encode a viral vector that can replicate in plant cells to form replicons of the viral vector. In order to be replicating, the viral vector and the replicons may contain an origin of replication that can be recognized by a nucleic acid polymerase present in plant cells, such as by the viral polymerase expressed from the replicon. In case of RNA viral vectors (referred to as "RNA replicons"), the replicons may be formed by transcription under the control of a promoter active in plant cells, from the DNA construct after the latter has been introduced into plant cell nuclei. In case of DNA replicons, the replicons may be formed by recombination between two recombination sites flanking the sequence encoding the viral replicon in the DNA construct, e.g. as described in WO00/17365 and WO 99/22003. If the replicon is encoded by the DNA construct, RNA replicons are preferred. Use of DNA and RNA viral vectors (DNA or RNA replicons) has been extensively described in the literature over the years. Some examples are the following patent publications: WO2008028661, WO2007137788, WO 2006003018, WO2005071090, WO2005049839, WO02097080, WO02088369, WO02068664. Examples of DNA viral vectors are those based on geminiviruses. For the present invention, viral vectors or replicons based on plant RNA viruses, notably those based on plus-sense single-stranded RNA viruses may be preferably used. Accordingly, the viral replicon may be a plus-sense single-stranded RNA replicon. Examples of such viral vectors are those based on tobacco mosaic virus (TMV) and potexvirus X (PVX). "Based on" means that the viral vector uses the replication system such as the replicase and/or other proteins involved in replication of these viruses. Potexvirus-based viral vectors and expression systems are described in EP2061890 or WO2008/028661.

The salmocin may be expressed in a multi-cellular plant or a part thereof, notably a higher plant or parts thereof. Both monocot and dicot (crop) plants can be used. Common plants usable for expressing the protein of interest include *Nicotiana benthamiana, Nicotiana tabacum*, spinach, *Brassica campestris, B. juncea*, beets (*Beta vulgaris*), cress, arugula, mustard, strawberry, *Chenopodium capitatum*, lettuce, sunflower, cucumber, chinese cabbage, cabbage, carrot, green onion, onion, radish, lettuce, field peas, cauliflower, broccoli, burdock, turnip, tomato, eggplant, squash, watermelon, prince melon, and melon. Preferred plants are spinach, chard, beetroot, carrot, sugar beet, *Nicotiana tabacum*, and *Nicotiana benthamiana*. Expression in edible plants may be used for preventing contamination of the plants or food made therefrom with *Salmonella*. In one embodiment, plants are used that do not normally enter the human or animal food chain such as *Nicotiana* species such as *N. tabacum* and *N. benthamiana.*

Generally, the salmocin as a protein of interest is expressed in the cytosol of cells of the plants or plant parts. In this case, no signal peptide directing the protein of interest into a particular compartment is added to the protein. Alternatively, the protein of interest can be expressed in or targeted into chloroplasts of the plants; in the latter case, an N-terminal pre-sequence, generally referred to as plastid transit peptide or chloroplast targeting peptide, is added to the N-terminal or C-terminal end, preferably the N-terminal end, of the salmocin as the protein of interest.

The salmocin may be co-expressed together with an immunity protein as described in the experimental section, notably if the salmocin has nuclease activity, for preventing toxicity on plant tissue. Suitable immunity proteins that may be co-expressed are those given in Table 2 below.

In the process of producing a composition comprising at least one salmocin, a salmocin is, in the first step, expressed in a plant or cells of a plant, such as an edible plant. In the next step, plant material containing expressed salmocin from a plant having expressed the salmocin is harvested. Plant material may e.g. be leaves, roots, tubers, or seeds, or a crushed, milled or comminuted product of leaves, roots, tubers, or seeds. In step (iii), the salmocin is extracted from the plant material using an aqueous buffer. This may include that the plant material is homogenized and insoluble material may be removed by centrifugation or filtration. Soluble components including the salmocin will be extracted into the aqueous buffer to produce a salmocin solution in the aqueous buffer. The aqueous buffer may contain an inorganic or organic acid or salts thereof and may have a pH as defined above for the aqueous solution as a composition of the invention. Further, the aqueous buffer may contain salt and/or a sulfhydryl compound as also described above for the aqueous solution as a composition of the invention. If a relatively pure salmocin composition is desired, the salmocin solution in the aqueous buffer may be further purified by removing undesired components in step (iv) according to known methods of protein purification.

Accordingly, the invention provides a process of producing a composition comprising a protein according to the invention, said process comprising the following steps:

(i) expressing said protein in a plant as described above, preferably an edible plant or *Nicotiana,*

(ii) harvesting plant material containing expressed protein from said plant, (iii) extracting said protein from said plant material using an aqueous buffer to obtain a composition containing said protein, optionally removing undesired contaminants from said composition.

If a salmocin is expressed in plants, the plants or tissue thereof having expressed protein is harvested, the tissue may be homogenized and insoluble material may be removed by centrifugation or filtration. If relatively pure salmocin is desired, the salmocin may be further purified by generally known method of protein purification such as by chromatographic methods which can remove other host-cell proteins and plant metabolites such as alkaloids and polyphenols. Purified salmocin solutions may be concentrated and/or freeze-dried.

If salmocins are expressed in edible plants, crude protein extracts from the edible plants or semi-purified concentrates may be used for preventing or reducing contamination of an object such as food with *Salmonella.*

The following examples are offered by way of illustration and not by way of limitation.

EXAMPLES

Example 1: Plasmid Constructs (Salmocins)

Six salmocins representing four activity groups were selected (Table 1).

TABLE 1

List of *Salmonella* bacteriocins (salmocins) used in examples.

| No./SEQ ID NO: | Salmocin | Activity | GenBank Accession No |
|---|---|---|---|
| 1/1 | ScolE2 | DNase | KTM78572.1 |
| 2/2 | ScolE3 | RNase | GAS18013.1 |
| 3/3 | ScolE7 | DNase | KSU39545.1 |
| 4/4 | ScolE1a | pore-forming | KRG27003.1 |
| 5/5 | ScolE1b | pore-forming | KRG25604.1 |
| 6/6 | Spst | muramidase | ESF65298.1 |

The list comprises salmocins ScolE2, ScolE3, ScolE7, ScolE1a, ScolE1b and Spst. Respective amino acid sequences were retrieved from GenBank; corresponding nucleotide sequences with codon usage optimized for *Nicotiana benthamiana* were synthesized by Thermo Fisher Scientific Inc. In case of salmocins ScolE2, ScolE3 and ScolE7, the coding sequence was interrupted by insertion of the cat 1 intron (the first intron from *Ricinus communis* cat1 gene for catalase CAT1 (GenBank: D21161.1, nucleotide positions between 679 and 867)) to prevent the cytotoxicity in *Escherichia coli* cells used for cloning. Salmocin coding sequences were inserted into TMV-based assembled viral vector pNMD035 (described in detail in WO2012/019660) resulting in plasmid constructs depicted in FIG. 1 A-B.

In preliminary expression studies, it was found that bacteriocins with nuclease (RNase and DNase) activities are usually highly toxic for plant tissues where they are expressed. Their expression resulted in tissue necrosis and poor accumulation of recombinant protein. However, co-expression with appropriate immunity proteins reduced the toxic effect and increased the accumulation of these bacteriocins dramatically. Salmocin immunity proteins used in our studies are listed in the Table 2.

TABLE 2

List of immunity proteins used in examples

| No. | Immunity protein | Specificity | Accession No | SEQ ID NO: |
|---|---|---|---|---|
| 1 | SImmE2 | ScolE2 (DNase) | KTM78571.1 | 7 |
| 2 | SImmE7 | ScolE7 (DNase) | KSU39546.1 | 8 |

Immunity proteins SImmE2 and SImmE7 for salmocins ScolE2 and ScolE7, respectively. Amino acid sequences of immunity proteins were retrieved from GenBank; corresponding nucleotide sequences with codon usage optimized for *Nicotiana benthamiana* were synthesized by Thermo Fisher Scientific Inc. and subcloned into PVX-based assembled viral vector pNMD670 as described in WO2012/019660. Resulting plasmid constructs are shown in FIG. 1 A.

Example 2: Salmocin Expression Screen 6 week-old *Nicotiana benthamiana* plants were infiltrated using needleless syringe with diluted *Agrobacterium tumefaciens* cultures carrying TMV-based assembled vectors for cytosolic salmocin expression. In case of salmocins ScolE2 and ScolE7, *Agrobacterium* cultures carrying TMV-based vector for salmocin expression were mixed in equal proportions with other cultures carrying PVX-based vectors for the expression of the corresponding immunity proteins. Individual overnight cultures were adjusted to $OD_{600}$=1.5 and further diluted 1:100 with infiltration buffer containing 10 mM MES, pH 5.5 and 10 mM $MgSO_4$. Plasmid constructs used in this experiment are summarized in Table 3. For determination of optimal harvesting timepoint, plant material was harvested at several timepoints post infiltration and used for protein extraction with 5 volumes of buffer containing 50 mM HEPES (pH 7.0), 10 mM potassium acetate, 5 mM magnesium acetate, 10% (v/v) glycerol, 0.05% (v/v) Tween-20 and 300 mM NaCl. Total soluble protein (TSP) concentration was determined using the Bradford assay, and TSP extracts were analyzed using SDS-PAGE with Coomasssie staining. In our experiment, all tested salmocins were expressed on reasonably high levels varying between 1.2 and 1.8 mg recombinant colicin/g FW or between 18 and 47% of TSP (Table 4) as determined by comparison with bovine serum albumin (BSA) protein.

TABLE 3

Summary of salmocin expression screen.

| No. | Salmocin | Construct(s) | Construct (feature) |
|---|---|---|---|
| 1 | ScolE2/SImmE2 | pNMD28161/pNMD28222 | TMV/PVX |
| 2 | ScolE3 | pNMD28151 | TMV |
| 3 | ScolE7/SImmE7 | pNMD28172/pNMD28232 | TMV |
| 4 | ScolE1a | pNMD28191 | TMV/PVX |
| 5 | ScolE1b | pNMD28204 | TMV/PVX |
| 6 | Spst | pNMD28182 | TMV |

TABLE 4

Yield of recombinant salmocins expressed in *Nicotiana benthamiana* plants.

| | | Harvest | Yield (mg/g FW) | | | Yield (% TSP) | | |
|---|---|---|---|---|---|---|---|---|
| No. | Salmocin | (dpi) | AV | SD | N | AV | SD | N |
| 1 | ScolE2 | 6 | 1.7 | 0.2 | 3 | 25.0 | 0.0 | 3 |
| 2 | ScolE3 | 5 | 1.6 | 0.2 | 3 | 37.0 | 10.4 | 3 |
| 3 | ScolE7 | 5 | 1.4 | 0.3 | 3 | 18.0 | 6.9 | 3 |
| 4 | ScolE1a | 5 | 1.2 | 0.2 | 3 | 20.3 | 3.1 | 3 |
| 5 | ScolE1b | 4 | 1.2 | 0.1 | 3 | 25.7 | 3.1 | 3 |
| 6 | Spst | 6 | 1.8 | 0.3 | 3 | 47.0 | 23.6 | 3 |

FW stands for fresh weight, TSP for total soluble protein, dpi for days post infiltration, AV for average, SD for standard deviation, N for number of independent experiments.

Example 3: Salmocin Activity Screen

We analyzed the antimicrobial activity of plant-made recombinant salmocins against 36 strains of 33 different serotypes of *S. enterica* ssp. *enterica*. Details of strains used in the experiments are given in Tables 5A and 5B.

TABLE 5A

*Salmonella enterica* ssp. *enterica* strains used for antimicrobial activity screen.

| No. | culture collection reference # | Serovar | | Source of supply |
|---|---|---|---|---|
| 1 | ATCC ®13076 ™* | *Enteritidis* | I 1,9,12:g,m:- | (#0345P, Microbiologics Inc.) |
| 2 | ATCC ®49223 ™* | *Enteritidis* | I 9,12:g,m | (#01103P, Microbiologics Inc.) |
| 3 | ATCC ®14028 ™* | *Typhimurium* | I 4,5,12:i:1,2 | (#5068P, Microbiologics Inc.) |
| 4 | ATCC ®13311 ™* | *Typhimurium* | I 4,5,12:i:1,2 | (#0421P, Microbiologics Inc.) |
| 5 | ATCC ®6962 ™* | Newport | I 6,8:e,h:1,2 | (#01095P, Microbiologics Inc.) |
| 6 | ATCC ®10721 ™* | Javiana | I 1,9,12:l,z28:1,5 | LGC standards |
| 7 | ATCC ®BAA-1593 ™ | Javiana | I 9,12:-:1,5 | LGC standards |
| 8 | ATCC ®8387 ™* | Montevideo | I 6,7:g,m,s:- | LGC standards |
| 9 | ATCC ®BAA-1675 ™ | *Infantis* | | LGC standards |
| 10 | ATCC ®8388 ™* | Muenchen | I 6,8:d:1,2 | LGC standards |
| 11 | ATCC ®8326 ™* | Heidelberg | I 4,5,12:r:1,2 | (#01151P, Microbiologics Inc.) |
| 12 | ATCC ®9115 ™* | Bareilly | I 6,7:y:1,5 | LGC standards |
| 13 | ATCC ®8391 ™* | Thompson | I 6,7:k:1,5 | LGC standards |
| 14 | ATCC ®9712 ™* | Saintpaul | I 1,4,5,12:e,h:1,2 | LGC standards |
| 15 | ATCC ®9239 ™* | Oranienburg | I 6,7:m,t:- | LGC standards |
| 16 | ATCC ®BAA-2739 ™ | Mississippi | I 13,23:b:1,5 | LGC standards |
| 17 | ATCC ®9270 ™* | Anatum | I 3,10:e,h:1,6 | (#01095P, Microbiologics Inc.) |
| 18 | ATCC ®51957 ™* | Agona | I 4,12:f,g,s:- | (#01154P, Microbiologics Inc.) |

TABLE 5B

*Salmonella enterica* ssp. *enterica* strains used for antimicrobial activity screen.

| No. | culture collection reference # | Serovar | | Source of supply |
|---|---|---|---|---|
| 19 | ATCC ®8392 ™* | Berta | I 9,12:f,g,t:- | LGC standards |
| 20 | ATCC ®15480 ™* | Dublin | I 1,9,12:g,p:- | LGC standards |
| 21 | ATCC ®6960 ™* | Derby | I 1,4,12:f,g:- | LGC standards |
| 22 | ATCC ®10723 ™* | Cerro | I 18:z4,z23:- | LGC standards |
| 23 | DSM 10062 | Senftenberg | I 1,3,19:g,s,t:- | DSMZ, Braunschweig |
| 24 | ATCC ®9263 ™* | Kentucky | I (8),20:i:z6 | LGC standards |
| 25 | ATCC ®51958 ™* | Mbandaka | I 6,7:z10:e,n,z15 | LGC standards |
| 26 | ATCC ®10708 ™* | Cholerasius | I 6,7:C:1,5 | (#01095P, Microbiologics Inc.) |
| 27 | ATCC ®12002 ™* | Tallahassee | I 6,8:z4,z32:- | (#01095P, Microbiologics Inc.) |
| 28 | ATCC ®9150 ™* | *Paratyphi* A | I 1,2,12:a:- | (#01095P, Microbiologics Inc.) |
| 29 | NCTC 6017 | Abony | I 4,12,27:b:e,n,x | (#0890P, Microbiologics Inc.) |
| 30 | ATCC ®13036 ™* | *Pullorum* | I 9,12:-:- | (#0604P, Microbiologics Inc.) |
| 31 | ATCC ®15611 ™* | Vellore | I 1,4,12,27:z10:z35 | (#0342P, Microbiologics Inc.) |
| 32 | ATCC ®9842 ™* | Bispebjerg | I 4,12:a:enx | (#01056P, Microbiologics Inc.) |
| 33 | NCTC 4840 | Poona | I 13,22:z:1 | (#0851P, Microbiologics Inc.) |
| 34 | DSM 4883 | *Gallinarum* | I 9:-:- | DSMZ, Braunschweig |
| 35 | DSM 13674 | *Gallinarum* | I 9,12:-:- | DSMZ, Braunschweig |
| 36 | ATCC ®700136 ™* | Braenderup | I 6,7:e,h:e,n,z15 | LGC standards |

Antimicrobial activity of recombinant salmocin-containing plant extracts was tested in radial diffusion assays via spot-on-lawn-method. For this purpose, we prepared agar plates overlaid with soft agar containing cells of tested *Salmonella* strains. 10×10 cm quadratic petri dishes were poured with 15-20 ml LB agar medium (1.5% w/v agar). LB soft agar medium (0.8% (w/v) agar) was melted, 20 ml aliquots were transferred into 50 ml plastic tubes and their temperature was adapted to 50-55° C. *Salmonella* overnight cultures adjusted to $OD_{600}$=1.0 with LB medium were added to the soft agar medium with a ratio of 1:100 resulting in the final $OD_{600}$=0.01 or approximately $1\times10^7$ cells/ml and 20 ml LB softagar containing *Salmonella* test strain are poured on the pre-poured LB plate resulting in 0.14 mL bacterial solution of $1\times10^7$ cfu/mL per $cm^2$.

Plant leaf material was extracted as described in Example 2. We prepared 1:1 dilution series of plant extracts starting with undiluted samples by using same extraction buffer. 5 μl aliquots of TSP dilution series were applied to agar plates; plates were incubated at 37° C. overnight. Antimicrobial activity was evaluated based on clearing zones.

Among the 6 tested salmocins, one demonstrated narrow antimicrobial activity (Spst—12% of strains inhibited), one salmocin had medium activity spectrum (ScolE3—60% of strains inhibited), and 4 others had broad activity spectrum: ScolE2 and ScolE7—inhibited about 90% of strains and ScolE1a and ScolE1b—inhibited 100% of strains (FIG. 3).

Salmocins ScolE1 and ScolE1b demonstrated not only broad but also remarkably high activity against tested *Salmonella* strains (FIGS. 4, 5).

For semi-quantitative comparison, we represented relative antimicrobial activity of recombinant colicins in arbitrary units (AU), calculated as a dilution factor for the highest dilution of protein extract causing a detectable clearing effect in the radial diffusion assay. Salmocin antimicrobial activity against *Salmonella* strains calculated in AU per mg FW of the plant tissue is shown in FIGS. 6, 8, 10, 12 and 14 for ScolE2, ScolE3, ScolE7, ScolE1a, and ScolE1b, respectively. Thereby, the yield of specific active agent per unit of biomass; i. e. the specific production capacity of the host is reflected.

FIGS. 7, 9, 11, 13 and 15 demonstrate the same activity calculated in AU per μg of recombinant salmocin proteins ScolE2, ScolE3, ScolE7, ScolE1a and ScolE1b, respectively, reflecting the specific antimicrobial potency of salmocins.

Example 4: Plasmid Constructs (Colicins)

Six colicins representing two activity groups were selected (Table 6). The list comprises colicins colS4, col5, col10, colla, collb and colM. Respective amino acid sequences were retrieved from GenBank; corresponding nucleotide sequences with codon usage optimized for *Nicotiana benthamiana* were synthesized by Thermo Fisher Scientific Inc. Colicin coding sequences were inserted into TMV-based assembled viral vector pNMD035 (described in detail in WO2012/019660) resulting in plasmid constructs depicted in FIG. 16. The coding sequence of colicin M was interrupted by insertion of the cat 1 intron (the first intron from *Ricinus communis* cat1 gene for catalase CAT1 (GenBank: D21161.1, nucleotide positions between 679 and 867)).

TABLE 6

List of *E. coli* bacteriocins (colicins) used in Examples.

| No./ SEQ ID NO | colicin | Activity | Accession No. |
|---|---|---|---|
| 1/9 | colS4 | pore-forming | CAB46008.1 |
| 2/10 | col5 | pore-forming | CAA61102.1 |
| 3/11 | col10 | pore-forming | CAA57998.1 |
| 4/12 | colla | pore-forming | WP_001283344.1 |
| 5/13 | collb | pore-forming | AAA23188.1 |
| 6/14 | colM | cell wall-inhibition | AAA23589.1 |

Example 5: Colicin Expression Screen 6 week-old *Nicotiana benthamiana* plants were infiltrated using needleless syringe with diluted *Agrobacterium tumefaciens* cultures carrying TMV-based assembled vectors for cytosolic colicin expression. *Agrobacterium* overnight cultures were adjusted to $OD_{600}$=1.5 and further diluted 1:100 with infiltration buffer containing 10 mM MES, pH 5.5 and 10 mM $MgSO_4$. Plasmid constructs used in this experiment are summarized in Table 7. For determination of optimal harvesting timepoint, plant material was harvested at several timepoints post infiltration and used for protein extraction with 5 volumes of buffer containing 50 mM HEPES (pH 7.0), 10 mM potassium acetate, 5 mM magnesium acetate, 10% (v/v) glycerol, 0.05% (v/v) Tween-20 and 300 mM NaCl. Total soluble protein (TSP) concentration was determined using the Bradford assay, and TSP extracts were analyzed using SDS-PAGE with Coomasssie staining. In our experiment, all tested colicins were expressed on reasonably high levels varying between 1.5 and 4.7 mg recombinant colicin/g FW or 16 and 41% of TSP (Table 8) as determined by comparison with bovine serum albumin (BSA) protein.

TABLE 7

Summary of colicin expression screen.

| No. | Colicin | Construct(s) | Construct (feature) |
|---|---|---|---|
| 1 | colS4 | pNMD25856 | TMV |
| 2 | col5 | pNMD15311 | TMV |
| 3 | col10 | pNMD25848 | TMV |
| 4 | colla | pNMD19141 | TMV |
| 5 | collb | pNMD25861 | TMV |
| 6 | colM | pNMD10221 | TMV |

TABLE 8

Yield of recombinant colicins expressed in *Nicotiana benthamiana* plants.

| | | Harvest | Yield (mg/g FW) | | | Yield (% TSP) | | |
|---|---|---|---|---|---|---|---|---|
| No. | colicin | (dpi) | AV | SD | N | AV | SD | N |
| 1 | colS4 | 5 | 1.5 | 0.3 | 6 | 16.7 | 4.1 | 6 |
| 2 | col5 | 8 | 4.7 | 2.4 | 6 | 41.3 | 5.7 | 6 |
| 3 | col10 | 7 | 4.6 | 1.7 | 6 | 39.7 | 5.5 | 6 |
| 4 | colIa | 6 | 1.4 | 0.3 | 6 | 17.5 | 2.7 | 6 |
| 5 | colIb | 5 | 2.3 | 0.7 | 6 | 28.3 | 13.3 | 6 |
| 6 | colM | 6 | 2.9 | 1.4 | 6 | 30.8 | 5.8 | 6 |

FW stands for fresh weight, TSP for total soluble protein, dpi for days post infiltration, AV for average, SD for standard deviation, N for number of independent experiments.

Example 6: Colicin Activity Screen

We analyzed the antimicrobial activity of plant-made recombinant colicins against 35 strains of 32 different serotypes of *S. enterica* ssp. *enterica*. Details of strains used in our experiments are given in tables 5A and 5B (strain numbers 1-35).

Antimicrobial activity of recombinant colicin-containing plant extracts was tested in radial diffusion assays via spot-on-lawn-method as described in Example 3.

Among the 6 tested colicins, one demonstrated narrow antimicrobial activity (colS4—25% of strains inhibited), three colicins had medium activity spectrum (col5, col10 and colM—48%, 46% and 42% of strains inhibited, respectively), and two colicins had broad activity spectrum: colla and collb—inhibited 96% and 89% of strains, respectively (FIG. 17).

Example 7: Determination of Efficacy of Bactericidal Effect of Bacteriocins (Colicin Blends) on Pathogenic Strains of *S. enterica* Ssp. *Enterica* Applied to Meat Matrices Plant-produced colicins were tested for antibacterial activity on samples of chicken breast fillet contaminated with pathogenic *Salmonella*.

Evaluation of efficacy encompasses the analysis of pathogenic *S. enterica* ssp. *enterica* populations on contaminated meat samples subsequently treated with blends of plant-made recombinant colicins or a control carrier solution consisting of plant extract from the same production host but without colicins, and storage of treated meat samples for various time periods at 4° C.

No special sourcing of meat samples is used to ensure that bacteriocin activity is evaluated in representative consumer products. Raw chicken breast fillets are purchased at retail outlets (for these studies, ALDI supermarket, Halle, Germany), one day before the experiment. The meat is stored at 4° C. and the meat is not washed or pre-treated before experimental exposures.

The meat test matrices are experimentally contaminated with a 1:1 or 1:1:1:1 mixture of 2 or 4 *Salmonella enterica* ssp. *enterica* strains representing the serotypes *Typhimurium* and *Enteritidis* (ATCC® 9270™*, ATCC® 13076™*) or *Typhimurium, Enteritidis*, Newport and Anatum (ATCC® 9270™*, ATCC® 13076™*, ATCC® 6962™* and ATCC®9270™*), respectively (FIGS. 18 and 19, respectively). Prior to meat contamination, the strains are individually grown to $OD_{600}$=0.3 and mixed 1:1 or 1:1:1:1. The strain mix is further diluted to the desired cell number ($OD_{600}$=0.005-0.001, $2\times10^6$-$1.8\times10^5$ cfu/ml) with LB broth for use as meat contamination suspension to achieve an initial inoculum of ~$2\times10^4$ cfu/g meat. Chicken breast trims (3 pieces of ~25 g weight) are dipped into 12 ml of bacterial suspension and inverted and dipped again to inoculate both sides. Contaminated meat and bacteria are allowed to dry and colonize matrix samples, respectively, for 30 min at RT, during which time chicken breast trims are inverted every 15 min.

Contaminated meat is either treated with carrier or colicin blend solution (TSP extracts prepared 50 mM HEPES pH7.0, 10 mM K acetate, 5 mM Mg acetate, 10% (v/v) glycerol, 0.05% (v/v) Tween-20, 300 mM NaCl from *N. benthamiana* either non-treated plant material or plant material upon syringe-inoculation with *Agrobacterium* for colicin expression) by low-pressure spraying (2-4 bar) using atomizer flasks. Proposed application rates are 3 mg/kg for colicin M and 1 mg/kg for any other colicin used in the blend (colicin la and colicin 5). The meat is further incubated for 30 min at RT while inverted every 15 min.

Thirty minutes after colicin application, aliquots of ~25 g chicken breast trims are placed into sterile sample bags (BagFilter®400 P) in replicates, the exact weight of each sample is recorded, and sample bags are closed using a closing clip (BagClip®400). In total, meat samples are incubated at room temperature for 1 h upon colicin treatment before the sealed meat samples are then stored at 4° C.

Meat samples are sampled at 1 h, 48 h and 72 h of storage at 4° C. for determination of on-matrix microbial contamination levels. For recovery of pathogenic *Salmonella* from meat samples, to each ~25 g aliquot of meat sample ~100 ml buffered peptone water is added. The samples are homogenized in a laboratory blender (BagMixer®400CC®; settings: gap 0, time 30 s, speed 4). Microbial suspensions from filtered part of the storage bag are collected and a 1:10 dilution series is prepared. 100 μl aliquots of undiluted or diluted microbial suspensions are plated on XLD agar. The plates are incubated for 18-24 h at 37° C. and the CFU (colony forming units) are enumerated. The CFU number per g sample is calculated as follows:

$$\frac{\text{Total } CFU}{\text{g Meat}} = \frac{\text{Actual } CFU \times \text{Concentration Factor} \times \text{Dilution Factor}}{0.1 \text{ ml Plating Volume}} \times \frac{\text{Actual ml Peptone Water}}{\text{Actual g Sample}}$$

The efficacy of the colicin treatment in reducing the number of viable pathogenic *Salmonella* in the experimentally contaminated meat samples is evaluated by comparing the data obtained with the carrier-treated control samples and colicin-treated samples by one-way ANOVA (Tukey's multiple comparisons test) and unpaired parametric t-test using GraphPad Prism v. 6.01.

The results of bacterial counts are shown in FIGS. 18 and 19 for a two-strain or four-strain *Salmonella* contamination, respectively. Most significant reduction of bacterial population (1.8 logs) occurred already after 1 hour storage upon colicin treatment.

In summary, statistically significant reduction of *Salmonella* populations on contaminated meat could be achieved by treatment of meat with a colicin blend.

Salmocin blends or salmocin/colicin blends will be tested for decontamination of food products from *Salmonella* and are planned to be used in food industry for reducing *Salmonella* contamination. Salmocins ScolE1a and ScolE1b show the broadest antimicrobial activity against tested *Salmonella* strains. Thus, they can be used as a main ingredient of salmocin cocktails for the control of *Salmonella.*

Example 8: Production of Salmocins in Stable Transgenic Hosts

*N. benthamiana* was transformed by *Agrobacterium*-mediated leaf disk transformation using vectors for EtOH-inducible transgene expression and induction of detached leaves of TO generation transgenic plants for salmocin expression. This was done as described in Schulz et al. *Proc. Natl. Acad. Sci. USA.* 112, E5454-E5460 (2015).

Stable transgenic *Nicotiana benthamiana* plants containing the genomic insertion of TMV-based viral vector double-inducible with ethanol for ScolE1b expression (FIG. 21) exhibited normal growth and development, and selected transgenic lines accumulated salmocins upon induction with ethanol to the expected levels (FIG. 22).

Example 9: Production of Salmocins in Spinach

*Spinacia oleracea* cv. Frühes Riesenblatt plants were grown in the greenhouse (day and night temperatures of 19-23° C. and 17-20° C., respectively, with 12 h light and 35-70% humidity). Six-week-old plants were used for syringe infiltration as described in Example 2. Expression of recombinant proteins was confirmed using SDS-PAGE with Coomassie staining (FIG. 23).

Example 10: Extended Salmocin Activity Screen

We further analyzed the antimicrobial activity of plant-made recombinant salmocins against other strains of *Salmonella* as described in Example 6. To determine the salmocin antimicrobial activity spectrum, 109 strains representing 105 *S. enterica* ssp. *enterica* serotypes were selected and screened (Table 9). The screen included one strain each of all serotypes (except serotypes Typhi and 14, 5:12:r:-) that are documented at the U.S. Centers for Disease Control and Prevention (CDC) (www.cdc.gov/nationalsurveillance/pdfs/*salmonella*-annual-report-2013-508c.pdf) as having caused at least 100 incidences of human *Salmonella* infection from 2003-2012, two strains of serotypes *Typhimurium, Enteritidis* and *Javiana* and 6 serotypes causing less than 100 incidences or not reported to CDC.

TABLE 9

List of *Salmonella enterica* ssp. *enterica* strains analysed for antimicrobial susceptibility. Serotype antigenic formula is given in (Subspecies [space] O antigens [colon] Phase 1 H antigens [colon] Phase 2 H antigens) as provided by the supplier. Numbers in source of supply correspond to 1-Microbiologics, Inc. (St. Cloud, USA), 2-LGC Standards (Teddington, UK), 3-Robert Koch Institute, national reference centre for salmonellosis and other enteric pathogens (Wernigerode, Germany), 4-Leibnitz Institute DSMZ-German Collection of Microorganisms and Cell Cultures (Braunschweig, Germany), 5-National Collection of Type Cultures (Salisbury, UK). Strains marked with " were used for antmicrobial susceptibility testing in triplicate experiments. †The number of incidences refers to laboratory-confirmed human *Salmonella* infections (US) reported to CDC 2003-2012 published in National Enteric Disease Surveillance: *Salmonella* Annual Report, 2013 (CDC, June 2016; www.cdc.gov/nationalsurveillance/pdfs/salmonella-annual-report-2013-508c.pdf.

| No. | culture collection reference No. | serotype | serotype antigenic formula | source of supply | No. of incidences† |
|---|---|---|---|---|---|
| 1" | ATCC ® 13076 ™* | *Enteritidis* | I 1,9,12:g,m:- | 1 | 74450 |
| 2" | ATCC ® 49223 ™* | | I 9,12:g,m | 1 | |
| 3" | ATCC ® 14028 ™* | *Typhimurium* | I 4,5,12:i:1,2 | 1 | 70251 |
| 4" | ATCC ® 13311 ™* | | I 4,5,12:i:1,2 | 1 | |
| 5" | ATCC ® 6962 ™* | Newport | I 6,8:e,h:1,2 | 1 | 44675 |
| 6" | ATCC ® 10721 ™* | Javiana | I 1,9,12:l,z28:1,5 | 2 | 22868 |
| 7" | ATCC ® BAA-1593 ™ | | I 9,12:-:1,5 | 2 | |
| 8" | ATCC ® 8326 ™* | Heidelberg | I 4,5,12:r:1,2 | 1 | 15912 |
| 9 | 17-00918 | — | I 4,[5],12:i:- | 3 | 13567 |
| 10" | ATCC ® 8387 ™* | Montevideo | I 6,7:g,m,s:- | 2 | 11377 |
| 11" | ATCC ® 8388 ™* | Muenchen | I 6,8:d:1,2 | 2 | 9589 |
| 12" | ATCC ® 9712 ™* | Saintpaul | I 1,4,5,12:e,h:1,2 | 2 | 9420 |
| 13" | ATCC ® BAA-1675 ™ | *Infantis* | | 2 | 8106 |
| 14" | ATCC ® 9239 ™* | Oranienburg | I 6,7:m,t:- | 2 | 7514 |
| 15" | ATCC ® 700136 ™* | Braenderup | I 6,7:e,h:e,n,z15 | 2 | 7371 |
| 16" | ATCC ® BAA-2739 ™ | Mississippi | I 13,23:b:1,5 | 2 | 5693 |
| 17" | ATCC ® 8391 ™* | Thompson | I 6,7:k:1,5 | 2 | 5660 |
| 18" | ATCC ® 51957 ™* | Agona | I 4,12:f,g,s:- | 1 | 5072 |
| 19 | 16-04932 | *Paratyphi B* var. L(+) tartrate + | I 4,5:b:1,2 | 3 | 4624 |
| 20" | ATCC ® 9115 ™* | Bareilly | I 6,7:y:1,5 | 2 | 3704 |
| 21" | NCTC 4840 | Poona | I 13,22:z:1 | 1 | 2977 |
| 22 | 16-4909 | Hadar | I 6,8:z10:e,n,x | 3 | 2857 |
| 23 | 16-05099 | Schwarzengrund | I 4:d:1,7 | 3 | 2835 |
| 24" | ATCC ® 8392 ™* | Berta | I 9,12:f,g,t:- | 2 | 2779 |
| 25" | ATCC ® 9270 ™* | Anatum | I 3,10:e,h:1,6 | 1 | 2753 |
| 26 | 16-04966 | Stanley | I 4,5:d:1,2 | 3 | 2438 |
| 27 | 15-04731 | Litchfield | I 6,8:e,v:1,2 | 3 | 2386 |
| 28 | 10-03610 | Hartfort | I 6,7:y:e,n,x | 3 | 2312 |
| 29" | ATCC ® 51958 ™* | Mbandaka | I 6,7:z10:e,n,z15 | 2 | 2286 |
| 30 | 16-03044 | Panama | I 9:e,v:1,5 | 3 | 1903 |
| 31 | 16-04172 | — | I 4,[5],12:b:- | 3 | 1860 |
| 32 | 14-03918 | Sandiego | I 4,5:e,n:e,n,z15 | 3 | 1759 |
| 33" | ATCC ® 9150 ™* | *Paratyphi* A | I 1,2,12:a:- | 1 | 1731 |
| 34" | DSM 10062 | Senftenberg | I 1,3,19:g,s,t:- | 4 | 1594 |
| 35 | NCTC 7077 | Norwich | I 6,7:e,h:1,6 | 5 | 1481 |
| 36 | 16-05141 | Tennessee | I 6,7:z29:- | 3 | 1476 |
| 37 | 16-05288 | Rubislaw | I 11:r:e,n,x | 3 | 1394 |
| 38" | ATCC ® 6960 ™* | Derby | I 1,4,12:f,g:- | 2 | 1392 |
| 39 | 07-06267 | — | I 13,23:b:- | 3 | 1275 |
| 40 | 16-05246 | Give | I 3,10:1,v:1,7 | 3 | 1250 |
| 41 | 16-05252 | *Paratyphi* B | I 4,5:b:1,2 | 3 | 1249 |
| 42 | 14-04905 | Miami | I 9:a:1,5 | 3 | 1087 |
| 43" | ATCC ® 15480 ™* | Dublin | I 1,9,12:g,p:- | 2 | 1086 |
| 44" | ATCC ® 9263 ™ | Kentucky | I (8),20:i:z6 | 2 | 984 |
| 45 | 16-05080 | Brandenburg | I 4:l,v:e,n,z15 | 3 | 963 |
| 46 | 16-04827 | Virchow | I 6,7:r:1,2 | 3 | 961 |
| 47 | 16-02846 | Gaminara | I 16:d:1,7 | 3 | 953 |
| 48 | 17-00031 | Weltevreden | I 3,10:r:z6 | 3 | 876 |
| 49 | 16-05006 | *Bovismorbisficans* | I 6,8:r:1,5 | 3 | 839 |
| 50 | 17-00039 | Manhattan | I 6,8:d:1,5 | 3 | 836 |
| 51 | 14-05486 | Adelaide | I 35:f,g:- | 3 | 820 |
| 52 | 16-05394 | Uganda | I 3,10:e,z13:1,5 | 3 | 817 |
| 53 | 15-03669 | Pomona | I 28:Y:1,7 | 3 | 781 |
| 54 | 16-04580 | Muenster | I 3,10:e,h:1,5 | 3 | 756 |
| 55 | 15-01597 | Kiambu | I 4:z:1,5 | 3 | 699 |
| 56 | 15-02141 | Blockley | I 6,8:k:1,5 | 3 | 688 |
| 57 | 16-04687 | Ohio | I 6,7:b:e,w | 3 | 656 |
| 58 | 16-05313 | Hvittingfoss | | 3 | 620 |
| 59 | 16-01351 | Reading | I 4,5:e,h:1,5 | 3 | 619 |
| 60 | 11-00574 | Inverness | I 38:k:1,6 | 3 | 587 |
| 61 | 13-02698 | Urbana | I 30:b:e,n,x | 3 | 565 |

TABLE 9-continued

List of *Salmonella enterica* ssp. *enterica* strains analysed for antimicrobial susceptibility. Serotype antigenic formula is given in (Subspecies [space] O antigens [colon] Phase 1 H antigens [colon] Phase 2 H antigens) as provided by the supplier. Numbers in source of supply correspond to 1-Microbiologics, Inc. (St. Cloud, USA), 2-LGC Standards (Teddington, UK), 3-Robert Koch Institute, national reference centre for salmonellosis and other enteric pathogens (Wernigerode, Germany), 4-Leibnitz Institute DSMZ-German Collection of Microorganisms and Cell Cultures (Braunschweig, Germany), 5-National Collection of Type Cultures (Salisbury, UK). Strains marked with " were used for antmicrobial susceptibility testing in triplicate experiments. †The number of incidences refers to laboratory-confirmed human *Salmonella* infections (US) reported to CDC 2003-2012 published in National Enteric Disease Surveillance: *Salmonella* Annual Report, 2013 (CDC, June 2016; www.cdc.gov/nationalsurveillance/pdfs/salmonella-annual-report-2013-508c.pdf.

| No. | culture collection reference No. | serotype | serotype antigenic formula | source of supply | No. of incidences† |
|---|---|---|---|---|---|
| 62 | 16-05172 | London | I 3,10:e,v:1,6 | 3 | 480 |
| 63 | 14-05710 | Johannesburg | I 40:b:e,n,x | 3 | 443 |
| 64 | 16-05303 | Chester | | 3 | 435 |
| 65 | 16-02928 | Havana | I 13,23:f,g:- | 3 | 395 |
| 66 | 16-01712 | Bredeney | I 4:l,v:1,7 | 3 | 383 |
| 67 | 15-01962 | — | I6,7:-:1,5 | 3 | 366 |
| 68 | 15-02251 | Telelkebir | I 13,23:d:e,n,z15 | 3 | 361 |
| 69" | ATCC ® 10723 ™* | Cerro | I 18:z4,z23:- | 2 | 346 |
| 70 | 16-04988 | Albany | I 8,20:z4:z24 | 3 | 344 |
| 71 | 16-02205 | Agbeni | I 13,23:g,m:- | 3 | 343 |
| 72 | 14-02295 | Minnesota | I 21:b:e,n,x | 3 | 337 |
| 73 | 14-01914 | Worthington | I 13,23:z:e,w | 3 | 336 |
| 74 | 16-05041 | Rissen | I 6,7:f,g:- | 3 | 312 |
| 75 | 16-02392 | Oslo | I 6,7:a:e,n,x | 3 | 306 |
| 76 | 11-06323 | Baildon | I 9,46:a:e,n,x | 3 | 278 |
| 77 | 16-02147 | Cotham | I 28:i:1,5 | 3 | 253 |
| 78 | 15-03689 | Ealing | I 35:g,m,s | 3 | 237 |
| 79 | 418 | Lomalinda | I 9,12:a:e,n,x | 3 | 232 |
| 80 | 15-01471 | Cubana | I 13,23:z29 | 3 | 213 |
| 81 | 09-01912 | Carrau | I 6,14,24:y:1,7 | 3 | 209 |
| 82 | 16-02464 | Eastbourne | I 9:e,h:1,5 | 3 | 203 |
| 83 | 17-00172 | Monschaui | I 35:m,t:- | 3 | 201 |
| 84 | 15-01577 | Alachua | I 35:z4,z23:- | 3 | 193 |
| 85 | 16-03390 | Corvallis | I 8,20:z4,z23 | 3 | 189 |
| 86 | 16-00455 | Potsdam | I 6,7:e,v:e,n,z15 | 3 | 187 |
| 87 | 17-00107 | Meleagridis | I 3,10:e,n:e,w | 3 | 169 |
| 88 | 16-05286 | Indiana | | 3 | 158 |
| 89 | 15-02982 | Concord | I 6,7:l,v:1,2 | 3 | 157 |
| 90 | 03-08607 | — | I 6,7:k:- | 3 | 149 |
| 91" | ATCC ® 10708 ™* | Cholerasius | I 6,7:C:1,5 | 1 | 148 |
| 92 | 16-03583 | Altona | I 8,20:r:z6 | 3 | 145 |
| 93 | 11-07920 | Pensacola | I 9:m,t:- | 3 | 143 |
| 94 | 01-02501 | Othmarschen | I 6,7:g,m:- | 3 | 134 |
| 95 | 12-02378 | — | I 4,[5],12:-:1,2 | 3 | 130 |
| 96 | 16-05338 | Lovingstone | I 6,7:d:e,w | 3 | 123 |
| 97 | 15-03273 | Grumpensis | I 13,23:d:1,7 | 3 | 122 |
| 98 | 15-04797 | Wandsworth | I 39:b:1,2 | 3 | 118 |
| 99 | 13-04865 | Kintambo | I 13,23:m,t:- | 3 | 114 |
| 100 | 13-05516 | Edinburgh | | 3 | 113 |
| 101 | 16-04965 | Kottbus | I 6,8:e,h:1,5 | 3 | 109 |
| 102 | 15-00740 | Durban | I 9:a:e,n,z15 | 3 | 104 |
| 103" | NCTC 6017 | Abony | I 4,12,27:b:e,n,x | 1 | 60 |
| 104" | ATCC ® 9842 ™* | Bispebjerg | I 4,12:a:enx | 1 | 1 |
| 105" | ATCC ® 15611 ™* | Vellore | I 1,4,12,27:z10:z35 | 1 | — |
| 106" | ATCC ® 13036 ™* | *Pullorum* | I 9,12:-:- | 1 | — |
| 107 | ATCC ® 12002 ™* | Tallahassee | I 6,8:z4,z32:- | 1 | 67 |
| 108" | DSM 4883 | *Gallinarum* | I 9:-:- | 4 | — |
| 109" | DSM 13674 | | I 9,12:-:- | 4 | |

TABLE 10

List of *E. coli* STEC strains used in this study.

| No. | Culture collection reference # | Serotype | Characteristics | Source of supply |
|---|---|---|---|---|
| 1 | CDC 03-3014 | O26: H11 | Positive for | Big 7 STEC QC |
| 2 | CDC 00-3039 | O45: H2 | virulence | Set (#5219, |
| 3 | CDC 06-3008 | O103: H11 | genes stx1 | Microbiologics |
| 4 | CDC 2010C-3114 | O111: H8 | and/or | Inc., St. Cloud, |
| 5 | CDC 02-3211 | O121: H19 | stx2 and eae | Minnesota USA) |
| 6 | CDC 99-3311 | O145: NM | | |
| 7 | ATCC ® 35150 ™ | O157: H7 | | |

In order to estimate the breadth of the activity spectrum, all strains were tested at least once and 36 or 35 strains were subsequently re-screened in triplicate experiments with salmocins and colicins, respectively (FIG. 24). The broadest antimicrobial activity spectrum was again identified for salmocins ScolE1a and ScolE1b, which showed positive antibacterial activity against 100% and 99% of all strains evaluated, respectively. Significant breadth of activity was also observed for salmocins ScolE2 (94%), ScolE3 (70%) and ScolE7 (95%) as reflected by their activity on the subset of 36 strains represented in FIG. 24*e*.

The five salmocins analysed were divided into four groups based on their ability to control major pathogenic *Salmonella* strains. Salmocins ScolE1a and ScolE1b were universally active, each being able to kill all tested pathovars and showing the highest average activity of higher than $10^5$ AU/μg recombinant protein on all tested strains (FIG. 24*a*) and in most cases higher than $10^3$ AU/μg protein against individual strains. The remaining salmocins fell into two groups, with salmocins ScolE2 and ScolE7 in one group having a 100-fold lower average activity (<$10^5$ AU/μg protein, FIG. 24*a*), and ScolE3 in another group showing substantially lower average activity ($10^2$ AU/μg, FIG. 24*a*).

In contrast to the high potencies of salmocins in inhibiting enteropathogenic *S. enterica* strains, the specific activities of colicins la, lb, M, 5, 10 and S4 (Table 6) were 2-4 orders of magnitude lower (2-3 logs AU/μg, FIG. 24*b*), although most of the 109 strains were inhibited by colicins la (92%) and lb (90%) and about one third of strains by colicins S4 (45%), 5 (25%), 10 (29%) and M (34%), as also reflected in the susceptibility pattern of the subset of 35 strains (FIG. 24*f*). In general, salmocins demonstrated higher and broader activity against *Salmonella* than *E. coli* colicins. Conversely, salmocins showed low (below $10^2$ AU/μg) inter-specific and narrrow activity against *E. coli* STEC (Table 10) strains (FIG. 24*c, g*).

Example 11: Individual Salmocin ScolE1a and Salmocin Blends Control *Salmonella* on Contaminated Chicken Meat Matrices The bactericidal efficacy of plant-produced individual salmocin ScolE1a as well as salmocin blends for control of *Salmonella*-contaminated meat surfaces was analyzed in a simulation study.

Chicken breast fillet was purchased from a local supermarket. Nalidixic acid resistant mutants of strains of *S. enterica* ssp. *enterica* serovars *Enteritidis* (strain ATCC® 13076™*), *Typhimurium* (strain ATCC®14028 ™*), Newport (strain ATCC®6962 ™*), *Javiana* (strain ATCC® 10721™*), Heidelberg (strain ATCC®8326 ™*), Infantis (strain ATCC®BAA-1675™*) and Muenchen (strain ATCC® 8388™*) were individually grown in LB medium supplemented with 25 μg/ml nalidixic acid to stationary phase, diluted with fresh LB and grown to exponential phase. For contamination of poultry, bacterial cultures were diluted with LB medium to $OD_{600}$=0.001 (~2×$10^5$ cfu/ml) and mixed 1:1:1:1:1:1:1. A pool of chicken breast fillets cut into pieces of about 20 g weight was inoculated with 1 ml of a mixture of 7 *S. enterica* strains at ~2×$10^5$ CFU/ml density per 100 g of meat at room temperature resulting in an initial contamination level of meat matrices of about 3 log CFU/g of a 7-serotype mixture of pathogenic *S. enterica*; attachment of bacteria to meat surfaces was allowed for 30 min at room temperature. Subsequently, chicken breast trims were treated by spraying (10 ml/kg) with either plant extract control (TSP extract of WT *N. benthamiana* plant material with no salmocins, prepared with 50 mM HEPES pH 7.0, 10 mM K acetate, 5 mM Mg acetate, 10% (v/v) glycerol, 0.05% (v/v) Tween-20, 300 mM NaCl), or salmocin solutions (either individual or mixtures of TSP extracts of *N. benthamiana* plant material expressing salmocins ScolE1a, ScolE1b, ScolE2 and ScolE7 prepared with the same buffer as the plant extract control) at concentrations of 3 mg/kg ScolE1a, or 3 mg/kg ScolE1a, 1 mg/kg ScolE1b, 1 mg/kg ScolE2, 1 mg/kg ScolE7 or 0.3 mg/kg ScolE1a, 0.1 mg/kg ScolE1b, 0.1 mg/kg ScolE2, and 0.1 mg/kg ScolE7. Treated meat trims were further incubated at room temperature for 30 min. Aliquots of meat trims corresponding to ~40 g were packed into BagFilter®400P sterile bags (Interscience) and stored for 1 h, 1 d and 3 d at 10° C., which represents realistic industrial meat processing conditions that are permissive but suboptimal for bacterial growth.

In total, meat samples were incubated at room temperature for 1.5 h during salmocin treatment before they were sealed and stored at 10° C. For analysis of bacterial populations, poultry aliquots were homogenized with 4 vol. peptone water using Bag Mixer®400CC® homogenizer (settings: gap 0, time 30 s, speed 4; Interscience) and colony forming units (CFU) of *S. enterica* were enumerated on XLD medium (Sifin Diagnostics) supplemented with 25 μg/ml nalidixic acid upon plating of serial dilutions of microbial suspensions. Samples were analysed in quadruplicate.

The efficacy of the salmocin treatment in reducing the number of viable pathogenic *Salmonella* in the experimentally contaminated meat samples was evaluated by comparing the data obtained with the carrier-treated control samples and salmocin-treated samples by two-tailed unpaired parametric t-test with 6 degrees of freedom using GraphPad Prism v. 6.01.

Efficacy of salmocin treatment was assessed for the extent of reduction in the pathogenic bacterial population level on salmocin-treated (individual ScolE1a at an application rate of 3 mg/kg meat and salmocin blend consisting of ScolE1a+ScolE1b+ScolE2+ScolE7 applied at 3+1+1+1 mg/kg meat, respectively), both in relation to plant extract control-treated, meat samples and statistically significant net reductions in viable counts of 2-3 logs CFU/g meat at all time-points analysed were found (FIG. 25). The highest level of reduction of bacterial populations was observed for the 4-salmocin blend (concentration of 3+1+1+1 mg/kg meat) with up to 3.39 mean log reduction vs. carrier treatment upon 48 h of storage, which corresponds to a 99.6 mean percent reduction of bacteria. A single salmocin, ScolE1a (applied at 3 mg/kg meat), was able to control *Salmonella* contamination on meat with similar efficacy to the blend of four salmocins applied at double the concentration (6 mg/kg meat total salmocin). Even a treatment with salmocins at very low dose (total salmocin 0.6 mg/kg meat; 0.3+0.1+0.1+0.1 mg/kg meat for a blend of ScolE1a+ScolE1b+ScolE2+ScolE7) produced statistically significant reductions of bacterial populations of about 1 log CFU for up to 48 h of storage. Upon initial reduction of bacterial contamination, re-growth of viable bacteria was observed after 72 h, indicating that salmocins act quickly but have no prolonged technical effect on food.

Example 12: Recombinant Salmocins are Correctly Expressed by Plants

The primary structure including post-translational modifications of the plant-expressed recombinant salmocins contained in plant TSP extracts was analysed by Matrix-assisted laser desorption/ionization (MALDI) time-of-flight (TOF) mass spectrometry (MS).

For proteolytic digestion, TSP extracts prepared from plant material expressing salmocins with 5 vol. 20 mM Na citrate, 20 mM $NaH_2PO_4$, 30 mM NaCl, pH 5.5 were subjected to SDS-PAGE and Coomassie-stained SDS gel bands containing 5 μg of protein were excised and destained by consecutive washing with 100 mM $NH_4HCO_3$ and 100 mM $NH_4HCO_3$ in acetonitrile (ACN)/$H_2O$ (50; 50, v/v). Disulfide bonds were reduced with 10 mM DTT for 45 min at 50° C. followed by alkylation with 10 mg/ml of iodoacetamide for 60 min. Destained and alkylated gel bands were then subjected to proteolytic digestion with different sequencing grade endoproteinases (Promega, Madison, USA). Protease:protein ratio in the digestion solutions was adjusted to 1:20 (w/w) and digestions were carried out for 12 h at 25° C. (chymotrypsin) or 37° C. (Asp-N, Glu-C, Lys-C, trypsin). Proteolytic peptides were extracted by consecutive washing with $H_2O$, ACN/$H_2O$/trifluoroacetic acid (50; 45; 5, v/v/v) and ACN, respectively. Extraction solutions were combined, concentrated in a vacuum centrifuge and resolubilized in $H_2O$/acetic acid (90; 10, v/v).

Proteolytic salmocin peptides obtained as described above or purified intact plant-produced salmocin ScolE1a, ScolE1b and ScolE7 proteins were purified for mass spectrometry by solid-phase extraction using C4 or C18 bonded silica material (ZipTip®, Millipore, Darmstadt, Germany) and elution solutions were co-crystallized on a MALDI ground steel target with 2,5-dihydroxyacetophenone as well as 2,5-dihydroxybenzoic acid matrix (Bruker Daltonics, Bremen, Germany).

Mass spectra were acquired on a MALDI-TOF/TOF mass spectrometer (Autoflex Speed™, Bruker Daltonics, Bremen, Germany) with positive polarity in linear mode for molecular mass determination and in reflector mode for protein sequencing by In-source decay (ISD) analysis. The matrix crystals were irradiated with a Nd:YAG laser (Smart beam-II™, Bruker Daltonics, Bremen, Germany) at an emission wavelength of 355 nm and set to a pulse rate of 1 kHz.

MS and MS/MS spectra were recorded with flexControl (version 3.4, Bruker Daltonics, Bremen, Germany) by accumulation of at least 5000 or 10000 laser shots (per sample spot), respectively. Laser energy was set slightly above the threshold for MS experiments and set to maximum for MS/MS analyses. Spectra processing was carried out with flexAnalysis (version 3.4, Bruker Daltonics, Bremen, Germany) by applying baseline subtraction with TopHat algorithm, smoothing with Savitzky-Golay algorithm and peak detection with SNAP algorithm.

The mass spectrometer was calibrated using a set of standard peptides and proteins with known masses (Peptide Calibration Standard II, Protein Calibration Standard I and II, Bruker Daltonics, Bremen, Germany).

Determination of the intact molecular mass was based on the mass-to-charge-ratios (m/z) of single and multiple charged molecular ions.

Sequencing of protein termini was carried out by ISD analysis. The annotation of ISD fragment spectra was carried using BioTools (version 3.2, Bruker Daltonics, Bremen, Germany) by in silico generation of m/z values for fragment ions and their comparison with the m/z values of the fragment signals observed within the acquired ISD spectra. This approach enabled the identification of the terminal amino acid sequences as well as of present modifications.

For protein sequencing analysis, only fragment (MS/MS) spectra were used for the identification of proteolytic peptides and the annotation was carried out with PEAKS Studio (version 7.5, Bioinformatics Solutions Inc., Waterloo, Canada). Identification of proteins and verification of their amino acid sequences was performed by searching the MS/MS data against the NCBI nr database and the UniProt/SwissProt database to which the sequences of the salmocins were appended, respectively. Database search was performed with a parent mass error tolerance of 50 ppm and a fragment mass error tolerance of 0.5 Da. The maximum number for both missed cleavages as well as post-translational modifications for one proteolytic fragment was set to 3. Non-specific cleavage was allowed for both protein termini.

Search results of each MS/MS dataset from proteolytic peptides of salmocins against the UniProt/SwissProt database confirmed the identity of each of the analysed salmocins (Table 11). The integrity of purified salmocins ScolE1a, ScolE1b and ScolE7 was further analysed by MS-based sequencing of protein termini using ISD and molecular mass determination methods, which confirmed that all salmocin proteins were intact upon plant expression. Post-translational modifications observed were restricted to cleavage of N-terminal methionine in case of ScolE2, ScolE7, ScolE1a and ScolE1b and N-terminal acetylation for ScolE7 and ScolE1a (Table 11).

TABLE 11

Identity and integrity studies on plant-produced salmocins. MALDI-TOF/TOF mass spectrometry analysis of salmocin-containing TSP extracts of *N. benthamiana* or purified salmocins by peptide mass fingerprinting or by sequencing of protein termini by in-source decay and molecular mass determination, respectively. Proteases used for generation of peptide fragments are indicated. The identity of salmocins was confirmed by searching MS/MS datasets obtained against NCBI non-redundant database. Obtained molecular masses indicate that the proteins were intact.

| salmocin-containing TSP extracts of *N. benthamiana* | | | | | | |
|---|---|---|---|---|---|---|
| | | peptide mass fingerprinting | | | | |
| No. | salmocin | Peptides annotated | Amino acid coverage (trypsin, Asp-N, chymotrypsin, Glu-C, Lys-C, combined) | Proteoform | N-terminus (aa and PTM) | C-terminus (aa and PTM) |
| 1 | ScolE2 | 44 | 56.3% | 1<br>2 | $H_2N$-SGGDGIGHNS[. . .] (M cleaved, no PTM, part of SEQ ID NO: 1)<br>Acetyl-SGGDGIGHNS[. . .] (M cleaved, acetylation, part of SEQ ID NO: 1) | [. . .]KLHIDIHRGK-OH (intact, no PTM, part of SEQ ID NO: 1) |

TABLE 11-continued

Identity and integrity studies on plant-produced salmocins. MALDI-TOF/TOF mass spectrometry analysis of salmocin-containing TSP extracts of *N. benthamiana* or purified salmocins by peptide mass fingerprinting or by sequencing of protein termini by in-source decay and molecular mass determination, respectively. Proteases used for generation of peptide fragments are indicated. The identity of salmocins was confirmed by searching MS/MS datasets obtained against NCBI non-redundant database. Obtained molecular masses indicate that the proteins were intact.

| | | | | | | |
|---|---|---|---|---|---|---|
| 2 | ScolE7 | 31 | 33.3% | — | ND | [. . .]KRHIDIHRGQ-OH (intact, no PTM, part of SEQ ID NO: 3) |
| 3 | ScolE3 | 18 | 31.5% | — | ND | ND |
| 4 | ScolE1a | 14 | 34.2% | 1 | Acetyl-ADNTIAYYED[. . .] (M cleaved, acetylation, part of SEQ ID NO: 4) | ND |
| 5 | ScolE1b | 25 | 47.1% | — | ND | ND |

salmocins purified from *N. benthamiana*

| No. | salmocin | Batch | Theoretical mass of intact protein (Da) | Molecular mass: Average mass (Da) (PTM) | Molecular mass: Proteoform | in-source decay: N-terminus (aa and PTM) | in-source decay: C-terminus (aa and PTM) |
|---|---|---|---|---|---|---|---|
| 2 | ScolE7 | 1 | 62259.4 | 62111.0 | 1 | $H_2N$-SGGDGG[. . .] (M cleaved, no PTM, part of SEQ ID NO: 3) | [. . .]KRHIDIHRGQ-OH (intact, no PTM, part of SEQ ID NO: 3) |
| | | 2 | | 62126.9 | 1 | $H_2N$-SGGDGG[. . .] (M cleaved, no PTM, part of SEQ ID NO: 3) | [. . .]KRHIDIHRGQ-OH (intact, no PTM, part of SEQ ID NO: 3) |
| | | 3 | | 62137.8 (N-terminus: M cleaved) | 1 | ND | ND |
| 4 | ScolE1a | 1 | 52811.3 | ND | 1 | ND | ND |
| | | 2 | | ND | 1 | ND | ND |
| | | 3 | | 52722.1 (N-terminus: M cleaved, acetylation) | 1 | ND | ND |
| 5 | ScolE1b | 1 | 57583.1 | 57486.3 | 1 | ND | ND |
| | | 2 | | 57470.0 | 1 | ND | ND |
| | | 3 | | 57480.7 (N-terminus: M cleaved) | 1 | ND | ND |

ND, not detected; PTM post-translational modification; aa, amino acid sequence.

Example 13: Identification of Salmocins ScolE1c, ScolE1d ScolE1e and ScolMa

As it was shown in Example 10, two pore-forming salmocins ScolE1a and ScolE1b demonstrated the highest and broadest antimicrobial activity against all tested *Salmonella* strains. To identify other salmocins to control *Salmonella*, we performed a homology search in NCBI database for *Salmonella* proteins similar to ScolE1a and ScolE1b but different to colicins in the N-terminal part. This search revealed three new sequences, which we called ScolE1c (SEQ ID NO: 25), ScolE1d (SEQ ID NO: 26) and ScolE1e (SEQ ID NO: 27) (Table 12). The CLUSTAL Omega alignment of these sequences is shown in FIG. 26.

We also searched for *Salmonella* proteins similar to colicin M in order to have another functional domain expressing antimicrobial activity, which is not related to nuclease (as this often creates the need for co-expression of immunity proteins and most of these proteins were not easy to purify). This search resulted in ScolMa sequence (SEQ ID NO: 28) (Table 12).

TABLE 12

List of *Salmonella* bacteriocins (salmocins) used in examples.

| No./SEQ ID NO: | Salmocin | Activity | GenBank Accession No |
|---|---|---|---|
| 7/25 | ScolE1c | pore-forming | WP_079814137.1 |
| 8/26 | ScolE1d | pore-forming | WP_082328811.1 |
| 9/27 | ScolE1e | pore-forming | WP_079849790.1 |
| 10/28 | ScolMa | inhibition of murein biosynthesis | AXC71921.1 |

Example 14: Plasmid Constructs for Salmocins ScolE1c, ScolE1d ScolE1e and ScolMa Amino acid sequences of salmocins ScolE1c, ScolE1d, ScolE1e and ScolMa were retrieved from GenBank; corresponding nucleotide sequences with codon usage optimized for *Nicotiana benthamiana* were synthesized by Thermo Fisher Scientific Inc. SEQ ID NO: 29 encoded ScolE1c, SEQ ID NO: 30 encoded ScolE1d, SEQ ID NO: 31 encoded ScolE1e, and SEQ ID NO: 32 encoded ScolMa.

Salmocin coding sequences were inserted into TMV-based assembled viral vector pNMD035 (described in detail in WO2012/019660) resulting in plasmid constructs depicted in FIG. 28.

Example 15: Expression Screen for Salmocins ScolE1c, ScolE1d ScolE1e and ScolMa Salmocin expression screen was performed as described in Example 2. The accumulation of salmocins ScolE1c, ScolE1d and ScolMa in *Nicotiana benthamiana* leaves was high. In contrast, the expression of ScolE1e was poor (FIG. 29).

Example 16: Salmocin Activity Screen for ScolE1c, ScolE1d ScolE1e and ScolMa

We compared the antimicrobial activity of plant-made recombinant salmocins ScolE1c, ScolE1d, ScolE1e and ScolMa against ScolE1a and ScolE1b. For this comparison, we used 10 *Salmonella enterica* ssp. *enterica* strains (Table 13). The evaluation of antimicrobial activity in plant extracts containing salmocins was performed using a radial diffusion spot-on-lawn assay as described in Example 6. The extract from untransfected plant tissue (Wt) was used as a negative control. All tested new salmocins demonstrated significant antimicrobial activities, although they were not superior of ScolE1a and ScolEb (Table 13).

Based on the expression and antimicrobial activity levels, we selected ScolE1d and ScolMa for generation of ethanol-inducible stable transgenic *Nicotiana benthamiana* hosts.

TABLE 13

Antimicrobial activity of salmocins ScolE1c, ScolE1d ScolE1e and ScolMa against selected *Salmonella enterica* ssp. *enterica* strains.

| Culture collection reference # | Serotype | ScolE1c | ScolE1d | ScolE1e | ScolMa | ScolE1b | ScolE1a | Wt |
|---|---|---|---|---|---|---|---|---|
| ATCC ® 13076 ™* | Enteritidis | $2.68 \times 10^8$ | $2.14 \times 10^9$ | 8.00 | $6.4 \times 10^1$ | $2.14 \times 10^9$ | $2.14 \times 10^9$ | $6.4 \times 10^1$ |
| ATCC ® 14028 ™* | Typhimurium | $1.34 \times 10^8$ | $2.14 \times 10^9$ | $1.6 \times 10^1$ | $2.62 \times 10^5$ | $2.14 \times 10^9$ | $2.14 \times 10^9$ | $2.56 \times 10^2$ |
| ATCC ® 6962 ™* | Newport | $2.56 \times 10^2$ | $4.09 \times 10^3$ | 0 | 0 | $2.62 \times 10^5$ | $8.38 \times 10^6$ | 0 |
| ATCC ® 10721 ™* | Javiana | $2.56 \times 10^2$ | $2.56 \times 10^2$ | 0 | $6.55 \times 10^4$ | $8.19 \times 10^3$ | $2.14 \times 10^9$ | $1.6 \times 10^1$ |
| ATCC ® 8326 ™* | Heidelberg | $1.28 \times 10^2$ | $2.56 \times 10^2$ | 0 | $8.19 \times 10^3$ | $4.09 \times 10^3$ | $2.14 \times 10^9$ | 4.00 |
| ATCC ® 8387 ™* | Montevideo | $1.6 \times 10^1$ | $6.4 \times 10^1$ | 0 | $2.04 \times 10^3$ | $5.12 \times 10^2$ | $4.09 \times 10^3$ | 2.00 |
| ATCC ® 8388 ™* | Muenchen | 4.00 | $1.6 \times 10^1$ | 0 | $4.09 \times 10^3$ | $1.28 \times 10^2$ | $8.19 \times 10^3$ | 2.00 |
| ATCC ® 9712 ™* | Saintpaul | $6.4 \times 10^1$ | $1.28 \times 0^2$ | 0 | $1.63 \times 10^4$ | $5.12 \times 10^2$ | $4.19 \times 10^6$ | $1.6 \times 10^1$ |
| ATCC ®BAA-1675 ™ | Infantis | $3.2 \times 10^1$ | $6.4 \times 10^1$ | 0 | $2.04 \times 10^3$ | $4.09 \times 10^3$ | $5.24 \times 10^5$ | 1.00 |
| 13-04865 | Kintambo | 1.00 | 1.00 | 0 | $8.19 \times 10^3$ | 0 | $2.09 \times 10^6$ | 4.00 |

Example 17: Production of Salmocins ScolE1d and ScolMa in Stable Transgenic Hosts

*N. benthamiana* was transformed by *Agrobacterium*-mediated leaf disk transformation using vectors for EtOH-inducible transgene expression (pNMD49621 for ScolE1d and pNMD49632 for ScolMa, FIG. 30). The ethanol induction of detached leaves of TO generation transgenic plants for salmocin expression was performed. These experiments were done as described in Example 8. For 169 TO transgenic lines transformed with pNMD49621 construct which were used for analysis, 126 lines were positive for EtOH-inducible SalE1d expression (FIG. 31).

```
Amino acid and nucleotide sequences
Amino acid sequence of salmocin ScolE2
                                                          SEQ ID NO: 1
MSGGDGIGHN SGAHSTGGVN GSSSGRGGSS SGGGNNPNSG PGWGTTHTPD GHDIHNYNPG

EFGGGGHKPG GNGGNHSGGT GDGQPPGAAM AFGFPALVPA GAGGLAVTVS GDALAAAIAD

VLAVLKGPFK FGAWGIALYG ILPTEIAKDD PRMMSKIVTS LPADAVTESP VSSLPLDQAT

VSVTKRVTDV VKDERQHIAV VAGVPASIPV VDAKPTTHPG VFSVSVPGLP DLQVSTVKNA

PAMTALPRGV TDEKDRTVHP AGFTFGGSSH EAVIRFPKES GQAPVYVSVT DVLTPEQVKQ

RQDEENRRQQ EWDATHPVEV AERNYRLASD ELNRANVDVA GKQERQIQAA QAVAARKGEL

DAANKTFADA KEEIKKFERF AHDPMAGGHR MWQMAGLKAQ RAQNEVNQKQ AEFNAAEKEK

ADADAALNVA LESRKQKEQK AKDASDKLDK ENKRNHPGKA TGKGQPVGDK WLEDAGKEAG

APVPDRIADK LRDKEFKNFD DFRKKFWEEV SKDPELSKQF IPGNKKRMSQ GLAPRARNKD

TVGGRRSFEL HHDKPISQDG GVYDMDNIRV TTPKLHIDIH RGK

Amino acid sequence of salmocin ScolE3
                                                          SEQ ID NO: 2
MSGGDGRGHN TGAHSTSGNI NGGPTGLGVS GGASDGSGWS SENNPWGGGS GSGIHWGGGS

GRGNGGGNGN SGGGSGTGGN LSAVAAPVAF GFPALSTPGA GGLAVSISAS ELSAAIAGII

AKLKKVNLKF TPFGVVLSSL IPSEIAKDDP NMMSKIVTSL PADDITESPV SSLPLDKATV

NVNVRVVDDV KDERQNISVV SGVPMSVPVV DAKPTERPGV FTASIPGAPV LNISVNNSTP
```

-continued

AVQTLSPGVT NNTDKDVRPA GFTQGGNTRD AVIRFPKDSG HNAVYVSVSD VLSPDQVKQR

QDEENRRQQE WDATHPVEVA EREYENARAE LEAENKNVHS LQVALDGLKN TAEGLALSDA

GRHPLTSSES RFVAVPGYSG GGVHFDATAT VDSRDRLNSL LSLGGAAYVN NVLELGEVSA

PTEDGLKVGN AIKNAMIEVY DKLRQRLITR QNEINHAQVS LNTAIESRNK KEEKKRSAEN

KLNEERNKPR KGTKDYGHDY HPAPETEEIK GLGDIKKGIP KTPKQNGGGK RKRWIGDKGR

KIYEWDSQHG ELEGYRASDG QHLGSFDPKT GKQLKGPDPK RNIKKYL

Amino acid sequence of salmocin ScolE7

SEQ ID NO: 3

MSGGDGIGHN SGAHSTGGVN GSSSGSGGSS SGSGNNPNSG PGWGTTHTPN GDIHNYNPGE

FGGGGNKPGG HGGNSGNHDG SSGNGQPSAA PMAFGFPALA PAGAGSLAVT VSGEALSAAI

ADIFAALKGP FKFGAWGIAL YGIMPTEIAK DDPNMMSKIM TSLPADTVTD TPVSSLPLDQ

ATVSVTKRVA DVVKDERQHI AVVAGVPMSV PVVDAKPTTR PGIFSATVPG LPALEVSTGK

SIPASTALPR GITEDKDRTE HPAGFTFGGS SHDAVIRFPK ESGQAPVYVS VTDVLTPEQV

KQRQDEESRR QQEWDATHPV EVAERNYRLA SDELNRVNAD VAGKQERQAQ AGQAVAARKG

ELDAANKTFA DAKEEIKKFE HFARDPMAGG HRMWQMAGLK AQRAQNEVNQ KQAEFDAAEK

EKADADAALN AALESRKQKE QKAKDTKERL DKENKRNQPG KATGKGQPVS DKWLEDAGKE

SGSPIPDSIA DKLRDKEFRN FDDFRKKFWE EVSKDPELSK QFIKGNRDRM QVGKAPKSRK

KDAAGKRTSF ELHHDKPVSQ DGGVYDMDNL RITTPKRHID IHRGQ

Amino acid sequence of salmocin ScolE1a

SEQ ID NO: 4

MADNTIAYYE DGVPHSADGK VVIVIDGKMP VDTGAGGTGG GGGGKVGGTS ESSAAIHATA

KWSTAQLKKT LAEKAARERE TAAAMAAAKA KRDALTQHLK DIVNDVLRHN ASRTPSATDL

AHANNMAMQA EAQRLGRAKA EEKARKEAEA AELAFQEAER QREEAVRQLA ETERQLKQAE

EEKRLAALSD EARAVENARK NLDTAKSELA NVDSDIERQR SQLSSLDADV KKAEENLRLT

MRIKGRIGRK MQAKSQAIVD DKKRIYSDAE NVLNTMTVNR NLKAQQVTDA ENELKVAIDN

LNSSQMKNAV DATVSFYQTL TEKYGEKYSL IAQELAEKSK GKKIGNVDEA LAAFEKYKDV

LDKKFSKADR DAIVNALKSF NYDDWAKHLD QFAKYLKITG HVSFGYDVVS DVLKASETGD

WKPLFITLEQ KVLDTGMSYL VVLMFSLIAG TTLGIFGVAI ITAILCSFVD KYILNALNDA

LGI

Amino acid sequence of salmocin ScolE1b

SEQ ID NO: 5

MSDNTIAYYE DGVPYSADGQ VVIVIDGKMP VDTGAGGTGG GGGGKVGGTS ESSAAIHATA

KWSKAQLQKS LEEKAARERE TAAAMAAAKA KRDALTQHLK DIVNDVLRYN ASRTPSATDL

AHANNMAMQA EAQRLGRAKA EEKARKEAEA AEKSLQEAER QREEAARQRA EAERQLKQAE

AEEKRLAALS EEARAVEITQ KNLAAAQSEL SKMDGEIKSL NVRLSTSIHA RDAEMNSLSG

KRNELAQESA KYKELDELVK KLEPRANDPL QNRPFFDATS RRARAGDTLA EKQKEVTASE

TRINELNTEI NQVRGAISQA NNNRNLKVQQ VTETENALKV AIDNLNSSQM KNAVDATVSF

YQTLTAKYGE KYSLIAQELA EQSKGKKISN VDEALAAFEK YKDVLDKKFS KADRDAIVNA

LKSVDYADWA KHLDQFSRYL KISGRVSTGY DIYSDIRKGM DTNDWRPLFL TLEKLAVDAG

VGYIVALGFS VIASTALGIW GVAIITGVIC SFVDKKDLEK LNEALGI

Amino acid sequence of salmocin Spst

SEQ ID NO: 6

MFIKSGGNLT IRTFGGLGVG GDFDSDTWRR RSTDSWVPYS EYIAIECIVA PNQLYQLLTD

VAQVETVAAQ LAQVGYQYLQ GRLRLVREDG SCTDFSGKAM LDNLLNKSKD ILDLDFLHVS

-continued

EGYRSEAYWP GQSSGITIGY GVDIGHQSEE GLHKWGVPQS IIDKIKDYFG ITGEAANTLL

KGLKDKTLGL SDREIKQFSD IVKKQATADI INKYNAATKG ITFDKIPYNT RTAIIDLFYQ

YSAPKGAPKS WGFIINNDWN GFYNELMNFG DKHTTRRERE AALVLSDIVN NQYIYK

Amino acid sequence of salmocin ScolE2 immunity protein SImmE2

SEQ ID NO: 7

MELKKSISDY TEAEFKKIIE AIINCEGDEK TQDDNLEFFI RVTEYPSGSD LIYYPEGDND

GSTEAIIKEI KEWRAANGKP GFKQADSSYF VSFDYRDGDW

Amino acid sequence of salmocin ScolE7 immunity protein SImmE7

SEQ ID NO: 8

MELKNSISDY TEAEFIEFMK EIDKENVAET DDKLDLLLNH FEQVTEHPDG TDLIYYAASD

AESTPEAITK KIKEWRAANG KPGFKQG

Amino acid sequence of colicin S4

SEQ ID NO: 9

MAKELSVYGP TAGESMGGTG ANLNQQGGNN NSNSGVHWGG GSGSGNGGRE HGSQTGWGWS

KTNNPDVPPY VDDNGQVRIT ITNGLVKTPV YGVPGAGGNS DVQGGYIPEN PNDEVARKWD

KNNLPREIDV SIDGFKYRVT LNDNGRAIGI LRTGVRPYVG SEKAKAGIME KINHKTPEEI

YEALGFNKDE SQRQEKAKQQ AEDAWDRLPP NVRKFDVDVE QFHYLVVLDD YGNVLSVTRT

GVRPYVGSEK AKAGIMDKVD HKTPEEIYEA LGFNNEEPQR QNQAKKAAYD VFYSFSMNRD

RIQSDVLNKA AEVISDIGNK VGDYLGDAYK SLAREIADDV KNFQGKTIRS YDDAMASLNK

VLSNPGFKFN RADSDALANV WRSIDAQDMA NKLGNISKAF KFADVVMKVE KVREKSIEGY

ETGNWGPLML EVESWVLSGI ASAVALGVFS ATLGAYALSL GAPAIAVGIV GILLAAVVGA

LLDDKFADAL NKEIIKPAH

Amino acid sequence of colicin 5

SEQ ID NO: 10

MDKVTDNSPD VESTESTEGS FPTVGVDTGD TITATLATGT ENVGGGGGAF GGASESSAAI

HATAKWSTAQ LKKHQAEQAA RALAAEAALA KAKSQRDALT QRLKDIVNDA LRANAARSPS

VTDLAHANNM AMQAEAERLR LAKAEQKARE EAEAAEKALR EAERQRDEIA RQQAETAHLL

AMAEAAEAEK NRQDSLDEEH RAVEVAEKKL AEAKAELAKA ESDVQSKQAI VSRVAGELEN

AQKSVDVKVT GFPGWRDVQK KLERQLQDKK NEYSSVTNAL NSAVSIRDAK KTDVQNAEIK

LKEAKDALEK SQVKDSVDTM VGFYQYITEQ YGEKYSRIAQ DLAEKAKGSK FSSVDEALAA

FEKYKNVLDK KISKVDRDAI FNALESVNYD ELSKNLTKIS KSLKITSRVS FLYDVGSDFK

NAIETGNWRP LFVTLEKSAV DVGVAKIVAL MFSFIVGVPL GFWGIAIVTG IVSSYIGDDE

LNKLNELLGI

Amino acid sequence of colicin 10

SEQ ID NO: 11

MDKVTDNSPD VESTESTEGS FPTVGVDTGD TITATLATGT ENVGGGGGAF GGASESSAAI

HATAKWSTAQ LKKHQAEQAA RALAAEAALA KAKSQRDALT QRLKDIVNDA LRANAARSPS

VTDLAHANNM AMQAEAERLR LAKAEQKARE EAEAAEKALR EAERQRDEIA RQQAETAHLL

AMAEAAEAEK NRQDSLDEEH RAVEVAEKKL AEAKAELAKA ESDVQSKQAI VSRVAGELEN

AQKSVDVKVT GFPGWRDVQK KLERQLQDKK NEYSSVTNAL NSAVSIRDAK KTEVQNAEIK

LKEAKDALEK SQVKDSVDTM VGFYQYITEQ YGEKYSRIAQ DLAEKAKGSK FNSVDEALAA

FEKYKNVLDK KFSKVDRDDI FNALESITYD EWAKHLEKIS RALKVTGYLS FGYDVWDGTL

KGLKTGDWKP LFVTLEKSAV DFGVAKIVAL MFSFIVGAPL GFWGIAIITG IVSSYIGDDE

LNKLNELLGI

-continued

Amino acid sequence of colicin 1a

SEQ ID NO: 12

MSDPVRITNP GAESLGYDSD GHEIMAVDIY VNPPRVDVFH GTPPAWSSFG NKTIWGGNEW

VDDSPTRSDI EKRDKEITAY KNTLSAQQKE NENKRTEAGK RLSAAIAARE KDENTLKTLR

AGNADAADIT RQEFRLLQAE LREYGFRTEI AGYDALRLHT ESRMLFADAD SLRISPREAR

SLIEQAEKRQ KDAQNADKKA ADMLAEYERR KGILDTRLSE LEKNGGAALA VLDAQQARLL

GQQTRNDRAI SEARNKLSSV TESLNTARNA LTRAEQQLTQ QKNTPDGKTI VSPEKFPGRS

STNHSIVVSG DPRFAGTIKI TTSAVIDNRA NLNYLLTHSG LDYKRNILND RNPVVTEDVE

GDKKIYNAEV AEWDKLRQRL LDARNKITSA ESAVNSARNN LSARTNEQKH ANDALNALLK

EKENIRNQLA GINQKIAEEK RKQDELKATK DAINFTTEFL KSVSEKYGAK AEQLAREMAG

QAKGKKIRNV EEALKTYEKY RADINKKINA KDRAAIAAAL ESVKLSDISS NLNRFSRGLG

YAGKFTSLAD WITEFGKAVR TENWRPLFVK TETIIAGNAA TALVALVFSI LTGSALGIIG

YGLLMAVTGA LIDESLVEKA NKFWGI

Amino acid sequence of colicin 1b

SEQ ID NO: 13

MSDPVRITNP GAESLGYDSD GHEIMAVDIY VNPPRVDVFH GTPPAWSSFG NKTIWGGNEW

VDDSPTRSDI EKRDKEITAY KNTLSAQQKE NENKRTEAGK RLSAAIAARE KDENTLKTLR

AGNADAADIT RQEFRLLQAE LREYGFRTEI AGYDALRLHT ESRMLFADAD SLRISPREAR

SLIEQAEKRQ KDAQNADKKA ADMLAEYERR KGILDTRLSE LEKNGGAALA VLDAQQARLL

GQQTRNDRAI SEARNKLSSV TESLKTARNA LTRAEQQLTQ QKNTPDGKTI VSPEKFPGRS

STNHSIVVSG DPRFAGTIKI TTSAVIDNRA NLNYLLTHSG LDYKRNILND RNPVVTEDVE

GDKKIYNAEV AEWDKLRQRL LDARNKITSA ESAINSARNN VSARTNEQKH ANDALNALLK

EKENIRSQLA DINQKIAEEK RKRDEINMVK DAIKLTSDFY RTIYDEFGKQ ASELAKELAS

VSQGKQIKSV DDALNAFDKF RNNLNKKYNI QDRMAISKAL EAINQVHMAE NFKLFSKAFG

FTGKVIERYD VAVELQKAVK TDNWRPFFVK LESLAAGRAA SAVTAWAFSV MLGTPVGILG

FAIIMAAVSA LVNDKFIEQV NKLIGI

Amino acid sequence of colicin M

SEQ ID NO: 14

METLTVHAPS PSTNLPSYGN GAFSLSAPHV PGAGPLLVQV VYSFFQSPNM CLQALTQLED

YIKKHGASNP LTLQIISTNI GYFCNADRNL VLHPGISVYD AYHFAKPAPS QYDYRSMNMK

QMSGNVITPI VALAHYLWGN GAERSVNIAN IGLKISPMKI NQIKDIIKSG VVGTFPVSTK

FTHATGDYNV ITGAYLGNIT LKTEGTLTIS ANGSWTYNGV VRSYDDKYDF NASTHRGIIG

ESLTRLGAMF SGKEYQILLP GEIHIKESGK R

Nucleotide sequence used for salmocin ScolE2 expression in examples

SEQ ID NO: 15 atgtctggtggtgatggtatcggtcacaatagcggtgctcattctactggtggtgtgaacggttcttcat ctggtaggggtggtagttcttcaggtggtggtaacaaccctaactctggtcctggttggggtactactca tactcctgatggtcacgatatccacaactacaaccctggtgagtttggtggtggtggacataagcctggt ggaaacggtggtaatcactctggtggtactggtgatggacaacctcctggtgctgctatggcttttggtt tccctgctcttgttcctgctggtgctggtggtcttgctgttactgtttctggtgatgctctggctgctgc aattgctgatgtgcttgctgttctgaagggacctttcaagtttggtgcttggggtatcgctctgtacggt attcttcctaccgagatcgctaaggatgatccaaggatgatgagcaagatcgtgacctctttgcctgctg atgctgtgactgagtctcctgtgtcatctctgcctcttgatcaggctactgtgagcgttaccaagagggt taccgatgtggttaaggatgagaggcagcacattgctgttgttgctggtgtgcctgcttctatccctgtt -continued gttgatgctaagcctactacccaccctggtgtgttctctgtttctgttcctggtctgcctgatctgcagg tttcaactgtgaagaacgctcctgctatgactgctttgcctaggggtgttactgatgagaaggataggac tgttcaccctgctggtttcaccttcggtggttcttctcatgaggctgtgatcaggttccctaaagagtct ggtcaggctcctgtttacgtgtcagtgaccgatgttcttacccctgagcaggttaagcagagacaggatg aagagaatagaaggcagcaagagtgggatgctactcaccctgttgaagtggctgagaggaattacaggct ggcttctgatgagctgaacagggctaatgtggatgtggctggtaagcaagagaggcagattcaagctgct caagctgttgctgctagaaagggtgaactggatgctgctaacaagaccttcgctgatgctaaagaagaga tcaagaagttcgagaggttcgctcacgatcctatggctggtggacacagaatgtggcaaatggctggtct taaggctcagagggctcagaatgaggttaaccagaaacaagctgagttcaacgctgctgagaaagaaaag gctgatgcagatgctgctctgaacgtggcacttgagtctaggaagcagaaagaacaaaaggcaaaggatg ctagcgataagctggataaggaaaacaagaggaaccaccctggaaaggctactggtaagggtcaacctgt tggtgataagtggcttgaggatgctggtaaagaagctggagcacctgttccagataggatcgctgataag ctgagagataaggaattcaagaacttcgatgattttaggaagaagttctgggaagaggtaaatttctagt ttttctccttcatttcttggttaggacccttttctctttttatttttttgagctttgatctttctttaa actgatctatttttttaattgattggttatggtgtaaatattacatagctttaactgataatctgattact ttatttcgtgtgtctatgatgatgatgataactgcaggttagcaaggatcctgagctgagcaagcagttc atccctggtaacaagaaaaggatgagccagggtcttgctcctagggctagaaacaaggatactgtgggtg gtagaagatccttcgagctgcatcacgataagccaatctctcaggatggtggtgtttacgatatggataa catcagggtgaccaccccaaagctgcacatcgatattcatagggggaaagtaa nucleotide sequence used for salmocin ScolE3 expression in examples

SEQ ID NO: 16 atgtctggtggtgatggtaggggtcataataccggtgctcatagcaccagcggtaacattaacggtggtc ctactggtcttggtgtgtcaggtggtgcttctgatggttctggttggtcctctgagaacaatccttgggg tggtggtagcggttctggtattcactggggaggtggaagtggtagaggtaatggtggtggaaacggtaac agtggtggtggttctggaactggtggtaacctttctgctgttgctgctcctgttgctttcggtttccctg ctctttctactcctggtgctggtggtttggctgtgtctatttctgcttctgagctgagcgctgctatcgc tggtattatcgctaagctgaagaaggtgaacctgaagttcacccctttcggtgtggtgctgtcctctttg attcctagcgagatcgctaaggatgatcctaacatgatgagcaagatcgtgaccagcctgcctgctgatg atattaccgagtctcctgtgtcctctctgcctcttgataaggctactgtgaatgtgaacgtgagggtggt ggatgatgtgaaggatgagaggcagaacatcagcgttgtgtctggtgttcctatgtctgtgcctgttgtg gatgctaagcctactgaaaggcctggtgtgttcaccgcttctattccaggtgctcctgtgctgaacatct ccgtgaacaattctacccctgctgtgcagactctttctcctggtgtgactaacaacaccgataaggatgt taggcctgctggtttcactcagggtggtaataccagggatgctgtgatcaggttccctaaggattctggt cacaacgcagtgtacgtgtccgtgtctgatgtgttgtctccagatcaggttaagcagaggcaggatgaag agaatagaaggcagcaagagtgggatgctactcaccctgttgaagttgctgagagagagtacgagaacgc tagagctgaacttgaggctgaaaacaagaacgtgcacagccttcaggtggcacttgatggtcttaagaat accgctgagggtctggctctttctgatgctggtagacatcctctgaccagcagcgagtctagatttgttg ctgtgcctggttactccggtggtggtgttcattttgatgctaccgctaccgtggatagcagggataggct taactctcttctgtctcttggtggtgctgcttacgtgaacaacgtgttggagcttggtgaggtgtcagct cctactgaggatggtttgaaggtgggaaacgctatcaagaacgctatgatcgaggtgtacgataagctga ggcagaggcttattaccaggcagaacgagatcaaccacgctcaggtgtcacttaacaccgctatcgagtc taggaacaagaaagaggaaaagaagaggtccgcagagaacaagctgaacgaagagagaaacaagcctaga -continued aagggtactaaggattacggacacgattaccatcctgctccagagactgaagaaatcaagggtctgggtg atatcaagaagggtatccctaagacccctaagcagaacggtggtggtaagagaaagagatggatcggaga taagggtagaaagatctacgagtgggatagccagcatggtgagcttgaaggtaaatttctagtttttctc cttcattttcttggttaggacccttttctcttttttatttttttgagctttgatctttctttaaactgatc tattttttaattgattggttatggtgtaaatattacatagctttaactgataatctgattactttatttc gtgtgtctatgatgatgatgataactgcaggttatagggcttcagatggtcagcacctgggaagctttga tcctaagactggtaagcagctgaagggtcctgatccaaagaggaacatcaagaagtacctttaa nucleotide sequence used for salmocin ScolE7 expression in examples

SEQ ID NO: 17 atgtctggtggtgatggtatcggtcacaatagcggtgctcattctactggtggtgtgaacggttcctctt ctggttctggtggaagctcatctggaagcggtaacaaccctaattctggtcctggttggggtactactca taccccctaacggtgatatccacaactacaaccctggtgagtttggtggtggtggaaacaagcctggtgga catggtggtaactctggtaaccacgatggtagctctggaaacggtcaaccttctgctgctcctatggctt ttggtttccctgctcttgctcctgctggtgctggttctcttgctgttactgtttctggtgaggctctgtc tgctgctatcgctgatattttcgctgctctgaagggacctttcaagttcggtgcttggggtattgctctg tacggtattatgcctaccgagatcgctaaggatgatcctaacatgatgagcaagatcatgaccagcctgc ctgctgatactgtgactgatactcctgtgtcctctctgcctcttgatcaggctactgtgtctgtgactaa gagggttgcagatgtggtgaaggatgagaggcagcatattgctgttgttgctggtgtgcctatgtctgtg cctgttgttgatgctaagcctaccactaggcctggtatcttctctgctactgttcctggacttcctgctt tggaggtgtcaaccggtaagtctattcctgcttctaccgctctgcctaggggtattactgaggataagga taggactgagcaccctgctggtttcactttcggtggttcttctcacgatgctgtgatcaggttccctaaa gagtctggtcaggctccagtttacgtgtcagtgactgatgtgcttacccctgagcaggttaagcagagac aggatgaagagtctagaaggcagcaagagtgggatgctactcatcctgttgaagtggctgagaggaacta caggcttgcttctgatgagctgaacagggtgaacgctgatgtggctggtaagcaagaaagacaagctcaa gctggacaggctgttgctgctagaaagggtgaacttgatgctgctaacaagaccttcgctgatgctaaag aagagatcaagaagttcgagcacttcgctagggatccaatggctggtggtcatagaatgtggcagatggc tggtcttaaggctcagagggctcagaatgaggttaaccagaaacaagctgagttcgatgctgcagagaaa gaaaaggctgatgctgatgcagctctgaacgctgctcttgaatctaggaagcagaaagagcagaaggcta aggataccaaagagaggctggataaggaaaacaagaggaatcagcctggtaaggctaccggtaagggtca gccagtttctgataagtggcttgaggatgctggtaaagagagcggttctcctatccctgatagcattgct gataagcttagagataaggaattcagaaacttcgatgattttaggaagaagttctgggaggaagttagca aggatcctgagctgagcaagcagttcatcaagggtaacagagataggatgcaggtaaatttctagttttt ctccttcattttcttggttaggacccttttctcttttttatttttttgagctttgatctttctttaaactg atctattttttaattgattggttatggtgtaaatattacatagctttaactgataatctgattactttat ttcgtgtgtctatgatgatgatgataactgcaggttggaaaggctcctaagtccagaaagaaggatgctg ctggtaagaggacctctttcgagcttcatcacgataagcctgtgagccaggatggtggtgtttacgatat ggataacctgaggatcaccacccctaagaggcacatcgatattcataggggacagtaa nucleotide sequence used for salmocin ScolE1a expression in examples

SEQ ID NO: 18 atggctgataacaccattgcttactacgaggatggtgtgcctcacagcgctgatggtaaggtggtgattg tgatcgatggtaagatgcctgtggataccggtgctggtggtactggtggtggtggaggtggtaaggttgg aggaacttctgaaagctctgctgctattcacgctaccgctaagtggtctaccgctcagcttaagaaaacc -continued ctggctgagaaggctgctagagagagagaaactgctgctgcaatggctgctgctaaggctaagagagatg ctcttacccagcacctgaaggatatcgtgaacgatgtgcttaggcacaacgcttctaggaccccttctgc tactgatcttgctcacgctaacaacatggctatgcaggctgaagctcagagacttggtagagctaaggct gaggaaaaggctagaaaagaggctgaggctgctgagcttgctttccaagaagctgaaagacagagggaag aggctgttagacagcttgctgaaactgagaggcagcttaagcaagctgaggaagagaagaggcttgctgc tctttctgatgaggctagggctgttgagaacgctaggaagaatctggataccgcaaagtccgagctggct aatgtggattctgatatcgagaggcagaggtcccagctgtcatctcttgatgctgatgtgaagaaggctg aagagaacctgaggctgaccatgaggattaagggtaggatcggtaggaagatgcaggctaagtcacaggc tatcgtggatgataagaaaaggatctactccgatgctgagaacgtgctgaataccatgaccgtgaatagg aacctgaaggctcagcaggttaccgatgcagagaatgagcttaaggtggcaatcgataacctgaacagca gccagatgaagaacgctgtggatgctaccgtgtctttctaccagactctgaccgagaagtacggtgagaa gtacagccttatcgctcaagagctggcagagaagtccaagggtaagaaaatcggaaatgtggatgaggct ctggctgcattcgagaagtataaggatgtgctggataagaagttcagcaaggctgatagggatgctattg tgaacgctctgaagtccttcaactacgatgattgggctaagcacctggatcagttcgctaagtacctgaa gatcaccggtcacgtgagcttcggttacgatgttgtgtctgatgtgctgaaggctagcgagactggtgat tggaagcctctgttcattacccttgagcagaaggtgttggatactggtatgagctacctggtggtgctga tgttctctcttattgctggaaccaccctgggaatcttcggtgtggctattattaccgctatcctgtgcag cttcgtggataagtacatcctgaacgcactgaacgatgctctgggaatctaa nucleotide sequence used for salmocin ScolE1b expression in examples

SEQ ID NO: 19 atgagcgataacaccattgcttactacgaggatggtgtgccttacagcgctgatggtcaagtggtgattg tgatcgatggtaagatgcctgtggataccggtgctggtggtactggtggtggtggaggtggtaaggttgg aggaacttctgaaagctctgctgctattcacgctaccgctaagtggtctaaggctcagcttcagaagtcc ctggaagagaaggctgctagagagagagaaactgctgctgcaatggctgctgctaaggctaagagagatg ctcttacccagcacctgaaggatatcgtgaacgatgtgctgaggtacaacgcttctaggactccttctgc taccgatcttgctcacgctaacaacatggctatgcaggctgaagctcagagacttggtagagctaaggct gaggaaaaggctagaaaagaggctgaggctgctgagaagtctcttcaagaagctgagagacagagggaag aagctgctaggcaaagagctgaagcagagaggcaacttaagcaggcagaggctgaagagaagaggttggc tgctctttctgaagaggctagggcagttgagatcacccagaagaatcttgctgctgctcagagcgagctg tccaagatggatggtgagatcaagagccttaacgtgaggctgtctacctctatccatgctagggatgctg agatgaacagcctgtctggtaagaggaacgagctggctcaagagagcgctaagtacaaagaactggatga gctggtgaagaagcttgagcctagggctaatgatcctctgcagaacaggcctttcttcgatgctacatct agaagggcaagggctggtgatactttggctgagaagcagaaagaggtgaccgcttctgagactaggatca acgagcttaacaccgagatcaaccaggtgaggggtgctatttcacaggcaaacaacaataggaacctgaa ggtgcagcaggttaccgagactgagaacgctcttaaggtggcaatcgataacctgaacagcagccagatg aagaacgctgtggatgctaccgtgtctttctaccagaccctgactgctaagtacggtgagaagtacagcc tgatcgctcaagaacttgctgagcagtccaagggtaagaaaatcagcaatgtggatgaggctctggctgc attcgagaagtataaggatgtgctggataagaagttcagcaaggctgatagggatgcaattgtgaacgct ctgaagtccgtggattacgctgattgggctaagcacctggatcagttcagcagatacctgaagatcagcg gtagggtgtcaaccggttacgatatctacagcgatatcagaaagggtatggataccaacgattggaggcc -continued

```
tctgttcctgacccttgagaagcttgctgttgatgctggtgtgggttacatcgtggctcttggtttctct

gtgatcgcttctaccgctcttggtattttgggtgtggctattatcaccggtgtgatctgcagcttcgttg

ataagaaggatttggagaagctgaacgaggcactgggaatctaa
```

nucleotide sequence used for salmocin Spst expression in examples
SEQ ID NO: 20
```
atgttcatcaagagcggtggtaacctgaccatcaggacttttggtggtcttggtgtgggtggtg

atttcgatagcgatacttggagaagaaggtccaccgattcttgggtgccatacagcgagtacat

tgctatcgagtgcatcgtggctcctaaccagctttaccagcttcttactgatgtggctcaggtg

gaaactgtggctgctcaacttgctcaggttggataccagtatcttcagggtaggcttaggctgg

tgagagaggatggttcttgcaccgatttcagcggtaaggctatgctggataacctgctgaacaa

gagcaaggatattctggatctggatttcctgcacgtgagcgagggttataggtctgaagcttat

tggcctggtcagtcctctggtatcaccattggttacggtgtggatatcggtcaccagtctgaag

agggacttcataagtggggtgtgcctcagagcatcatcgataagatcaaggattacttcggtat

taccggtgaggctgctaacacccttcttaagggtctgaaggataagaccctgggactgagcgat

agagagatcaagcagttctccgatatcgtgaagaagcaggctaccgctgatatcatcaacaagt

acaacgctgctaccaagggtatcacctttgataagatcccttacaacaccaggaccgctatcat

cgatctgttctaccagtacagcgctcctaagggtgctcctaagtcttggggtttcattatcaac

aacgattggaacggtttctacaacgagctgatgaacttcggtgataagcacaccaccagaagag

agagggaagctgctctggttctgtctgatattgtgaacaaccagtacatctacaagtaa
```

nucleotide sequence used for salmocin ScolE2 immunity protein SImmE2 expression in examples
SEQ ID NO: 21
```
atggaactgaagaagtccatcagcgattacaccgaggctgagttcaagaagatcatcgaggcta

tcatcaactgcgagggtgatgagaaaacccaggatgataaccttgagttcttcatcagggtgac

cgagtacccttctggtagcgatcttatctactaccctgagggtgataacgatggtagcaccgag

gcaattatcaaagaaatcaaggaatggagggctgctaacggtaagcctggttttaagcaagctt

aa
```

nucleotide sequence used for salmocin ScolE7 immunity protein SImmE7 expression in examples
SEQ ID NO: 22
```
atggaactgaagaacagcatcagcgattacaccgaggctgagttcatcgagttcatgaaagaaa

tcgataaggaaaacgtggcagagactgatgataagctggatctgctgctgaaccacttcgagca

ggttacagaacaccctgatggaaccgatctgatctactacgctgcttccgatgctgagtctacc

cctgaggctatcaccaagaaaatcaaagaatggagggctgctaacggtaagcctggttttaagc

aaggttaa
```

nucleotide sequence of binary TMV-based vector used for salmocin ScolE1a expression in examples
SEQ ID NO: 23
```
catggctgataacaccattgcttactacgaggatggtgtgcctcacagcgctgatggtaaggtggtgatt

gtgatcgatggtaagatgcctgtggataccggtgctggtggtactggtggtggtggaggtggtaaggttg

gaggaacttctgaaagctctgctgctattcacgctaccgctaagtggtctaccgctcagcttaagaaaac

cctggctgagaaggctgctagagagagagaaactgctgctgcaatggctgctgctaaggctaagagagat

gctcttacccagcacctgaaggatatcgtgaacgatgtgcttaggcacaacgcttctaggaccccttctg

ctactgatcttgctcacgctaacaacatggctatgcaggctgaagctcagagacttggtagagctaaggc

tgaggaaaaggctagaaaagaggctgaggctgctgagcttgctttccaagaagctgaaagacagagggaa
```

-continued gaggctgttagacagcttgctgaaactgagaggcagcttaagcaagctgaggaagagaagaggcttgctg ctctttctgatgaggctagggctgttgagaacgctaggaagaatctggataccgcaaagtccgagctggc taatgtggattctgatatcgagaggcagaggtcccagctgtcatctcttgatgctgatgtgaagaaggct gaagagaacctgaggctgaccatgaggattaagggtaggatcggtaggaagatgcaggctaagtcacagg ctatcgtggatgataagaaaaggatctactccgatgctgagaacgtgctgaataccatgaccgtgaatag gaacctgaaggctcagcaggttaccgatgcagagaatgagcttaaggtggcaatcgataacctgaacagc agccagatgaagaacgctgtggatgctaccgtgtctttctaccagactctgaccgagaagtacggtgaga agtacagccttatcgctcaagagctggcagagaagtccaagggtaagaaaatcggaaatgtggatgaggc tctggctgcattcgagaagtataaggatgtgctggataagaagttcagcaaggctgatagggatgctatt gtgaacgctctgaagtccttcaactacgatgattgggctaagcacctggatcagttcgctaagtacctga agatcaccggtcacgtgagcttcggttacgatgttgtgtctgatgtgctgaaggctagcgagactggtga ttggaagcctctgttcattacccttgagcagaaggtgttggatactggtatgagctacctggtggtgctg atgttctctcttattgctggaaccaccctgggaatcttcggtgtggctattattaccgctatcctgtgca gcttcgtggataagtacatcctgaacgcactgaacgatgctctgggaatctaagcttactagagcgtggt gcgcacgatagcgcatagtgtttttctctccacttgaatcgaagagatagacttacggtgtaaatccgta ggggtggcgtaaaccaaattacgcaatgttttgggttccatttaaatcgaaaccccttatttcctggatc acctgttaacgcacgtttgacgtgtattacagtgggaataagtaaaagtgagaggttcgaatcctcccta accccgggtaggggcccagcggccgctctagctagagtcaagcagatcgttcaaacatttggcaataaag tttcttaagattgaatcctgttgccggtcttgcgatgattatcatataatttctgttgaattacgttaag catgtaataattaacatgtaatgcatgacgttatttatgagatgggtttttatgattagagtcccgcaat tatacatttaatacgcgatagaaaacaaaatatagcgcgcaaactaggataaattatcgcgcgcggtgtc atctatgttactagatcgacctgcatccaccccagtacattaaaaacgtccgcaatgtgttattaagttg tctaagcgtcaatttgtttacaccacaatatatcctgccaccagccagccaacagctccccgaccggcag ctcggcacaaaatcaccactcgatacaggcagcccatcagtcagatcaggatctcctttgcgacgctcac cgggctggttgccctcgccgctgggctggcggccgtctatggccctgcaaacgcgccagaaacgccgtcg aagccgtgtgcgagacaccgcggccgccggcgttgtggatacctcgcggaaaacttggccctcactgaca gatgaggggcggacgttgacacttgaggggccgactcacccggcgcggcgttgacagatgaggggcaggc tcgatttcggccggcgacgtggagctggccagcctcgcaaatcggcgaaaacgcctgattttacgcgagt ttcccacagatgatgtggacaagcctggggataagtgccctgcggtattgacacttgaggggcgcgacta ctgacagatgaggggcgcgatccttgacacttgaggggcagagtgctgacagatgaggggcgcacctatt gacatttgaggggctgtccacaggcagaaaatccagcatttgcaagggtttccgcccgtttttcggccac cgctaacctgtcttttaacctgcttttaaaccaatatttataaaccttgtttttaaccagggctgcgccc tgtgcgcgtgaccgcgcacgccgaaggggggtgcccccccttctcgaaccctcccggcccgctaacgcgg gcctcccatcccccccaggggctgcgcccctcggccgcgaacggcctcaccccaaaaatggcagcgctggc caattcgtgcgcggaacccctatttgtttatttttctaaatacattcaaatatgtatccgctcatgagac aataaccctgataaatgcttcaataatattgaaaaaggaagagtatggctaaaatgagaatatcaccgga attgaaaaaactgatcgaaaaataccgctgcgtaaaagatacggaaggaatgtctcctgctaaggtatat aagctggtgggagaaaatgaaaacctatatttaaaaatgacggacagccggtataaagggaccacctatg atgtggaacgggaaaaggacatgatgctatggctggaaggaaagctgcctgttccaaaggtcctgcactt tgaacggcatgatggctggagcaatctgctcatgagtgaggccgatggcgtcctttgctcggaagagtat gaagatgaacaaagccctgaaaagattatcgagctgtatgcggagtgcatcaggctctttcactccatcg -continued acatatcggattgtccctatacgaatagcttagacagccgcttagccgaattggattacttactgaataa cgatctggccgatgtggattgcgaaaactgggaagaagacactccatttaaagatccgcgcgagctgtat gatttttaaagacggaaaagcccgaagaggaacttgtcttttcccacggcgacctgggagacagcaaca tctttgtgaaagatggcaaagtaagtggctttattgatcttgggagaagcggcagggcggacaagtggta tgacattgccttctgcgtccggtcgatcagggaggatatcggggaagaacagtatgtcgagctatttttt gacttactggggatcaagcctgattgggagaaaataaaatattatattttactggatgaattgttttagc tgtcagaccaagtttactcatatatactttagattgatttaaaacttcatttttaatttaaaaggatcta ggtgaagatcctttttgataatctcatgaccaaaatcccttaacgtgagttttcgttccactgagcgtca gaccccgtagaaaagatcaaaggatcttcttgagatcctttttttctgcgcgtaatctgctgcttgcaaa caaaaaaaccaccgctaccagcggtggtttgtttgccggatcaagagctaccaactctttttccgaaggt aactggcttcagcagagcgcagataccaaatactgtccttctagtgtagccgtagttaggccaccacttc aagaactctgtagcaccgcctacatacctcgctctgctaatcctgttaccagtggctgctgccagtggcg ataagtcgtgtcttaccgggttggactcaagacgatagttaccggataaggcgcagcggtcgggctgaac ggggggttcgtgcacacagcccagcttggagcgaacgacctacaccgaactgagatacctacagcgtgag ctatgagaaagcgccacgcttcccgaagggagaaaggcggacaggtatccggtaagcggcagggtcggaa caggagagcgcacgagggagcttccagggggaaacgcctggtatctttatagtcctgtcgggtttcgcca cctctgacttgagcgtcgatttttgtgatgctcgtcaggggggcggagcctatggaaaaacgccagcaac gcggcctttttacggttcctggcagatcctagatgtggcgcaacgatgccggcgacaagcaggagcgcac cgacttcttccgcatcaagtgttttggctctcaggccgaggcccacggcaagtatttgggcaaggggtcg ctggtattcgtgcagggcaagattcggaataccaagtacgagaaggacggccagacggtctacgggaccg acttcattgccgataaggtggattatctggacaccaaggcaccaggcgggtcaaatcaggaataagggca cattgccccggcgtgagtcggggcaatcccgcaaggagggtgaatgaatcggacgtttgaccggaaggca tacaggcaagaactgatcgacgcggggttttccgccgaggatgccgaaaccatcgcaagccgcaccgtca tgcgtgcgccccgcgaaaccttccagtccgtcggctcgatggtccagcaagctacggccaagatcgagcg cgacagcgtgcaactggctccccctgccctgcccgcgccatcggccgccgtggagcgttcgcgtcgtctc gaacaggaggcggcaggtttggcgaagtcgatgaccatcgacacgcgaggaactatgacgaccaagaagc gaaaaaccgccggcgaggacctggcaaaacaggtcagcgaggccaagcaggccgcgttgctgaaacacac gaagcagcagatcaaggaaatgcagctttccttgttcgatattgcgccgtggccggacacgatgcgagcg atgccaaacgacacggcccgctctgccctgttcaccacgcgcaacaagaaaatcccgcgcgaggcgctgc aaaacaaggtcattttccacgtcaacaaggacgtgaagatcacctacaccggcgtcgagctgcgggccga cgatgacgaactggtgtggcagcaggtgttggagtacgcgaagcgcacccctatcggcgagccgatcacc ttcacgttctacgagctttgccaggacctgggctggtcgatcaatggccggtattacacgaaggccgagg aatgcctgtcgcgcctacaggcgacggcgatgggcttcacgtccgaccgcgttgggcacctggaatcggt gtcgctgctgcaccgcttccgcgtcctggaccgtggcaagaaaacgtcccgttgccaggtcctgatcgac gaggaaatcgtcgtgctgtttgctggcgaccactacacgaaattcatatgggagaagtaccgcaagctgt cgccgacggcccgacggatgttcgactatttcagctcgcaccgggagccgtacccgctcaagctggaaac cttccgcctcatgtgcggatcggattccacccgcgtgaagaagtggcgcgagcaggtcggcgaagcctgc gaagagttgcgaggcagcggcctggtggaacacgcctgggtcaatgatgacctggtgcattgcaaacgct agggccttgtggggtcagttccggctgggggttcagcagccagcgcctgatctggggaaccctgtggttg gcacatacaaatggacgaacggataaaccttttcacgcccttttaaatatccgattattctaataaacgc -continued tcttttctcttaggtttacccgccaatatatcctgtcaaacactgatagtttaaactgaaggcgggaaac gacaatctgatctaagctagcttggaattggtaccacgcgtttcgacaaaatttagaacgaacttaatta tgatctcaaatacattgatacatatctcatctagatctaggttatcattatgtaagaaagttttgacgaa tatggcacgacaaaatggctagactcgatgtaattggtatctcaactcaacattatacttataccaaaca ttagttagacaaaatttaaacaactatttttatgtatgcaagagtcagcatatgtataattgattcaga atcgttttgacgagttcggatgtagtagtagccattatttaatgtacatactaatcgtgaatagtgaata tgatgaaacattgtatcttattgtataaatatccataaacacatcatgaaagacactttctttcacggtc tgaattaattatgatacaattctaatagaaaacgaattaaattacgttgaattgtatgaaatctaattga acaagccaaccacgacgacgactaacgttgcctggattgactcggtttaagttaaccactaaaaaaacgg agctgtcatgtaacacgcggatcgagcaggtcacagtcatgaagccatcaaagcaaaagaactaatccaa gggctgagatgattaattagtttaaaaattagttaacacgagggaaaaggctgtctgacagccaggtcac gttatctttacctgtggtcgaaatgattcgtgtctgtcgattttaattatttttttgaaaggccgaaaat aaagttgtaagagataaacccgcctatataaattcatatattttcctctccgctttgaagttttagtttt attgcaacaacaacaacaaattacaataacaacaaacaaaatacaaacaacaacaacatggcacaatttc aacaaacaattgacatgcaaactctccaagccgctgcgggacgcaacagcttggtgaatgatttggcatc tcgtcgcgtttacgataatgcagtcgaggagctgaatgctcgttccagacgtcccaaggtaataggaact ttctggatctactttatttgctggatctcgatcttgttttctcaatttccttgagatctggaattcgttt aatttggatctgtgaacctccactaaatcttttggttttactagaatcgatctaagttgaccgatcagtt agctcgattatagctaccagaatttggcttgaccttgatggagagatccatgttcatgttacctgggaaa tgatttgtatatgtgaattgaaatctgaactgttgaagttagattgaatctgaacactgtcaatgttaga ttgaatctgaacactgtttaaggttagatgaagtttgtgtatagattcttcgaaactttaggatttgtag tgtcgtacgttgaacagaaagctatttctgattcaatcagggtttatttgactgtattgaactcttttttg tgtgtttgcaggtccacttctccaaggcagtgtctacggaacagaccctgattgcaacaaacgcatatcc ggagttcgagatttcctttactcatacgcaatccgctgtgcactccttggccggaggccttcggtcactt gagttggagtatctcatgatgcaagttccgttcggttctctgacgtacgacatcggcggtaacttttccg cgcaccttttcaaagggcgcgattacgttcactgctgcatgcctaatctggatgtacgtgacattgctcg ccatgaaggacacaaggaagctatttacagttatgtgaatcgtttgaaaaggcagcagcgtcctgtgcct gaataccagagggcagctttcaacaactacgctgagaacccgcacttcgtccattgcgacaaacctttcc aacagtgtgaattgacgacagcgtatggcactgacacctacgctgtagctctccatagcatttatgatat ccctgttgaggagttcggttctgcgctactcaggaagaatgtgaaaacttgtttcgcggcctttcatttc catgagaatatgcttctagattgtgatacagtcacactcgatgagattggagctacgttccagaaatcag gtaacattccttagttacctttcttttctttttccatcataagtttatagattgtacatgctttgagatt tttctttgcaaacaatctcaggtgataacctgagcttcttcttccataatgagagcactctcaattacac ccacagcttcagcaacatcatcaagtacgtgtgcaagacgttcttccctgctagtcaacgcttcgtgtac cacaaggagttcctggtcactagagtcaacacttggtactgcaagttcacgagagtggatacgttcactc tgttccgtggtgtgtaccacaacaatgtggattgcgaagagttttacaaggctatggacgatgcgtggca ctacaaaaagacgttagcaatgcttaatgccgagaggaccatcttcaaggataacgctgcgttaaacttc tggttcccgaaggtgctcttgaaattggaagtcttcttttgttgtctaaacctatcaatttctttgcgga aatttatttgaagctgtagagttaaaattgagtcttttaaacttttgtaggtgagagacatggttatcgt ccctctctttgacgcttctatcacaactggtaggatgtctaggagagaggttatggtgaacaaggacttc gtctacacggtcctaaatcacatcaagacctatcaagctaaggcactgacgtacgcaaacgtgctgagct -continued tcgtggagtctattaggtctagagtgataattaacggtgtcactgccaggtaagttgttacttatgattg ttttcctctctgctacatgtattttgttgttcatttctgtaagatataagaattgagttttcctctgatg atattattaggtctgaatgggacacagacaaggcaattctaggtccattagcaatgacattcttcctgat cacgaagctgggtcatgtgcaagatgaaataatcctgaaaaagttccagaagttcgacagaaccaccaat gagctgatttggacaagtctctgcgatgccctgatggggggttattccctcggtcaaggagacgcttgtgc gcggtggttttgtgaaagtagcagaacaagccttagagatcaaggttagtatcatatgaagaaataccta gtttcagttgatgaatgctattttctgacctcagttgttctcttttgagaattatttcttttctaatttg cctgatttttctattaattcattaggttcccgagctatactgtaccttcgccgaccgattggtactacag tacaagaaggcggaggagttccaatcgtgtgatctttccaaacctctagaagagtcagagaagtactaca acgcattatccgagctatcagtgcttgagaatctcgactcttttgacttagaggcgtttaagactttatg tcagcagaagaatgtggacccggatatggcagcaaaggtaaatcctggtccacacttttacgataaaaac acaagattttaaactatgaactgatcaataatcattcctaaaagaccacacttttgttttgtttctaaag taatttttactgttataacaggtggtcgtagcaatcatgaagtcagaattgacgttgcctttcaagaaac ctacagaagaggaaatctcggagtcgctaaaaccaggagaggggtcgtgtgcagagcataaggaagtgtt gagcttacaaaatgatgctccgttcccgtgtgtgaaaaatctagttgaaggttccgtgccggcgtatgga atgtgtcctaagggtggtggtttcgacaaattggatgtggacattgctgatttccatctcaagagtgtag atgcagttaaaaagggaactatgatgtctgcggtgtacacagggtctatcaaagttcaacaaatgaagaa ctacatagattacttaagtgcgtcgctggcagctacagtctcaaacctctgcaaggtaagaggtcaaaag gtttccgcaatgatccctctttttttgtttctctagtttcaagaatttgggtatatgactaacttctgag tgttccttgatgcatatttgtgatgagacaaatgtttgttctatgttttaggtgcttagagatgttcacg gcgttgacccagagtcacaggagaaatctggagtgtgggatgttaggagaggacgttggttacttaaacc taatgcgaaaagtcacgcgtggggtgtggcagaagacgccaaccacaagttggttattgtgttactcaac tgggatgacggaaagccggtttgtgatgagacatggttcagggtggcggtgtcaagcgattccttgatat attcggatatgggaaaacttaagacgctcacgtcttgcagtccaaatggtgagccaccggagcctaacgc caaagtaattttggtcgatggtgttcccggttgtggaaaaacgaaggagattatcgaaaaggtaagttct gcatttggttatgctccttgcattttaggtgttcgtcgctcttccatttccatgaatagctaagattttt tttctctgcattcattcttcttgcctcagttctaactgtttgtggtatttttgttttaattattgctaca ggtaaacttctctgaagacttgattttagtccctgggaaggaagcttctaagatgatcatccggagggcc aaccaagctggtgtgataagagcggataaggacaatgttagaacggtggattccttcttgatgcatcctt ctagaagggtgtttaagaggttgtttatcgatgaaggactaatgctgcatacaggttgtgtaaatttcct actgctgctatctcaatgtgacgtcgcatatgtgtatggggacacaaagcaaattccgttcatttgcaga gtcgcgaactttccgtatccagcgcattttgcaaaactcgtcgctgatgagaaggaagtcagaagagtta cgctcaggtaaagcaactgtgttttaatcaatttcttgtcaggatatatggattataacttaatttttga gaaatctgtagtatttggcgtgaaatgagtttgctttttggtttctcccgtgttataggtgcccggctga tgttacgtatttccttaacaagaagtatgacggggcggtgatgtgtaccagcgcggtagagagatccgtg aaggcagaagtggtgagaggaaagggtgcattgaacccaataaccttaccgttggagggtaaaattttga ccttcacacaagctgacaagttcgagttactggagaagggttacaaggtaaagtttccaactttccttta ccatatcaaactaaagttcgaaactttttatttgatcaacttcaaggccacccgatctttctattcctga ttaatttgtgatgaatccatattgacttttgatggttacgcaggatgtgaacactgtgcacgaggtgcaa ggggagacgtacgagaagactgctattgtgcgcttgacatcaactccgttagagatcatatcgagtgcgt -continued cacctcatgttttggtggcgctgacaagacacacaacgtgttgtaaatattacaccgttgtgttggaccc gatggtgaatgtgatttcagaaatggagaagttgtccaatttccttcttgacatgtatagagttgaagca ggtctgtctttcctatttcatatgtttaatcctaggaatttgatcaattgattgtatgtatgtcgatccc aagactttcttgttcacttatatcttaactctctctttgctgtttcttgcaggtgtccaatagcaattac aaatcgatgcagtattcaggggacagaacttgtttgttcagacgcccaagtcaggagattggcgagatat gcaattttactatgacgctcttcttcccggaaacagtactattctcaatgaatttgatgctgttacgatg aatttgagggatatttccttaaacgtcaaagattgcagaatcgacttctccaaatccgtgcaacttccta aagaacaacctatttcctcaagcctaaaataagaactgcggcagaaatgccgagaactgcaggtaaaat attggatgccagacgatattctttcttttgatttgtaacttttcctgtcaaggtcgataaattttattt tttttggtaaaaggtcgataattttttttggagccattatgtaattttcctaattaactgaaccaaaat tatacaaaccaggtttgctggaaaatttggttgcaatgatcaaaagaaacatgaatgcgccggatttgac agggacaattgacattgaggatactgcatctctggtggttgaaaagttttgggattcgtatgttgacaag gaatttagtggaacgaacgaaatgaccatgacaagggagagcttctccaggtaaggacttctcatgaata ttagtggcagattagtgttgttaaagtctttggttagataatcgatgcctcctaattgtccatgttttac tggttttctacaattaaaggtggctttcgaaacaagagtcatctacagttggtcagttagcggactttaa ctttgtggatttgccggcagtagatgagtacaagcatatgatcaagagtcaaccaaagcaaaagttagac ttgagtattcaagacgaatatcctgcattgcagacgatagtctaccattcgaaaaagatcaatgcgattt tcggtccaatgttttcagaacttacgaggatgttactcgaaaggattgactcttcgaagtttctgttcta caccagaaagacacctgcacaaatagaggacttcttttctgacctagactcaacccaggcgatggaaatt ctggaactcgacatttcgaagtacgataagtcacaaaacgagttccattgtgctgtagagtacaagatct gggaaaagttaggaattgatgagtggctagctgaggtctggaaacaaggtgagttcctaagttccatttt tttgtaatccttcaatgttattttaacttttcagatcaacatcaaaattaggttcaattttcatcaacca aataatatttttcatgtatatataggtcacagaaaaacgaccttgaaagattatacggccggaatcaaaa catgtctttggtatcaaaggaaaagtggtgatgtgacaacctttattggtaataccatcatcattgccgc atgtttgagctcaatgatccccatggacaaagtgataaaggcagctttttgtggagacgatagcctgatt tacattcctaaaggtttagacttgcctgatattcaggcgggcgcgaacctcatgtggaacttcgaggcca aactcttcaggaagaagtatggttacttctgtggtcgttatgttattcaccatgatagaggagccattgt gtattacgatccgcttaaactaatatctaagttaggttgtaaacatattagagatgttgttcacttagaa gagttacgcgagtctttgtgtgatgtagctagtaacttaaataattgtgcgtatttttcacagttagatg aggccgttgccgaggttcataagaccgcggtaggcggttcgtttgctttttgtagtataattaagtattt gtcagataagagattgtttagagatttgttctttgtttgataatgtcgatagtctcgtacgaacctaagg tgagtgatttcctcaatctttcgaagaaggaagagatcttgccgaaggctctaacgaggttaaaaaccgt gtctattagtactaaagatattatatctgtcaaggagtcggagactttgtgtgatatagatttgttaatc aatgtgccattagataagtatagatatgtgggtatcctaggagccgtttttaccggagagtggctagtgc cagacttcgttaaaggtggagtgacgataagtgtgatagataagcgtctggtgaactcaaaggagtgcgt gattggtacgtacagagccgcagccaagagtaagaggttccagttcaaattggttccaaattactttgtg tccaccgtggacgcaaagaggaagccgtggcaggtaaggatttttatgatatagtatgcttatgtatttt gtactgaaagcatatcctgcttcattgggatattactgaaagcatttaactacatgtaaactcacttgat gatcaataaacttgattttgcaggttcatgttcgtatacaagacttgaagattgaggcgggttggcagcc gttagctctggaagtagtttcagttgctatggtcaccaataacgttgtcatgaagggtttgagggaaaag gtcgtcgcaataaatgatccggacgtcgaaggtttcgaaggtaagccatcttcctgcttatttttataat -continued gaacatagaaataggaagttgtgcagagaaactaattaacctgactcaaaatctaccctcataattgttg tttgatattggtcttgtattttgcaggtgtggttgacgaattcgtcgattcggttgcagcatttaaagcg gttgacaactttaaaagaaggaaaaagaaggttgaagaaaagggtgtagtaagtaagtataagtacagac cggagaagtacgccggtcctgattcgtttaatttgaaagaagaaaacgtcttacaacattacaaacccga atcagtaccagtatttcgataagaaacaagaaac nucleotide sequence of binary PVX-based vector used for salmocin ScolE2 immunity protein ImmScolE2 expression in examples

SEQ ID NO: 24 gatcggtcgtatcactggaacaacaaccgctgaggctgttgtcactctaccaccaccataactacgtcta cataaccgacgcctaccccagtttcatagtattttctggtttgattgtatgaataatataaataaaaaaa aaaaaaaaaaaaaaaaactagtgagctcttctgtcagcgggcccactgcatccaccccagtacattaaaa acgtccgcaatgtgttattaagttgtctaagcgtcaatttgtttacaccacaatatatcctgccaccagc cagccaacagctccccgaccggcagctcggcacaaaatcaccactcgatacaggcagcccatcagtcaga tcaggatctcctttgcgacgctcaccgggctggttgccctcgccgctgggctggcggccgtctatggccc tgcaaacgcgccagaaacgccgtcgaagccgtgtgcgagacaccgcggccgccggcgttgtggatacctc gcggaaaacttggccctcactgacagatgaggggcggacgttgacacttgaggggccgactcacccggcg cggcgttgacagatgaggggcaggctcgatttcggccggcgacgtggagctggccagcctcgcaaatcgg cgaaaacgcctgattttacgcgagtttcccacagatgatgtggacaagcctggggataagtgccctgcgg tattgacacttgaggggcgcgactactgacagatgaggggcgcgatccttgacacttgaggggcagagtg ctgacagatgaggggcgcacctattgacatttgaggggctgtccacaggcagaaaatccagcatttgcaa gggtttccgcccgtttttcggccaccgctaacctgtcttttaacctgcttttaaaccaatatttataaac cttgtttttaaccagggctgcgccctgtgcgcgtgaccgcgcacgccgaaggggggtgcccccccttctc gaaccctcccggcccgctaacgcgggcctcccatccccccaggggctgcgcccctcggccgcgaacggcc tcaccccaaaaatggcagcgctggccaattcgtgcgcggaacccctatttgtttatttttctaaatacat tcaaatatgtatccgctcatgagacaataaccctgataaatgcttcaataatattgaaaaaggaagagta tggctaaaatgagaatatcaccggaattgaaaaaactgatcgaaaaataccgctgcgtaaaagatacgga aggaatgtctcctgctaaggtatataagctggtgggagaaaatgaaaacctatatttaaaaatgacggac agccggtataaagggaccacctatgatgtggaacgggaaaaggacatgatgctatggctggaaggaaagc tgcctgttccaaaggtcctgcactttgaacggcatgatggctggagcaatctgctcatgagtgaggccga tggcgtcctttgctcggaagagtatgaagatgaacaaagccctgaaaagattatcgagctgtatgcggag tgcatcaggctctttcactccatcgacatatcggattgtccctatacgaatagcttagacagccgcttag ccgaattggattacttactgaataacgatctggccgatgtggattgcgaaaactgggaagaagacactcc atttaaagatccgcgcgagctgtatgatttttttaaagacggaaaagcccgaagaggaacttgtcttttcc cacggcgacctgggagacagcaacatctttgtgaaagatggcaaagtaagtggctttattgatcttggga gaagcggcagggcggacaagtggtatgacattgccttctgcgtccggtcgatcagggaggatatcgggga agaacagtatgtcgagctatttttttgacttactggggatcaagcctgattgggagaaaataaaatattat attttactggatgaattgttttagctgtcagaccaagtttactcatatatactttagattgatttaaaac ttcatttttaatttaaaaggatctaggtgaagatcctttttgataatctcatgaccaaaatcccttaacg tgagttttcgttccactgagcgtcagaccccgtagaaaagatcaaaggatcttcttgagatcctttttt ctgcgcgtaatctgctgcttgcaaacaaaaaaaccaccgctaccagcggtggtttgtttgccggatcaag agctaccaactctttttccgaaggtaactggcttcagcagagcgcagataccaaatactgtccttctagt gtagccgtagttaggccaccacttcaagaactctgtagcaccgcctacatacctcgctctgctaatcctg -continued ttaccagtggctgctgccagtggcgataagtcgtgtcttaccgggttggactcaagacgatagttaccgg ataaggcgcagcggtcgggctgaacggggggttcgtgcacacagcccagcttggagcgaacgacctacac cgaactgagatacctacagcgtgagctatgagaaagcgccacgcttcccgaagggagaaaggcggacagg tatccggtaagcggcagggtcggaacaggagagcgcacgagggagcttccagggggaaacgcctggtatc tttatagtcctgtcgggtttcgccacctctgacttgagcgtcgatttttgtgatgctcgtcaggggggcg gagcctatggaaaaacgccagcaacgcggcctttttacggttcctggcagatcctagatgtggcgcaacg atgccggcgacaagcaggagcgcaccgacttcttccgcatcaagtgttttggctctcaggccgaggccca cggcaagtatttgggcaaggggtcgctggtattcgtgcagggcaagattcggaataccaagtacgagaag gacggccagacggtctacgggaccgacttcattgccgataaggtggattatctggacaccaaggcaccag gcgggtcaaatcaggaataagggcacattgccccggcgtgagtcggggcaatcccgcaaggagggtgaat gaatcggacgtttgaccggaaggcatacaggcaagaactgatcgacgcggggttttccgccgaggatgcc gaaaccatcgcaagccgcaccgtcatgcgtgcgccccgcgaaaccttccagtccgtcggctcgatggtcc agcaagctacggccaagatcgagcgcgacagcgtgcaactggctccccctgccctgcccgcgccatcggc cgccgtggagcgttcgcgtcgtctcgaacaggaggcggcaggtttggcgaagtcgatgaccatcgacacg cgaggaactatgacgaccaagaagcgaaaaaccgccggcgaggacctggcaaaacaggtcagcgaggcca agcaggccgcgttgctgaaacacacgaagcagcagatcaaggaaatgcagctttccttgttcgatattgc gccgtggccggacacgatgcgagcgatgccaaacgacacggcccgctctgccctgttcaccacgcgcaac aagaaaatcccgcgcgaggcgctgcaaaacaaggtcattttccacgtcaacaaggacgtgaagatcacct acaccggcgtcgagctgcgggccgacgatgacgaactggtgtggcagcaggtgttggagtacgcgaagcg caccccctatcggcgagccgatcaccttcacgttctacgagctttgccaggacctgggctggtcgatcaat ggccggtattacacgaaggccgaggaatgcctgtcgcgcctacaggcgacggcgatgggcttcacgtccg accgcgttgggcacctggaatcggtgtcgctgctgcaccgcttccgcgtcctggaccgtggcaagaaaac gtcccgttgccaggtcctgatcgacgaggaaatcgtcgtgctgtttgctggcgaccactacacgaaattc atatgggagaagtaccgcaagctgtcgccgacggcccgacggatgttcgactatttcagctcgcaccggg agccgtacccgctcaagctggaaaccttccgcctcatgtgcggatcggattccacccgcgtgaagaagtg gcgcgagcaggtcggcgaagcctgcgaagagttgcgaggcagcggcctggtggaacacgcctgggtcaat gatgacctggtgcattgcaaacgctagggccttgtggggtcagttccggctgggggttcagcagccagcg cctgatctggggaaccctgtggttggcacatacaaatggacgaacggataaaccttttcacgccctttta aatatccgattattctaataaacgctcttttctcttaggtttacccgccaatatatcctgtcaaacactg atagtttaaactgaaggcgggaaacgacaatctgatctaagctaggcatgcctgcaggtcaacatggtgg agcacgacacgcttgtctactccaaaaatatcaaagatacagtctcagaagaccaaagggcaattgagac ttttcaacaaagggtaatatccggaaacctcctcggattccattgcccagctatctgtcactttattgtg aagatagtggaaaaggaaggtggctcctacaaatgccatcattgcgataaaggaaaggccatcgttgaag atgcctctgccgacagtggtcccaaagatggacccccacccacgaggagcatcgtggaaaaagaagacgt tccaaccacgtcttcaaagcaagtggattgatgtgatatctccactgacgtaagggatgacgcacaatcc cactatccttcgcaagacccttcctctatataaggaagttcatttcatttggagaggagaaaactaaacc atacaccaccaacacaaccaaacccaccacgcccaattgttacacacccgcttgaaaaagaaagtttaac aaatggccaaggtgcgcgaggtttaccaatcttttacagactccaccacaaaaactctcatccaagatga ggcttatagaaacattcgccccatcatggaaaaacacaaactagctaaccccttacgctcaaacggttgaa gcggctaatgatctagaggggttcggcatagccaccaatccctatagcattgaattgcatacacatgcag -continued ccgctaagaccatagagaataaacttctagaggtgcttggttccatcctaccacaagaacctgttacatt
tatgtttcttaaacccagaaagctaaactacatgagaagaaacccgcggatcaaggacattttccaaaat
gttgccattgaaccaagagacgtagccaggtaccccaaggaaacaataattgacaaactcacagagatca
caacggaaacagcatacattagtgacactctgcacttcttggatccgagctacatagtggagacattcca
aaactgcccaaaattgcaaacattgtatgcgaccttagttctccccgttgaggcagcctttaaaatggaa
agcactcacccgaacatatacagcctcaaatacttcggagatggtttccagtatataccaggcaaccatg
gtggcggggcataccatcatgaattcgctcatctacaatggctcaaagtgggaaagatcaagtggaggga
ccccaaggatagctttctcggacatctcaattacacgactgagcaggttgagatgcacacagtgacagta
cagttgcaggaatcgttcgcggcaaaccacttgtactgcatcaggagaggagacttgctcacaccggagg
tgcgcactttcggccaacctgacaggtacgtgattccaccacagatcttcctcccaaaagttcacaactg
caagaagccgattctcaagaaaactatgatgcagctcttcttgtatgttaggacagtcaaggtcgcaaaa
aattgtgacatttttgccaaagtcagacaattaattaaatcatctgacttggacaaatactctgctgtgg
aactggtttacttagtaagctacatggagttccttgccgatttacaagctaccacctgcttctcagacac
actttctggtggcttgctaacaaagacccttgcaccggtgagggcttggatacaagagaaaaagatgcag
ctgtttggtcttgaggactacgcgaagttagtcaaagcagttgatttccacccggtggatttttctttca
aagtggaaacttgggacttcagattccaccccttgcaagcgtggaaagccttccgaccaagggaagtgtc
ggatgtagaggaaatggaaagtttgttctcagatggggacctgcttgattgcttcacaagaatgccagct
tatgcggtaaacgcagaggaagatttagctgcaatcaggaaaacgcccgagatggatgtcggtcaagaag
ttaaagagcctgcaggagacagaaatcaatactcaaaccctgcagaaactttcctcaacaagctccacag
gaaacacagtagggaggtgaaacaccaggccgcaaagaaagctaaacgcctagctgaaatccaggagtca
atgagagctgaaggtgatgccgaaccaaatgaaataagcgggacgatgggggcaatacccagcaacgccg
aacttcctggcacgaatgatgccagacaagaactcacactcccaaccactaaacctgtccctgcaaggtg
ggaagatgcttcattcacagattctagtgtggaagaggagcaggttaaactccttggaaaagaaaccgtt
gaaacagcgacgcaacaagtcatcgaaggacttccttggaaacactggattcctcaattaaatgctgttg
gattcaaggcgctggaaattcagagggataggagtggaacaatgatcatgcccatcacagaaatggtgtc
cgggctggaaaaagaggacttccctgaaggaactccaaaagagttggcacgagaattgttcgctatgaac
agaagccctgccaccatccctttggacctgcttagagccagagactacggcagtgatgtaaagaacaaga
gaattggtgccatcacaaagacacaggcaacgagttggggcgaatacttgacaggaaagatagaaagctt
aactgagaggaaagttgcgacttgtgtcattcatggagctggaggttctggaaaaagtcatgccatccag
aaggcattgagagaaattggcaagggctcggacatcactgtagtcctgccgaccaatgaactgcggctag
attggagtaagaaagtgcctaacactgagccctatatgttcaagacctctgaaaaggcgttaattggggg
aacaggcagcatagtcatctttgacgattactcaaaacttcctcccggttacatagaagccttagtctgt
ttctactctaaaatcaagctaatcattctaacaggagatagcagacaaagcgtctaccatgaaactgctg
aggacgcctccatcaggcatttgggaccagcaacagagtacttctcaaaatactgccgatactatctcaa
tgccacacaccgcaacaagaaagatcttgcgaacatgcttggtgtctacagtgagagaacgggagtcacc
gaaatcagcatgagcgccgagttcttagaaggaatcccaactttggtaccctcggatgagaagagaaagc
tgtacatgggcaccgggaggaatgacacgttcacatacgctggatgccaggggctaactaagccgaaggt
acaaatagtgttggaccacaacacccaagtgtgtagcgcgaatgtgatgtacacggcactttctagagcc
accgataggattcacttcgtgaacacaagtgcaaattcctctgccttctgggaaaagttggacagcaccc
cttacctcaagactttcctatcagtggtgagagaacaagcactcagggagtacgagccggcagaggcaga
gccaattcaagagcctgagccccagacacacatgtgtgtcgagaatgaggagtccgtgctagaagagtac -continued aaagaggaactcttggaaaagtttgacagagagatccactctgaatcccatggtcattcaaactgtgtcc aaactgaagacacaaccattcagttgttttcgcatcaacaagcaaaagatgagactctcctctgggcgac tatagatgcgcggctcaagaccagcaatcaagaaacaaacttccgagaattcctgagcaagaaggacatt ggggacgttctgtttttaaactaccaaaaagctatgggtttacccaaagagcgtattcctttttcccaag aggtctgggaagcttgtgcccacgaagtacaaagcaagtacctcagcaagtcaaagtgcaacttgatcaa tgggactgtgagacagagcccagacttcgatgaaaataagattatggtattcctcaagtcgcagtgggtc acaaaggtggaaaaactaggtctacccaagattaagccaggtcaaaccatagcagccttttaccagcaga ctgtgatgctttttggaactatggctaggtacatgcgatggttcagacaggctttccagccaaaagaagt cttcataaactgtgagacgacgccagatgacatgtctgcatgggccttgaacaactggaatttcagcaga cctagcttggctaatgactacacagctttcgaccagtctcaggatggagccatgttgcaatttgaggtgc tcaaagccaaacaccactgcataccagaggaaatcattcaggcatacatagatattaagactaatgcaca gattttcctaggcacgttatcaattatgcgcctgactggtgaaggtcccacttttgatgcaaacactgag tgcaacatagcttacacccatacaaagtttgacatcccagccggaactgctcaagtttatgcaggagacg actccgcactggactgtgttccagaagtgaagcatagtttccacaggcttgaggacaaattactcctaaa gtcaaagcctgtaatcacgcagcaaaagaagggcagttggcctgagttttgtggttggctgatcacacca aaaggggtgatgaaagacccaattaagctccatgttagcttaaaattggctgaagctaagggtgaactca agaaatgtcaagattcctatgaaattgatctgagttatgcctatgaccacaaggactctctgcatgactt gttcgatgagaaacagtgtcaggcacacacactcacttgcagaacactaatcaagtcagggagaggcact gtctcactttcccgcctcagaaactttctttaaccgttaagttaccttagagatttgaataagatgtcag caccagctagtacaacacagcccatagggtcaactacctcaactaccacaaaaactgcaggcgcaactcc tgccacagcttcaggcctgttcactatcccggatggggatttctttagtacagcccgtgccatagtagcc agcaatgctgtcgcaacaaatgaggacctcagcaagattgaggctatttggaaggacatgaaggtgccca cagacactatggcacaggctgcttgggacttagtcagacactgtgctgatgtaggatcatccgctcaaac agaaatgatagatacaggtccctattccaacggcatcagcagagctagactggcagcagcaattaaagag gtgtgcacacttaggcaattttgcatgaagtatgccccagtggtatggaactggatgttaactaacaaca gtccacctgctaactggcaagcacaaggtttcaagcctgagcacaaattcgctgcattcgacttcttcaa tggagtcaccaacccagctgccatcatgcccaaagaggggctcatccggccaccgtctgaagctgaaatg aatgctgcccaaactgctgcctttgtgaagattacaaaggccagggcacaatccaacgactttgccagcc tagatgcagctgtcactcgaggaaggatcaccggaacgaccacagcagaggcagtcgttactctgcctcc tccataacagaaactttctttaaccgttaagttaccttagagatttgaataagatggatattctcatcag tagtttgaaaagtttaggttattctaggacttccaaatctttagattcaggacctttggtagtacatgca gtagccggagccggtaagtccacagccctaaggaagttgatcctcagacacccaacattcaccgtgcata cactcggtgtccctgacaaggtgagtatcagaactagaggcatacagaagccaggacctattcctgaggg caacttcgcaatcctcgatgagtatactttggacaacaccacaaggaactcataccaggcactttttgct gacccttatcaggcaccggagtttagcctagagccccacttctacttggaaacatcatttcgagttccga ggaaagtggcagatttgatagctggctgtggcttcgatttcgagacgaactcaccggaagaagggcactt agagatcactggcatattcaaagggcccctactcggaaaggtgatagccattgatgaggagtctgagaca acactgtccaggcatggtgttgagtttgttaagccctgccaagtgacgggacttgagttcaaagtagtca ctattgtgtctgccgcaccaatagaggaaattggccagtccacagctttctacaacgctatcaccaggtc aaagggattgacatatgtccgcgcagggccataggctgaccgctccggtcaattctgaaaaagtgtacat -continued agtattaggtctatcatttgctttagtttcaattacctttctgctttctagaaatagcttaccccacgtc ggtgacaacattcacagcttgccacacggaggagcttacagagacggcaccaaagcaatcttgtacaact ccccaaatctagggtcacgagtgagtctacacaacggaaagaacgcagcatttgctgccgttttgctact gactttgctgatctatggaagtaaatacatatctcaacgcaatcatacttgtgcttgtggtaacaatcat agcagtcattagcacttccttagtgaggactgaaccttgtgtcatcaagattactggggaatcaatcaca gtgttggcttgcaaactagatgcagaaaccataagggccattgccgatctcaagccactctccgttgaac ggttaagtttccattgatactcgaaagaggtcagcaccagctagcaacaaacaagaacatggaactgaag aagtccatcagcgattacaccgaggctgagttcaagaagatcatcgaggctatcatcaactgcgagggtg atgagaaaacccaggatgataaccttgagttcttcatcagggtgaccgagtacccttctggtagcgatct tatctactaccctgagggtgataacgatggtagcaccgaggcaattatcaaagaaatcaaggaatggagg gctgctaacggtaagcctggttttaagcaagcttaa Amino acid sequence of salmocin ScolE1c

SEQ ID NO: 25

MSDNTIAYYEDGVPYSADGKVLIIIDGKMPVDTGGTGGGGGGKAGVTSESSAAIHATAKWSKAQLQKSLE

EKAARERETAAAMAAAKAKRDALTQHLKDIVNDVLYHNAHPPAVIDLAHANNMAMQAEAQRLGRAKAEEK

ARKEAEAAEKSLQEAERQCEEAARQRAEAERQLKQAEAEEKRLAALSEEARAVEIAQKNLAAAQSELSKM

DGEIMSLNVRLSTSIHARDAEMNSLSGKRNELAQASAKYKELDELVKKLEPRANDPLQNRPFFDAASRRA

RAGDTLAEKQKEVTASETRINELNTEINQVQGAISQANNNRNLNVQQVTETENALKVAIDNLNSSQMKNA

VDATVSFYQTLTEKYGEKYSLIAQELAEKSKGKKIGNVDEALAAFEKYKDVLDRKFSKADRDAIVNALKS

FNYDDWAKHLDQFAKYLKITGHVSFGYDVVSDVLKARETGDWKPLFITLEQKALDTGMSYLVVLMFSLIA

GTTLGIFGVAIITAILCSFVDKYILNALNDALGI

Amino acid sequence of salmocin ScolE1d

SEQ ID NO: 26

MSDNTIAYYEDGVPYSADGKVLIIIDGKMPVDTGGTGGGGGGKAGVTSESSAAIHATAKWSKAQLQKSLE

EKAARERETAAAMAAAKAKRDALTQHLKDIVNDVLYHNAHPPAVIDLAHANNMAMQAEAQRLGRAKAEEK

ARKEAEAAEKSLQEAERQREEAARQRAEAERQLKQAEAEEKRLAALSEEARAVEIAQKNLAAAQSELSKM

DGEIMSLNVRLSTSIHARDAEMNSLSGKRNELAQASAKYKELDELVKKLEPRANDPLQNRPFFDAASRRA

RAGDTLAEKQKEVTASETRINELNTEINQVQGAISQANNNRNLNVQQVTETENALKVAIDNLNSSQMKNA

VDATVSFYQTLTEKYGEKYSLIAQELAEKSKGKKIGNVDEALAAFEKYKDVLDRKFSKADRDAIVNALKS

FNYDDWAKHLDQFAKYLKITGHVSFGYDVVSDVLKARETGDWKPLFITLEQKALDTGMSYLVVLMFSLIA

GTTLGIFGVAIITAILCSFVDKYILNALNDALGI

Amino acid sequence of salmocin ScolE1e

SEQ ID NO: 27

MSGSIAYYEDGVPYSADGKVVIVITGKLPEGTGGSLTADLGSAGVSESSAAIHATAKWSTAQLQKTKAEQ

AVKVKEAAVAQAKAKEKRDALTQYLKDIVNQALSHNSRPPAVTDLAHANNMAMQAEAERLRLAKAEAKAR

EEAEAAEKAFQLAEQQRLASEREQAETERQLKLAEAEEKRLAALSEEARAVEIAQKNLAATQSELTNMDG

EIQNLNIRLNNNIHERDAETSSLSARRNELFQVSEQYKEIDAQVKKLEPRANDPLQSRPFFAAMTRRANV

YTVVQEKQGLVTASETRINQFNADISRLQEEIVKANEKRNMIITHIHEAEEQLKIAKINLINSQIKDATD

SVIGFYQTLTEKYGQKYSLLAQELAEKSKGKKIGNVNEALAAFEKYQDVLNKKFSKADRDAIFNALESVK

YDDWAKHLDQFAKYLKITGRVSFGYDLVSDVLKVRDTGDWKPLEMILEKKALDTGLSYLVVLMFSLIAGT

TLGIWGVAIVTGILCSFIDKSMLNDLNEALGI

Amino acid sequence of salmocin ScolMa

SEQ ID NO: 28

MIDIITVVAPVPPSGSALAGNYSASTMSAGNRISSGPTFLQFAYPYYQSPQLAVNCAKWILDFVESHDMK

NANNQKIFSENVGHFCFADKNLVNYPAMKVLDAFGGDRKFIYSQDQISRLSGDVTTPITAWAHFLWGDGA

-continued

ARTVNLTDVGLRIQANQISPVMDLVKGGAVGTFPVNAKFTRDTMLDGIIPASYLGNITLQTTGTLTINSL

GAMSYDGVVKAYNDTYDANPSTHRGLLGEYSTSVLGHFSGTPYEIQMPGMIPVKGNGMR

Nucleotide sequence used for salmocin ScolE1c expression in examples

SEQ ID NO: 29 atgagcgacaacaccattgcctactacgaggatggtgtgccttacagcgctgatggtaaggtgctgatca tcatcgatggcaagatgcctgttgataccggtggtactggtggtggtggcggtggtaaggctggtgttac ttctgaatctagcgctgctattcacgctaccgccaagtggtctaaggctcagcttcagaagtctctggaa gagaaggctgctagagagagggaaactgctgctgctatggctgctgcaaaggctaagagagatgctctta cccagcacctgaaggacatcgtgaacgatgtgctttaccataacgctcaccctccagctgtgattgatct tgctcacgctaacaacatggctatgcaggctgaagctcagaggcttggtagagctaaggctgaggaaaag gctcgtaaagaagctgaggctgctgagaagtcacttcaagaggctgaaagacagtgcgaggaagctgcta gacaaagagctgaagcagagaggcaacttaagcaggctgaggcagaagagaagaggcttgctgctctttc tgaagaggctagggctgttgagatcgctcagaagaatcttgctgctgcacagagcgagctgtccaagatg gatggtgagatcatgtctctgaacgtgcggctgtctacttctatccatgctagggatgccgagatgaaca gcctttctggtaagaggaatgagctggctcaggctagcgccaagtacaaagaacttgatgagctggtgaa gaagctcgagcctagggctaatgatccacttcagaacaggccattcttcgacgctgctagtagaagggct agagctggcgatactcttgccgagaagcagaaagaggttaccgcttctgagactcggatcaacgagctta acaccgagattaaccaggtgcagggtgctatctcacaggccaacaacaataggaacctcaacgtgcagca ggtcaccgagactgagaacgctcttaaggtggcaatcgacaacctgaacagcagccagatgaagaacgct gtggatgctaccgtgagcttctaccagactttgaccgagaagtacggggagaagtacagccttattgctc aagagctggccgagaagtccaagggtaagaaaattggtaacgtggacgaggctctcgctgccttcgaaaa gtacaaggatgtgctggaccggaagttcagcaaggctgatagggatgctattgtgaacgccctgaagtcc ttcaactacgacgattgggctaagcacctggaccagttcgctaagtaccttaagatcaccggccacgtgt ccttcggttacgatgttgtttctgacgtgctgaaggctcgtgagactggtgattggaagcctctgttcat taccctcgagcagaaggctttggataccggcatgtcttaccttgtggtgctgatgttctctctgatcgct ggtactacccttggcattttcggtgtggctatcatcaccgctatcctgtgctcattcgtggacaagtaca tcctgaacgctctgaacgatgctctgggaatctaa Nucleotide sequence used for salmocin ScolE1d expression in examples

SEQ ID NO: 30 atgagcgacaacaccattgcctactacgaggatggtgtgccttacagcgctgatggtaaggtgctgatca tcatcgatggcaagatgcctgttgataccggtggtactggtggtggtggcggtggtaaggctggtgttac ttctgaatctagcgctgctattcacgctaccgccaagtggtctaaggctcagcttcagaagtctctggaa gagaaggctgctagagagagggaaactgctgctgctatggctgctgcaaaggctaagagagatgctctta cccagcacctgaaggacatcgtgaacgatgtgctttaccataacgctcaccctccagctgtgattgatct tgctcacgctaacaacatggctatgcaggctgaagctcagaggcttggtagagctaaggctgaggaaaag gctcgtaaagaagctgaggctgctgagaagtcacttcaagaggctgaaaggcagagagaggaagctgcaa gacaaagagcagaggctgagagacaacttaagcaggctgaggcagaagagaagaggcttgctgctctttc tgaagaggctagggctgttgagatcgctcagaagaatcttgctgctgcacagagcgagctgtccaagatg gatggtgagatcatgtctctgaacgtgcggctgtctacttctatccatgctagggatgccgagatgaaca gcctttctggtaagaggaatgagctggctcaggctagcgccaagtacaaagaacttgatgagctggtgaa gaagctcgagcctagggctaatgatccacttcagaacaggccattcttcgacgctgctagtagaagggct agagctggcgatactcttgccgagaagcagaaagaggttaccgcttctgagactcggatcaacgagctta -continued acaccgagattaaccaggtgcagggtgctatctcacaggccaacaacaataggaacctcaacgtgcagca ggtcaccgagactgagaacgctcttaaggtggcaatcgacaacctgaacagcagccagatgaagaacgct gtggatgctaccgtgagcttctaccagactttgaccgagaagtacggggagaagtacagccttattgctc aagagctggccgagaagtccaagggtaagaaaattggtaacgtggacgaggctctcgctgccttcgaaaa gtacaaggatgtgctggaccggaagttcagcaaggctgatagggatgctattgtgaacgccctgaagtcc ttcaactacgacgattgggctaagcacctggaccagttcgctaagtaccttaagatcaccggccacgtgt ccttcggttacgatgttgtttctgacgtgctgaaggctcgtgagactggtgattggaagcctctgttcat taccctcgagcagaaggctttggataccggcatgtcttaccttgtggtgctgatgttctctctgatcgct ggtactacccttggcattttcggtgtggctatcatcaccgctatcctgtgctcattcgtggacaagtaca tcctgaacgctctgaacgatgctctgggaatctaa Nucleotide sequence used for salmocin ScolE1e expression in examples

SEQ ID NO: 31 atgagcggctctatcgcttactacgaggatggtgttccttacagcgctgatggtaaggtggtgatcgtga ttaccggcaagcttcctgaaggtactggtggttctcttaccgctgatcttggatctgctggtgtgtctga aagctctgctgctattcatgctaccgccaagtggtctactgctcagcttcaaaagactaaggctgagcag gccgtgaaggtgaaagaagctgctgttgctcaggccaaggccaaagaaaagagggatgctcttacccagt acctgaaggatatcgtgaaccaggctctgagccataactctagacctccagctgtgactgatctggctca cgctaacaatatggctatgcaggctgaggctgagaggcttagacttgctaaagctgaggctaaggctcgt gaagaagctgaagctgcagagaaggcttttcagcttgctgaacagcagaggcttgcttctgaaagagaac aggctgagacagagcggcagcttaagttggctgaagcagaggaaaagaggctggctgctctttctgaaga ggctagggctgttgagatcgctcagaagaatcttgctgctacccagtctgagctgaccaacatggatggt gagatccagaacctgaacatccggctgaacaacaacatccatgagagggacgctgagacaagctctctgt ctgctagacggaacgagcttttccaggttagcgagcagtacaaagagatcgacgcccaggttaagaagct tgagcctagggctaatgaccctcttcagtctaggcctttcttcgctgctatgaccagacgggctaatgtg tacactgtggtgcaagagaagcagggtcttgtgactgcttctgagactcggatcaaccagttcaacgctg acatctctaggctgcaagaagagatcgtcaaggccaacgagaagcggaacatgatcattacccacatcca cgaggctgaggaacagctgaagatcgctaagatcaacctgatcaactcccagatcaaggacgctaccgat agcgtgatcggtttctaccagactctgaccgagaagtacggccagaagtactctttgcttgctcaagagc tggccgagaagtccaagggtaagaaaatcggtaacgtgaacgaggcccttgctgcctttgagaagtacca ggatgtgctgaacaagaagttctccaaggctgacagggacgctatcttcaacgctcttgagtccgtgaag tacgacgattgggctaagcaccttgaccagttcgccaagtaccttaagatcaccggtagggtgagcttcg gttacgatcttgtgtccgatgtcctcaaggtgagagatactggtgattggaagccgctgttcttgaccct tgagaagaaggctcttgataccggcctgtcttaccttgtggtgctgatgttctctcttatcgccggtact acccttggcatttggggtgttgctattgtgaccggtatcctgtgctccttcatcgacaagagcatgctga acgacctcaacgaggctcttggtatctaa Nucleotide sequence used for salmocin ScolMa expression in examples

SEQ ID NO: 32 atgaccgacactattactgtggttgctcctgtgcctccttctggttctgctcttgctggtaactacagcg cctctactatgtctgctggcaacaggatttctagcggtcctacctttctgcagttcgcttacccttacta ccagtctcctcagcttgctgtgaattgcgctaagtggatcctggacttcgttgagagccacgacatgaag aacgccaacaaccagaaaatcttcagcgagaacgtgggccacttctgcttcgctgataagaaccttgtga actacccggccatgaaggtgttggatgcttttggtggtgaccggaagttcatctacagccaggatcagat ctctcggctgtctggtgatgtgactactcctattactgcttgggctcacttcctgtggggtgatggtgct -continued

```
gctaggactgtgaatcttaccgatgttggtctgcggatccaggccaatcagatttctcctgtgatggacc

tggtgaaaggtggtgctgttggtactttccctgtgaacgctaagttcaccagggataccatgctggacgg

tatcatccctgctagctaccttggtaacattacccttcagaccaccggcaccttgaccatcaattctctt

ggtgcttggagctacgatggcgtggtgaaggcttacaacgatacctacgatgctaacccgtctactcaca

ggggtttgcttggtgagtacagcacttctgtgctcggtcatttctctggaaccccttacgagattcagat

gcctggtatgatcccggtgaaaggcaatggtatgaggtaa
```

The article “a” and “an” are used herein to refer to one or more than one (i.e., to at least one) of the grammatical object of the article. By way of example, “an element” means one or more element.

Throughout the specification the word “comprising,” or variations such as “comprises” or “comprising,” will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. A composition comprising one or more proteins selected from the group consisting of ScolE1a, ScolE1b, ScolE1c, ScolE1d, and a derivative of ScolE1a, ScolE1b, ScolE1c, or ScolE1d; said one or more proteins comprising or consisting of any one of the following amino acid sequences:

(A-iv) the amino acid sequence set forth in SEQ ID NO: 4 (ScolE1a), (A-v) the amino acid sequence set forth in SEQ ID NO: 5 (ScolE1b), (A-vii) the amino acid sequence set forth in SEQ ID NO: 25 (ScolE1c), (A-viii) the amino acid sequence set forth in SEQ ID NO: 26 (ScolE1d), (B-iv) an amino acid sequence having at least 70% sequence identity to the amino acid sequence of SEQ ID NO: 4, (B-v) an amino acid sequence having at least 70% sequence identity to the amino acid sequence of SEQ ID NO: 5, (B-vii) an amino acid sequence having at least 80% sequence identity to the amino acid sequence of SEQ ID NO: 25, (B-viii) an amino acid sequence having at least 80% sequence identity to the amino acid sequence of SEQ ID NO: 26, (C-iv) an amino acid sequence having at least 80% sequence similarity to the amino acid sequence of SEQ ID NO: 4, (C-v) an amino acid sequence having at least 80% sequence similarity to the amino acid sequence of SEQ ID NO: 5, (C-vii) an amino acid sequence having at least 80% sequence similarity to the amino acid sequence of SEQ ID NO: 25, (C-viii) an amino acid sequence having at least 80% sequence similarity to the amino acid sequence of SEQ ID NO: 26, (D-iv) an amino acid sequence having from 1 to 40 amino acid substitutions, additions, insertions or deletions to the amino acid sequence of SEQ ID NO: 4, (D-v) an amino acid sequence having from 1 to 40 amino acid substitutions, additions, insertions or deletions to the amino acid sequence of SEQ ID NO: 5, (D-vii) an amino acid sequence having from 1 to 40 amino acid substitutions, additions, insertions or deletions to the amino acid sequence of SEQ ID NO: 25, (D-viii) an amino acid sequence having from 1 to 40 amino acid substitutions, additions, insertions or deletions to the amino acid sequence of SEQ ID NO: 26, (E-iv) an amino acid sequence comprising or consisting of at least 390 contiguous amino acid residues of SEQ ID NO: 4, (E-v) an amino acid sequence comprising or consisting of at least 425 contiguous amino acid residues of SEQ ID NO: 5, (E-vii) an amino acid sequence comprising or consisting of at least 425 contiguous amino acid residues of SEQ ID NO: 25, and (E-viii) an amino acid sequence comprising or consisting of at least 425 contiguous amino acid residues of SEQ ID NO: 26.

2. The composition according to claim 1, wherein said composition is a plant material or extract thereof, wherein the plant material is a material from a plant having expressed said one or more proteins; or wherein said composition is an aqueous solution containing said protein.

3. A method of preventing or reducing infection or contamination of an object with *Salmonella*, comprising contacting said object with composition according to claim 1.

4. The method according to claim 3, wherein said object is sprayed with said aqueous solution or is immersed into said aqueous solution, or said object is immersed for at least 10 seconds into an aqueous solution of said composition.

5. The method according to claim 3, wherein said object is food or animal feed; or said food is whole animal carcass, meat, eggs, raw fruit or vegetable.

6. A method of treating infection with *Salmonella* of a subject in need thereof, comprising administering to said subject a composition according to claim 1.

7. The method according to claim 3, wherein said *Salmonella* is *Salmonella enterica.*

8. The method according to claim 6, wherein said *Salmonella* is *Salmonella enterica.*

9. A composition comprising a first protein and a second protein, said first protein comprising or consisting of an amino acid sequence selected from the group consisting of (A-iv) the amino acid sequence set forth in SEQ ID NO: 4 (ScolE1a), (A-v) the amino acid sequence set forth in SEQ ID NO: 5 (ScolE1b), (A-vii) the amino acid sequence set forth in SEQ ID NO: 25 (ScolE1c), (A-viii) the amino acid sequence set forth in SEQ ID NO: 26 (ScolE1d), (B-iv) an amino acid sequence having at least 70% sequence identity to the amino acid sequence of SEQ ID NO: 4, (B-v) an amino acid sequence having at least 70% sequence identity to the amino acid sequence of SEQ ID NO: 5, (B-vii) an amino acid sequence having at least 70% sequence identity to the amino acid sequence of SEQ ID NO: 25, (B-viii) an amino acid sequence having at least 70% sequence identity to the amino acid sequence of SEQ ID NO: 26, (C-iv) an amino acid sequence having at least 80% sequence similarity to the amino acid sequence of SEQ ID NO: 4, (C-v) an amino acid sequence having at least 80% sequence similarity to the amino acid sequence of SEQ ID NO: 5, (C-vii) an amino acid sequence having at least 80% sequence similarity to the amino acid sequence of SEQ ID NO: 25, (C-viii) an amino acid sequence having at least 80% sequence similarity to the amino acid sequence of SEQ ID NO: 26, (D-iv) an amino acid sequence having from 1 to 40 amino acid substitutions, additions, insertions or deletions to the amino acid sequence of SEQ ID NO: 4, (D-v) an amino acid sequence having from 1 to 40 amino acid substitutions, additions, insertions or deletions to the amino acid sequence of SEQ ID NO: 5, (D-vii) an amino acid sequence having from 1 to 40 amino acid substitutions, additions, insertions or deletions to the amino acid sequence of SEQ ID NO: 25, (D-viii) an amino acid sequence having from 1 to 40 amino acid substitutions, additions, insertions or deletions to the amino acid sequence of SEQ ID NO: 26, (E-iv) an amino acid sequence comprising or consisting of at least 390 contiguous amino acid residues of SEQ ID NO: 4, (E-v) an amino acid sequence comprising or consisting of at least 425 contiguous amino acid residues of SEQ ID NO: 5, (E-vii) an amino acid sequence comprising or consisting of at least 425 contiguous amino acid residues of SEQ ID NO: 25, and (E-viii) an amino acid sequence comprising or consisting of at least 425 contiguous amino acid residues of SEQ ID NO: 26;

and said second protein comprising or consisting of an amino acid sequence selected from the group consisting of (A-i) the amino acid sequence set forth in SEQ ID NO: 1 (ScolE2), (B-i) an amino acid sequence having at least 75% sequence identity to the amino acid sequence of SEQ ID NO: 1, (C-i) an amino acid sequence having at least 85% sequence similarity to the amino acid sequence of SEQ ID NO: 1, (D-i) an amino acid sequence having from 1 to 40 amino acid substitutions, additions, insertions or deletions to the amino acid sequence of SEQ ID NO: 1, and (E-i) an amino acid sequence comprising or consisting of at least 470 contiguous amino acid residues of SEQ ID NO: 1.

10. A composition comprising a first protein and a second protein, said first protein comprising or consisting of an amino acid sequence selected from the group consisting of (A-iv) the amino acid sequence set forth in SEQ ID NO: 4 (ScolE1a), (A-v) the amino acid sequence set forth in SEQ ID NO: 5 (ScolE1b), (A-vii) the amino acid sequence set forth in SEQ ID NO: 25 (ScolE1c), (A-viii) the amino acid sequence set forth in SEQ ID NO: 26 (ScolE1d), (B-iv) an amino acid sequence having at least 70% sequence identity to the amino acid sequence of SEQ ID NO: 4, (B-v) an amino acid sequence having at least 70% sequence identity to the amino acid sequence of SEQ ID NO: 5, (B-vii) an amino acid sequence having at least 70% sequence identity to the amino acid sequence of SEQ ID NO: 25, (B-viii) an amino acid sequence having at least 70% sequence identity to the amino acid sequence of SEQ ID NO: 26, (C-iv) an amino acid sequence having at least 80% sequence similarity to the amino acid sequence of SEQ ID NO: 4, (C-v) an amino acid sequence having at least 80% sequence similarity to the amino acid sequence of SEQ ID NO: 5, (C-vii) an amino acid sequence having at least 80% sequence similarity to the amino acid sequence of SEQ ID NO: 25, (C-viii) an amino acid sequence having at least 80% sequence similarity to the amino acid sequence of SEQ ID NO: 26, (D-iv) an amino acid sequence having from 1 to 40 amino acid substitutions, additions, insertions or deletions to the amino acid sequence of SEQ ID NO: 4, (D-v) an amino acid sequence having from 1 to 40 amino acid substitutions, additions, insertions or deletions to the amino acid sequence of SEQ ID NO: 5, (D-vii) an amino acid sequence having from 1 to 40 amino acid substitutions, additions, insertions or deletions to the amino acid sequence of SEQ ID NO: 25, (D-viii) an amino acid sequence having from 1 to 40 amino acid substitutions, additions, insertions or deletions to the amino acid sequence of SEQ ID NO: 26, (E-iv) an amino acid sequence comprising or consisting of at least 390 contiguous amino acid residues of SEQ ID NO: 4, (E-v) an amino acid sequence comprising or consisting of at least 425 contiguous amino acid residues of SEQ ID NO: 5, (E-vii) an amino acid sequence comprising or consisting of at least 425 contiguous amino acid residues of SEQ ID NO: 25, and (E-viii) an amino acid sequence comprising or consisting of at least 425 contiguous amino acid residues of SEQ ID NO: 26;

and said second protein comprising or consisting of an amino acid sequence selected from the group consisting of (A-x) the amino acid sequence set forth in SEQ ID NO: 28 (ScolMa), (B-x) an amino acid sequence having at least 70% sequence identity to the amino acid sequence of SEQ ID NO: 28, (C-x) an amino acid sequence having at least 80% sequence similarity to the amino acid sequence of SEQ ID NO: 28, (D-x) an amino acid sequence having from 1 to 40 amino acid substitutions, additions, insertions or deletions to the amino acid sequence of SEQ ID NO: 28, and (E-x) an amino acid sequence comprising or consisting of at least 215 contiguous amino acid residues of SEQ ID NO: 28.

11. A method of preventing or reducing infection or contamination of an object with *Salmonella*, comprising contacting said object with a composition according to claim 9.

12. The method according to claim 11, wherein said object is sprayed with said aqueous solution or is immersed into said aqueous solution, or said object is immersed for at least 10 seconds into an aqueous solution of said composition.

13. The method according to claim 11, wherein said object is food or animal feed; or said food is whole animal carcass, meat, eggs, raw fruit or vegetable.

14. The method according to claim 11, wherein said *Salmonella* is *Salmonella enterica*.

15. A method of treating infection with *Salmonella* of a subject in need thereof, comprising administering to said subject a composition according to claim 9.

16. A method of preventing or reducing infection or contamination of an object with *Salmonella*, comprising contacting said object with a composition according to claim 10.

17. The method according to claim 16, wherein said object is sprayed with said aqueous solution or is immersed into said aqueous solution, or said object is immersed for at least 10 seconds into an aqueous solution of said composition.

18. The method according to claim 16, wherein said object is food or animal feed; or said food is whole animal carcass, meat, eggs, raw fruit or vegetable.

19. The method according to claim 16, wherein said *Salmonella* is *Salmonella enterica*.

20. A method of treating infection with *Salmonella* of a subject in need thereof, comprising administering to said subject a composition according to claim 10.

* * * * *